US011505782B2

(12) United States Patent
Draganov et al.

(10) Patent No.: US 11,505,782 B2
(45) Date of Patent: Nov. 22, 2022

(54) CELL-BASED VEHICLES FOR POTENTIATION OF VIRAL THERAPY

(71) Applicant: CALIDI BIOTHERAPEUTICS, INC., La Jolla, CA (US)

(72) Inventors: Dobrin Draganov, San Diego, CA (US); Aladar A. Szalay, Highland, CA (US)

(73) Assignee: Calidi Biotherapeutics, Inc., La Jolla, CA (US)

( * ) Notice: Subject to any disclaimer, the term of this patent is extended or adjusted under 35 U.S.C. 154(b) by 665 days.

(21) Appl. No.: 16/536,073

(22) Filed: Aug. 8, 2019

(65) Prior Publication Data

US 2019/0367880 A1 Dec. 5, 2019
US 2020/0318073 A9 Oct. 8, 2020

Related U.S. Application Data

(63) Continuation of application No. PCT/US2019/035464, filed on Jun. 4, 2019.

(60) Provisional application No. 62/680,570, filed on Jun. 4, 2018.

(51) Int. Cl.

| C12N 5/0775 | (2010.01) |
| C12N 5/09 | (2010.01) |
| C12N 7/00 | (2006.01) |
| G01N 33/50 | (2006.01) |
| A61P 35/00 | (2006.01) |
| A61K 35/28 | (2015.01) |
| A61P 35/02 | (2006.01) |
| A61K 35/13 | (2015.01) |
| C12N 5/078 | (2010.01) |

(52) U.S. Cl.
CPC ............ *C12N 5/0667* (2013.01); *A61K 35/13* (2013.01); *A61K 35/28* (2013.01); *A61P 35/00* (2018.01); *A61P 35/02* (2018.01); *C12N 5/0634* (2013.01); *C12N 5/0693* (2013.01); *C12N 5/0694* (2013.01); *C12N 7/00* (2013.01); *G01N 33/5005* (2013.01); *C12N 2501/231* (2013.01); *C12N 2501/24* (2013.01); *C12N 2501/999* (2013.01); *C12N 2510/00* (2013.01); *C12N 2710/24132* (2013.01)

(58) Field of Classification Search
CPC .................................................... C12N 5/0667
See application file for complete search history.

(56) References Cited

U.S. PATENT DOCUMENTS

| 5,023,252 A | 6/1991 | Hsieh ............................ 514/183 |
| 5,716,613 A | 2/1998 | Guber et al. ................. 424/93.2 |
| 5,716,826 A | 2/1998 | Guber et al. ................. 424/93.2 |
| 5,851,529 A | 12/1998 | Guber et al. ............... 424/188.1 |
| 6,428,968 B1 | 8/2002 | Molnar-Kimber et al. . 435/7.23 |
| 6,632,670 B1 | 10/2003 | Wadsworth .................... 435/455 |
| 6,635,472 B1 | 10/2003 | Lauermann ................. 435/320.1 |
| 6,653,103 B2 | 11/2003 | Petersen et al. ............. 435/69.1 |
| 6,689,871 B1 | 2/2004 | Wolfe et al. .................... 530/412 |
| 6,723,316 B2 | 4/2004 | Laquerre et al. ............. 424/93.2 |
| 6,723,325 B1 | 4/2004 | Weltzin et al. ............. 424/232.1 |
| 6,897,045 B2 | 5/2005 | Engelhardt et al. ......... 435/69.6 |
| 7,001,765 B2 | 2/2006 | Maass et al. ............... 435/320.1 |
| 7,033,826 B2 | 4/2006 | Perricaudet et al. ...... 435/320.1 |
| 7,115,270 B2 | 10/2006 | Welzin et al. ............. 424/232.1 |
| 7,153,510 B1 | 12/2006 | Rose .......................... 424/199.1 |
| 7,172,893 B2 | 2/2007 | Rabinowitz et al. ....... 435/235.1 |
| 7,238,526 B2 | 7/2007 | Wilson et al. ................. 435/382 |
| 7,241,447 B1 | 7/2007 | Engelhardt et al. ........ 424/193.1 |
| 7,537,924 B2 | 5/2009 | Coffin ........................ 435/235.1 |
| 7,550,296 B2 | 7/2009 | Hermiston et al. ........... 435/473 |
| 7,588,767 B2 | 9/2009 | Szalay et al. ............... 424/199.1 |
| 7,588,771 B2 | 9/2009 | Szalay et al. ............... 424/232.1 |
| 7,645,456 B2 | 1/2010 | Weltzin et al. ............. 424/232.1 |
| 7,662,398 B2 | 2/2010 | Szalay et al. ............... 424/232.1 |
| 7,662,627 B2 | 2/2010 | Johnson ......................... 435/367 |
| 7,731,952 B2 | 6/2010 | Mohr et al. ................... 424/93.2 |
| 7,731,974 B2 | 6/2010 | Bell et al. ................... 424/199.1 |
| 7,754,221 B2 | 7/2010 | Szalay et al. ............... 424/199.1 |
| 7,811,814 B2 | 10/2010 | Bohn et al. ................. 435/320.1 |
| 7,897,146 B2 | 3/2011 | Brown et al. ................. 424/93.1 |
| 7,906,111 B2 | 3/2011 | Wilson et al. ................. 424/93.2 |
| 7,927,585 B2 | 4/2011 | Snyder .......................... 424/93.2 |
| 7,943,374 B2 | 5/2011 | Hildinger ................... 435/320.1 |
| 7,968,340 B2 | 6/2011 | Hallek et al. ................. 435/440 |
| 8,007,780 B2 | 8/2011 | Arbetman et al. ........... 424/93.2 |
| 8,021,662 B2 | 9/2011 | Szalay et al. ............... 424/138.1 |
| 8,052,968 B2 | 11/2011 | Chen et al. ................. 424/93.21 |
| 8,221,769 B2 | 7/2012 | Szalay et al. ............... 424/232.1 |
| 8,859,256 B2 | 10/2014 | Szalay et al. ................. 435/210 |

(Continued)

FOREIGN PATENT DOCUMENTS

| EP | 1520175 | 11/2007 |
| EP | 1385466 | 3/2011 |

(Continued)

OTHER PUBLICATIONS

Letter/Written Disclosure of the Supplemental Information Disclosure Statement for the above-referenced application, filed herewith on Nov. 2, 2021, 2 pages.

News Release, entitled "Calidi Biotherapeutics Announces Partnership with GenScript ProBio for Distribution of its SuperNova-1 Technology." Published Jun. 8, 2021 [online]; retrieved on Jun. 16, 2021, from: <URL:businesswire.com/news/home/20210608005504/en/Calidi-Biotherapeutics-Announces-Partnership-with-GenScript-ProBio-for-Distribution-of-its-SuperNova-1-Technology, 2 pages.

(Continued)

*Primary Examiner* — Scott Long
(74) *Attorney, Agent, or Firm* — Dentons US LLP; Stephanie Seidman

(57) ABSTRACT

Provided herein are carrier cells and virus combinations and methods for treatment of cancers. Also provided are modified carrier cells for such treatment, and methods of selecting carrier cells that are matched to subjects for such treatment.

63 Claims, No Drawings

(56) References Cited

U.S. PATENT DOCUMENTS

| | | | |
|---|---|---|---|
| 9,492,534 B2 | 11/2016 | Szalay et al. | 424/199.1 |
| 10,105,436 B2 | 10/2018 | Szalay et al. | 424/186.1 |
| 2004/0009604 A1 | 1/2004 | Zhang et al. | 435/456 |
| 2004/0234455 A1 | 11/2004 | Szalay | 424/9.6 |
| 2005/0220818 A1 | 10/2005 | Lorence | 424/214.1 |
| 2005/0260601 A1 | 11/2005 | Whitt et al. | 435/6 |
| 2006/0039894 A1 | 2/2006 | Mohr et al. | 424/93.6 |
| 2007/0086984 A1 | 4/2007 | Coffey et al. | 424/93.2 |
| 2007/0098743 A1 | 5/2007 | Bell et al. | 424/224.1 |
| 2007/0110720 A1 | 5/2007 | Brown et al. | 424/93.2 |
| 2008/0206201 A1 | 8/2008 | Beler et al. | 424/93.6 |
| 2009/0010889 A1 | 1/2009 | Brown et al. | 424/93.2 |
| 2009/0162288 A1 | 6/2009 | Chen et al. | 424/9.3 |
| 2009/0215147 A1 | 8/2009 | Zhang et al. | 435/235.1 |
| 2009/0274728 A1 | 11/2009 | Brown et al. | 424/231.1 |
| 2009/0285860 A1 | 11/2009 | Martuza et al. | 424/277.1 |
| 2009/0324616 A1 | 12/2009 | Stassi et al. | 424/174.1 |
| 2010/0055102 A1 | 3/2010 | Langermann | 424/174.1 |
| 2010/0092515 A1 | 4/2010 | Conner et al. | 424/231.1 |
| 2010/0113567 A1 | 5/2010 | Barber | 514/44 |
| 2010/0172877 A1 | 7/2010 | Van den Pol et al. | 424/93.6 |
| 2010/0178684 A1 | 7/2010 | Woo et al. | 435/235.1 |
| 2010/0297072 A1 | 11/2010 | Depinho | 424/85.2 |
| 2011/0064650 A1 | 3/2011 | Szalay | 424/1.11 |
| 2011/0158948 A1 | 7/2011 | Brown et al. | 424/93.2 |
| 2011/0171219 A1 | 7/2011 | Merchant et al. | 435/325 |
| 2011/0177032 A1 | 7/2011 | Martuza et al. | 424/93.2 |
| 2011/0212530 A1 | 9/2011 | Baltimore et al. | 435/455 |
| 2011/0293527 A1 | 12/2011 | Chen et al. | 424/9.3 |
| 2012/0087901 A1 | 4/2012 | Nelson | 424/93.21 |
| 2013/0273007 A1 | 10/2013 | Szalay et al. | 424/93.2 |
| 2014/0017787 A1 | 1/2014 | Betancourt | 435/375 |
| 2015/0086541 A1 | 3/2015 | Aguilar-Cordova | 424/133.1 |
| 2015/0352206 A1 | 12/2015 | Gajewski et al. | 424/173.1 |
| 2017/0043010 A1 | 2/2017 | Szalay et al. | 424/186.1 |
| 2017/0239338 A1 | 8/2017 | Szalay et al. | 424/93.2 |
| 2018/0092951 A1 | 4/2018 | Szalay et al. | 424/138.1 |
| 2018/0326048 A1 | 11/2018 | Szalay et al. | 424/186.1 |
| 2020/0140824 A1 | 5/2020 | Fernandez Santidrian et al. | 424/93.21 |

FOREIGN PATENT DOCUMENTS

| | | |
|---|---|---|
| WO | WO 2002/046455 | 6/2002 |
| WO | WO 2004/085659 | 10/2004 |
| WO | WO 2008/009115 | 1/2008 |
| WO | WO 2008/052054 | 5/2008 |
| WO | WO 2009/13 9921 | 11/2009 |
| WO | WO 2014/022138 | 2/2014 |
| WO | WO 2015/089280 | 6/2015 |
| WO | WO 2016/008976 | 1/2016 |
| WO | WO 2016/065330 | 4/2016 |
| WO | WO 2016/149559 | 9/2016 |
| WO | WO 2017/027757 | 2/2017 |
| WO | WO 2019/236633 | 12/2019 |
| WO | WO 2020/097269 | 5/2020 |

OTHER PUBLICATIONS

News Release, entitled "Calidi Biotherapeutics Announces Agreement with Northwestern University for Exclusive Commercial Rights to their IND for Treatment of Malignant Glioma." Published Aug. 4, 2021 [online]; retrieved on Oct. 6. 2021, from: <URL:calidibio.com/2021/08/04/calidi-biotherapeutics-announces-agreement-with-northwestern-university-for-exclusive-commercial-rights-to-their-ind-for-treatment-of-malignant-glioma, 4 pages.
News Release, entitled "Calidi Biotherapeutics Announces Exclusive License Agreement with City of Hope and the University of Chicago for Novel Oncolytic Virotherapy Technology." Published Aug. 16, 2021 [online]; retrieved on Oct. 6, 2021, from: <URL:calidibio.com/2021/08/16/calidi-biotherapeutics-announces-exclusive-license-agreement-with-city-of-hope-and-the-university-of-chicago-for-novel-oncolytic-virotherapy-technology, 5 pages.
Response, filed Dec. 14, 2020, to Written Opinion of the International Preliminary Examining Authority, dated Oct. 12, 2020, in connection with related International Patent Application No. PCT/US2019/060160, 56 pages.
International Preliminary Report on Patentability (Chapter II of the PCT), dated Jan. 26, 2021, in connection with related International Application No. PCT/US2019/060160, 11 pages.
Examiner's Report, dated Apr. 28, 2021, in connection with corresponding Canadian Patent Application No. 3,100,046, 7 pages.
Response, filed Aug. 30, 2021, to Examiner's Report, dated Apr. 28, 2021, in connection with corresponding Canadian Patent Application No. 3,100,046, 128 pages.
Communication pursuant to Rules 161(1) and 162 EPC, dated Feb. 12, 2021, issued in connection with corresponding European Patent Application No. 19 759 071.4, 3 pages.
Response, filed Aug. 20, 2021, to Communication pursuant to Rules 161(1) and 162 EPC, dated Feb. 12, 2021, issued in connection with corresponding European Patent Application No. 19 759 071.4, 19 pages.
Letter/Written Disclosure of the Information Disclosure Statement for the above-referenced application, filed herewith on Nov. 7, 2019, 2 pages.
Agranovski et al., "Rapid detection of airborne viruses by personal bioaerosol sampler combined with the PCR device," Atmospheric Environment 40:3924-3929 (2006).
Angelova et al., "The Oncolytic Virotherapy Era in Cancer Management: Prospects of Applying H-1 Parvovirus to Treat Blood and Solid Cancers," Front. Oncol. 7:93 (2017) [8 pages].
Angelova et al., "Tumor Selectivity of Oncolytic Parvoviruses: From in vitro and Animal Models to Cancer Patients," Frontiers in Bioengineering and Biotechnology 3:55 (2015) [14 pages].
Aref et al., "Measles to the Rescue: A Review of Oncolytic Measles Virus," Viruses 8:294 (2016) [16 pages].
Balvers et al., "Locally-delivered T-cell-derived cellular vehicles efficiently track and deliver adenovirus delta24-RGD to infiltrating glioma," Viruses 6:3080-3096 (2014).
Baroudy et al., "Incompletely base-paired flip-flop terminal loops link the two DNA strands of the vaccinia virus genome into one uninterrupted polynucleotide chain," Cell 28:315-324 (1982).
Benson Jr., D.M. and M.A. Caligiuri, "Cancer Immunology at the Crossroads: Killer immunoglobulin-like receptors and tumor immunity," Cancer Immunol Res. 2(2):99-104 (2014).
Berglund et al., "Immunoprivileged no more: measuring the immunogenicity of allogeneic adult mesenchymal stem cells," Stem Cell Research & Therapy 8:288 (2017) [7 pages].
Bishnoi et al., "Oncotargetingby Vesicular Stomatitis Virus (VSV): Advances in Cancer Therapy," Viruses 10(2):90 (2018) [20 pages].
Bolontrade et al., "A specific subpopulation of mesenchymal stromal cell carriers overrides melanoma resistance to an oncolytic adenovirus," Stem cells and development 21(14): 2689-2702 (2012), 28 pages.
Bradley et al., "Applications of coxsackievirus A21 in oncology," Oncolytic Virotherapy 3:47-55 (2014).
Broder, C.C. and P.L. Earl, "Recombinant vaccinia viruses. Design, generation, and isolation," Mol. Bioteclmol. 13:223-245 (1999).
Brown, M.C. and M. Gromeier, "Oncolytic immunotherapy through tumor-specific translation and cytotoxicity of poliovirus," Discov. Med. 19(106):359-365 (2015).
Brown, M.C. and M. Gromeier, "Cytotoxic and immunogenic mechanisms of recombinant oncolytic poliovirus," Curr. Opin. Virol. 13:81-85 (2015).
Brown et al., "Oncolytic polio virotherapy of cancer," Cancer 120(21):3277-3286 (2014).
Burke, M. J., "Oncolytic Seneca Valley Virus: past perspectives and future directions," Oncolytic Virotherapy 5:81-89 (2016).
Burke et al., "Phase I Trial of Seneca Valley Virus (NTX-010) in Children with Relapsed / Refractory Solid Tumors: A Report of the Children's Oncology Group," Pediatr. Blood Cancer 62(5):743-750 (2015).
Casteilla et al., "Adipose-derived stromal cells: Their identity and uses in clinical trials, an update," World J Stem Cells 3(4):25-33 (2011).
Campadelli-Fiume et al., "Retargeting Strategies for Oncolytic Herpes Simplex Viruses," Viruses 8(3):63 (2016) [11 pages].

(56) References Cited

OTHER PUBLICATIONS

Cattaneo et al., "Reprogrammed viruses as cancer therapeutics: targeted, armed and shielded," Nat. Rev. Microbiol. 6(7):529-540 (2008).

Cecil et al., "Vaccinia virus injected human tumors: oncolytic virus efficiency predicted by antigen profiling analysis fitted boolean models," Bioengineered 10(1):190-196 (2019).

Cheng et al., "Genetic Modification of Oncolytic Newcastle Disease Virus for Cancer Therapy," J. Virol. 90(1):5343-5352 (2016).

Chkheidze et al., "Identification of DNA binding proteins in vaccinia virus by DNA-protein crosslinking," FEBS 336(2):340-342 (1993).

Choi et al., "Use of an anti-CD 16 antibody for in vivo depletion of natural killer cells in rhesus macaques," Immunology 124(2): 215-222 (2008).

Choi et al., "Polymeric oncolytic adenovirus for cancer gene therapy," J. Control. Release 10(219): 181-191 (2015).

Christaki et al., "NK and NKT Cell Depletion Alters the Outcome of Experimental Pneumococcal Pneumonia: Relationship with Regulation of Interferon-γ Production," J. Immunol. Res. 2015 Art. ID. 532717 (2015) [10 pages].

Correia et al., "Differentiation of human peripheral blood Vδ1+ T cells expressing the natural cytotoxicity receptor NKp30 for recognition of lymphoid leukemia cells," Blood 118(4):992-1001 (2011).

Dorer, D.E. and D.M. Nettelbeck, "Targeting cancer by transcriptional control in cancer gene therapy and viral oncolysis," Adv. Drug Deliv. Rev. 61(7-8):554-571 (2009).

Draghiciu et al., "Therapeutic immunization and local low-dose tumor irradiation, a reinforcing combination," Int J Cancer 134: 859-872 (2014).

Draganov et al., "Delivery of oncolytic vaccinia virus by matched allogeneic stem cells overcomes critical innate and adaptive immune barriers," Transl Med. 17 (1): 100 (2019), 22 pages.

Dold et al., "Application of interferon modulators to overcome partial resistance of human ovarian cancers to VSV-GP oncolytic viral therapy," Molecular Therapy—Oncolytics 3, 16021 (2016).

Eissa et al., "Genomic Signature of the Natural Oncolytic Herpes Simplex Virus HF10 and Its Therapeutic Role in Preclinical and Clinical Trials," Front. Oncol. 7:149 (2017) [12 pages].

Felt, S.A. and V.Z. Grdzelishvili, "Recent advances in vesicular stomatitis virus-based oncolytic virotherapy: a 5-year update," Journal of General Virology 98:2895-2911 (2017).

Field et al., "NNKTT120, an anti-iNKT cell monoclonal antibody, produces rapid and sustained iNKT cell depletion in adults with sickle cell disease," PLoS One 12(2):e0171067 (2017).

Beck et al., "Red Bone Marrow and Male Breast Doses for a Cohort of Atomic Veterans," Radiation Research 187: 221-228 (2017).

Fu et al., "Effective treatment of pancreatic cancer xenografts with a conditionally replicating virus derived from type 2 herpes simplex virus," Clin. Cancer Res. 12(10):3152-3157 (2006).

Fujiwara et al., "Carrier cell-based delivery of replication-competent HSV-1 mutants enhances antitumor effect for ovarian cancer," Cancer Gene Therapy 18:77-86 (2011).

Galanis et al., "Oncolytic measles virus expressing the sodium iodide symporter to treat drug-resistant ovarian cancer," Cancer Res. 75(1):22-30 (2015).

Geiss et al., "Preclinical Testing of an Oncolytic Parvovirus: Standard Protoparvovirus H-1PV Efficiently Induces Osteosarcoma Cell Lysis In Vitro," Viruses 9:301 (2017), 18 pages.

Geletneky et al., "Oncolytic H-1 Parvovirus Shows Safety and Signs of Immunogenic Activity in a First Phase I/IIa Glioblastoma Trial," Mol. Ther. 25(12):2620-2634 (2017).

Ginting et al., "Proinflammatory response induced by Newcastle disease virus in tumor and normal cells,"Oncolytic Virotherapy 6:21-30 (2017).

Gong et al., "Clinical development of reovirus for cancer therapy: An oncolytic virus with immune-mediated antitumor activity," World J. Methodol. 6(1):25-42 (2016).

Guo et al., "The combination of immunosuppression and carrier cells significantly enhances the efficacy of oncolytic poxvirus in the pre-immunized host," Gene Ther. 17(12): 1465-1475 (2010).

Guo et al., "Oncolytic virotherapy: molecular targets in tumor-selective replication and carrier cell-mediated delivery of oncolytic viruses," Biochim Biophys Acta 1785(2):217-231 (2008).

Heo et al., "Sequential therapy with JX-594, a targeted oncolytic poxvirus, followed by sorafenib in hepatocellular carcinoma: preclinical and clinical demonstration of combination efficacy," Mol. Ther. 19(6):1170-1179 (2011).

Huang, T., "Vaccinia Virus-mediated Therapy of Solid Tumor Xenografts: Intra-tumoral Delivery of Therapeutic Antibodies," Dissertation (2013), 172 pages.

Huang et al., "The use of hypoxic cultured mesenchymal stem cell for oncolytic virus therapy," Cancer Gene Therapy 20: 308-316 (2013).

Hutzen et al., "Advances in the design and development of oncolytic measles viruses," Oncolytic Virotherapy 4:109-118 (2015).

Ichise et al., "NK Cell Alloreactivity against KIR-Ligand-Mismatched HLA-Haploidentical Tissue Derived from HLA Haplotype-Homozygous iPSCs," Stem Cell Reports 9:853-867 (2017).

Ilett et al., "Internalization of oncolytic reovirus by human dendritic cell carriers protects the virus from neutralization," Clin. Cancer Res. 17(9):2767-2776 (2011).

Ilett et al., "Dendritic cells and T cells deliver oncolytic reovirus for tumour killing despite pre-existing anti-viral immunity," Gene Ther. 16(5):689-699 (2009).

Iupac-Iub, Commission on Biochemical Nomenclature, Biochemistry:"Symbols for Amino-Acid Derivatives and Peptides Recommendations," 11:1726-1731 (1972).

Jacobson et al., "Cap-dependent translational control of oncolytic measles virus infection in malignant mesothelioma," Oncotarget 8(38):63096-63109 (2017).

Janeway et al., "The major histocompatibility complex and its fucntions," Immunobiology: The Immune System in Health and Disease. 5th edition. New York: Garland Science; 2001. Retrieved from URL:<ncbi.nlm.nih.gov/books/NBK27156/, 13 pages.

Jennings et al., "Lymphokine-activated killer and dendritic cell carriage enhances oncolytic reovirus therapy for ovarian cancer by overcoming antibody neutralization in ascites," Int. J. Cancer 134:1091-1101 (2014).

Jiang et al., "Oncolytic adenovirus research evolution: from cell-cycle checkpoints to immune checkpoints," Curr. Opin. Virol. 13:33-39 (2015).

Josiah et al., "Adipose-derived Stem Cells as Therapeutic Delivery Vehicles of an Oncolytic Virus for Glioblastoma," Mol Ther 18(2): 377-85 (2010).

Kaczmarek et al., "CD1: A Singed Cat of the Three Antigen Presentation Systems," Arch. Immunol. Ther. Exp. 65:201-214 (2017).

Kazimirsky et al., "Mesenchymal stem cells enhance the oncolytic effect of Newcastle disease virus in glioma cells and glioma stem cells via the secretion of TRAIL," Stem Cell Research & Therapy 7:149 (2016), 10 pages.

Kelly, E.J. and S. J. Russell, "MicroRNAs and the regulation of vector tropism," Mol. Ther., 17(3):409-416 (2009).

Kelly et al., "Novel oncolytic agent GLV-1h68 is effective against malignant pleural mesothelioma," Hum. Gene Ther. 19:774-782 (2008).

Kemp et al., "Exploring Reovirus Plasticity for Improving Its Use as Oncolytic Virus," Viruses 8(1):4 (2016), 16 pages.

Kerrigan et al., "Mesenchymal stem cells for the delivery of oncolytic viruses in gliomas," Cytotherapy 19(4)445-457 (2017).

Kilinc et al., "The ratio of ADSCs to HSC-progenitors in adipose tissue derived SVF may provide the key to predict the outcome of stem-cell therapy," Clin Transl Med 7(1):5 (2018) 20 pages.

Kim et al., "Stem Cell-Based Cell Carrier for Targeted Oncolytic Virotherapy: Translational Opportunity and Open Questions," Viruses 7: 6200-6217 (2015).

Kim et al., "Overview analysis of adjuvant therapies for melanoma—a special reference to results from vaccinia melanoma oncolysate adjuvant therapy trials," Surgical Oncol. 10:53-59 (2001).

(56) References Cited

OTHER PUBLICATIONS

Kim et al., "Suppression of human anti-porcine natural killer cell xenogeneic responses by combinations of monoclonal antibodies specific to CD2 and NKG2D and extracellular signal-regulated kinase kinase inhibitor," Immunology 130:545-555 (2010).
Kimpel et al., "The Oncolytic Virus VSV-GP Is Effective against Malignant Melanoma," Viruses 10:108 (2018), 16 pages.
Koenecke et al., "In vivo application of mAb directed against the gammadelta TCR does not deplete but generates "invisible" gammadelta T cells," Eur. J. Immunol. 39(2):372-9 (2009).
Kohler, G and C. Milstein, "Continuous cultures of fused cells secreting antibody of predefined specificty," Nature 256:495-97 (1975).
Kohlhapp, F.J. and H.L. Kaufman, "Molecular Pathways: Mechanism of Action for Talimogene Laherparepvec, A New Oncolytic Virus Immunotherapy," Clin. Cancer Res. 22(5):1048-1054 (2016).
Kozlova et al., "Inactivation and mineralization of aerosol deposited model pathogenic microorganisms over TiO2 and Pt/TiO2," Environ. Sci. Technol. 44:5121-5126 (2010).
Kutinova et al., "Search for optimal parent for recombinant vaccinia virus vaccines. Study of three vaccinia virus vaccinal strains and several virus lines derived from them," Vaccine 13(5)487-493 (1995).
Kutinova et al., "Hepatitis B virus proteins expressed by recombinant vaccinia viruses: influence of preS2 sequence on expression surface and nucleocapsid proteins in human diploid cells," Arch. Virol. 134:1-15 (1994).
Lam et al., "Safety and clinical usage of newcastle disease virus in cancer therapy," J Biomed Biotechnol 2011: Article ID: 718710 (2011), 13 pages.
Laurie et al., "A phase 1 clinical study of intravenous administration of PV701, an oncolytic virus, using two-step desensitization," Clin. Cancer Res. 12(8):2555-2562 (2006).
Li et al., "Coadministration of a Herpes Simplex Virus-2-Based Oncolytic Virus and Cyclophosphamide Produces a Synergistic Antitumor Effect and Enhances Tumor-Specific Immune Responses," Cancer Res. 67(16):7850-7855 (2007).
Lin et al., "Ovarian cancer-related hypophosphatemic osteomalacia—a case report," J. Clin. Endocrinol. Metab. 99(12)4403-7 (2014).
Lin et al., "Treatment of anaplastic thyroid carcinoma in vitro with a mutant vaccinia virus," Surgery 142(6):976-983 (2007).
Liu et al., "The targeted oncolytic poxvirus JX-594 demonstrates antitumoral, antivascular, and anti-HBV activities in patients with hepatocellular carcinoma," Mol. Ther. 16(9):1637-1642 (2008).
Mader et al., "Mesenchymal stem cell carriers protect oncolytic measles viruses from antibody neutralization in an orthotopic ovarian cancer therapy model," Clin Cancer Res 15(23): 7246-7255 (2009), 18 pages.
Mader et al., "Optimizing patient derived mesenchymal stem cells as virus carriers for a Phase I clinical trial in ovarian cancer," J Trans Med 11: 20 (2013), 14 pages.
Matveeva et al., "Oncolysis by paramyxoviruses: preclinical and clinical studies," Molecular Therapy—Oncolytics 2, 150017 (2015),14 pages.
McCart et al., "Systemic cancer therapy with a tumor-selective vaccinia virus mutant lacking thymidine kinase and vaccinia growth factor genes," Cancer Res. 61:8751-8757 (2001).
Meyer et al., "A genomic perspective on HLA evolution," Immunogenetics 70:5-27 (2018).
Miles et al., "Anthrax toxin receptor 1 is the cellular receptor for Seneca Valley virus," J. Clin Invest. 127(8):2957-2967 (2017).
Minev et al., "First-in-human study of TK-positive oncolytic vaccinia virus delivered by adipose stromal vascular fraction cells," Transl Med 17 (1): 271 (2019), 15 pages.
Moehler et al., "Oncolytic virotherapy as emerging immunotherapeutic modality: potential of parvovirus h-1," Frontiers in Oncology 4:92 (2014), 10 pages.
Moser, B. and M. Eberl, "gammadelta T cells: novel initiators of adaptive immunity," Immunol. Reviews 215(1):89-102 (2007).

Moss, B., "Poxvirus vectors: cytoplasmic expression of transferred genes," Curr. Opin. Genet. Dev. 3:86-90 (1993).
Msaouel et al., "Oncolytic measles virus strains as novel anticancer agents," Expert Opin. Biol. Ther. 13(4)483-502 (2013), 28 pages.
Munguia et al., "Cell carriers to deliver oncolytic viruses to sites of myeloma tumor growth," Gene Ther 15(10): 797-806 (2008).
Muik et al., "Re-engineering vesicular stomatitis virus to abrogate neurotoxicity, circumvent humoral immunity, and enhance oncolytic potency," Cancer Res. 74(13):3567-3578 (2014).
Naik, S. and S. J. Ruseell, "Engineering oncolytic viruses to exploit tumor specific defects in innate immune signaling pathways," Expert Opin. Biol. Ther. 9(9):1163-1176 (2009).
Nakashima et al., "Directing systemic oncolytic viral delivery to tumors via carrier cells," Cytokine Growth Factor Reviews 21(2-3): 119-126(2010), 17 pages.
Park et al., "Use of a targeted oncolytic poxvirus, JX-594, in patients with refractory primary or metastatic liver cancer: a phase I trial," Lancet Oncol. 9:533-542 (2008).
Henderson, D.A. and B. Moss, "Recombinant Vaccinia Virus Vaccines," Plotkin SA, Orenstrin WA, editors. Vaccines. $3^{rd}$ Edition. Philadephia: Saunders (1999), 3 pages.
Power, A.T. and J.C. Bell, "Cell-based Delivery of Oncolytic Viruses: A New Strategic Alliance for a Biological Strike Against Cancer," Mol. Ther. 15(4): 660-665 (2007).
Power et al., "Carrier cell-based delivery of an oncolytic virus circumvents antiviral immunity," Molecular Therapy 15(1):123-130 (2007).
Protest Documents Submitted Under 37 CFR § 1.99 on Aug. 5, 2009 in connection with U.S. Appl. No. 12/218,953, 53 pages.
Qian et al., "Seneca Valley Virus Suppresses Host Type I Interferon Production by Targeting Adaptor Proteins MAVS, TRIF, and TANK for Cleavage," J. Virol. 91(16):e00823-17 (2017), 17 pages.
Ramirez et al., "Patient-derived mesenchymal stem cells as delivery vehicles for oncolytic virotherapy: novel state-of-the-art technology," Oncolytic Virotherapy 4:149-155 (2015).
Raykov et al., "Carrier cell-mediated delivery of oncolytic parvoviruses for targeting metastases," Int. J. Cancer 109:742-749 (2004).
Reeves, E. and E. James, "Antigen processing and immune regulation in the response to tumours," Immunology 150:16-24 (2016).
Response, filed Aug. 17, 2009, to Third Party Submission of Protest Documents Submitted Under 37 CFR § 1.99 on Aug. 7, 2009 in connection with U.S. Appl. No. 12/218,953, 5 pages.
Roy, D. G. and J. C. Bell, "Cell carriers for oncolytic viruses: current challenges and future directions," Oncolytic Virother 2: 47-56 (2013).
Qiao et al., "Loading of oncolytic vesicular stomatitis virus onto antigen-specific T cells enhances the efficacy of adoptive T-cell therapy of tumors," Gene Ther. 15(8):604-616 (2008).
Shaw, A.R. and M. Suzuki, "Recent advances in oncolytic adenovirus therapies for cancer," Curr. Opin. Virol. 21:9-15 (2016).
Shehelkunov et al., "The gene encoding the late nonstructural 36K protein of vaccinia virus is essential for virus reproduction," Virus Research 28:273-283 (1993).
Shulman et al., "A better cell line for making hybridomas secreting specific antibodies," Nature 276:269-270 (1978).
Sokolowski et al., "Oncolytic virotherapy using herpes simplex virus: how far have we come?" Oncolytic Virotherapy 4:207-219 (2015).
Sroller et al., "Effect of 3-beta-hydroxysterol dehydrogenase gene deletion on virulence and immunogenicity of different vaccinia viruses and their recombinants," Archives Virology 143:1311-1320 (1998).
Strassmann et al., "Depletion of human NK cells with monoclonal antibodies allows the generation of cytotoxic T lymphocytes without NK-like cells in mixed cultures," J. Immunol. 130(4): 1556-60 (1983).
Studeny et al., "Mesenchymal Stem Cells: Potential Precursors for Tumor Stroma and Targeted-Delivery Vehicles for Anticancer Agents," J. Natl Cancer Inst 96(21): 1593-1603 (2004).
Tayeb et al., "Therapeutic potential of oncolytic Newcastle disease virus: a critical review," Oncolytic Virotherapy 4:49-62 (2015).
Thorne et al., "Vaccinia virus and oncolytic virotherapy of cancer," Curr Opin Mol Ther 7(4): 359-365 (2005).

(56) References Cited

OTHER PUBLICATIONS

Thorne et al., "Targeting localized immune suppression within the tumor through repeat cycles of immune cell-oncolytic virus combination therapy," Molecular Therapy 18(9): 1698-1705 (2010).
Timiryasova et al., "Construction of Recombinant Vaccinia Viruses Using PUV-Inactivated Virus as a Helper," Biotechniques 31(3):534-540 (2001).
Traktman, P., Chapter 27, "Poxvirus DNA Replication," pp. 775-798, in DNA Replication in Eukaryotic Cells, Cold Spring Harbor Laboratory Press (1996), 24 pages.
Tsoneva et al., "Humanized Mice with Subcutaneous Human Solid Tumors for Immune Response Analysis of Vaccinia Virus-Mediated Oncolysis," Mol Ther Oncolytics 5:41-61 (2017).
Uusi-Kerttula et al., "Oncolytic Adenovirus: Strategies and Insights for Vector Design and Immuno-Oncolytic Applications," Viruses 7:6009-6042 (2015).
Veinalde et al., "Oncolytic measles virus encoding interleukin-12 mediates potent antitumor effects through T cell activation," Oncoimmunology 6(4):e1285992 (2017), 11 pages.
Volk et al., "Monoclonal antibodies to the glycoprotein of vesicular stomatitis virus: comparative neutralizing activity," J. Virol. 42(1):220-227 (1982).
Wang et al., "Oncolytic vaccinia virus GLV-1h68 strain shows enhanced replication in human breast cancer stem-like cells in comparison to breast cancer cells," J Transl Med 10:167 (2012), 15 pages.
Wasserstein, R. L. and N.A. Lazar, "The ASA's Statement on p-Values: Context, Process, and Purpose," The American Statistician 70(2): 129-33 (2016).
Waterman et al., "A New Mesenchymal Stem Cell (MSC) Paradigm: Polarization into a Pro-Inflammatory MSC1 or an Immunosuppressive MSC2 Phenotype," PLoS One 5(4):e10088 (2010) [14 pages].
Willmon et al., "Cell carriers for oncolytic viruses: Fed Ex for cancer therapy," Molecular Therapy 17(10):1667-1676 (2009).
Wu et al., "γδT cells and their potential for immunotherapy," Int. J. Biol. Sci. 10(2):119-135 (2014).
Yamamoto et al., "Recent advances in genetic modification of adenovirus vectors for cancer treatment," Cancer Sci. 108:831-837 (2017).
Yang et al., "Adult neural stem cells expressing IL-10 confer potent immunomodulation and remyelination in experimental autoimmune encephalitis," J Clin Invest 119(12): 3678-3691 (2009).
Yin et al., "Modulation of the Intratumoral Immune Landscape by Oncolytic Herpes Simplex Virus Virotherapy," Front. Oncol. 7:136 (2017), 7 pages.
Yla-Pelto et al., "Therapeutic Use of Native and Recombinant Enteroviruses," Viruses 8(3):57 (2016), 15 pages.
Yokoda et al., "Oncolytic Adenoviruses in Gastrointestinal Cancers," Biomedicines 6:33 (2018), 13 pages.
Yu et al., "Oncolytic vaccinia therapy of squamous cell carcinoma," Mol. Cancer 8:45 (2009), 9 pages.
Yu et al., "Regression of human pancreatic tumor xenografts in mice after a single systemic injection of recombinant vaccinia virus GLV-1h68," Mol. Cancer Ther. 8(1):141-151 (2009).
Yu et al., "Visualization of tumors and metastases in live animals with bacteria and vaccinia virus encoding light-emitting proteins," Nat. Biotech. 22(3):313-320 (2004).
Yu, Y.A. and A.A. Szalay, "A Renilla luciferase-Aequorea GFP (ruc-gfp) fusion gene construct permits real-time detection of promoter activation by exogenously administered mifepristone in vivo," Mol Genet Genomics 268:169-178 (2002).
Yuan et al., "Interleukin-23-Expressing Bone Marrow-Derived Neural Stem-Like Cells Exhibit Antitumor Activity Against Intracranial Glioma," Cancer Research 66(5): 2630-2638 (2006).
Zhao et al., "Strategic Combinations: The Future of Oncolytic Virotherapy with Reovirus," Mol. Cancer Ther. 15(5):767-773 (2016).
Zinoviev et al., "Identification of the gene encoding vaccinia virus immunodominant protein p35," Gene 147:209-214 (1994).

Minev et al., "First in man study of TK positive oncolytic vaccinia virus delivered by adipose stromal vascular fraction cells," [abstract] Journal for ImmunoTherapy of Cancer 2018, 6(Suppl 1):115, Abstract No. P609, Nov. 2018, 2 pages.
Minev et al., "First in man study of TK positive oncolytic vaccinia virus delivered by adipose stromal vascular fraction cells," poster presented at The Society for Immunotherapy of Cancer's (SITC) 33rd Annual Meeting | Nov. 7-11, 2018 Washington, D.C. [poster and individual panels], 8 pages.
Santidrian et al., "A cell-based platform to protect and enhance oncolytic virus therapies," [abstract] Journal for ImmunoTherapy of Cancer 2018, 6(Suppl 1):115, Abstract No. P617, Nov. 2018, 1 page.
Santidrian et al., "A cell-based platform to protect and enhance oncolytic virus therapies," poster presented at The Society for Immunotherapy of Cancer's (SITC) 33rd Annual Meeting |Nov. 7-11, 2018 Washington, D.C. [poster and individual panels], 9 pages.
News Release, Calidi Biotherapeutics "Calidi Biotherapeutics Announces Two Abstracts Accepted for Presentation at the Society for Immunotherapy of Cancer's (SITC) 33rd Annual Meeting." Published Nov. 6, 2018 [online] Retrieved from: <URL: calidibio.com/2018/11/06/calidi-biotherapeutics-inc-granted-new-patent-from-uspto-for-cell-based-delivery-of-oncolytic-vaccinia-viruses-2/ [retrieved on Nov. 29, 2018], 3 pages.
News Release, "Calidi Biotherapeutics Announces a Collaborative Study With the National Institutes of Health (NIH) on the Therapeutic Potential of Oncolytic Viruses Delivered by Mesenchymal Stem Cells," Published May 28, 2019 [online] Retrieved from: <URL: prnewswire.com/news-releases/calidi-biotherapeutics-amiounces-a-collaborative-study-with-the-national-institutes-of-health-nih-on-the-therapeutic-potential-of-oncolytic-viruses-delivered-by-mesenchymal-stem-cells-300857135.html [retrieved on May 28, 2019], 3 pages.
Guse et al., "Oncolytic vaccinia virus for the treatment of cancer," Expert Opin Biol Ther 11(5):595-608 (2011).
Wennier et al., "Bugs and Drugs: Oncolytic Virotherapy in Combination with Chemotherapy," Curr Pharm Biotechnol 13(9):1817-1833 (2012).
U.S. Appl. 16/676,413, filed Nov. 6, 2019, 2020-0140824, May 7, 2020.
Letter/Written Disclosure of the Supplemental Information Disclosure Statement for the above-referenced application, filed herewith dated Mar. 26, 2020, 2 pages.
Ahmed et al., "A Comparative Study of Neural and Mesenchymal Stem Cell-Based Carriers for Oncolytic Adenovirus in a Model of Malignant Glioma," Mol Pharm 8(5): 1559-72 (2011).
W. M. Chan and G. McFadden, "Oncolytic Poxviruses," Annu Rev Virol 1(1): 119-141 (2014).
Freeman et al., "Phase I/II Trial of Intravenous NDV-HUJ Oncolytic Virus in Recurrent Glioblastoma Multiforme," Mol Ther 13(1): 221-28 (2006).
Guo et al., "Neoantigen Vaccine Delivery for Personalized Anticancer Immunotherapy," Front. Immunol. 9:1499 (2018), 8 pages.
Kiline et al., "Colonization of xenograft tumors by oncolytic vaccinia virus (VACV) results in enhanced tumor killing due to the involvement of myeloid cells," J Transl Med 14(1):340 (2016), 12 pages.
Lu et al., "Genetic engineering of dendritic cells to express immunosuppressive molecules (viral IL-10, TGF-beta, and CTLA4Ig)," J Leukoc Biol 66(2): 293-96 (1999).
Nguyen et al., "Vaccinia virus-mediated expression of human erythropoietin in tumors enhances virotherapy and alleviates cancer-related anemia in mice," Mol Ther 21(11): 2054-62 (2013).
Payne et al., "Human adipose-derived mesenchymal stem cells engineered to secrete IL-10 inhibit APC function and limit CNS autoimmunity," Brain Behavior and Immunity 30(1): 103-114 (2013).
Rincon et al., "Mesenchymal Stem Cell Carriers Enhance Antitumor Efficacy of Oncolytic Adenoviruses in an Immunocompetent Mouse Model," Oncotarget 8(28): 45415-45431 (2017).
Wang et al., "Optical detection and virotherapy of live metastatic tumor cells in body fluids with vaccinia strains," PLoS One 8(9):e71105 (2013), 12 pages.

(56) References Cited

OTHER PUBLICATIONS

Nguyen et al., "A cell-based platform to potentiate oncolytic virus therapies," poster presented at ASCO-SITC Clinical Immuno-Oncology Symposium Feb. 6-8. 2020 Orlando, Florida, 1 page.

Nguyen et al., "A cell-based platform to potentiate oncolytic virus: Potential approach for cancer therapies," abstract presented at ASCO-SITC Clinical Immuno-Oncology Symposium Feb. 6, 2020, Orlando, Florida. Abstract No. 21, 2 pages.

News Release, "Calidi Biotherapeutics Presents Data at the 2020 ASCO-SITC Clinical Immuno-Oncology Symposium," Published Feb. 13, 2020 [online] Retrieved from: <URL: calidibio.com/2020/02/13/calidi-biotherapeutics-presents-data-at-the-2020-asco-site-clinical-immuno-oncology-symposium/ [retrieved on Mar. 11, 2020], 4 pages.

Invitation to Pay Additional Fees and Protest Fees, International Search Report and Provisional Written Opinion, dated Dec. 13, 2019, in connection with International Patent Application No. PCT/US2019/035464, 28 pages.

Response, filed Jan. 10, 2020, to Invitation to Pay Additional Fees and Protest Fees, and International Search Report and Provisional Written Opinion, dated Dec. 13, 2019, in connection with International Patent Application No. PCT/US2019/035464, 14 pages.

International Search Report and Written Opinion, dated Mar. 9, 2020, in connection with International Patent Application No. PCT/US2019/035464, 40 pages.

Letter/Written Disclosure of the Supplemental Information Disclosure Statement for the above-referenced application, filed herewith on Oct. 27, 2020, 2 pages.

Cho et al., "Role of Toll-Like Receptors on Human Adipose-Derived Stromal Cells," Stem Cells 24(12):2744-52 (2006).

Dias et al., "Targeted Cancer Immunotherapy With Oncolytic Adenovirus Coding for a Fully Human Monoclonal Antibody Specific for CTLA-4," Gene Ther 19:988-98 (2012).

Gao et al., "Recombinant Vesicular Stomatitis Virus Targeted to Her2/neu Combined With anti-CTLA4 Antibody Eliminates Implanted Mammary Tumors," Cancer Gene Ther 16(1): 44-52 (2009).

Lesterhuis et al., "Synergistic Effect of CTLA-4 Blockade and Cancer Chemotherapy in the Induction of Anti-Tumor Immunity," PLoS One 8(4):e61895 (2013), 8 pages.

Li et al., "Complement enhances in vitro neutralizing potency of antibodies to human cytomegalovirus glycoprotein B (gB) and immune sera induced by gB/MF59 vaccination," NPJ Vaccines 2:36 (2017), 8 pages.

Mehlhop et al., "Complement protein C1q reduces the stoichiometric threshold for antibody-mediated neutralization of West Nile virus," Cell Host Microbe 6(4):381-91 (2009).

Meyer et al., "Complement-mediated enhancement of antibody function for neutralization of pseudotype virus containing hepatitis C virus E2 chimeric glycoprotein," J Virol 76(5):2150-8 (2002).

Petrov et al., "Canine Adipose-Derived Mesenchymal Stem Cells (cAdMSCs) as a "Trojan Horse" in Vaccinia Virus Mediated Oncolytic Therapy against Canine Soft Tissue Sarcomas," Viruses 12(7):750 (2020), 13 pages.

Rogers et al., "Rationale for the clinical use of adipose-derived mesenchymal stem cells for COVID-19 patients," J Transl Med 18(1):203 (2020), 19 pages.

VanBlargen et al., "Deconstructing the Antiviral Neutralizing-Antibody Response: Implications for Vaccine Development and Immunity," Microbiol & Mol. Bio. Reviews 80(4):989-1010 (2016).

Draganov et al., "Evaluation of the potential of oncolytic vaccinia virus delivered by autologous SVF to modulate innate and adaptive immunity in patients with diverse solid and hematological malignancies," Abstract No. 4473 presented at AACR meeting Jun. 22, 2020. Virtual Meeting, 2 pages.

Nguyen et al., "CAL1 vaccinia virus as oncolytic agent and potential use of cell-based platform to enhance its therapeutic effects," Abstract No. 6542 presented at AACR meeting Jun. 22, 2020. Virtual Meeting, 2 pages.

News Release, "Calidi Biotherapeutics Announces Two Abstracts Accepted for Presentation at AACR 2020 Virtual Annual Meeting II," Published Jun. 22, 2020 [online] Retrieved from: <URL: businesswire.com/news/home/20200622005121/cn/Calidi-Biotherapeutics-Announces-Abstracts-Accepted-Presentation-AACR [retrieved on Jun. 23, 2020], 2 pages.

International Search Report and Written Opinion, dated Apr. 7, 2020, in connection with International Patent Application No. PCT/US2019/060160, 20 pages.

Demand for International Preliminary Exam, filed Sep. 7, 2020, to International Search Report and Written Opinion, dated Apr. 7, 2020, in connection with International Patent Application No. PCT/US2019/060160, 78 pages.

Written Opinion of the International Preliminary Examining Authority, dated Oct. 12, 2020, in connection with International Patent Application No. PCT/US2019/060160, 78 pages.

Response, filed Jun. 9, 2020, to International Search Report and Written Opinion, dated Mar. 9, 2020, in connection with International Patent Application No. PCT/US2019/035464, 74 pages.

Written Opinion, dated Jul. 3, 2020, in connection with International Patent Application No. PCT/US2019/035464, 10 pages.

Response, filed Sep. 3, 2020, to Written Opinion, dated Jul. 3, 2020, in connection with International Patent Application No. PCT/US2019/035464, 42 pages.

International Preliminary Report on Patentability, dated Sep. 28, 2020, in connection with International Patent Publication No. PCT/US2019/035464, 10 pages.

U.S. Appl. No. 15/521,602, filed Apr. 24, 2017, Publ. No. 2017-0239338, dated Aug. 24, 2017.

U.S. Appl. No. 16/044,136, filed Jul. 24, 2018, Publ. No. 2018-0326048, dated Nov. 15, 2018.

U.S. Appl. No. 16/676,413, filed Nov. 6, 2019.

CELL-BASED VEHICLES FOR POTENTIATION OF VIRAL THERAPY

RELATED APPLICATIONS

This application is a continuation of International PCT application No. PCT/US2019/035464, filed Jun. 4, 2019, to Dobrin Draganov and Aladar A. Szalay, and entitled "CELL-BASED VEHICLES FOR POTENTIATION OF VIRAL THERAPY," which claims priority to U.S. Provisional Application Ser. No. 62/680,570. Benefit of priority to PCT application No. PCT/US2019/035464, filed Jun. 4, 2019, and to U.S. Provisional Application Ser. No. 62/680,570, filed Jun. 4, 2018, to Dobrin Draganov and Aladar A. Szalay, and entitled "CELL-BASED VEHICLES FOR POTENTIATION OF VIRAL THERAPY" is claimed. The subject matter of each of these applications is incorporated by reference in its entirety.

FIELD OF THE INVENTION

Provided herein are carrier cells (cell vehicles) and virus combinations and methods for treatment of cancers, and methods of matching such to subjects for treatment.

BACKGROUND

Oncolytic viruses show promise as cancer therapeutics. Oncolytic viruses are designed to accumulate and replicate in cancerous cells. The oncolytic viruses can lyse cancerous cells and also can be used to encode and deliver anti-cancer agents. The efficacy of oncolytic viruses, however, can be impeded by circulating neutralizing antibodies, innate and adaptive immune mechanisms, and other clearing mechanisms that interfere with the delivery and/or accumulation of the viruses in cancerous tumors/cells. There is a need for improved delivery methods for effecting oncolytic therapy.

SUMMARY

A challenge of oncolytic therapy is that the immune system of the treated subject functions to eliminate viral infections. Oncolytic viruses preferentially replicate in tumor tissue and other immunoprivileged environments, but, particularly if they are systemically administered, they must escape from, avoid, or otherwise be protected from the host's immune (innate and adaptive) responses so that sufficient virus reaches tumors and metastases. This has been addressed by infecting cells and employing them as delivery vehicles (also referred to herein as carrier cells, or cell vehicles) for the virus. Cancer cells, tumor cells, as well as various types of stem cells and normal cells can carry oncolytic viruses in order to help protect them from complement and antibody mediated neutralization in circulation. The virus must be able to replicate in the cells, and at the same time escape the host's immune system, for a sufficient time to reach a tumor or tumor cells, and deliver virus. It is these properties that render cells suitable as carrier cells for oncolytic or therapeutic viruses. In general, however, when cells are administered, particularly systemically, but even locally, there are problems, including, but not limited to:

limited efficiency of delivery despite preferential homing to tumor environments: most infected cells get trapped in lungs or other organs and only a small percentage make it successfully to the tumor. Intratumoral injection only partially improves delivery, for reasons including poor retention of the administered carrier cells in the tumor, or leaks in circulation.

most cancers have limited subject- and cancer-type-specific permissiveness for oncolytic viruses (intrinsic resistance).

Efficient control and elimination of the virus by innate and adaptive immunity including interferon-gamma (IFNγ) production when only a limited number of viruses or infected carrier cells colonize the tumor.

Proper tumor colonization requires not only delivery, but also an initial boost or critical amplification of virus step to overcome the intrinsic tumor cell resistance as well as the innate and adaptive immune barriers.

The survival and virus amplification potential of off-the-shelf stem or cancer cells, if used as delivery vehicles, would be affected by allogeneic immune responses, including, for example, inactivation and/or immunological rejection.

Provided herein are methods, cells and strategies to address these problems and provide improved carrier cells and cells containing virus for oncolytic therapy. The cells include any that can be used to deliver virus to tumors, and, include stem cells, tumor cells, cell lines, primary cells, and cultured primary cells. The cells include stem cells, with the proviso that, where embryonic stem cells or cells derived from embryonic stem cells or cell lines are not permitted, reference to stem cells does not include such cells. Thus in some embodiments, the cells include any stem cells, except for embryonic stem cells and/or cells derived from embryonic stem cells or cell lines. The cells can be autologous or allogeneic. Methods herein render it possible to use allogeneic cells, including off-the-shelf allogeneic stem and cancer cell lines, not only to deliver, but also to provide potent intratumoral amplification of oncolytic viruses, thereby overcoming the existent allogeneic barriers. The cells provided herein have improved properties for delivery of oncolytic viruses to tumors. While any route of administration is contemplated, the cells can be administered via systemic administration. The cells are modified and/or treated (sensitized) to eliminate, reduce or avoid the host immune system, including complement, and host anti-virus immune responses. The cells also are modified or engineered or selected so that the particular oncolytic virus of interest can replicate in the cells, so that therapeutic amounts are delivered to tumors, metastases, and/or the tumor microenvironment.

Among the findings herein, it is shown herein that:

High intrinsic virus amplification ability of the cell-based delivery vehicle (stem cells or cancer cells) is not sufficient to guarantee ability for intratumoral amplification of the oncolytic virus by the carrier cells in situ/in vivo. The amplification potential of the cell-based delivery vehicle can be restricted or completely blocked by the immune responses of individual subjects against the virus or the cells, particularly allogeneic carrier cells. This problem can be overcome by employing alternative and complementing strategies involving, one or more of: 1) an assay-based matching between the patient and the allogeneic cell-based delivery vehicle; 2) sensitization and protection of the cell-based delivery vehicle for improved oncolytic virus amplification and delivery; and 3) engineered resistance to the innate and adaptive immune barriers by introduction of specific genetic modifications into the cell-based delivery vehicle.

It is shown herein that oncolytic therapy is improved and problems solved by factors and treatments and/or by modifications that increase or maintain viral amplification in the cell, and/or that can decrease host immune response, such as complement, or allogeneic recognition, and/or that sensitize or engineer cells to evade allogeneic recognition or complement, and/or other such responses, to permit sufficient time for the cells to deliver virus to tumors and for virus to replicate. Type I and type II interferons (IFNs) are potent inducers of the anti-viral state in stem cells, and in some tumor cells. This interferes with the ability of these cells to get infected and support virus amplification. It is shown herein that blocking the detection of virus infection and the induction of an anti-viral state can augment the therapeutic potential of various stem cells as well as tumor cells to function as carriers of oncolytic viruses, by sensitizing them to virus infection, amplification and spread. The carrier cells (cell vehicles) can be sensitized, for example, treated or pre-treated, and/or engineered, to enhance virus amplification and/or to suppress induction of the anti-viral state upon administration of cells containing virus to the host. Target(s) for achieving this include, for example, inhibiting interferon signaling and/or inhibiting the JAK-STAT signaling pathway, such as inhibiting JAK1/2. The cells can be treated or engineered to express inhibitors of interferon or interferon signaling pathways. For example, the cells, tumor cells and/or stem cells can be pre-treated, prior to administration, with a JAK1/2 inhibitor, and/or an interferon inhibitor. Exemplary of such is Ruxolintib, Oclactinib, and Baricitinib.

Human serum can have numerous deleterious effects on stem cell carriers, including directly attacking and killing the virus infected carrier cells before they have completed their virus amplification and/or release of virus particles, thus limiting virus spread into the target tumor cells. The cells can be pre-treated or engineered to protect against or evade complement. Targets include the classical and alternative pathways for complement activation, such as complement proteins C3 or C5. Inhibitory antibodies, such as an anti-C5 antibody marketed under the name Soliris® (Alexion), and inhibitors of C3 cleavage, such as compstatin, and other such inhibitors of complement activation, can be used to protect cells against complement. Various inhibitors of complement activation are well-known in the art.

The cells can be treated or engineered to suppress and/or eliminate the determinants responsible for allogeneic recognition and rejection. This can augment the therapeutic potential of allogeneic stem or tumor cells to deliver oncolytic viruses in an off-the-shelf fashion, evading allogeneic recognition and rejection. Such allogeneic rejection determinants include the highly polymorphic and patient-specific MHC Class I and Class II molecules recognized by CD8 and CD4 T cells, and a broad spectrum of less polymorphic determinants recognized by various innate T cell subpopulations like NKT, iNKT, and mixed innate/adaptive populations like γδ (gd) T cells, including, but not limited to, MHC-like MICA/MICB and CD1a, b, c, d molecules, as well as various other stress-related or stress-sensing molecules, such as butyrophilins and Annexin A2. Thus, the cells can be sensitized/engineered to evade or inhibit allogeneic recognition/rejection targets. Such targets include, for example, determinants of allogeneic rejection by T and NK cells, including HLA-A, HLA-B, HLA-C, and NKG2D, which is an activating receptor expressed on NK cells, CD8+ cells, subsets of CD4+ cells, and gamma-delta T cells (gd T cells or γδ T cells). Immune responses to HLA determinants can be blocked, for example, with pan HLA-A, B, C blockade, such as with a pan-HLA blocking antibody, such as Tü39 (BioLegend).

Immunologic responses and rejection of allogeneic and virus-infected stem or tumor carrier cells can be enhanced by engagement of various non-MHC markers, which typically are up-regulated on the surface of virally infected or transformed tumor cells, and that serve as immune co-stimulatory molecules. Such markers can directly modulate the ability of the carrier cells to evade immunological rejection. For example, NKG2D molecules (receptors) recognize various MHC Class I-related proteins, such as human MICA and MICB, that function as co-stimulatory molecules involved in the recognition and rejection of virus-infected and transformed tumor cells. As shown herein, they play a role in regulating the immune-evasive potential of oncolytic virus carriers. NKG2D molecules have complex biology and can sensitize cells to be targeted by innate and adaptive cellular immunity mediated by NK and CD8 T cells or, when shed from the surface and secreted, also function as potent immune-suppressors. NKG2D can be inhibited directly by blocking its activation, and/or by inhibiting its ligands, such as MICA, MICB and others. The HLA blockade enhances immune evasion by the cells; NKG2D engagement compromises immune evasion by the cells.

Stem cells and tumor cells use various strategies for immune suppression and evasion, including IDO expression and IL-10 secretion. Virus amplification in the carrier cells causes a gradual loss of cell viability and immunosuppressive potential.

To overcome this limitation, cells are treated or engineered to express immunosuppressive agents. For example, cells are treated with a high dose of the immunosuppressive cytokine IL-10 to reverse the virus-mediated loss of immunosuppressive properties and improve the ability of virus-infected carrier cells to avoid allogeneic rejection/responses or early immune recognition. The cells can be sensitized with or engineered to secrete immunosuppressive factors, such as IL-10, or members of the PDL-1/PD-1 pathway. For example, pre-treatment with or engineering the cells to express IL-10, which suppresses immune responses to the cells.

Above are examples of the ways in which cell carriers, including tumor cells and stem cells, including allogeneic stem and tumor cells, can be treated or modified to improve or increase delivery of therapeutically effective amounts of virus to the target tumor cells, and also can be treated/engineered to increase or maintain viral amplification. Treatments can be effected prior to administration of the cells, or can be effected by co-administration of the agent(s). The following tables provide examples of targets, treatments and modifications. These and others are detailed in the description and examples below.

| Improvement/ Modification | Mechanism of Action or target | Exemplary Treatment |
|---|---|---|
| Enhancing virus amplification ability of the cells | Immunosuppression to protect cells, using immune-suppressive factors, and/or inhibitors of immune activation | Pre-treating/loading the cell vehicles with one or more of: IL-10; TGFβ; VEGF; FGF-2; PDGF; HGF; IL-6; GM-CSF; Growth factors; receptor tyrosine kinase (RTK)/mTOR agonists; wnt protein ligands; and GSK3 inhibitors/antagonists (e.g., Tideglusib, Valproic acid). |
| Suppressing/ blocking induction of the anti-viral state | Inhibition of IFN Type I/Type II receptors and downstream signaling/ responsiveness | Pre-treating/loading the cell vehicles with small molecule or protein inhibitors of, for e.g., IFNAR1/IFNAR2 signaling; IFNGR1/IFNGR2 signaling; STAT1/2 signaling; Jak1 signaling (e.g., Tofacitinib, Ruxolitinib, Baricitinib); Jak2 signaling (e.g., SAR302503, LY2784544, CYT387, NS-018, BMS-911543, AT9283); IRF3 signaling; IRF7 signaling; IRF9 signaling; TYK2 signaling (e.g., BMS-986165); and TBK1 signaling (e.g., BX795, CYT387, AZ13102909). Pretreatment/loading with HDAC inhibitors, e.g., Vorinostat, Romidepsin, Chidamide, Panobinostat, Belinostat, Valproic acid, Mocetinostat, Abexinostat, Entinostat, SB939, Resminostat, Givinostat, Quisinostat, HBI-8000, Kevetrin, CUDC-101, AR-42, CHR-2845, CHR-3996, 4SC-202, CG200745, ACY-1215, ME-344, Sulforaphane and/or Trichostatin. |
| | Inhibition of virus sensing and/or anti-virus defense pathways mediated by, e.g., STING, PKR, RIG-1 MDA-5, OAS-1/2/3, AIM2, MAVS, RIP-1/3, DAI (ZBP1) | Pretreatment/loading of the cells with antagonists of viral origin, including, but not limited to, one or more of: K1, E3L, K3L proteins (Vaccinia); NS1/NS2 proteins (Influenza); NS3-4A (Hepatitis C); NP and Z proteins (Arenavirus); VP35 (Ebola virus); US11, ICP34.5, ICP0 (HSV); M45 (MCMV); and X protein (BDV: Borna Disease Virus). |
| Protection against allogeneic inactivation/ rejection determinants | MHC/HLA Antagonism | Pre-treating/loading the cells with MHC antagonists of viral origin, e.g., one or more of: A40R (Vaccinia); Nef and TAT (HIV); E3-19K (Adenovirus); ICP47 (HSV-1/2); CPXV012, CPXV203 (Cowpox); ORF66 (VZV); EBNA1, BNLF2a, BGLF5, BILF1 (EBV); US2/gp24, US3/gp23, US6/gp21, US10, US11/gp33 (hCMV); Rh178/VIHCE (RhCMV); U21 (HHV-6/7); LANA1, ORF37/SOX, kK3/MIR1, kK5/MIR2 (KSHV); mK3 (MHV-68); UL41/vhs (a-herpesvirus, HSV, BHV-1, PRV); UL49.5 (Varicellovirus, BHV-1, EHV-1/4, PRV); m4/gp34, m6/gp48, m27, m152/gp40 (mCMV); and UL18 (HCMV; β2 microglobulin antagonist). |
| | Antagonism of MIC-A and MIC-B/ NKG2D modulation | Pre-treating/loading the cells with MIC-A and MIC-B antagonists, e.g., kK5 (KHSV). |
| Immune suppression and evasion | Immunosuppression using various immunosuppressive factors | Pre-treatment/loading with one or more immunosuppressing factors of viral origin including, but not limited to: inhibitors of immune FAS/TNF/Granzyme B-induced apoptosis (e.g., Ectromelia/Vaccinia virus SP1-2/CrmA); IL-1/NFkB/IRF3 antagonists (e.g., Vaccinia virus-encoded N1); IL-1 and TLR antagonists (e.g., IL-18 binding protein, A46R, A52R); IL-1β antagonists (e.g., B15R/B16R); TNF -continued

| | | Cell Vehicles Sensitized (Treated) for Improved Viral Amplification and/or Immunomodulation |
|---|---|---|
| Improvement/Modification | Mechanism of Action or target | Exemplary Treatment |
| | | peptidic C3 inhibitors of the compstatin family (e.g., Cp40); Human soluble membrane (s/m) proteins (e.g., s/mCR1 (CD35), s/mCR2 (CD21), s/mCD55, s/mCD59); Human Factor H and derivatives; and Cobra venom factors and derivatives with complement inhibitory activity. |

| | Cell Vehicles Sensitized (Treated) for Resistance to Virus-Mediated Killing | |
|---|---|---|
| Improvement/Modification | Mechanism of Action | Treatment |
| Pretreatment with Type I and/or Type II interferons | Provides extended survival and/or improved local immunosuppression | Pre-treatment/loading with Type I IFN (e.g., IFNα, IFNβ) and/or Type II IFN (e.g., IFNγ). |
| Pretreatment with agonists/inducers of anti-viral state | Provides extended survival and/or improved local immunosuppression | Pre-treatment/loading with agonists of STING, PKR, RIG-I, MDA-5, OAS-1/2/3, AIM-2, MAVS, RIP-1/3, and/or DAI (ZBP1) pathways. |

| | Cell Vehicles Engineered for Improved Viral Amplification and/or Immunomodulation | |
|---|---|---|
| Improvement/Modification | Mechanism of Action | Exemplary Genetic Modification |
| Engineered to be unresponsive to an IFN-induced antiviral state | Transient or permanent suppression of Type I/Type II IFN receptors and/or downstream signaling | Engineering the cells to suppress expression of one or more of: IFNα, IFNβ, IFNγ receptors; IFNAR1/IFNAR2 receptors; IFNGR1/IFNGR2 receptors; STAT1/2 receptors; Jak1/2 receptors; IRF3 receptors; IRF7 receptors; IRF9 receptors; TYK2 kinase; and TBK1 kinase. |
| | Transient or permanent suppression of elements of the cytosolic viral DNA/RNA-sensing and anti-viral defense machinery | Engineering the cells to suppress expression of one or more of: PKR, RIG-I, MDA-5, cGAS, STING, TBK1, IRF3, OAS-1/2/3, AIM2, MAVS, RIP-1/3 and DAI (ZBP1). |
| | Transient or permanent expression of antagonists of virus-sensing and anti-viral defense pathways mediated by, e.g., STING, PKR, RIG-1, MDA-5, OAS-1/2/3, AIM2, MAVS, RIP-1/3, DAI (ZBP1) | Engineering cells to express one or more of K1, E3L, K3L (Vaccinia); NS1/NS2 (Influenza A); NS3-4A (Hepatitis C); NP, Z protein (Arenavirus); VP35 (Ebola virus); US11, ICP34.5, ICP0 (HSV); M45 (MCMV); and X protein (BDV: Borna Disease Virus). |
| Engineered to evade allogeneic recognition by T cells and/or NKT cells and/or adaptive immune responses of γδ T cells | Transient or permanent suppression of expression of MHC Class I molecules | Engineering cells to suppress expression of HLA-A, B, C molecules. |
| | Transient or permanent suppression of expression of MHC Class II molecules | Engineering cells to suppress expression of HLA-DP, DQ, DR molecules. |
| | Transient or permanent suppression of expression of MHC-like molecules | Engineering cells to suppress expression of CD1a/b/c/d molecules. |

-continued

Cell Vehicles Engineered for Improved Viral Amplification and/or Immunomodulation

| Improvement/ Modification | Mechanism of Action | Exemplary Genetic Modification |
|---|---|---|
| | Transient or permanent suppression of expression of regulators of transcription or expression of MHC Class I, MHC Class II, and MHC-like molecules | Engineering cells to suppress expression of, for example, TAP1/2, Tapasin, Beta-2 microglobulin, CIITA, RFXANK, RFX5 and RFXAP. |
| | Transient or permanent expression of antagonists of MHC and MHC-like molecules | Engineering cells to express $\beta_2M$ antagonists of viral origin, e.g., UL18 (HCMV). Engineering cells to express MHC antagonists of viral origin, e.g., one or more of: A40R MHCI (Vaccinia); Nef, TAT (HIV); E3-19K (Adenovirus); ICP47 (HSV-1/2); CPXV012, CPXV203 (Cowpox); EBNA1, BNLF2a, BGLF5, BILF1 (EBV); ORF66 (VZV); US2/gp24, US3/gp23, US6/gp21, US10, US11/gp33 (hCMV); rh178/VIHCE (RhCMV); U21 (HHV-6/7); LANA1, ORF37/SOX, kK3/MIR1, kK5/MIR2 (KHSV); mK3 (MHV-68); UL41/vhs (a-herpesvirus, HSV, BHV-1, PRV); UL49.5 (Varicellovirus, BHV-1, EHV-1/4, PRV); and m4/gp34, m6/gp48, m27, m152/gp40 (mCMV). Engineering cells to express anti-HLA, anti-MHC, and/or anti-MHC-like molecule antibodies. |
| Engineered to evade allogeneic recognition by NK cells and/or innate immune responses of γδ T cells. | Transient or permanent suppression of expression of ligands of NK cell and/or γδ T cell receptors | Engineering cells to suppress expression of, e.g., membrane-bound MICA/B (NKG2D ligands); membrane-bound PVR (DNAM-1 ligand); and/or membrane-bound Nectin-2 (DNAM-1 ligand). |
| | Transient or permanent expression of antagonists of NK receptor and/or γδ T cell receptor ligands | Engineering cells to express antagonists of MIC-A and MIC-B (NKG2D ligands), e.g., kK5 (KHSV). |
| | Transient or permanent expression of antagonists of NK cell and/or γδ T cell receptors | Engineering cells to express antagonists of NKG2D receptors, e.g., Cowpox OMCP. Engineering cells to express antagonists of NCR - targeting NKp30, NKp44, NKp46 receptors, e.g., HA (hemagglutinin - in vaccinia and other viruses). |
| | Transient or permanent expression of ligands for NK and/or γδ T cell inhibitory receptors | Engineering cells to express ligands for KIR (NK inhibitory receptors), e.g., HLA-Bw4; HLA-C2. Engineering cells to express ligands for NKG2a/CD94 (NK inhibitory receptors), e.g., HLA-E and derivatives alone, or combined with 21M HLA-B ligands to generate HLA-E binding peptides and stabilize HLA-E surface expression. |
| Engineered to express immunosuppressive factors of human or viral origin | Prevention/inhibition of allogeneic anti-cell vehicle or anti-viral immune responses | Engineering cells to express factors of human origin, including but not limited to, IDO, Arginase, TRAIL, iNOS, IL-10, TGFβ, VEGF, FGF-2, PDGF, HGF, IL-6, sMICA, sMICB, sHLA-G, HLA-E, PD-L1, FAS-L, B7-H4, and single-chain antibodies (scFv) that target or deplete NK and/or NKT cells. Engineering cells to express factors of viral origin, including but not limited to, Ectromelia/Vaccinia virus SPI-2/CrmA (inhibitor of immune FAS/TNF/Granzyme B induced apoptosis); Vaccinia Virus encoded N1 (IL-1/NFkB/IRF3 antagonist); HA (NCR |

-continued

| Cell Vehicles Engineered for Improved Viral Amplification and/or Immunomodulation | | |
| --- | --- | --- |
| Improvement/ Modification | Mechanism of Action | Exemplary Genetic Modification |
| | | antagonists targeting NKp30, NKp44, NKp46); IL-18 binding protein; A40R; A46R; A52R; B15R/B16R; TNFα blockers (e.g., Vaccinia virus CmrC/CmrE); IFNα/β blockers (e.g., Vaccinia virus B18R/B19R); IFNγ blockers (e.g., Vaccinia virus B8R); and other IL-1/IL-1β/NFKB/IRF3/NCR/MHCI/TLR/NKG2D antagonists. |
| Engineered to express cancer or stem cell-derived factors that facilitate viral infection of otherwise non-permissive (impermissive) cells | Facilitating viral infection of otherwise non-permissive (impermissive) cell vehicles and/or tumor cells | Engineering cells to express one or more of: cancer associated antigens, e.g., cancer testis antigens (MAGE-A1, MAGE-A3, MAGE-A4, NY-ESO-1, PRAME, CT83, SSX2, BAGE family, CAGE family); oncofetal antigens (AFP, CEA); oncogene/tumor suppressors (myc, Rb, Ras, p53, Telomerase); differentiation antigens (MELAN, Tyrosinase, TRP-1/2, gp100, CA-125, MUC-1, ETA); GM-CSF; IL-10; TGFβ; VEGF; FGF-2; PDGF; HGF; IL-6; growth factors; RTK/mTOR agonists; and wnt protein ligands. |
| Engineered to express factors interfering with the function of complement and/or neutralizing antibodies | Protection of cells against complement and serum neutralizing antibodies | Engineering cells to express one or more of: protein antagonists of complement factors (e.g., antagonists of C1, C2, C3, C4, C5, MBL); Vaccinia virus complement control protein (VCP); Vaccinia virus complement inhibitor (B5R); scFv anti-CD1q/CD1r/CD1s; anti-C3 antibodies; anti-C5 antibodies (e.g., Eculizumab); peptidic C3 inhibitors of the compstatin family (e.g., Cp40); human soluble membrane (s/m) proteins (e.g., s/mCR1 (CD35), s/mCR2 (CD21), s/mCD55, s/mCD59); Human Factor H and derivatives; and cobra venom factors and derivatives with complement inhibitory activity. |

Provided herein are methods that capture patient-specific differences in the immune responses to the virus and stem cells, providing proper subject-carrier cell matching and permitting the effective use of off-the-shelf allogeneic cell-based delivery platforms and/or development of allogeneic cells for use as viral cell carriers that address the problems discussed above. The use of allogeneic stem cells for oncolytic virus delivery is facilitated by the lack of requirement for long-term survival and engraftment of the cells; hence the methods herein can work across insignificant WIC mismatch barriers. Subjects and carrier cells can be treated and modified as described herein and matched to subjects for effective delivery of virus. Thus, provided is a viable alternative to the autologous stem cell approach. The methods and cells also can be practiced with autologous cells. Also provided are the carrier cells, and the carrier cells containing viruses.

Provided herein are methods for improving delivery of oncolytic viruses to tumor cells. Cell vehicles have been used as carriers (carrier cells) to deliver virus, helping the virus evade circulating antibodies and immune mechanisms and delivering the virus to the cancerous tumors/cells. The carrier cells can boost amplification of the virus at the tumor site, thereby increasing its therapeutic efficacy and permitting the virus to overcome intrinsic tumor cell resistance as well as innate and adaptive immune barriers. Provided herein are carrier cells (cell vehicles) that have improved ability to evade the treated subject's immune responses. Provided are methods for matching the carrier cells to a subject to best evade the immune system and also to match carrier cell with virus, and to match the carrier cell and virus with a subject to be treated. In particular, provided are methods of treatment of subjects with allogeneic carrier cells that comprise an oncolytic virus. The allogeneic carrier cells are matched to subject by methods described herein. The virus and carrier cells generally are co-cultured prior to administration, but they can be administered separately, such as sequentially, in different compositions. Also, carrier cells co-cultured with or infected with virus can be administered, and additional carrier cells that have not been co-cultured with or infected with virus can be administered.

It is shown herein that oncolytic therapy is improved and problems solved, by factors and treatments and/or by modifications of cells that increase or maintain viral amplification in the cell, and/or decrease host immune response, such as complement and/or HLA responses and other such responses, against the cells to permit sufficient time for delivery of virus to tumors.

Also provided are methods for matching allogeneic cells to a subject to avoid or reduce host immune responses that kill or inhibit the cells before the cells can amplify and deliver the virus to the cells. The methods also can aid in selecting an appropriate virus for a particular cell type.

Provided herein are carrier cells and carrier cells that comprise an oncolytic virus, wherein: the virus can replicate in the cell; the cell can be administered to a human subject; the cell has been treated or modified or both to enhance the immunosuppressive properties or immunoprivileged properties of the cell for administration to a human subject; and, optionally, the cell has been treated or modified to enhance amplification of the virus in the cell. Carrier cells that have been treated or modified or both to enhance the immunosuppressive properties or immunoprivileged properties of the cell for administration to a human subject; and that have been treated or modified to enhance amplification of the virus in the cell, are provided. Also provided are carrier cells that are permissive for oncolytic virus amplification, and that accumulate in tumors and/or carrier cells that are not recognized by the immune system of the subject for a time sufficient to deliver virus to a tumor in a subject. A goal is for the cells to survive long enough to amplify the virus and deliver virus to tumors, and metastases. Ultimately, the cells will dissipate in number as they are lysed by virus. The carrier cells are treated or modified stem cells, immune cells, and tumor cells. In some embodiments in which the carrier cells are stem cells, the cells are not embryonic or fetal stem cells, or derived from an embryonic cell line. The carrier cells can be removed or harvested from a subject and infected with the oncolytic virus, or they can be allogeneic. The stem cells can be adult stem cells, or, where permitted, embryonic stem cells or fetal stem cells. Exemplary carrier cells can be selected from among mesenchymal, neural, totipotent, pluripotent, induced pluripotent, multipotent, oligopotent, unipotent, adipose stromal, endothelial, bone marrow, cord blood, adult peripheral blood, myoblast, small juvenile, epithelial, embryonic epithelial, and fibroblast stem cells. In some embodiments, the carrier cell is a mesenchymal stem cell. Exemplary of mesenchymal stem cells are mesenchymal cells from adult bone marrow, adipose tissue, blood, dental pulp, neonatal umbilical cord, cord blood, placenta, placenta-derived adherent stromal cells, placenta-derived decidual stromal cells, endometrial regenerative cells, placental bipotent endothelial/mesenchymal progenitor cells, amniotic membrane or fluid mesenchymal stem cells, amniotic fluid derived progenitors, Wharton's Jelly mesenchymal stem cells, pelvic girdle stem cells, Chorionic Villus Mesenchymal Stromal cells, subcutaneous white adipose mesenchymal stem cells, pericytes, adventitial reticular stem cells, hair follicle-derived stem cells, hematopoietic stem cells, periosteum-derived mesenchymal stem cells, lateral plate mesenchymal stem cells, exfoliated deciduous teeth stem cells, periodontal ligament stem cells, dental follicle progenitor cells, stem cells from apical papilla, or muscle satellite cells, or mixtures thereof.

In some embodiments, the carrier cell is an adipose stromal cell, such as an adipose stromal mesenchymal cell. For example, the cells can be supra adventitial-adipose stromal cells (SA-ASC; $CD235a^-/CD45^-/CD34^+/CD146^-/CD31^-$), and/or pericytes ($CD235a^-/CD45^-/CD34^-/CD146^+/CD31^-$), such as supra adventitial-adipose stromal cells ($CD34^+$ SA-ASC). In other embodiments, the carrier cells can be selected from among endothelial Progenitor Cells, Placental Endothelial Progenitor cells, Angiogenic Endothelial Cells, and pericytes. Where permitted, the carrier cells can be embryonic epithelial cells.

In other embodiments, the carrier cells can be immune cells. Immune cells can be selected from among granulocytes, mast cells, monocytes, dendritic cells, natural killer cells, lymphocytes, T-cell receptor (TCR) transgenic cell targeting tumor-specific antigens, and CAR-T cell targeting tumor-specific antigens.

In some embodiments, the carrier cell is a modified or treated cell from a hematological malignancy cell line. Generally, malignant cells are treated so that they cannot replicate.

In all embodiments, the carrier cells can be allogeneic to the subject to be treated or they can be autologous. Where allogeneic, they can be treated or sensitized or engineered to avoid or to not be subjected to the treated subject's immune response, and/or matched to the subject to avoid such response for a sufficient time to deliver virus to the tumor.

The carrier cells can be a cell from a cell line, such as, but not limited to, a human leukemia, T-cell leukemia, myelomonocytic leukemia, lymphoma, non-Hodgkin's lymphoma, Burkitt lymphoma, diffuse large B cell lymphoma, acute myeloid leukemia (AML), chronic myelogenous leukemia (CML), acute lymphoblastic leukemia (ALL), erythroleukemia, myelomonoblastic leukemia, malignant non-Hodgkin's NK Lymphoma, myeloma/plasmacytoma, multiple myeloma and a macrophage cell line. Exemplary of such cell lines is one selected from among:

a leukemia cell line that is KASUMI-1, HL-60, THP-1, K-562, RS4;11, MOLT-4, CCRF-CEM, JVM-13, 31E9, ARH-77, MoB, JM1, NALM-1, or ProPak-X.36;

a T cell leukemia cell line that is HM-2, CEM-CM3, Jurkat/Jurkat clone E6-1, J.CaM1.6, BCL2 Jurkat, BCL2 S87A Jurkat, BCL2 S70A Jurkat, Neo Jurkat, BCL2 AAA Jurkat, J.RT3-T3.5, J45.01, J.gamma1, J.gamma1.WT, JK28, P116, P116.c139, A3, JX17, D1.1, I9.2, or I2.1;

a myelomonocytic leukemia cell line that is MV-4-11;

a lymphoma cell line that is HT, BC-3, CA46, Raji, Daudi, GA-10-Clone-4, HH, or H9;

a Non-Hodgkin's Lymphoma cell line that is SU-DHL-1, SU-DHL-2, SU-DHL-4, SU-DHL-5, SU-DHL-6, SU-DHL-8, SU-DHL-10, SU-DHL-16, NU-DUL-1, NCEB-1, EJ-1, BCP-1, TUR, or U-937;

a Burkitt lymphoma cell line that is Ramos/RA 1, Ramos.2G6.4C10, P3HR-1, Daudi, ST486, Raji, CA46, human gamma-herpesvirus 4/HHV-4 cheek tumor from Burkitt Lymphoma Patient, DG-75, GA-10, NAMALWA, HS-Sultan, Jiyoye, NC-37, 20-B8, EB2, 1G2, EB1, EB3, 2B8, GA-10 clone 20, or HKB-11/Kidney-B cell Hybrid;

a diffuse large B cell lymphoma cell line that is Toledo or Pfeiffer;

a mantle Cell Lymphoma cell line that is JeKo-1, JMP-1, PF-1, JVM-2, REC-1, Z-138, Mino, or MAVER-1;

an AML cell line that is AML-193, BDCM, KG-1, KG-1a, Kasumi-6, or HL-60/S4;

a CML cell line that is K562, K562-r, K562-s, LAMA84-r, LAMA84-s, AR230-r, or AR230-s;

an ALL cell line that is N6/ADR, RS4;11, NALM6 clone G5, Loucy, SUP-B15, or CCRF-SB;

an erythroleukemia cell line that is an IDH2-mutant-TF-1 Isogenic cell line;

a myelomonoblastic leukemia cell line that is GDM-1;

a malignant Non-Hodgkin's NK Lymphoma cell line that is NK-92, or NK-92MI;

a Myeloma/Plasmacytoma cell line that is U266B1/U266, HAA1, SA13, RPMI-8226, NCI-H929, or MC/CAR;

a multiple myeloma cell line that is MM.1R, IM-9, or MM.1S; and a macrophage cell line that is MD, SC, or WBC264-9C.

The carrier cells can be a modified or treated cell selected from among:

a mesenchymal stem cell line that is APCETH-201 (APCETH), APCETH-301 (APCETH), Cx601 (TIGENIX), TEMCELL, MSC-100-IV, or Prochymal (MESOBLAST); or an induced pluripotent stem cell (iPSC) that is ToleraCyte (Fate Therapeutics); or a fibroblast cell line that is CCD-16Lu or WI-38; or a tumor-associated fibroblast cell line that is Malme-3M, COLO 829, HT-144, Hs 895.T, hTERT or PF179T CAF; or an endothelial cell line that is HUVEC, HUVEC/TERT 2 or TIME; or an embryonic epithelial cell line that is HEK-293, HEK-293 STF, 293T/17, 293T/17 SF, or HEK-293.2sus; or an embryonic stem cell line that is hESC BG01V; or an epithelial cell line that is NuLi-1, ARPE-19, VK2/E6E7, Ect1/E6E7, RWPE-2, WPE-stem, End1/E6E7, WPMY-1, NL20, NL20-TA, WT 9-7, WPE1-NB26, WPE-int, RWPE2-W99, or BEAS-2B.

The carrier cells can be a modified or treated cell from a cell line that is a human hematological malignancy cell line. The carrier cells can be a modified or treated cell from a human tumor cell line. Cell lines include, but are not limited to, a cell line selected from an NCI-60 panel, a fibrosarcoma, a hepatocarcinoma, a prostate cancer, a breast cancer, a head and neck cancer, a lung cancer, a pancreatic cancer, an ovarian cancer, a colon cancer, a gastric cancer, a gynecological cancer, a sarcoma, a melanoma, a squamous cell carcinoma, a hepatocellular carcinoma, a bladder cancer, a renal cell carcinoma, an embryonal carcinoma, a testicular teratoma, a glioblastoma, an astrocytoma, a thyroid carcinoma, or a mesothelioma cell line.

The carrier cells can be a modified or treated cell from a GM-CSF whole tumor cell vaccine (GVAX). The GVAX can be modified or treated as described herein so that it does not induce an anti-viral response or other immune response for a sufficient time to deliver the virus to the tumors. Exemplary GVAXs include, GVAX prostate; GVAX pancreas; GVAX lung; or GVAX renal cell, each modified or treated as described herein.

The oncolytic virus can be any known to those of skill in the art. Included are oncolytic viruses selected from among new castle disease virus, parvovirus, measles virus, reovirus, vesicular stomatitis virus (VSV), adenovirus, poliovirus, herpes simplex virus (HSV), poxvirus, coxsackie virus (CXV) and Seneca Valley virus (SVV). In some embodiments, the oncolytic virus is a vaccinia virus, such as, but not limited to, a smallpox vaccine. Exemplary vaccinia viruses include those derived from a Lister strain, Western Reserve (WR) strain, Copenhagen (Cop) strain, Bern strain, Paris strain, Tashkent strain, Tian Tan strain, Wyeth strain (DRYVAX), IHD-J strain, IHD-W strain, Brighton strain, Ankara strain, CVA382 strain, Dairen I strain, LC16m8 strain, LC16M0 strain, modified vaccinia Ankara (MVA) strain, ACAM strain, WR 65-16 strain, Connaught strain, New York City Board of Health (NYCBH) strain, EM-63 strain, NYVAC strain, Lister strain LIVP, JX-594 strain, GL-ONC1 strain, and vvDD TK mutant strain with deletions in VGF and TK (see, e.g., McCart et al. (2001) *Cancer Res.* 61:8751-8757). For example, the vaccinia virus can be ACAM2000 or ACAM1000.

The viruses can be oncolytic adenovirus, such as, for example, ONYX-015, CG00070, Oncorin (H101), ColoAd1, ONCOS-102, or Delta24-RGD/DNX-2401. The virus can be a modified HSV-1 virus, or a measles virus.

The oncolytic viruses can be modified to express a heterologous gene product and/or to have increased tumorigenicity and/or to have reduced toxicity (increased attenuation). The viruses can encode a detectable marker for detection in culture or in a subject. For example, the marker can be a fluorescent protein, such as Turbo-Red or GFP.

The carrier cells can be sensitized or treated, or engineered, to achieve, enhance or improve (compared to virus not sensitized, treated or engineered) one or more of: virus amplification in the cell, blocking the induction of an anti-viral state in a subject or in the tumor microenvironment, immune suppression/immune evasion, protection against allogeneic inactivation/rejection determinants, and/or protection against complement. Provided are carrier cells sensitized or engineered to enhance or improve virus amplification; or sensitized or treated or engineered to block induction of an anti-viral state in the subject or in the tumor microenvironment; or treated, sensitized or engineered to enhance virus amplification by pre-treatment or treatment with one or more of a cytokine or growth factor. For example, the carrier cells can be treated to inhibit, or modified to express an inhibitor of, interferon-γ and/or interferon-β. In some embodiments, instead of treating the cells with an agent, the agent and cell can be co-administered to the host.

Exemplary of carrier cells sensitized to enhance virus amplification, are those sensitized by pre-treatment or treatment to load the cell with one or more of IL-10, TGFβ, VEGF, FGF-2, PDGF, HGF, IL-6, GM-CSF, a RTK/mTOR agonist, a Wnt protein ligand, and a GSK3 inhibitor/antagonist. Exemplary of carrier cells that have been sensitized to block induction of an anti-viral state are those sensitized by pre-treatment or treatment to load the cell with one or more small molecule or protein inhibitors that interfere with IFN Type I/Type II receptors, interfere with downstream IFN signaling, interfere with IFNAR1/IFNAR2 signaling, interfere with IFNGR1/IFNGR2 signaling, interfere with STAT1/2 signaling, interfere with Jak1 signaling, interfere with Jak2 signaling, interfere with IRF3 signaling, interfere with IRF7 signaling, interfere with IRF9 signaling, interfere with TYK2 signaling, interfere with TBK1 signaling, or interfere with other signaling pathways that effect an immune response against the oncolytic virus in the cell or subject. Exemplary of cells sensitized to block induction of an anti-viral state, are those sensitized by pre-treatment or treatment to load the cell with one or more HDAC inhibitors, for interfering with/deregulating IFN signaling/responsiveness. Exemplary HDAC inhibitors include, but are not limited to, those selected from among vorinostat, romidepsin, chidamide, panobinostat, belinostat, valproic acid, mocetinostat, abexinostat, entinostat, SB939, resminostat, givinostat, quisinostat, HBI-8000, Kevetrin, CUDC-101, AR-42, CHR-2845, CHR-3996, 4SC-202, CG200745, ACY-1215, ME-344, sulforaphane, or trichostatin. Exemplary of carrier cells sensitized to block induction of an anti-viral state or enhance virus amplification are those sensitized by pre-treatment or treatment to load the cell with antagonists of virus sensing and/or anti-virus defense pathways. Virus sensing and/or defense pathway(s) include those that is/are induced or modulated by one or more of STING, PKR, RIG-1, MDA-5, OAS-1/2/3, AIM2, MAVS, RIP-1/3, and DAI (ZBP1). Antagonists that affect one or more of these pathways include, for example, one or more of K1, E3L, and K3L vaccinia proteins; NS1/NS2 influenza proteins; hepatitis C NS3-4A; arenavirus NP and Z proteins; Ebola virus VP35; HSV US11, ICP34.5 and ICP0; MCMV M45; and Borna disease virus X protein.

Exemplary of carrier cells that have been sensitized to protect them against inactivation/rejection determinants, are those sensitized by pre-treatment or treatment to load the cell with one or more viral major histocompatibility (MHC) antagonists. Exemplary MHC antagonists include those selected from among one or more of A40R MHCI antagonist from vaccinia; Nef and TAT from HIV; E3-19K from adenovirus; ICP47 from HSV 1 and HSV2; CPXV012 and CPXV203 from Cowpox; ORF66 from varicella zoster virus (VZV); EBNA1, BNLF2a, BGLF5, and BILF1 from Epstein Barr virus (EBV); US2/gp24, US3/gp23, US6/gp21, US10, and US11/gp33 from human cytomegalovirus (hCMV); Rh178/VIHCE from rhesus CMV (RhCMV); U21 from human herpes virus-6 (HHV6) or HHV7; LANA1, ORF37/SOX, kK3/MIR1, and kK5/MIR2 from Kaposi's sarcoma associated herpes virus (KSHV); mK3 from mouse hepatitis virus-68 (MHV-68); UL41/vhs from alpha-herpesvirus, herpes simplex virus (HSV), bovine herpes virus-2 (BHV-1), and pseudorabies virus (PRV); UL49.5 from Varicellovirus, BHV-1, equine herpes virus 1 and 4 (EHV-1/4) and PRV; and m4/gp34, m6/gp48, m27, m152/gp40 from murine CMV (mCMV). Other antagonists for pre-treatment or treatment are those that are treated to load the cell with antagonists of human MEW class I chain related genes MIC-A and MIC-B or with beta-2 microglobulin (B2M) antagonists of viral origin.

Exemplary of carrier cells that have been sensitized to enhance immune suppression/immune evasion are those sensitized by pre-treatment or treatment to load the cell with immunosuppressing factors of viral origin. Exemplary of such factors is/are one or more of an inhibitor of immune FAS/TNF/granzyme B-induced apoptosis, an IL-1/NFkB/IRF3 antagonist, an IL-1 and toll-like receptor (TLR) antagonist, an IL-1β antagonist, a TNFα blocker, an IFNα/β blocker, and an IFNγ blocker.

Exemplary of carrier cells that have been sensitized to enhance immune suppression/immune evasion are those sensitized by pre-treatment or treatment to load the cell with one or more small molecule inhibitor(s) of one or more of antigen peptide transporter-1/2 (TAP-1 and TAP-2) and tapasin.

The carrier cells also can be sensitized to protect against complement. This can be effected, for example, by pre-treatment or treatment to load the cell with an antibody or small molecule or other inhibitor of a complement protein. Complement proteins that can be targeted include C3 and C5. As described above and below, and exemplified herein, there are numerous known inhibitors of C3 and C5, including antagonist antibodies specific for each, and small molecule inhibitors.

The carrier cells generally are pre-treated with the agent that sensitizes or protects. Pre-treatment can be effected for 15 min to 48 hours before viral infection, after viral infection, or before administration to the subject, or before storage.

The carrier cells also can be sensitized or engineered for extended survival and improved local immunosuppression to reduce or limit virus-mediated killing. Agents for effecting this include agonist(s), such as of one or more of STING, PKR, RIG-I, MDA-5, OAS-1/2/3, AIM2, MAVS, RIP-1/3, and DAI (ZBP1), which can be engineered for expression by the cell or virus under control of a promoter that appropriately times expression, or by administration to the subject, so that the carrier cells are not killed too soon by virus, but are not killed or inhibited by the host's immune system before delivering virus to the tumors.

The carrier cells provided herein also can be engineered for improved viral amplification and/or immunomodulation. This can be effected, for example, by one or more of: a) engineering to prevent or to be unresponsive to an interferon-induced antiviral state; b) engineering to evade allogeneic recognition by one or more of T and NKT cells and/or adaptive immune responses of γδ T cells; c) engineering to evade allogeneic recognition by NK Cells and/or innate immune responses of γδ T cells; d) engineering to express immunosuppressive factors of human or viral origin to prevent/inhibit allogeneic anti-carrier cell or anti-viral immune responses; e) engineering to express cancer or stem cell-derived factors that facilitate viral infection of otherwise non-permissive carrier cells and/or tumor cells; and f) engineering to express factors interfering with the function of complement and/or neutralizing antibodies.

For example for a), the carrier cells can be engineered to prevent or to be unresponsive to an interferon-induced antiviral state by transient or permanent suppression of IFN Type I/Type II receptors and/or downstream signaling, wherein permanent suppression can be effected by deleting the locus that is suppressed. Suppression can be effected by suppression of one or more of Type I/Type II interferon receptor expression, IFN α/β receptor expression, IFNγ receptor expression, IFNAR1/IFNAR2 receptor expression, IFNGR1/IFNGR2 receptor expression, STAT1/2 receptor expression, Jakl/2 receptor expression, IRF3 receptor expression, IRF7 receptor expression, IRF9 receptor expression, TYK2 kinase expression, and TBK1 kinase expression. In another example for a) the carrier cells can be engineered to prevent or to be unresponsive to an interferon-induced antiviral state by transient or permanent suppression of elements of the cytosolic viral DNA/RNA-sensing and anti-viral defense machinery. This can be effected by suppression of one or more of STING, PKR, RIG-1, MDA-5, OAS-1/2/3, AIM2, MAVS, RIP-1/3, and DAI (ZBP1). In other embodiments, the carrier cells can be a) engineered to prevent or to be unresponsive to an interferon-induced antiviral state by transient or permanent expression of antagonists of virus-sensing and anti-viral defense pathways mediated by STING, PKR, RIG-1, MDA-5, OAS-1/2/3, AIM2, MAVS, RIP-1/3, DAI (ZBP1). Antagonists include, but are not limited to, one or more of K1, E3L, and K3L vaccinia proteins; NS1/NS2 influenza proteins; hepatitis C NS3-4A; arenavirus NP and Z proteins; Ebola virus VP35; HSV US11, ICP34.5 and ICP0; MCMV M45; and Borna disease virus X protein.

For example for b) the carrier cells can be engineered to evade allogeneic recognition by one or more of T and NKT cells and/or adaptive immune responses of γδ T cells. This can be effected, for example by either or both of: (i) transient or permanent suppression of one or more of: MHC Class I molecules, MHC Class II molecules, MHC-like molecules, and regulators of transcription or expression of MHC Class I, MHC Class II, and MHC-like molecules; and/or (ii) transient or permanent expression of B2M antagonists of viral origin and/or MHC antagonists of viral origin. Transient or permanent suppression of one or more of MHC Class I molecules can be effected for example, by permanent or transient suppression of HLA-A, B, and/or C; transient or permanent suppression of one or more of MHC Class II molecules is effected by suppression of one or more of HLA-DP, DQ and DR; transient or permanent suppression of one or more of MHC-like molecules is effected by suppression of CD1a/b/c/d; transient or permanent suppression of one or more of regulators of transcription or expression of MEW Class I, MHC Class II, and MHC-like molecules is effected by suppression of one or more of TAP1/2, Tapasin, Beta-2 microglobulin, CIITA, RFXANK, RFX5 and RFXAP.

Transient or permanent suppression of B2M and/or MEW can be effected, for example, by transient or permanent expression of one or more of B2M antagonists of viral origin selected from UL18 from hCMV, and one or more of MHC antagonists selected from among one or more of A40R MHCI antagonist from vaccinia; Nef and TAT from HIV; E3-19K from adenovirus; ICP47 from HSV 1 and HSV2; CPXV012 and CPXV203 from Cowpox; ORF66 from varicella zoster virus (VZV); EBNA1, BNLF2a, BGLF5, and BILF1 from Epstein Barr virus (EBV); US2/gp24, US3/gp23, US6/gp21, US10, and US11/gp33 from human cytomegalovirus (hCMV); Rh178/VIHCE from rhesus CMV (RhCMV); U21 from human herpes virus-6 or HHV7; LANA1, ORF37/SOX, kK3/MIR1, and kK5/MIR2 from Kaposi's sarcoma associated herpes virus (KSHV); mK3 from mouse hepatitis virus-68 (MHV-68); UL41/vhs from alpha-herpesvirus, herpes simplex virus (HSV), bovine herpes virus-2 (BHV-1), and pseudorabies virus (PRV); UL49.5 from varicella zoster virus, BHV-1, equine herpes virus 1 and 4 (EHV-1/4) and PRV; and m4/gp34, m6/gp48, m27, and m152/gp40 from murine CMV (mCMV).

For example for c), the carrier cells can be engineered to evade allogeneic recognition by NK cells and/or innate immune responses of γδ T cells by either or both: (i) transient or permanent suppression of: membrane-bound MICAS or membrane-bound PVR, or membrane-bound Nectin-2, wherein permanent suppression can be effected by deleting the locus; and (ii) transient or permanent expression of: antagonists of MIC-A and MIC-B, antagonists of the NKG2D receptor, antagonists of NCR, ligands for the NK inhibitory receptors (KIR), and ligands for the NK inhibitory receptors NKG2a/CD94. For example, the carrier cells can be engineered to evade allogeneic recognition by NK cells and/or innate immune responses of γδ T cells by either or both of: (i) transient or permanent suppression of NKG2D ligands and/or DNAM-1 ligands; and (ii) transient or permanent expression of the antagonist of MIC-A and MIC-B, kK5 (from Kaposi's sarcoma virus (KHSV)); the antagonist of the NKG2D receptor Cowpox OMCP; the antagonists of NCR targeting NKp30, NKp44, NKp46 receptors, hemagglutinin (HA from vaccinia and other viruses); ligands for the NK inhibitory receptors (KIR) selected from HLA-Bw4 and HLA-C2; and ligands for the NK inhibitory receptors (NKG2a/CD94) selected from HLA-E and derivatives alone or combined with 21M HLA-B ligands to generate HLA-E binding peptides and stabilize HLA-E surface expression.

For example for d), the carrier cells can be engineered to express immunosuppressive factors of human or viral origin to prevent/inhibit allogeneic anti-carrier cell or anti-viral immune responses. This can be effected, for example, by engineering the carrier cells to express immunosuppressive factors of human or viral origin to prevent/inhibit allogeneic anti-cell vehicle or anti-viral immune responses. Factors of human origin, include, but are not limited to, one or more of: IDO, Arginase, TRAIL, iNOS, IL-10, TGFβ, VEGF, FGF-2, PDGF, HGF, IL-6, sMICA, sMICB, sHLA-G, HLA-E, PD-L1, FAS-L, B7-H4, and single-chain antibodies (scFv) that target or deplete NK and/or NKT cells, and/or γδ T cells. Factors of viral origin include, but are not limited to, one or more of: ectromelia/vaccinia virus SPI-2/CrmA (inhibitor of immune FAS/TNF/Granzyme B induced apoptosis), Vaccinia Virus encoded N1 (IL-1/NFkB/IRF3 antagonist), HA (NCR antagonists targeting NKp30, NKp44, NKp46), IL-18 binding protein, A40R, A46R, A52R, B15R/B16R, TNFα blockers (e.g., Vaccinia virus CmrC/CmrE), IFN α/β blockers (e.g., Vaccinia virus B18R/B19R), IFNγ blockers (e.g., Vaccinia virus B8R), and other IL-1/IL-1β/NFκB/IRF3/NCR/MHCI/TLR/NKG2D antagonists.

For example for e), the carrier cells can be engineered to express cancer or stem cell-derived factors that facilitate viral infection of otherwise non-permissive (impermissive) carrier cells and/or tumor cells. This can be effected, for example, by engineering the carrier cells to express cancer or stem cell-derived factors that facilitate viral infection of otherwise non-permissive (impermissive) cell vehicles and/or tumor cells, wherein the factors are selected from among one or more growth factors and cytokines that facilitate viral infection. Exemplary factors include, but are not limited to, one or more of cancer associated antigens, oncofetal antigens, oncogene/tumor suppressors, differentiation antigens, GM-CSF, IL-10, TGFβ, VEGF, FGF-2, PDGF, HGF, IL-6, RTK/mTOR agonists and Wnt protein ligands.

For example for f), the carrier cells can be engineered to express factors interfering with the function of complement and/or neutralizing antibodies. This can be effected, for example, by engineering carrier cells to express factors interfering with the function of complement and/or neutralizing antibodies selected from protein antagonists of a complement protein and/or an antibody that inhibits a complement protein. For example, factors interfering with the function of complement and/or neutralizing antibodies include, but are not limited to, protein antagonists of complement factors (e.g., complement proteins C1, C2, C3, C4, C5, MBL), vaccinia virus complement control protein (VCP), vaccinia virus complement inhibitor (B5R), scFv anti-CD1q/CD1r/CD1s, anti-C3 antibodies, anti-CS antibodies (e.g., Eculizumab), peptidic C3 inhibitors of the compstatin family (e.g., Cp40), human soluble membrane (s/m) proteins (e.g., s/mCR1 (CD35), s/mCR2 (CD21), s/mCD55, s/mCD59), human Factor H and derivatives, and cobra venom factors and derivatives with complement inhibitory activity.

Also provided are modified cell vehicles or carrier cells that include, one or more modifications selected from among: a) sensitization of the cell vehicle to enhance virus amplification ability; b) sensitization of the cell vehicle to block induction of anti-viral responses and/or to improve immune evasion/immune suppression; c) protection of the cell vehicle against allogeneic inactivation and/or rejection by the subject; d) protection of the cell vehicle against complement; and/or e) rendering the cell vehicle resistant to virus-mediated killing.

Also provided are carrier cells engineered for: a) transient or permanent expression or suppression of a gene that renders the cell vehicle unresponsive to an interferon-induced antiviral response; b) transient or permanent expression or suppression of a gene to facilitate evading allogeneic recognition by T cells and NKT cells, and γδ T cells; c) transient or permanent expression or suppression of a gene to facilitate evading allogeneic recognition by NK cells; d) transient or permanent expression of immunosuppressive factors; e) transient or permanent expression of factors that facilitate viral association with the cell vehicle; and f) transient or permanent expression of factors that interfere with the function of complement and/or neutralizing antibodies. Further modifications can include one or more of: a) sensitization of the cell vehicle to enhance virus amplification ability; b) sensitization of the cell vehicle to block induction of anti-viral responses and/or to enhance immune suppression/immune evasion of the cell vehicle; c) protection of the cell vehicle against allogeneic inactivation and/or rejection by the subject; d) protection of the cell vehicle against complement; and/or e) rendering the cell vehicle resistant to virus-mediated killing.

Any of the carrier cells containing oncolytic virus provided herein can be used in methods of treatment comprising administering the carrier cells to a subject who has cancer. Also provided are uses of the cells for treatment of cancer. Administration can be systemic or local, and can be parenteral, such as intravenous. The cancers include solid tumors and hematologic malignancies, and include metastatic cancer. The carrier cells can be allogeneic or autologous to the subject. When allogeneic, the carrier cells can be matched to the subject. In particular, matching can be effected by methods described below. Hence, provided are uses and methods of treating cancer, where the carrier cells that comprise an oncolytic virus are administered to a subject, and the carrier cell matches or has been matched to the subject; and a carrier cell is: a cell in which the virus can replicate; and a cell that has been treated or modified or both to enhance the immunosuppressive properties or immunoprivileged properties of the cell, and/or has been treated or modified to enhance amplification of the virus in the cell, whereby the cell overcomes innate/adaptive immune barriers of the subject to deliver virus to the tumor. The carrier cells include any described herein.

Subjects for treatment include animals, particularly mammals, including pets, zoo animals, and farm animals, and humans. Non-humans, include, for example, dogs, cats, horses, pigs, cows, goats, and non-human primates, such as chimpanzees, gorillas, bonobos, and baboons.

The methods of treatment and uses of the carrier cells include those in which the carrier cells comprising oncolytic virus are administered to a subject who has cancer, where: the carrier cells are allogeneic to the subject and have been matched to the subject; and a carrier cell is: a cell in which the virus can replicate; and a cell that has been treated or modified or both to enhance the immunosuppressive properties or immunoprivileged properties of the cell, and/or has been treated or modified to enhance amplification of the virus in the cell, whereby the cell overcomes innate/adaptive immune barriers of the subject to deliver virus to the tumor.

The methods of treatment and uses of the carrier cells include those in which the carrier cells comprising oncolytic virus are administered to a subject who has cancer, where the carrier cells are allogeneic to the subject and have been matched to the subject. Matching can be effected by the methods herein.

Also provided are uses of carrier cells for treatment of cancer, wherein: the carrier cell comprises an oncolytic virus; the carrier cell matches or has been matched to the subject; and a carrier cell is: a cell in which the virus can replicate; and a cell that has been treated or modified or both to enhance the immunosuppressive properties or immunoprivileged properties of the cell, and/or has been treated or modified to enhance amplification of the virus in the cell, whereby the cell overcomes innate/adaptive immune barriers of the subject to deliver virus to the tumor. Provided are uses where: the carrier cells comprise an oncolytic virus; the carrier cells match or have been matched to the subject; and the carrier cells are any described herein. The carrier cells can be autologous or allogeneic. When allogeneic, they can be matched to the subject, such as by the methods of matching described herein.

Cancers that can be treated by the carrier cells, methods, and uses provided herein, include solid tumors, hematologic malignancies, and metastatic cancers. The cancers include, but are not limited to, those selected from among leukemias, lymphomas, melanomas, carcinomas, sarcomas, myelomas, and neuroblastomas. Other cancers include, but are not limited to, pancreatic cancer, lung cancer, ovarian cancer, breast cancer, cervical cancer, bladder cancer, prostate cancer, brain cancer, central nervous system cancer, adenocarcinomas, liver cancer, skin cancer, hematological cancers, biliary tract cancer, bone cancer, choriocarcinoma, colon and rectal cancers, connective tissue cancer, cancer of the digestive system, endometrial cancer, esophageal cancer, eye cancer, head and neck cancer, gastric cancer, intra-epithelial neoplasm, kidney cancer, larynx cancer, oral cavity cancer, retinoblastoma, rhabdomyosarcoma, cancer of the respiratory system, stomach cancer, testicular cancer, thyroid cancer, uterine cancer, and urinary system cancers. Others include, but are not limited to, Hodgkin's lymphoma, non-Hodgkin's lymphomas, colon cancer, basal cell carcinoma, small cell lung cancer, non-small cell lung cancer, cancer of the lip, cancer of the tongue, cancer of the mouth, gliomas, and cancer of the pharynx.

As described herein, the carrier cells can be treated or modified to have improved viral amplification properties and/or to have enhanced immunosuppressive or immune privileged properties. The carrier cells can be sensitized by pretreatment with factors that promote viral amplification and/or immunosuppressive or immune privileged properties of the carrier cells. The carrier cells can be engineered to improve their virus amplification potential.

In the methods and uses the carrier cells with virus can be administered with or sequentially or after administration of carrier cells, not infected with virus, that first is pretreated with IFN-gamma, and is administered or used prior to administration of the carrier cell comprising virus or concurrently with the carrier cell comprising virus.

The, carrier cells, methods and uses provided herein can be used in combination therapies with another anti-cancer agent or treatment with another anti-cancer therapy, such as radiation therapy and/or surgery. Exemplary of further anti-cancer agents or treatments include, but are not limited to, immune costimulation agonists, BiTEs, CAR-T cells and TCR transgenic T cell targeting tumor-specific antigens, checkpoint inhibitors, chemotherapeutic compounds/antibodies, and immunosuppressive drugs. Further anti-cancer agents include, but are not limited to, immunotherapy and/or an immunosuppressive drug. Further anti-cancer agents or treatments include, but are not limited to, those selected from among the B7 family (CD28, ICOS); the TNFR family selected from among 4-1BB, OX40, GITR, CD40, CD30 and CD27; LIGHT; LT-alpha; checkpoint inhibitors that target one or more of PD-1, PD-2, PD-L1, PD-L2, CTLA-4, IDO 1 and 2, CTNNB1 (β-catenin), SIRPα, VISTA, LIGHT, HVEM, LAG3, TIM3, TIGIT, Galectin-9, KIR, GITR, TIM1, TIM4, CEACAM1, CD27, CD40/CD40L, CD48, CD70, CD80, CD86, CD112, CD137 (4-1BB), CD155, CD160, CD200, CD226, CD244 (2B4), CD272 (BTLA), B7-H2, B7-H3, B7-H4, B7-H6, ICOS, A2aR, A2bR, HHLA2, ILT-2, ILT-4, gp49B, PIR-B, HLA-G, ILT-2/4 and OX40/OX-40L, MDR1, Arginasel, iNOs, IL-10, TGF-β, pGE2, STAT3, VEGF, KSP, HER2, Ras, EZH2, NIPP1, PP1, TAK1 and PLK1a; chemotherapeutic compounds and antibodies selected from among cytokines, chemokines, growth factors, photosensitizing agents, toxins, anti-cancer antibiotics, chemotherapeutic compounds, radionuclides, angiogenesis inhibitors, signaling modulators, antimetabolites, anti-cancer vaccines, anti-cancer oligopeptides, mitosis inhibitor proteins, antimitotic oligopeptides, anti-cancer antibodies, immunotherapeutic agents; and immunosuppressive drugs selected from glucocorticoids (e.g., prednisone, dexamethasone, hydrocortisone), calcineurin inhibitors (e.g., cyclosporin, tacrolimus), mTOR Inhibitors (e.g., sirolimus, everolimus), methotrexate, lenalidomide, azathioprine, mercaptopurine, fluorouracil, cyclophosphamide, TNFα blocking antibodies (e.g., infliximab/Remicade, etanercept/Enbrel, adalimumab/Humira), and fludarabine.

As discussed above, for use in the methods and uses, the carrier cells, when allogeneic, can be matched to the subject to whom they are to be administered or to whom they are administered. Methods of matching also are provided.

The carrier cells can be matched to immune cells from the subject to whom the cell is administered to identify a carrier cell that is sufficiently immunologically compatible to immune cells from the subject to deliver virus to the subject. Also, the carrier cells can be matched with a virus, wherein the ability of the cell to amplify virus is measured. The cell/virus combination also can be matched to the subject. Immune cell from the subject include, for example, peripheral blood mononuclear cells (PBMCs). The method of matching can include testing ability of the virus to replicate in the cell and/or the ability of the cell to promote viral amplification. The methods and uses and cells, include methods of matching where the ability of the virus to replicate in the cell and/or the ability of the cell to promote viral amplification is tested by co-culturing the cell and a virus and measuring the rate of viral amplification. The ability of the virus to replicate in the cell and/or the ability of the cell to promote viral amplification is measured by, for example: a) measuring rates of virus amplification using a multiplicity of infection (MOI) of at or about 0.01-10, and co-culturing for periods of 1 day to about or at 1 week (24h-1 week) under equivalent assay conditions; and b) normalizing against the number of infected cell carriers, where: normalized Pfu per cell values measured under equivalent assay conditions can be used to compute a virus amplification score (VAS), which is for ranking a carrier cell+virus combination as suitable (or not) for therapy; a plaque forming units (pfu) per carrier cell value of 1-10 is considered limited potency (as a cell carrier for a particular virus); a Pfu per cell of 10-100 is good potency; a Pfu per cell of 100-1000 is very good potency; a Pfu per cell of more than 1000 is extremely high potency; and combinations of carrier cells and viruses demonstrating Pfu/cell of at least 10 are considered for testing in the subject compatibility screens of the cells with the subject.

In accord with these methods: the carrier cell/virus combination is matched to the subject to be treated by a) assessing patient-specific genetic polymorphism to identify MHC I/II haplotype, KIR haplotype and ligands, and non-classical MHC Haplotype, including one or more of HLA-E, CD1a, b, c, d, MICA/B; b) comparing the genetic polymorphism profile of the subject with the profile of the available carrier cells to identify from among carrier cells, cells most compatible with the subject; c) assessing the compatibility of the carrier cells and subject immune cells by co-culturing the cells, virus and immune cells; and d) assessing the level of viral amplification. Thus method of matching can further include: e) measuring carrier cell+live tumor biopsy+/−virus by detecting vehicle-directed migration of tumor cells and virus amplification, to identify carrier cells/virus for administration, where: viral amplification in the subject tumor biopsy+cell vehicles is either: 5% or more greater than the sum of viral amplification in the tumor biopsy alone under equivalent conditions+viral amplification in the cell vehicles alone under equivalent conditions; or is at least 5% or more greater than viral amplification in the tumor biopsy alone under equivalent conditions.

The method of matching can further include analyzing co-culture to assess subject permissivity to the carrier cell-mediated virotherapy by culturing subject-derived PBMCs+carrier cell+virus. The methods, uses, cells can include: measuring viral amplification in co-cultures of subject-derived PMBCs+carrier cell+virus, where a match is: compatible if virus amplification in the co-cultures of carrier cell and patient PBMC is in excess of 80% of the virus amplification when the same carrier cell is infected in the absence of PBMC; moderately compatible if virus amplification in the co-cultures of carrier cell and patient PBMC is in the range of 30-80% of the virus amplification when the same carrier cell is infected in the absence of PBMC; minimally compatible if virus amplification in the co-cultures of carrier cell and patient PBMC is in the range of 10-30% of the virus amplification when the same carrier cell is infected in the absence of PBMC; incompatible if virus amplification in the co-cultures of carrier cell and patient PBMC is less than 10% of the virus amplification when the same carrier cell is infected in the absence of PBMC; and the % compatibility can be used to rank carrier cells from the least to the most compatible carrier cells for each individual patient and for each particular virus.

Also provided are carrier cells, methods, including the matching methods, and uses herein, where a match between carrier cell and the subject by selecting a cell vehicle (carrier cell) as suitable for delivery of an oncolytic virus to a subject having cancer is effected by a method, comprising identifying one or more of the following determinants (a)-(f) as indicative of a match between the cell vehicle (carrier cell) and the subject:

a) the cell vehicle and the subject have identical alleles at 50% or more of the following genetic loci combined:
  (i) MHC I and/or MHC II haplotypes;
  (ii) KIR haplotype and/or KIR ligand haplotypes; and
  (iii) HLA-E, CD1a, CD1b, CD1c and/or CD1d haplotypes;

b) incubating the cell vehicle in a co-culture with cancerous cells from the subject results in one or more of the following:
  (i) a cell to tumor migration score (CTMS) of 20% or more of the cell vehicle cells migrating toward the cancerous cells;
  (ii) a tumor to cell migration score (TCMS) of 20% or more of the cancerous cells migrating toward the cell vehicle cells; and/or
  (iii) a cumulative migration score (MRS) of [(i)+(ii)]/2 of at least 20%;

c) incubating the cell vehicle in a co-culture with the oncolytic virus and cancerous cells from the subject results in one or more of the following:
  (i) a virus loaded cell to tumor migration score (V-CTMS) of 20% or more of the cell vehicle cells migrating toward the cancerous cells;
  (ii) a virus loaded tumor to cell migration score (V-TCMS) of 20% or more of the cancerous cells migrating toward the cell vehicle cells; and/or
  (iii) a cumulative virus loaded migration score (V-MRS) of [(i)+(ii)]/2 of at least 20%;

d) when the cell vehicle is incubated in a co-culture with the oncolytic virus and immune cells obtained from the subject, an immunological viral amplification score (IVAS) representing the amount of viral amplification in the presence of immune cells obtained from the subject relative to the amount of viral amplification obtained under equivalent conditions except in the absence of immune cells obtained from the subject, is at least 20%;

e) when the cell vehicle is incubated in a co-culture with the oncolytic virus and immune cells obtained from the subject, an immunological compatibility score (ICS) representing the immune response in the presence of the cell vehicle relative to the immune response under equivalent conditions except in the absence of the cell vehicle, is ≤200%, wherein the immune response is determined by the amount of expression of one or more of the following:
   (i) IFNγ;
   (ii) one or more markers associated with T cell, γδ T cell, NK cell and/or NKT cell-mediated cytotoxicity; and/or
   (iii) one or more markers associated with T cell, γδ T cell, NK cell and/or NKT cell activator/effector function(s);
f) when the cell vehicle is incubated in a co-culture with the oncolytic virus and immune cells obtained from the subject, the cell vehicle does not augment an anti-viral immune response and/or suppresses an anti-viral immune response relative to identical conditions except in the absence of the cell vehicle, as measured by an immunological suppression score (ISS) of ≥0% according to the equation:

ISS %=[(IV+IC)−ICV]/(IV+IC)×100, wherein:

IV=the marker expression level in a co-culture of the virus+immune cells obtained from the subject;
IC=the marker expression level in a co-culture of immune cells obtained from the subject+the cell vehicle;
ICV=the marker expression level in a co-culture of immune cells obtained from the subject+the cell vehicle+the virus; and
the marker expression level is the expression level of one or more of the markers set forth in (i), (ii) and (iii) of e); and if one or more of a)-f) is satisfied, identifying a match between the cell vehicle and the subject and selecting the cell vehicle as suitable for delivery of an oncolytic virus to the subject having cancer.

Prior to one or more of a)-f), the method can include: determining a viral amplification score (VAS) as the Pfu/cell when the cell vehicle is incubated with the virus; and if the VAS score is at least 10, selecting the cell vehicle for screening using one or more of the determinants (a)-(f) and identifying whether there is a match between the cell vehicle and the subject.

The matching methods can be multiplexed for a panel of possible carrier cells to rank them based on the effectiveness for, or delivery of, an oncolytic virus to a subject, wherein a rank of 1 is the most desirable, highest rank and larger numbers represent less desirable ranks, by a multiplexed method comprising:
(i) measuring the value(s) of one or more of a)-f) for each cell vehicle in the panel and ranking each cell vehicle according to the measured value(s), wherein:
   for a), the higher the identity of the alleles between a cell vehicle and the subject, the higher the rank of the cell vehicle;
   for b), the higher the CTMS, TCMS and/or MRS scores for a cell vehicle, the higher the rank of the cell vehicle;
   for c), the higher the V-CTMS, V-TCMS and/or V-MRS scores for a cell vehicle, the higher the rank of the cell vehicle;
   for d), the higher the IVAS score for a cell vehicle, the higher the rank of the cell vehicle;
   for e), the lower the ICS score for a cell vehicle, the higher the rank of the cell vehicle; and
   for f), the higher the ISS score for a cell vehicle, the higher the rank of the cell vehicle; and/or (ii) for each cell vehicle in the panel, obtaining a cumulative rank that is the average of two or more ranks based on measuring the value(s) of two or more of a)-f), and ranking the cell vehicles of the panel according to their cumulative rank.

The multiplexed method can further comprise:
(i) for each cell vehicle in the panel, obtaining a viral amplification score (VAS) as the Pfu/cell when the cell vehicle is incubated with the virus;
(ii) for each cell vehicle in the panel, obtaining a cumulative rank that is the average of two or more ranks based on measuring the VAS score and the value of one or more of a)-f); and
(iii) ranking the cell vehicles of the panel according to their cumulative rank.

In the methods of matching, the ICS score and/or the ISS score is/are obtained based on measuring marker expression in the cell co-culture.

The ICS score and/or the ISS score can be obtained based on measuring marker expression in the supernatants of the co-culture(s); and/or the IVAS score corrected for the effect of the subject's serum on viral amplification by a method comprising: (i) to the co-culture of d), adding serum from the subject in an amount of between 10-50% by weight (or v/v) of the co-culture volume; (ii) computing a Subject Serum Resistance Score (SSRS) according to the formula:

$$SSRS = \frac{pfu/\text{cell without serum} - pfu/\text{cell with serum}}{pfu/\text{cell without serum}};$$

and
(iii) computing a percent SSRS-corrected IVAS score according to the formula:

IVAS(SSRS corrected)=IVAS×(1−SSRS)×100.

Methods of selecting a cell vehicle as suitable for delivery of an oncolytic virus to a subject having cancer (methods of matching) are provided. The methods include identifying one or more of the following determinants (a)-(f) as indicative of a match between the cell vehicle and the subject:
a) the cell vehicle and the subject have identical alleles at 50% or more of the following genetic loci combined:
   (i) MHC I and/or MHC II haplotypes;
   (ii) KIR haplotype and/or KIR ligand haplotypes; and
   (iii) HLA-E, CD1a, CD1b, CD1c and/or CD1d haplotypes;
b) incubating the cell vehicle in a co-culture with cancerous cells from the subject results in one or more of the following:
   (i) a cell to tumor migration score (CTMS) of 20% or more of the cell vehicle cells migrating toward the cancerous cells;
   (ii) a tumor to cell migration score (TCMS) of 20% or more of the cancerous cells migrating toward the cell vehicle cells; and/or
   (iii) a cumulative migration score (MRS) of [(i)+(ii)]/2 of at least 20%;
c) incubating the cell vehicle in a co-culture with the oncolytic virus and cancerous cells from the subject results in one or more of the following:
   (i) a virus loaded cell to tumor migration score (V-CTMS) of 20% or more of the cell vehicle cells migrating toward the cancerous cells;

(ii) a virus loaded tumor to cell migration score (V-TCMS) of 20% or more of the cancerous cells migrating toward the cell vehicle cells; and/or (iii) a cumulative virus loaded migration score (V-MRS) of [(i)+(ii)]/2 of at least 20%;

d) when the cell vehicle is incubated in a co-culture with the oncolytic virus and immune cells obtained from the subject, an immunological viral amplification score (IVAS) representing the amount of viral amplification in the presence of immune cells obtained from the subject relative to the amount of viral amplification obtained under equivalent conditions except in the absence of immune cells obtained from the subject, is at least 20%;

e) when the cell vehicle is incubated in a co-culture with the oncolytic virus and immune cells obtained from the subject, an immunological compatibility score (ICS) representing the immune response in the presence of the cell vehicle relative to the immune response under equivalent conditions except in the absence of the cell vehicle, is ≤200%, wherein the immune response determined by the amount of expression of one or more of the following:

(i) IFNγ;

(ii) one or more markers associated with T cell, γδ T cell, NK cell and/or NKT cell-mediated cytotoxicity; and/or (iii) one or more markers associated with T cell, γδ T cell, NK cell and/or NKT cell activator/effector function(s);

f) when the cell vehicle is incubated in a co-culture with the oncolytic virus and immune cells obtained from the subject, the cell vehicle does not augment an anti-viral immune response and/or suppresses an anti-viral immune response relative to identical conditions except in the absence of the cell vehicle, as measured by an immunological suppression score (ISS) of ≥0% according to the equation:

$$ISS\ \% = [(IV+IC)-ICV]/(IV+IC) \times 100, \text{ wherein}$$

IV=the marker expression level in a co-culture of the virus+immune cells obtained from the subject;

IC=the marker expression level in a co-culture of immune cells obtained from the subject+the cell vehicle;

ICV=the marker expression level in a co-culture of immune cells obtained from the subject+the cell vehicle+the virus; and the marker expression level is the expression level of one or more of the markers set forth in (i), (ii) and (iii) of e); and if one or more of a)-f) is satisfied, identifying a match between the cell vehicle and the subject and selecting the cell vehicle as suitable for delivery of an oncolytic virus to the subject having cancer.

As above, the method of matching can further include, prior to one or more of a)-f): determining a viral amplification score (VAS) as the Pfu/cell when the cell vehicle is incubated with the virus; and if the VAS score is at least 10, selecting the cell vehicle for screening using one or more of the determinants (a)-(f) and identifying whether there is a match between the cell vehicle and the subject. The multiplexed methods described above, also are provided.

Also provided are pharmaceutical compositions containing any of the carrier cells provided herein in a pharmaceutically acceptable vehicle. The pharmaceutical compositions are for use for treating cancer and in methods of treating cancers as described above, and, below. The compositions can be administered systemically, locally, intratumorally, intrahepatically, intravenously, rectally or subcutaneously.

The carrier cells can be matched to the subject by the methods of matching described herein or any other such methods.

Provided are methods for matching, for treatment, a subject having cancer with a cell vehicle for delivery of an oncolytic virus to the subject. The methods include steps of: determining whether the cell vehicle overcomes immune barriers in the subject by detecting, in a co-culture of the cell vehicle, the oncolytic virus and cells, such as PMBC, from the subject, one or more of: (a) a reduced level of one or more markers for T cell activation compared to otherwise equivalent conditions except the cell vehicle is not present; (b) a reduced level of one or more markers for NK cell activation compared to otherwise equivalent conditions except the cell vehicle is not present; and (c) a reduced level of one or more markers for NKT cell activation compared to otherwise equivalent conditions except the cell vehicle is not present, If one or more of (a), (b) and (c) is/are satisfied, the cell vehicle is a match for the subject.

Also provided are methods of matching a subject having cancer with a cell vehicle for delivery of an oncolytic virus for treatment of the subject, that include the steps of: (a) measuring the amount of viral amplification obtained when the virus and the cell vehicle are incubated together with cells from the subject; (b) measuring the amount of viral amplification obtained when the virus and the cell vehicle are incubated under equivalent conditions, except in the absence of cells from the subject; and (c) comparing the amounts measured in (a) and (b), wherein the cell vehicle is a match for treating the subject if the amount of amplification measured in (a) is at least 20% of the amount of amplification measured in (b).

These methods of matching can further include identifying identical alleles, where at least 10% of the alleles in the cell vehicle and the subject are identical. The alleles are one or more major histocompatibility complex (MHC) and/or killer cell inhibitory receptor (KIR) genetic loci. The identity between and among alleles can be performed prior to measuring the level of markers or amount of viral amplification. It can be performed afterwards, or concurrently.

Other methods of matching also are provided. For example, methods, comprising: identifying identical alleles at major histocompatibility complex (MEW) and/or killer cell inhibitory receptor (KIR) genetic loci in the cell vehicle and the subject; and if at least 50% of the alleles are identical, selecting the cell vehicle as a match for the subject. In other methods, the methods comprise: determining whether the cell vehicle overcomes immune barriers in the subject by detecting, in a co-culture comprising the cell vehicle, the oncolytic virus and cells from the subject, a level of expression of one or more immunological markers that is ≤200% the level of expression detected under equivalent conditions except in the absence of the cell vehicle, wherein the markers are selected from among one or more of: (1) markers for T cell activation; (2) markers for NK cell activation; and (3) markers for NKT cell activation, wherein if the expression level of at least one marker selected from among (1), (2) and (3) in the co-culture is ≤200% the level of expression detected under equivalent conditions except in the absence of the cell vehicle, the cell vehicle is a match for the subject. This methods can further include identifying at least one of the alleles at major histocompatibility complex (MHC) and/or killer cell inhibitory receptor (KIR) genetic loci as being identical in the cell vehicle and the subject, where if at least one of the loci is identical and the level of expression of one or more immunological markers in the co-culture is ≤200% the level of expression detected under equivalent conditions except in the absence of the cell vehicle, the cell vehicle is a match for the subject. This step can be performed prior to detecting the expression level of the one or more immunological markers; it can be performed after, or concurrently.

Any of the methods of matching described herein, can be performed to identify carrier cells that are provided herein for administration to a particular subject. Generally, the carrier cells are allogeneic to the subject.

Where permitted, the claims set forth below and in priority applications, International PCT application No. PCT/US2019/035464, and U.S. provisional application Ser. No. 62/680,570 are incorporated by reference into this section.

DETAILED DESCRIPTION

Outline
A. Definitions
B. Selection of Components for Viral Therapy Using Cell-Based Vehicles ("Cell Vehicles" or "Carrier Cells")
   (1) Cell-based Vehicles
      Types of Cell Vehicles (Autologous or Allogeneic)
   (2) Viruses
      Types of Viruses
C. Assays for Matching Cell Vehicles and Viruses with Subjects
   Overview
    A. Haplotype Analysis
      (a) Overview of Haplotypes
      (b) Haplotype Matching Analysis
    B. Ability to Recruit/Sensitize Resistant Tumor Cells and/or Promote Viral Amplification
    C. Ability of Subject-Derived Immune Cells to Promote Viral Amplification
    D. Measurement of Immunological Compatibility with the Subject
    E. Measurement of Cell Vehicle-mediated Suppression of Anti-Viral Immunity
    F. Measurement of Immunomodulative Effects of Cell Vehicles by Analyzing Supernatants
   Detailed Methods for the Matching Assays
    a. General methods for measurements performed in the assays
    b. Selection of Subject-Derived Immune Cells
    c. Matching Cell Vehicle with Virus
    d. Matching Cell Vehicle/Viruns Combination with Subject
   (I) Selection of Subject-Derived Immune Cells
      Types of Cells
      Methods of obtaining cells
   (II) General Culturing and Labeling Methods
   (III) Matching a Cell-based Vehicle ("Cell Vehicle") with a Virus
   (IV) Matching a Cell Vehicle/Virus Combination with a Subject
    1. Haplotype Matching
    2. Conditions and Methods for co-culturing Cell Vehicles, Viruses and Subject-derived Immune Cells
    3. Measurement of Ability/Efficiency of being Recruited to Tumor Cells and Sensitizing otherwise resistant Tumor Cells to Viral Infection.
    4. Analysis of Subject/Cell Vehicle Match
      a. Measurement of Viral Amplification
      b. Measurement of Immunomodulation of Co-cultures
      c. Measurement of Immunomodulation of Supernatants of Co-cultures
      d. Selection of Subject-specific Cell Vehicle
   D. Modified Cell Vehicles with Improved Matching Capabilities
    (i) Sensitized for improved Viral Amplification and/or Immunomodulation
      1. Types
        a. Cell Vehicles sensitized to Enhance Virus Amplification Ability
        b. Cell Vehicles sensitized to Block induction of the Anti-Viral State
        c. Cell Vehicles protected against Allogeneic Inactivation/Rejection Determinants
        d. Cell Vehicles protected against Complement
      2. Methods of Making
    (ii) Sensitized for Resistance to Virus-Mediated Killing
      a. Cell Vehicles pretreated with Type I and/or Type II interferons
      b. Cell Vehicles pretreated with agonists/inducers of anti-viral state (STING, PKR, RIG-I, MDA-5, etc.)
      2. Methods of Making
    (iii) Engineered for improved Viral Amplification and/or Immunomodulation
      1. Types
        a. Engineered to be unresponsive to an interferon-induced antiviral state
        b. Engineered to evade allogeneic recognition by T cells, γδ (gd) T cells (adaptive immune responses) and NKT cells
        c. Engineered to evade allogeneic recognition by NK cells and γδ (gd) T cells (innate immune responses)
        d. Engineered to express immunosuppressive factors of human or viral origin
        e. Engineered to Express Cancer or Stem Cell-Derived Factors that Facilitate viral infection of otherwise impermissive Tumor Cells
        f. Engineered to Express Factors interfering with the function of Complement and/or Neutralizing Antibodies
      2. Methods of Making
   E. Modes of Administration of Cell Vehicle/Virus for Therapy
   F. Treatment Methods and Monitoring Coordinated with Treatment
   G. Pharmaceutical Compositions, Combinations and Kits
   H. Additional Therapies Administered with Cell Vehicle+Virus Treatment
   I. Types of Cancers to be treated
   J. Examples

A. DEFINITIONS

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, a "virus" refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. Viruses include, but are not limited to, poxviruses, herpesviruses, adenoviruses, adeno-associated viruses, lentiviruses, retroviruses, rhabdoviruses, papillomaviruses, vesicular stomatitis virus, measles virus, Newcastle disease virus, picornavirus, Sindbis virus, papillomavirus, parvovirus, reovirus, coxsackievirus, influenza virus, mumps virus, poliovirus, Seneca Valley Virus, and semliki forest virus.

As used herein, oncolytic viruses refer to viruses that replicate selectively in tumor cells in tumorous subjects. Some oncolytic viruses can kill a tumor cell following infection of the tumor cell. For example, an oncolytic virus can cause death of the tumor cell by lysing the tumor cell or inducing cell death of the tumor cell.

As used herein, the term "therapeutic virus" refers to a virus that is administered for the treatment of a disease or disorder, such as a neoplastic disease, such as cancer, a tumor and/or a metastasis or inflammation or wound or diagnosis thereof and or both. Generally, a therapeutic virus herein is one that exhibits anti-tumor activity and minimal toxicity.

As used herein the term "vaccinia virus" or "VACV" or "VV" denotes a large, complex, enveloped virus belonging to the poxvirus family. It has a linear, double-stranded DNA genome approximately 190 kbp in length, which encodes approximately 200 proteins. Vaccinia virus strains include, but are not limited to, strains of, derived from, or modified forms of Western Reserve (WR), Copenhagen (Cop), Bern, Paris, Tashkent, Tian Tan, Lister, Wyeth, IHD-J, IHD-W, Brighton, Ankara, modified vaccinia Ankara (MVA), CVA382, Dairen I, LIPV, LC16M8, LC16M0, LIVP, ACAM, WR 65-16, Connaught, JX-594, GL-ONC1, vvDD TK mutant, New York City Board of Health (NYCBH), EM-63, and NYVAC vaccinia virus strains.

As used herein, Lister Strain of the Institute of Viral Preparations (LIVP) or LIVP virus strain refers to a virus strain that is the attenuated Lister strain (ATCC Catalog No. VR-1549) that was produced by adaption to calf skin at the Institute of Viral Preparations, Moscow, Russia (Al'tshtein et al. (1985) *Dokl. Akad. Nauk USSR* 285:696-699). The LIVP strain can be obtained, for example, from the Institute of Viral Preparations, Moscow, Russia (see. e.g., Kutinova et al. (1995) *Vaccine* 13:487-493); the Microorganism Collection of FSRI SRC VB Vector (Kozlova et al. (2010) *Environ. Sci. Technol.* 44:5121-5126); or can be obtained from the Moscow Ivanovsky Institute of Virology (C0355 K0602; Agranovski et al. (2006) *Atmospheric Environment* 40:3924-3929). It also is well-known to those of skill in the art; as it was the vaccine strain used for vaccination in the USSR and throughout Asia and India. The strain now is used by researchers and is well-known (see e.g., Altshteyn et al. (1985) *Dokl. Akad. Nauk USSR* 285:696-699; Kutinova et al. (1994) *Arch. Virol.* 134:1-9; Kutinova et al. (1995) *Vaccine* 13:487-493; Shchelkunov et al. (1993) *Virus Research* 28:273-283; Sroller et al. (1998) *Archives Virology* 143:1311-1320; Zinoviev et al., (1994) *Gene/*47:209-214; and Chkheidze et al. (1993) *FEBS* 336:340-342). Among the LIVP strains are those described in WO 2012/142529, now EP 2697368, and viruses that contain a sequence that is at least or at least about 97%, 98% or 99% identical to any LIVP strains. An LIVP virus strain encompasses any virus strain or virus preparation that is obtained by propagation of an LIVP through repeat passage in cell lines.

As used herein, the term "modified virus" refers to a virus that is altered compared to a parental strain of the virus. Typically modified viruses have one or more truncations, mutations, insertions or deletions in the genome of virus. A modified virus can have one or more endogenous viral genes modified and/or one or more intergenic regions modified. Exemplary modified viruses can have one or more heterologous nucleic acid sequences inserted into the genome of the virus. Modified viruses can contain one or more heterologous nucleic acid sequences in the form of a gene expression cassette for the expression of a heterologous gene.

As used herein, the term "carrier cell," used interchangeably with "cell vehicle," "carrier vehicle," cell-based delivery vehicle" and "cell-based vehicle" refers to any cell that can be or is infected with virus or otherwise associated with virus, such as through chemical or physical interaction between the virus and a surface protein, or by infection of the cytoplasm or nucleus of the cell with the virus.

As used herein, "sensitized" or "sensitizing a cell" to alter a property of the cell, refers to treating the cell by treatment, generally before use, with an agent to modify a property of the cell, such as by inducing expression of a gene.

As used herein, a match between a particular cell carrier (also referred to herein as a cell vehicle) and a subject with cancer to be treated with the carrier cell and virus means that the cell carrier is sufficiently compatible with the immune system of the host to evade the subject's immune system to deliver virus to a tumor in the subject. Assays to identify matched carrier cells matched to a subject to be treated are provided herein. The carrier cell also can be matched to a virus, where a matched virus can replicate in the cell. A matched carrier cell with virus is a match for administration to a subject if the virus amplifies/replicates in the cell and the cell delivers virus to a tumor in the subject. Assays to select carrier cell/virus combinations also are provided herein.

As used herein, amplification of a virus in a carrier cell means that the virus replicates in the cell to sustain the virus or increase the amount of virus in the cell. As used herein, a "host cell" or "target cell" are used interchangeably to mean a cell that can be infected by a virus.

As used herein, the term "tissue" refers to a group, collection or aggregate of similar cells generally acting to perform a specific function within an organism.

As used herein, the term, "therapeutic gene product" or "therapeutic polypeptide" or "therapeutic agent" refers to any heterologous protein expressed by the therapeutic virus that ameliorates the symptoms of a disease or disorder or ameliorates the disease or disorder. Therapeutic agents include, but are not limited to, moieties that inhibit cell growth or promote cell death, that can be activated to inhibit cell growth or promote cell death, or that activate another agent to inhibit cell growth or promote cell death. Optionally, the therapeutic agent can exhibit or manifest additional properties, such as, properties that permit its use as an imaging agent, as described elsewhere herein. Exemplary therapeutic agents include, for example, cytokines, growth factors, photosensitizing agents, radionuclides, toxins, antimetabolites, signaling modulators, anti-cancer antibiotics, anti-cancer antibodies, angiogenesis inhibitors, chemotherapeutic compounds or a combination thereof.

As used herein, therapeutic agents are agents that ameliorate the symptoms of a disease or disorder or ameliorate the disease or disorder. Therapeutic agent, therapeutic compound, or therapeutic regimens include conventional drugs and drug therapies, including vaccines for treatment or prevention (i.e., reducing the risk of getting a particular disease or disorder), which are known to those skilled in the art and described elsewhere herein. Therapeutic agents for the treatment of neoplastic disease include, but are not limited to, moieties that inhibit cell growth or promote cell death, that can be activated to inhibit cell growth or promote cell death, or that activate another agent to inhibit cell growth or promote cell death. Therapeutic agents for use in the methods provided herein can be, for example, an anti-cancer agent. Exemplary therapeutic agents include, for example, therapeutic microorganisms, such as therapeutic viruses and bacteria, cytokines, growth factors, photosensitizing agents, radionuclides, toxins, antimetabolites, signaling modulators, anticancer antibiotics, anticancer antibodies, angiogenesis inhibitors, radiation therapy, chemotherapeutic compounds or a combination thereof.

As used herein, a tumor cell or cancer cell refers to a cell that divides and reproduces abnormally because growth and division are not regulated or controlled, i.e. cells that are susceptible to uncontrolled growth. A tumor cell can be a benign or malignant cell. Typically, the tumor cell is a malignant cell that can spread to other parts of the body, a process known as metastasis.

As used herein, a virus preparation or virus composition, refers to a virus composition obtained by propagation of a virus strain, for example a vaccinia virus strain, a vaccinia virus clonal strain or a modified or recombinant virus strain, in vivo or in vitro in a culture system. For example, a vaccinia virus preparation refers to a viral composition obtained by propagation of a virus strain in host cells, typically upon purification from the culture system using standard methods known in the art. A virus preparation generally is made up of a number of virus particles or virions. If desired, the number of virus particles in the sample or preparation can be determined using a plaque assay to calculate the number of plaque forming units per sample unit volume (pfu/mL), assuming that each plaque formed is representative of one infective virus particle. Each virus particle or virion in a preparation can have the same genomic sequence compared to other virus particles (i.e., the preparation is homogenous in sequence) or can have different genomic sequences (i.e., the preparation is heterogeneous in sequence). It is understood to those of skill in the art that, in the absence of clonal isolation, heterogeneity or diversity in the genome of a virus can occur as the virus reproduces, such as by homologous recombination events that occur in the natural selection processes of virus strains (Plotkin & Orenstein (eds) "Recombinant Vaccinia Virus Vaccines" in Vaccines, 3$^{rd}$ edition (1999)).

As used herein, plaque forming unit (pfu) or infectious unit (IU) refers to the number of infectious or live viruses. It thus reflects the amount of active virus in the preparation. The pfu can be determined using a virus plaque assay (plaque formation assay) or an end-point dilution assay, which are standard assays known to one of skill in the art.

As used herein, a nanoparticle refers to a colloidal particle for delivery of a molecule or agent that is microscopic in size of between or about between 1 and 1000 nanometers (nm), such as between 1 and 100 nm and behave as a whole unit in terms of transport and properties. Nanoparticles include those that are uniform in size. Nanoparticles include those that contain a targeting molecule attached to the outside.

As used herein, "targeting molecule" or "targeting ligand" refers to any molecular signal directing localization to specific cells, tissues or organs. Examples of targeting ligands include, but are not limited to, proteins, polypeptides or portions thereof that bind to cell surface molecules, including, but not limited to, proteins, carbohydrates, lipids or other such moieties. For example, targeting ligands include proteins or portions thereof that bind to cell surface receptors or antibodies directed to antigens expressed selectively on a target cell. Targeting ligands include, but are not limited to growth factors, cytokines, adhesion molecules, neuropeptides, protein hormones and single-chain antibodies (scFv).

For purposes herein, recitation of "antibody" (e.g., antibody directed to an antigen expressed on an immune cell population such as, for example, T cells, γδ (gd) T cells, NK cells, NKT cells to be depleted or inhibited for suppression of an immune response) includes full-length antibodies and portions thereof including antibody fragments. Antibody fragments, include, but are not limited to, Fab fragments, Fab' fragments, F(ab')2 fragments, Fv fragments, disulfide-linked Fvs (dsFv), Fd fragments, Fd' fragments, single-chain Fvs (scFv), single-chain Fabs (scFab), diabodies, anti-idiotypic (anti-Id) antibodies, or antigen-binding fragments of any of the above. Antibody also includes synthetic antibodies, recombinantly produced antibodies, multispecific antibodies (e.g., bispecific antibodies), human antibodies, non-human antibodies, humanized antibodies, chimeric antibodies, and intrabodies. Antibodies provided herein include members of any immunoglobulin type (e.g., IgG, IgM, IgD, IgE, IgA and IgY), any class (e.g., IgG1, IgG2, IgG3, IgG4, IgA1 and IgA2) or subclass (e.g., IgG2a and IgG2b).

Antibodies, such as monoclonal antibodies, can be prepared using standard methods known to those with skill in the art (see, e.g., Kohler et al., Nature 256:495-497 (1975); Kohler et al., Eur. J. Immunol. 6:511-519 (1976); and WO 02/46455). For example, an animal is immunized by standard methods to produce antibody-secreting somatic cells. These cells then are removed from the immunized animal for fusion to myeloma cells. Somatic cells that can produce antibodies, particularly B cells, can be used for fusion with a myeloma cell line. These somatic cells can be derived from the lymph nodes, spleens and peripheral blood of primed animals. Specialized myeloma cell lines have been developed from lymphocytic tumors for use in hybridoma-producing fusion procedures (Kohler and Milstein, Eur. J. Immunol. 6:511-519 (1976); Shulman et al., Nature, 276: 269-282 (1978); Volk et al., J. Virol., 42:220-227 (1982)). These cell lines have three useful properties. The first is they facilitate the selection of fused hybridomas from unfused and similarly indefinitely self-propagating myeloma cells by having enzyme deficiencies that render them incapable of growing in selective medium that support the growth of hybridomas. The second is they have the ability to produce antibodies and are incapable of producing endogenous light or heavy immunoglobulin chains. A third property is they efficiently fuse with other cells. Other methods for producing hybridomas and monoclonal antibodies are well known to those of skill in the art. It is routine to produce antibodies against any polypeptide, e.g., antigenic marker on an immune cell population.

Exemplary immune cell depleting antibodies include, but are not limited to:
  anti-asialo GM1 (Thermofisher Scientific), which depletes NK cells in mice in vivo and in a variety of species, including humans, in vitro;
  anti-NK1.1 which depletes NK cells in mice, and also depletes NKT cells;

OKM1 (anti-CD11b, human) and B73.1 (anti-CD16, human) antibodies for depleting NK cells (Strassmann et al., *J. Immunol.*, 130(4):1556-60 (1983));

DJ130c or 3G8 (anti-CD16, human) antibodies to deplete NK cells (Choi et al., *Immunology*, 124(2): 215-222 (2008));

IMMU510 or B1.1 (anti-TCRγδ) which block γδ (gd) T cells. Also, for receptor blocking, γδ PBLs were incubated with the blocking antibodies anti-NKp30 (clone F252), anti-NKp44 (clone KS38), anti-NKp46 (clone KL247), anti-TCRγδ (Beckman Coulter, clones IMMU510 or B1.1), or anti-Vδ1 TCR (Fisher Scientific, clones TCS1 or TS8.2) (Correia et al., *Blood*, 118:992-1001 (2011));

B1 antibody which blocks antigen-mediated activation of TCR;

GL3 and UC7-13D5 antibodies which deplete γδ (gd) T cells or internalize them in vivo in mice (Koenecke et al., *Eur. J. Immunol.*, 39(2):372-9 (2009));

anti-CD1d, clone 1B1 which depletes NKT cells in mice (Christaki et al., *J. Immunol. Res.*, 2015, Article ID 532717); and NKTT120 which depletes iNKT cells in humans. NKTT120 is a humanized IgG1κ monoclonal antibody targeted to the Vα24-Jα18 gene rearranged invariant TCR that has the potential to rapidly and specifically deplete iNKT cells (Field et al., *PLoS One*, 12,2.e0171067 (2017)).

As used herein, a delivery vehicle for administration refers to a lipid-based or other polymer-based composition, such as liposome, micelle or reverse micelle, that associates with an agent, such as a virus provided herein, for delivery into a host subject.

As used herein, accumulation of a virus in a particular tissue refers to the distribution or colonization of the virus in particular tissues of a host organism after a time period following administration of the virus to the host, long enough for the virus to infect the host's organs or tissues. As one skilled in the art will recognize, the time period for infection of a virus will vary depending on the virus, the organ(s) or tissue(s) to be infected, the immunocompetence of the host, and the dosage of the virus. Generally, accumulation can be determined at time points from about less than 1 day, about 1 day to about 2, 3, 4, 5, 6 or 7 days, about 1 week to about 2, 3 or 4 weeks, about 1 month to about 2, 3, 4, 5, 6 months or longer after infection with the virus. For purposes herein, the viruses preferentially accumulate in immunoprivileged tissue, such as inflamed tissue or tumor tissue, but are cleared from other tissues and organs, such as non-tumor tissues, in the host to the extent that toxicity of the virus is mild or tolerable and at most, not fatal.

As used herein, "preferential accumulation" refers to accumulation of a virus at a first location at a higher level than accumulation at a second location (i.e., the concentration of viral particles, or titer, at the first location is higher than the concentration of viral particles at the second location). Thus, a virus that preferentially accumulates in immunoprivileged tissue (tissue that is sheltered from the immune system), such as inflamed tissue, and tumor tissue, relative to normal tissues or organs, refers to a virus that accumulates in immunoprivileged tissue, such as a tumor, at a higher level (i.e., concentration or viral titer) than the virus accumulates in normal tissues or organs.

As used herein, activity refers to the in vitro or in vivo activities of a compound or virus provided herein. For example, in vivo activities refer to physiological responses that result following in vivo administration of a compound or virus provided herein (or of a composition or other mixture thereof). Activity, thus, encompasses resulting therapeutic effects and pharmaceutical activity of such compounds, compositions and mixtures. Activities can be observed in in vitro and/or in vivo systems designed to test or use such activities.

As used herein, "anti-tumor activity" or "anti-tumorigenic" refers to virus strains that prevent or inhibit the formation or growth of tumors in vitro or in vivo in a subject. Anti-tumor activity can be determined by assessing a parameter or parameters indicative of anti-tumor activity.

As used herein, "greater" or "improved" activity with reference to anti-tumor activity or anti-tumorigenicity means that a virus strain is capable of preventing or inhibiting the formation or growth of tumors in vitro or in vivo in a subject to a greater extent than a reference or control virus or to a greater extent than absence of treatment with the virus. Whether anti-tumor activity is "greater" or "improved" can be determined by assessing the effect of a virus and, if necessary, a control or reference virus, on a parameter indicative of anti-tumor activity. It is understood that when comparing the activity of two or more different viruses, the amount of virus (e.g., pfu) used in an in vitro assay or administered in vivo is the same or similar, and the conditions (e.g., in vivo dosage regimen) of the in vitro assay or in vivo assessment are the same or similar.

As used herein, "toxicity" (also referred to as virulence or pathogenicity herein) with reference to a virus refers to the deleterious or toxic effects to a host upon administration of the virus. For an oncolytic virus, such as vaccinia virus, the toxicity of a virus is associated with its accumulation in non-tumorous organs or tissues, which can impact the survival of the host or result in deleterious or toxic effects. Toxicity can be measured by assessing one or more parameters indicative of toxicity. These include accumulation in non-tumorous tissues and effects on viability or health of the subject to whom it has been administered, such as effects on body weight.

As used herein, "reduced toxicity" means that the toxic or deleterious effects upon administration of the virus to a host are attenuated or lessened compared to a host not treated with the virus or compared to a host that is administered with another reference or control virus. Whether toxicity is reduced or lessened can be determined by assessing the effect of a virus and, if necessary, a control or reference virus, on a parameter indicative of toxicity. It is understood that when comparing the activity of two or more different viruses, the amount of virus (e.g., pfu) used in an in vitro assay or administered in vivo is the same or similar and the conditions (e.g., in vivo dosage regimen) of the in vitro assay or in vivo assessment are the same or similar. For example, when comparing effects upon in vivo administration of a virus and a control or reference virus the subjects are the same species, size, gender and the virus is administered in the same or similar amount under the same or similar dosage regimen. In particular, a virus with reduced toxicity can mean that upon administration of the virus to a host, such as for the treatment of a disease, the virus does not accumulate in non-tumorous organs and tissues in the host to an extent that results in damage or halm to the host, or that impacts survival of the host to a greater extent than the disease being treated does or to a greater extent than a control or reference virus does. For example, a virus with reduced toxicity includes a virus that does not result in death of the subject over the course of treatment.

As used herein, a "control" or "standard" refers to a sample that is substantially identical to the test sample, except that it is not treated with a test parameter, or, if it is a plasma sample, it can be from a normal volunteer not affected with the condition of interest. A control also can be an internal control. For example, a control can be a sample, such as a virus, that has a known property or activity.

As used herein, dosing regimen refers to the amount of agent, for example, a carrier cell or virus or other agent, administered, and the frequency of administration over the course of a cycle of administration. The dosing regimen is a function of the disease or condition to be treated, and thus can vary.

As used herein, frequency of administration refers to the number of times an agent is administered during the cycle of administration. For example, frequency can be days, weeks or months. For example, frequency can be administration once during a cycle of administration, two times, three times, four times, five times, six times or seven times. The frequency can refer to consecutive days during the cycle of administration. The particular frequency is a function of the particular disease or condition treated.

As used herein, a "cycle of administration" refers to the repeated schedule of the dosing regimen of administration of a virus that is repeated over successive administrations. For example, an exemplary cycle of administration is a 28 day cycle.

As used herein, the terms immunoprivileged cells and immunoprivileged tissues refer to cells and tissues, such as solid tumors, which are sequestered from the immune system. Generally, administration of a virus to a subject elicits an immune response that clears the virus from the subject. Immunoprivileged sites, however, are shielded or sequestered from the immune response, permitting the virus to survive and generally to replicate. Immunoprivileged tissues include proliferating tissues, such as tumor tissues and other tissues and cells involved in other proliferative disorders, wounds and other tissues involved in inflammatory responses.

As used herein, a wound or lesion refers to any damage to any tissue in a living organism. The tissue can be an internal tissue, such as the stomach lining or a bone, or an external tissue, such as the skin. As such, a wound or lesion can include, but is not limited to, a gastrointestinal tract ulcer, a broken bone, a neoplasia, and cut or abraded skin. A wound or lesion can be in a soft tissue, such as the spleen, or in a hard tissue, such as bone. The wound or lesion can have been caused by any agent, including traumatic injury, infection or surgical intervention.

As used herein, a tumor, also known as a neoplasm, is an abnormal mass of tissue that results when cells proliferate at an abnormally high rate. Tumors can show partial or total lack of structural organization and functional coordination with normal tissue. Tumors can be benign (not cancerous), or malignant (cancerous). As used herein, a tumor is intended to encompass hematopoietic tumors as well as solid tumors.

Malignant tumors can be broadly classified into three major types. Carcinomas are malignant tumors arising from epithelial structures (e.g., breast, prostate, lung, colon, and pancreas). Sarcomas are malignant tumors that originate from connective tissues, or mesenchymal cells, such as muscle, cartilage, fat or bone. Leukemias and lymphomas are malignant tumors affecting hematopoietic structures (structures pertaining to the formation of blood cells), including components of the immune system. Other malignant tumors include, but are not limited to, tumors of the nervous system (e.g., neurofibromatomas), germ cell tumors, and blastic tumors.

As used herein, a resected tumor refers to a tumor in which a significant portion of the tumor has been excised. The excision can be effected by surgery (i.e., a surgically resected tumor). The resection can be partial or complete.

As used herein, a disease or disorder refers to a pathological condition in an organism resulting from, for example, infection or genetic defect, and characterized by identifiable symptoms. An exemplary disease as described herein is a neoplastic disease, such as cancer.

As used herein, a cell involved in a disease or disease process refers to cells whose presence contributes to, exacerbates, causes or otherwise is involved in the etiology of a disease or disease process. Inhibition or killing of such cells can ameliorate the symptoms of the disease or can ameliorate the disease. Examples of such cells are tumor cells. Killing or inhibiting the growth or proliferation of tumor cells effects treatment of tumors. Other examples are immune effector cells, which participate in inflammatory responses that contribute to the pathology of a variety of diseases. Inhibiting or killing immune effector cells can treat diseases that have an inflammatory component.

As used herein, "killing or inhibiting growth or proliferation of cells" means that the cells die or are eliminated. Inhibiting growth or proliferation means that the number of such cells does not increase, and can decrease.

As used herein, a "tumor cell" is any cell that is part of a tumor. Typically, carrier cells provided herein preferentially home to tumor cells and the viruses provided herein preferentially infect tumor cells in a subject compared to normal cells.

As used herein, a "metastatic cell" is a cell that has the potential for metastasis. Metastatic cells have the ability to metastasize from a first tumor in a subject and can colonize tissue at a different site in the subject to form a second tumor at the site.

As used herein, "tumorigenic cell," is a cell that, when introduced into a suitable site in a subject, can form a tumor. The cell can be non-metastatic or metastatic.

As used herein, a "normal cell" is a cell that is not derived from a tumor. As used herein, neoplastic disease refers to any disorder involving cancer, including tumor development, growth, metastasis and progression.

As used herein, cancer is a term for diseases caused by or characterized by any type of malignant tumor, including metastatic cancers, lymphatic tumors, and blood cancers. Exemplary cancers include, but are not limited to, acute lymphoblastic leukemia, acute lymphoblastic leukemia, acute myeloid leukemia, acute promyelocytic leukemia, adenocarcinoma, adenoma, adrenal cancer, adrenocortical carcinoma, AIDS-related cancer, AIDS-related lymphoma, anal cancer, appendix cancer, astrocytoma, basal cell carcinoma, bile duct cancer, bladder cancer, bone cancer, osteosarcoma/malignant fibrous histiocytoma, brainstem glioma, brain cancer, carcinoma, cerebellar astrocytoma, cerebral astrocytoma/malignant glioma, ependymoma, medulloblastoma, supratentorial primitive neuroectodermal tumor, visual pathway or hypothalamic glioma, breast cancer, bronchial adenoma/carcinoid, Burkitt lymphoma, carcinoid tumor, carcinoma, central nervous system lymphoma, cervical cancer, chronic lymphocytic leukemia, chronic myelogenous leukemia, chronic myeloproliferative disorder, colon cancer, cutaneous T-cell lymphoma, desmoplastic small round cell tumor, endometrial cancer, ependymoma. epidermoid carcinoma, esophageal cancer, Ewing's sarcoma, extracranial germ cell tumor, extragonadal germ cell tumor, extrahepatic bile duct cancer, eye cancer/intraocular melanoma, eye cancer/retinoblastoma, gallbladder cancer, gallstone tumor, gastric/stomach cancer, gastrointestinal carcinoid tumor, gastrointestinal stromal tumor, giant cell tumor, glioblastoma multiforme, glioma, hairy-cell tumor, head and neck cancer, heart cancer, hepatocellular/liver cancer, Hodgkin lymphoma, hyperplasia, hyperplastic corneal nerve tumor, in situ carcinoma, hypopharyngeal cancer, intestinal ganglioneuroma, islet cell tumor, Kaposi's sarcoma, kidney/renal cell cancer, laryngeal cancer, leiomyoma tumor, lip and oral cavity cancer, liposarcoma, liver cancer, non-small cell lung cancer, small cell lung cancer, lymphomas, macroglobulinemia, malignant carcinoid, malignant fibrous histiocytoma of bone, malignant hypercalcemia, malignant melanomas, marfanoid habitus tumor, medullary carcinoma, melanoma, merkel cell carcinoma, mesothelioma, metastatic skin carcinoma, metastatic squamous neck cancer, mouth cancer, mucosal neuromas, multiple myeloma, mycosis fungoides, myelodysplastic syndrome, myeloma, myeloproliferative disorder, nasal cavity and paranasal sinus cancer, nasopharyngeal carcinoma, neck cancer, neural tissue cancer, neuroblastoma, oral cancer, oropharyngeal cancer, osteosarcoma, ovarian cancer, ovarian epithelial tumor, ovarian germ cell tumor, pancreatic cancer, parathyroid cancer, penile cancer, pharyngeal cancer, pheochromocytoma, pineal astrocytoma, pineal germinoma, pineoblastoma, pituitary adenoma, pleuropulmonary blastoma, polycythemia vera, primary brain tumor, prostate cancer, rectal cancer, renal cell tumor, reticulum cell sarcoma, retinoblastoma, rhabdomyosarcoma, salivary gland cancer, seminoma, Sezary syndrome, skin cancer, small intestine cancer, soft tissue sarcoma, squamous cell carcinoma, squamous neck carcinoma, stomach cancer, supratentorial primitive neuroectodermal tumor, testicular cancer, throat cancer, thymoma, thyroid cancer, topical skin lesion, trophoblastic tumor, urethral cancer, uterine/endometrial cancer, uterine sarcoma, vaginal cancer, vulvar cancer, Waldenström's macroglobulinemia or Wilm's tumor. Exemplary cancers commonly diagnosed in humans include, but are not limited to, cancers of the bladder, brain, breast, bone marrow, cervix, colon/rectum, kidney, liver, lung/bronchus, ovary, pancreas, prostate, skin, stomach, thyroid, or uterus. Exemplary cancers commonly diagnosed in dogs, cats, and other pets include, but are not limited to, lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumor, testicular tumor, seminoma, Sertoli cell tumor, hemangiopericytoma, histiocytoma, chloroma (e.g., granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma, follicular lymphoma, intestinal lymphosarcoma, fibrosarcoma and pulmonary squamous cell carcinoma. Exemplary cancers diagnosed in rodents, such as a ferret, include, but are not limited to, insulinoma, lymphoma, sarcoma, neuroma, pancreatic islet cell tumor, gastric MALT lymphoma and gastric adenocarcinoma. Exemplary neoplasias affecting agricultural livestock include, but are not limited to, leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticuloendotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lymphadenitis (CLA): chronic, infectious, contagious disease of sheep and goats caused by the bacterium Corynebacterium pseudotuberculosis, and contagious lung tumor of sheep caused by jaagsiekte.

As used herein, a "metastasis" refers to the spread of cancer from one part of the body to another. For example, in the metastatic process, malignant cells can spread from the site of the primary tumor in which the malignant cells arose and move into lymphatic and blood vessels, which transport the cells to normal tissues elsewhere in an organism where the cells continue to proliferate. A tumor formed by cells that have spread by metastasis is called a "metastatic tumor," a "secondary tumor" or a "metastasis."

As used herein, an anticancer agent or compound (used interchangeably with "antitumor or antineoplastic agent") refers to any agent or compound used in anticancer treatment. These include any agents, when used alone or in combination with other compounds or treatments, that can alleviate, reduce, ameliorate, prevent, or place or maintain in a state of remission of clinical symptoms or diagnostic markers associated with neoplastic disease, tumors and cancer, and can be used in methods, combinations and compositions provided herein. Anticancer agents include antimetastatic agents. Exemplary anticancer agents include, but are not limited to, chemotherapeutic compounds (e.g., toxins, alkylating agents, nitrosoureas, anticancer antibiotics, antimetabolites, antimitotics, topoisomerase inhibitors), cytokines, growth factors, hormones, photosensitizing agents, radionuclides, signaling modulators, anticancer antibodies, anticancer oligopeptides, anticancer oligonucleotides (e.g., antisense RNA and siRNA), angiogenesis inhibitors, radiation therapy, or a combination thereof. Exemplary chemotherapeutic compounds include, but are not limited to, Ara-C, cisplatin, carboplatin, paclitaxel, doxorubicin, gemcitabine, camptothecin, irinotecan, cyclophosphamide, 6-mercaptopurine, vincristine, 5-fluorouracil, and methotrexate. As used herein, reference to an anticancer or chemotherapeutic agent includes combinations or a plurality of anticancer or chemotherapeutic agents unless otherwise indicated.

As used herein, a subject includes any organism, including an animal for whom diagnosis, screening, monitoring or treatment is contemplated. Animals include mammals such as primates and domesticated animals. An exemplary primate is a human. A patient refers to a subject, such as a mammal, primate, human, or livestock subject afflicted with a disease condition or for which a disease condition is to be determined or risk of a disease condition is to be determined.

As used herein, a patient refers to a human subject exhibiting symptoms of a disease or disorder.

As used herein, treatment of a subject that has a condition, disorder or disease means any manner of treatment in which the symptoms of the condition, disorder or disease are ameliorated or otherwise beneficially altered. Treatment encompasses any pharmaceutical use of the viruses described and provided herein.

As used herein, treatment of a subject that has a neoplastic disease, including a tumor or metastasis, means any manner of treatment in which the symptoms of having the neoplastic disease are ameliorated or otherwise beneficially altered.

Typically, treatment of a tumor or metastasis in a subject encompasses any manner of treatment that results in slowing of tumor growth, lysis of tumor cells, reduction in the size of the tumor, prevention of new tumor growth, or prevention of metastasis of a primary tumor, including inhibition of vascularization of the tumor, tumor cell division, tumor cell migration or degradation of the basement membrane or extracellular matrix.

As used herein, therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, amelioration or alleviation of the symptoms of a particular disorder, such as by administration of a particular pharmaceutical composition, refers to any lessening, whether permanent or temporary, lasting or transient that can be attributed to or associated with administration of the composition.

As used herein, efficacy means that upon administration of a virus or virus composition, the virus will colonize proliferating or immunoprivileged cells, such as tumor cells, and replicate. Colonization and replication in tumor cells is indicative that the treatment is or will be an effective treatment.

As used herein, effective treatment with a cell carrier/virus is one that can increase survival compared to the absence of treatment therewith. For example, a virus is an effective treatment if it stabilizes disease, causes tumor regression, decreases severity of disease or slows down or reduces metastasizing of the tumor.

As used herein, an effective amount, or therapeutically effective amount, of a virus or compound for treating a particular disease is an amount to ameliorate, or in some manner reduce the symptoms associated with the disease. The amount will vary from one individual to another and will depend upon a number of factors, including, but not limited to, age, weight, the overall physical condition of the patient and the severity of the disease. A therapeutically effective amount can be administered as a single dosage or can be administered in multiple dosages according to a regimen, whereby it is effective. The amount can cure the disease but, typically, is administered in order to ameliorate the symptoms of the disease. Repeated administration can be required to achieve the desired amelioration of symptoms.

As used herein, an effective amount, or therapeutically effective amount, of a virus or compound for treating a neoplastic disease, including a tumor or metastasis is an amount to ameliorate, or in some manner reduce the symptoms associated with the neoplastic disease, including, but not limited to slowing of tumor growth, lysis of tumor cells, reduction in the size of the tumor, prevention of new tumor growth, or prevention of metastasis of a primary tumor.

As used herein, a "composition" refers to any mixture of two or more products or compounds. It can be a solution, a suspension, liquid, powder, a paste, aqueous, non-aqueous, or any combination thereof.

As used herein, a formulation refers to a composition containing at least one active pharmaceutical or therapeutic agent and one or more excipients.

As used herein, a co-formulation refers to a composition containing two or more active or pharmaceutical or therapeutic agents and one or more excipients.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related. Exemplary combinations include, but are not limited to, two or more pharmaceutical compositions, a composition containing two or more active ingredients, such as two viruses, or a virus and an anticancer agent, such as a chemotherapeutic compound, two or more viruses, a virus and a therapeutic agent, a virus and an imaging agent, a virus and a plurality of therapeutic and/or imaging agents, or any association thereof. Such combinations can be packaged as kits.

As used herein, direct administration refers to administration of a composition without dilution.

As used herein, a kit is a packaged combination, optionally, including instructions for use of the combination and/or other reactions and components for such use.

As used herein, an "article of manufacture" is a product that is made and sold. As used throughout this application, the term is intended to encompass articles containing a carrier cell and vaccinia virus alone or in combination with a second therapy or a therapeutic energy source contained in the same or separate articles of packaging.

As used herein, a device refers to a thing made or adapted for a particular task. Exemplary devices herein are devices that cover or coat or are capable of contacting the epidermis or surface of the skin. Examples of such devices include, but are not limited to, a wrap, bandage, bind, dress, suture, patch, gauze or dressing.

As used herein, the singular forms "a," "an" and "the" include plural referents unless the context clearly dictates otherwise.

As used herein, ranges and amounts can be expressed as "about" or "approximately" a particular value or range. "About" or "approximately" also includes the exact amount. Hence, "about 5 milliliters" means "about 5 milliliters" and also "5 milliliters." Generally "about" includes an amount that would be expected to be within experimental error.

As used herein, "about the same" means within an amount that one of skill in the art would consider to be the same or to be within an acceptable range of error. For example, typically, for pharmaceutical compositions, within at least 1%, 2%, 3%, 4%, 5% or 10% is considered about the same. Such amounts can vary depending upon the tolerance for variation in the particular composition by subjects.

As used herein, "optional" or "optionally" means that the subsequently described event or circumstance does or does not occur, and that the description includes instances where said event or circumstance occurs and instances where it does not.

As used herein, the abbreviations for any protective groups, amino acids and other compounds are, unless indicated otherwise, in accord with their common usage, recognized abbreviations, or the IUPAC-IUB Commission on Biochemical Nomenclature (see, (1972) *Biochem.* 11:1726).

Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, "allogeneic cells" are cells that are genetically different with respect to a particular subject because they are derived from a genetically different individual of the same species. For example, allogeneic stem cells are stem cells that are derived from a donor other than the patient (or identical twin).

As used herein, "autologous cells" are cells obtained from the same individual, for example, the subject to be treated (i.e., the patient). For example, autologous stem cells are stem cells that are derived from the patient.

As used herein, the term "engineered," with respect to cell vehicles or carrier cells, denotes the genetic modification of the cells, such that they express proteins that can improve or enhance the performance of the cells. For example, cells can be engineered for improved viral amplification and/or improved immunomodulation.

As used herein, "immunomodulation" refers to any process in which an immune response is modified to a desired level, for example by inducing, enhancing or suppressing an immune response.

As used herein, "'immune suppression" or "immunosuppression" refers to the suppression or reduction of the immune response.

As used herein, "immune privileged" or "immunoprivileged" refers to cells or tissues that do not elicit an immune response and can evade the immune system. Immunoprivileged cells and tissues refer to cells and tissues, such as solid tumors and the tumor microenvironment, which are sequestered from the immune system by virtue of immunosuppressive properties of tumors. As a result, oncolytic viruses preferentially accumulate in tumors in the tumor microenvironment because they are shielded from the immune system. Immunoprivileged tissues and cells, however, are shielded or sequestered from the immune response, permitting the viruses to survive and generally to replicate.

As used herein, oncolytic viruses refer to viruses that replicate selectively in tumor cells.

As used herein, "disease or disorder" refers to a pathological condition in an organism resulting from, e.g., infection or genetic defect, and characterized by identifiable symptoms.

As used herein, cancer is a general term for diseases caused by or characterized by any type of malignant tumor or hematological malignancy, such as a leukemia.

As used herein, malignant, as applies to tumors, refers to primary tumors that have the capacity of metastasis with loss of growth control and positional control.

As used herein, metastasis refers to a growth of abnormal or neoplastic cells distant from the site primarily involved by the morbid process.

As used herein, an anti-cancer agent or compound (used interchangeably with "anti-tumor or anti-neoplastic agent") refers to any agents or compounds used in anti-cancer treatment. These include any agents, when used alone or in combination with other compounds, that can alleviate, reduce, ameliorate, prevent, or place or maintain in a state of remission of clinical symptoms or diagnostic markers associated with neoplastic disease, tumors and cancer, and can be used in methods, combinations and compositions provided herein.

As used herein, "resistant" with respect to viral infection refers to a cell that is not infected, or is infected to a very low degree, with a virus upon exposure to the virus.

As used herein, "permissive" with respect to viral infection refers to a cell that is readily infected upon exposure to the virus.

As used herein, a "haplotype" is a set of DNA variations or polymorphisms that are inherited together, and can refer to a group of alleles or a set of single nucleotide polymorphisms (SNPs) located on the same chromosome.

As used herein, a "matched haplotype" denotes an immunological compatibility between the haplotype of the donor and the haplotype of the recipient or patient, such that the haplotype of the donor is sufficiently compatible with the immune system of the recipient or patient to evade the recipient's immune system.

As used herein, a "mismatched haplotype" denotes an immunological incompatibility between the haplotype of the donor and the haplotype of the recipient or patient, such that the haplotype of the donor is not sufficiently compatible with the immune system of the recipient or patient and the donor cells cannot evade the recipient's immune system. An "immunocompromising mismatch" is defined as a mismatch between the subject and the carrier cells at a genetic polymorphism locus that is associated with a significant (e.g., 10% or more) reduction in the % compatibility as determined by the matching assay methods provided herein.

As used herein, immunologically compatible refers to a cell or virus that is sufficiently compatible with the immune system of the subject/host, to evade the subject's immune system for a sufficient time to deliver virus to a tumor or cancerous cell in the subject.

As used herein, "co-culture" refers to a cell culture in which two or more different populations of cells are grown.

As used herein the term "loading," with respect to cells, can refer to the association of a cell with an agent, such as a virus, small molecule, therapeutic agent, antibody etc., through a chemical or physical interaction between the cell and the agent on the surface of the cell or inside the cell.

As used herein, adipose-derived stem cells or ADSCs are mesenchymal stem cells that are obtained from the adipose tissue of a donor.

As used herein, a peripheral blood mononuclear cell or PBMC is any peripheral blood cell having a round nucleus, for example, lymphocytes, monocytes or macrophages.

As used herein, "L14 VV" is a TK-inserted Turbo-FP635 engineered LIVP strain of vaccinia virus.

As used herein, "WT1," also called "ACAM2000," is a wild type thymidine kinase (TK)-positive Wyeth strain of vaccinia virus. It is a smallpox vaccine strain that is available from the CDC.

As used herein, a virus plaque assay (VPA) is an assay used to determine the quantity of infectious virus or the viral titer, given as plaque-forming units (pfu) per ml or per sample.

As used herein, a "primed" or "protected" cell vehicle or carrier cell is one that has been pre-treated and/or loaded with an agent, such as a cytokine, for example interferon (IFN), or antagonists of allogeneic inactivation/rejection determinants, to protect the cell from the immune response.

As used herein, treatment refers to amelioration of the symptoms of a disease or disorder.

As used herein, prevention refers to prophylactic treatment to reduce the risk of getting a disease or condition or reducing the severity thereof.

As used herein, a subject refers to any mammal that can be treated by the methods and uses herein. Mammals include humans, other primates, such as chimpanzees, bonobos, and gorillas, dogs, cats, cows, pigs, goats and other farm animals and pets. Patients refer to human subjects.

For clarity of disclosure, and not by way of limitation, the detailed description is divided into the subsections that follow.

B. SELECTION OF COMPONENTS FOR VIRAL THERAPY USING CELL-BASED VEHICLES ("CELL VEHICLES" OR "CARRIER CELLS")

1. Cell Vehicles

Oncolytic viruses (OVs) have the ability to preferentially infect, accumulate in and kill tumor cells, relative to normal cells. This ability can be a natural feature of the virus (e.g., reovirus, Newcastle disease virus and mumps virus), or the viruses can be genetically attenuated so that they circumvent antiviral immune and other defenses in the subject (e.g., vesicular stomatitis virus, herpes simplex virus, adenovirus) or the preference for tumor cells can be selected for or engineered into the virus using, e.g., tumor-specific cell surface molecules, transcription factors and tissue-specific microRNAs (see, e.g., Cattaneo et al., *Nat. Rev. Microbiol.*, 6(7):529-540 (2008); Dorer et al., *Adv. Drug Deliv. Rev.*, 61(7-8):554-571 (2009); Kelly et al., *Mol. Ther.*, 17(3):409-416 (2009) and Naik et al., *Expert Opin. Biol. Ther.*, 9(9): 1163-1176 (2009)).

Delivery of oncolytic viruses can be effected via direct intratumoral injection. While direct intratumoral delivery can minimize the exposure of normal cells to the virus, there often are limitations due to, e.g., inaccessibility of the tumor site (e.g., brain tumors) or for tumors that are in the form of several small nodules spread out over a large area. Systemic delivery, on the other hand, has the potential of the virus reaching not only the primary tumor site, but disseminated metastases as well. Regardless of the mode of delivery, however, the success of treatment using oncolytic viruses can be compromised by the host's immune system, which rapidly induces an immune response and neutralizes the virus (Kerrigan et al. (2017) *Cytotherapy* 19(4):445-457; Roy and Bell (2013) *Oncolytic Virotherapy* 2:47-56). For example, intravenously delivered viruses are exposed to neutralizing antibodies, complement and various immune cells, and are sequestered and subsequently cleared by organs such as the lung, spleen and liver (Roy and Bell (2013) *Oncolytic Virotherapy* 2:47-56). Neutralizing antibodies (NAbs) bind viruses, block their attachment to cell surface receptors and inhibit viral infection, thus limiting the therapeutic potential of OVs (Jennings et al. (2014) *Int. J. Cancer* 134:1091-1101). In addition to the innate immune response, previous exposure, resulting in adaptive immunity, can be more specific and potent and also limiting of the therapeutic potential of OVs. Additionally, physical barriers, such as the extracellular matrix and high interstitial fluid pressure of tumors, can prevent the efficient delivery of viral particles to tumor cells (Roy and Bell (2013) *Oncolytic Virotherapy* 2:47-56).

The majority of individuals have been exposed to a number of viruses, including measles virus, adenovirus, vaccinia virus, and reovirus, and as a result, exhibit pre-existing antiviral immunity, which can diminish the therapeutic potential of oncolytic virotherapy. For example, most older subjects have been vaccinated against smallpox, resulting in pre-existing antiviral immunity against orthopoxviruses, including vaccinia virus. Even if a subject does not already possess pre-existing immunity to a specific OV, the initial dose of virus results in a robust anti-viral immune response, limiting the effectiveness of repeated doses, which are often required to achieve a potent antitumor response. Strategies to circumvent this include the use of immune suppressants, such as cyclophosphamide, and the use of carrier cells (cell vehicles) to bypass the immune system and deliver OVs to tumor sites.

Transient immunosuppression using immunosuppressive drugs such as cyclophosphamide, tacrolimus, mycophenolate mofetil and methylprednisolone sodium succinate, have been used successfully in organ transplantation, but have demonstrated limited success in enhancing the tumoral delivery of systemically administered OVs (Guo et al. (2010) *Gene Ther.* 17(12):1465-1475; Guo et al. (2010) *Gene Ther.* 17(12):1465-1475). The use of immunosuppressive drugs also can increase the potential toxicity of viruses and, in addition, can reduce any antitumor responses mounted by the immune system that would otherwise aid in oncolysis (Thorne et al. (2010) *Molecular Therapy* 18(9): 1698-1705).

The use of carrier cells for the delivery of OVs can mimic the way viruses have evolved to spread within the host. For example, the human immunodeficiency virus binds circulating dendritic cells (DCs) and macrophages, which can migrate to the lymph nodes and allow the virus to reach its target: $CD4^+$ T cells. Additionally, viruses that replicate by spreading from cell to cell can successfully evade neutralizing antibodies. Clinical trials have shown that oncolytic reovirus, upon i.v. administration, binds circulating cells, retaining its infectivity and reaching tumor cells even in the presence of neutralizing antibodies (Roy and Bell (2013) *Oncolytic Virotherapy* 2:47-56). The advantages of using cell-based vehicles include the specific delivery of OVs to tumor cells, increasing their therapeutic potential and preventing off-target toxicities, and the ability to shield the OVs from pre-existing antiviral immunity. Chemokines and adhesion molecules such as integrins play a vital role in the trafficking of cells within the immune system and into tumors. Cancer cells have been shown to secrete a variety of cytokines and chemokines that attract carrier cells to the tumor. Other factors, such as hypoxia also can contribute to the tumor homing abilities of carrier cells.

OVs can be associated with carrier cells by loading onto the surface of carrier cells via specific or nonspecific interactions, or can be internalized by them. Internalization of the OVs sometimes provides better protection against circulating NAbs and allows for viral replication within the cells, increasing the amount of delivered virus. However, viral infection can kill the carrier cells before they reach their target site(s), preventing the successful delivery of OVs for oncolysis. On the other hand, loading onto the carrier cell surface precludes viral amplification prior to arrival at the tumor site and can reduce the amount of virus that is delivered (Jennings et al. (2014) *Int. J. Cancer* 134:1091-1101; Willmon et al. (2009) *Molecular Therapy* 17(10): 1667-1676).

The effectiveness of a carrier cell for the delivery of an OV relies on several factors, including: (1) successful ex vivo loading of the virus; (2) in vivo accumulation of the virus at the tumor site; and (3) virus amplification/production at the tumor site (Guo et al. (2010) *Gene Ther.* 17(12): 1465-1475). The ideal carrier cell not only shields the OV from neutralization by the immune system, but also specifically delivers it to the tumor and possesses antitumor activity of its own. The carrier cell should be safe to administer, easy to isolate and/or manufacture, be susceptible to infection by the virus, allow the virus to replicate, and release the virus at the tumor site before being destroyed. Different viruses replicate at different speeds and, ideally, the kinetics of cell trafficking and viral replication should be compatible such that the carrier cell arrives at the tumor site while the virus is replicating. For example, VSV is a rapidly replicating virus, and successful delivery via carrier cells can be achieved if the cells are injected after 1-2 hours of infection. With slower replicating viruses such as vaccinia virus, there is more flexibility in optimizing the timing for infection and delivery of the carrier cells (Roy and Bell (2013) *Oncolytic Virotherapy* 2:47-56). Choosing a compatible virus and carrier cell pair also can ensure that viral replication does not negatively impact the carrier cell's circulation and effector functions, or hinder its tumor trafficking. For example, premature viral replication and/or expression can result in the destruction of carrier cells via direct cytotoxicity, or via indirect clearance by the immune system, once the carrier cells have been identified as "infected" (Willmon et al. (2009) *Molecular Therapy* 17(10):1667-1676). In cases where viral infection causes the expression of viral antigens on the surface of carrier cells, one can engineer the virus such that it replicates once it reaches the tumor, in order to reduce or prevent the immune-mediated destruction of the carrier cells. For example, tumor-specific and hypoxia-induced promoters can be used to drive viral replication at the tumor site (Roy and Bell (2013) *Oncolytic Virotherapy* 2:47-56).

In addition to considerations of virus-carrier cell compatibility with respect to kinetic parameters, as discussed above, the carrier cell, like the associated oncolytic virus, must be able to overcome innate and adaptive immune barriers, while promoting viral amplification in the tumor cells/cancer cells. The use of autologous carrier cells (cells obtained from the subject to be treated) can minimize innate and immune responses directed against the carrier cells, but can be onerous to the subject, expensive and limiting in their availability. Allogeneic carrier cells, which can include a variety of readily isolable and/or commercially available cells/cell lines, offer the ease of availability and non-invasiveness to the subject; however, the greater magnitude of the innate and/or adaptive immune responses can compromise their therapeutic efficacy and clinical applicability. The methods provided herein permit the screening, identification and selection of "matched" carrier cells that can potentiate viral therapy in a subject-specific and/or cancer-specific manner. According to the methods provided herein, available potential carrier cell candidates are screened in a manner that identifies carrier cells whose ability to promote amplification of the virus and/or show therapeutic efficacy of the virus in the subject is not significantly compromised by the immune responses of the subject against the carrier cell and/or the carrier cell/virus combination. The carrier cells so identified can then be used for subject and/or cancer specific carrier cell-mediated virotherapy, in accordance with the methods of treatment provided herein.

The methods of selecting carrier cells that are provided herein can be used to screen any cell types that have been used as carrier cells for the delivery of OVs. As described herein, the screened carrier cell types can be ranked based on their ability to promote viral amplification and/or evade immune attack in a particular subject who is to be treated using carrier cell-mediated viral oncotherapy; the higher the ability, the higher the "rank." One or more carrier cell types ranked as "high" are then selected as a match for the particular subject and/or the particular cancer to be treated. Methods of treatment using the carrier cell types so selected also are provided herein A variety of cell types have been used as carrier cells, and any of these can be screened in the methods provided herein. In some examples, as discussed herein, the carrier cells can be modified to provide a better "match" for a subject of interest. Then screened and/or modified carrier cells can be used in the methods of treatment provided herein. Exemplary carrier cell types for the delivery of OVs, which can include, for example, stem/progenitor cells, immune cells and cancer/transformed cells, are described below. The carrier cells screened according to the methods provided herein can be autologous, i.e., derived from the subject to be treated, or allogeneic, i.e., derived from a donor other than the subject to be treated. Exemplary carrier cells for use in the methods, combinations and compositions provided herein are as follows:

Types of Cell-Based Vehicles

Stem Cells, Immune Cells, Cancer Cell Lines

Stem cells, immune cells and tumor/cancerous cells can be utilized as delivery vehicles for oncolytic viruses (OVs), including HSV-1, parvovirus, measles virus, vesicular stomatitis virus (VSV), vaccinia virus, reovirus, New Castle Disease virus and adenovirus, among others. The delivery vehicles used in the compositions and methods provided herein are isolated and administered as compositions formed by incubating the isolated delivery vehicles/carrier cells with oncolytic viruses; they are not part of a plant or animal. In embodiments, the cells can be cultured for use as carriers.

These cells demonstrate tumor-homing properties, which enhance the therapeutic effect of OVs. This tumor selectivity is due to the attraction of these cells to the tumor microenvironment, which is characterized by hypoxia, inflammation and an abundance of chemoattractant molecules, such as cytokines and chemokines.

Stem Cells

Stem cells possess an intrinsic tumor-homing ability, making them attractive as carrier cells for oncolytic virotherapy. This is due to the tumor microenvironment being rich in various growth factors, angiogenic factors, cytokines and chemokines, which support the uncontrolled growth of tumors. The hypoxic nature of the TME also promotes the migration of stem cells towards tumors. Stem cells also are attractive as carrier cells also because they are highly immunosuppressive and express lower levels of the molecules necessary for antigen processing and presentation, delaying the recognition of the viruses they harbor by the immune system (Kim et al. (2015) *Viruses* 7:6200-6217). Examples of stem cells that can be used as carrier cells for OVs include endothelial progenitor cells, neural stem cells and mesenchymal stem cells.

Endothelial progenitor cells have been shown to home to sites of tumor neovasculature and have successfully been utilized to delivery oncolytic measles virus in a murine model of human glioma (Guo et al. (2008) *Biochim Biophys Acta* 1785(2):217-231). These cells divide rapidly in vivo, but are not immortal, and new cells must be repeatedly isolated from clinical samples (Kim et al. (2015) *Viruses* 7:6200-6217).

Neural stem cells (NSCs), which differentiate into various different cells of the nervous system, including neurons and glial cells, were the first stem cells investigated as carrier cells for the delivery of therapeutic agents to brain tumors (Kerrigan et al. (2017) *Cytotherapy* 19(4):445-457). NSCs display a strong tropism towards glioblastoma tumors, due to the hypoxia-inducible factor (HIF)-mediated expression of stromal cell-derived factor-1 (SDF-1), vascular endothelial growth factor (VEGF) and urokinase plasminogen activator (uPA) in glioma cells (Kim et al. (2015) *Viruses*

7:6200-6217). NSCs have been utilized in the delivery of IL-4, IL-12, IL-23, cytosine deaminase, the antiangiogenic protein thrombospondin and OVs such as adenovirus to gliomas, for example. However, NSCs must be isolated from the brain tissues of fetuses or from the periventricular zone of adult brains during surgery, which is a disadvantage for their utility as carrier cells.

Adult human bone marrow has been utilized as an alternative source for stem cells, as bone marrow stem cells are easily acquired and can be sourced from the patients themselves for autologous transplant, precluding immune rejection (Kerrigan et al. (2017) *Cytotherapy* 19(4):445-457). Of the various bone marrow stem cells available, mesenchymal stem cells (MSCs) are attractive as carrier cells because they are easily isolated from patients and expanded in vitro, they support the replication of OVs and their protection from immediate neutralization by the immune system, they can be engineered easily and they inherently home to tumors in vivo due to the tumor-associated expression of inflammatory cytokines. MSCs can even be utilized as standalone anticancer agents. For example, studies have demonstrated the tumor-homing ability and oncolytic effects of MSCs expressing IFN-β (Nakashima et al. (2010) *Cytokine Growth Factor Rev.* 21(2-3):119-126).

MSCs express low levels of MHC class I molecules and do not express MHC class II molecules on their cell surfaces, allowing for allogeneic transplant. MSCs also can inhibit T-cell proliferation and differentiation of monocytes into dendritic cells (DCs), and can suppress the expression of interferon-gamma and tumor necrosis factor produced by CD4+ T-helper cells (Kim et al. (2015) *Viruses* 7:6200-6217). MSCs also are capable of degrading the extracellular matrix via the secretion of proteases, which can help overcome the physical barriers to oncolytic viral delivery (Ramirez et al. (2015) *Oncolytic Virotherapy* 4:149-155). Another advantage to the use of MSCs is that they can be frozen after viral infection and, upon thawing, retain active viral replication and antitumor activity, allowing for their storage (Roy and Bell (2013) *Oncolytic Virotherapy* 2:47-56). In addition to bone marrow, MSCs also can be isolated from adipose tissue, umbilical cord blood, peripheral blood, muscle, cartilage and amniotic fluid, with adipose tissue being the most attractive source, due to the ease of access and abundance of adipose tissue (Kerrigan et al. (2017) *Cytotherapy* 19(4):445-457; Nakashima et al. (2010) *Cytokine Growth Factor Rev.* 21(2-3):119-126).

MSCs have served as carriers of oncolytic adenovirus for the treatment of pancreatic cancer, brain cancer, renal cell carcinoma, glioblastoma, and ovarian cancer, and as carriers of measles virus for the treatment of ovarian cancer and hepatocellular carcinoma (Kim et al. (2015) *Viruses* 7:6200-6217). For example, MSCs have been utilized as carriers of the oncolytic adenovirus ICOVIR-5 for the treatment of children with advanced metastatic neuroblastoma (Kerrigan et al. (2017) *Cytotherapy* 19(4):445-457; Ramirez et al. (2015) *Oncolytic Virotherapy* 4:149-155).

One downside to the use of MSCs, however, is their potential for promoting tumor growth, which has been demonstrated in models of breast cancer, endometrial tumors and glioma. In order to overcome this potential downfall, MSCs can be engineered to ensure their destruction upon delivery of the OV, for example, by carrying suicide genes (Kerrigan et al. (2017) *Cytotherapy* 19(4):445-457).

Examples of stem cells (autologous or allogeneic) that can be utilized as carrier cells include: adult stem cells; embryonic stem cells; fetal stem cells; neural stem cells; mesenchymal stem cells (for example, isolated/derived from: adult bone marrow, adipose tissue, blood, dental pulp, neonatal umbilical cord, umbilical cord blood, placenta, placenta-derived adherent stromal cells, placenta-derived decidual stromal cells, endometrial regenerative cells, placental bipotent endothelial/mesenchymal progenitor cells, amniotic membrane or fluid mesenchymal stem cells, amniotic fluid derived progenitors, Wharton's Jelly mesenchymal stem cells, pelvic girdle stem cells, Chorionic Villus Mesenchymal Stromal cells, subcutaneous white adipose mesenchymal stem cells, pericytes, adventitial reticular stem cells, hair follicle-derived stem cells, hematopoietic stem cells, periosteum-derived mesenchymal stem cells, lateral plate mesenchymal stem cells, exfoliated deciduous teeth stem cells, periodontal ligament stem cells, dental follicle progenitor cells, stem cells from apical papilla, muscle satellite cells, etc.); neural stem cells; totipotent stem cells; pluripotent stem cells; induced pluripotent stem cells; multipotent stem cells; oligopotent stem cells; unipotent stem cells; adipose stromal stem cells; endothelial stem cells (for example, endothelial progenitor cells, placental endothelial progenitor cells, angiogenic endothelial Cells, pericytes); adult peripheral blood stem cells; myoblasts; small juvenile stem cells; skin fibroblast stem cells; tissue/tumor-associated fibroblasts; epithelial stem cells; and embryonic epithelial stem cells, for example. In embodiments of the compositions and methods provided herein, the carrier cells are not one or more of embryonic stem cells, fetal stem cells, cord blood derived stem cells, amniotic fluid derived stem cells or placenta derived stem cells.

Immune Cells

Immune cells, which respond to "danger signals" released from tumors by trafficking to cancer sites, have been extensively investigated as carrier cells for OVs. These immune cells include T cells, including γδ T cells, CAR-T cells targeting tumor-specific antigens, TCR transgenic cells targeting tumor-specific antigens; NKT cells, lymphocytes, monocytes, macrophages, mast cells, granulocytes, dendritic cells (DCs), natural killer (NK) cells, myeloid-derived suppressor cells, lymphokine-activated killer (LAK) cells, and cytokine-induced killer (CIK) cells, for example. Immune cells are attractive as carrier cells because they circulate systemically and can recognize tumors (Roy and Bell (2013) *Oncolytic Virotherapy* 2:47-56). The use of immune cells as carriers for OVs can also provide additional antitumor activity in the form of direct cytotoxicity, or by priming adaptive antitumor immune responses (Jennings et al. (2014) *Int. J. Cancer* 134:1091-1101).

Tumor antigen-specific T cells, for example, display direct anticancer effector functions, and activated T cells have been extensively investigated in the delivery of OVs to tumors. It has been shown that loading adoptively transferred T cells with OVs can help combat the immunosuppressive nature of the tumor microenvironment, because the proinflammatory nature of viral infection can prevent the silencing and inactivation of T cells (Roy and Bell (2013) *Oncolytic Virotherapy* 2:47-56). The intratumoral expression of chemokines such as CCL3, CCL21 and CXCL10 (IP-10) enhances the tumor-specific trafficking of adoptive T cells. T cells also can be genetically engineered to express chemokine receptors such as CXCR2, in order to help direct them towards tumors (Guo et al. (2008) *Biochim Biophys Acta* 1785(2):217-231). Studies have demonstrated that vesicular stomatitis virus, reovirus, herpes simplex virus, Newcastle disease virus, and retrovirus particles can attach to the surface of T cells and be delivered to tumor cells either passively or via cellular synapses between the carrier and tumor cells (Roy and Bell (2013) *Oncolytic Virotherapy* 2:47-56). Despite the advantages of using T cells as carriers for OV, it remains very expensive and difficult to raise T-cell populations against highly tumor-specific antigens from patients, limiting their use (Willmon et al. (2009) *Molecular Therapy* 17(10):1667-1676).

Lymphokine-activated killer cells (LAK cells) have shown promise in combination with IL-2 in the treatment of ovarian cancer. Immature dendritic cells (iDCs), LAK cells and their co-cultures (LAKDC) were tested as carriers for reovirus in the treatment for ovarian cancer, and it was shown that reovirus-loaded LAKDC were able to protect the reovirus from neutralizing antibodies, induce a proinflammatory cytokine milieu and generate an innate and adaptive antitumor immune response (Jennings et al. (2014) *Int. J. Cancer* 134:1091-1101). DC cells also have been successfully used as carriers of reovirus for the treatment of melanoma (Jennings et al. (2014) *Int. J. Cancer* 134:1091-1101).

CIK cells are another type of immune cell that can be used as carriers for OVs. Whereas tumor antigen-specific T cells recognize one antigen, CIK cells recognize NKG2D ligands, which are often upregulated on a variety of tumor cells, making them more versatile. CIK cells also are easier to isolate from patients and expand ex vivo, can produce high titers of virus, and have successfully been used to deliver measles and vaccinia viruses to tumors (Roy and Bell (2013) *Oncolytic Virotherapy* 2:47-56; Willmon et al. (2009) *Molecular Therapy* 17(10):1667-1676; Power and Bell (2007) *Mol. Ther.* 15(4):660-665). One disadvantage to the use of CIK cells, however, is that their generation requires the expansion of primary leukocytes using cytokines in vivo (Kim et al. (2015) *Viruses* 7:6200-6217).

Macrophages represent yet another potential class of carrier cells for OVs. Since tumors often secrete monocyte chemotactic protein-1, macrophage colony-stimulating factor and VEGF, monocytes naturally migrate to tumor sites, localizing to hypoxic regions, and differentiating into tumor-associated macrophages, which can enhance tumor growth inhibition (Roy and Bell (2013) *Oncolytic Virotherapy* 2:47-56). As a result, macrophages have been investigated preclinically for the delivery of oncolytic adenovirus and measles virus. In addition to the other types of immune cells discussed, myeloid-derived suppressor cells also have been investigated as carrier cells for the delivery of oncolytic VSV.

Cancer Cells

Cancer cells, often inactivated with y-irradiation before administration for safety, also have successfully been used as carrier cells for OVs. The y-irradiation can prevent tumorigenicity, but preserve viral production. Another safety measure involves the engineering of OVs to express suicide genes, such as thymidine kinase, to ensure that the cancer cells do not remain indefinitely in the subject (i.e., are killed and no longer immortal). Alternatively, allogeneic cancer cells, which typically are cleared by the recipient's immune system, can be used ((Power and Bell (2007) *Mol. Ther.* 15(4):660-665).

Cancer cells can readily be obtained in large amounts and display higher levels of viral infectivity and amplification than normal cells (Guo et al. (2010) *Gene Ther.* 17(12): 1465-1475; Roy and Bell (2013) *Oncolytic Virotherapy* 2:47-56). Additionally, some tumor cells migrate specifically to certain organs, as is seen with metastatic disease. For example, myeloma cells express high levels of the chemokine receptor CXCR4, resulting in bone marrow metastases, and have been utilized in the delivery of oncolytic measles virus (Roy and Bell (2013) *Oncolytic Virotherapy* 2:47-56). A variety of transformed cell lines have been shown to successfully deliver oncolytic parvovirus, measles virus, and vesicular stomatitis virus in immune-competent as well as immune-deficient animals. For example, carcinoma cells infected with VSV or adenovirus have been used to effectively deliver the virus to lung metastases in mice (Willmon et al. (2009) *Molecular Therapy* 17(10):1667-1676; Power and Bell (2007) *Mol. Ther.* 15(4):660-665). Cells derived from solid tumors, however, have been shown to accumulate in the lungs of mice following IV administration, due to their large diameters. As a result, cancer cells of hematopoietic/hematological origin can be a better alternative, as they are more widely distributed in the body and can deliver OVs to anatomical locations outside the lungs (Power and Bell (2007) *Mol. Ther.* 15(4):660-665).

Examples of allogeneic human hematological malignancy cell lines that can be used as carrier cells include: leukemia cells (such as, for example, KASUMI-1, HL-60, THP-1, K-562, RS4;11, MOLT-4, CCRF-CEM, JVM-13, 31E9, ARH-77, MoB, JM1, NALM-1, ProPak-X.36); T cell leukemia cells (such as, for example, HM-2, CEM-CM3, Jurkat/Jurkat clone E6-1, J.CaM1.6, BCL2 Jurkat, BCL2 S87A Jurkat, BCL2 S70A Jurkat, Neo Jurkat, BCL2 AAA Jurkat, J.RT3-T3.5, J45.01, J.gamma1, J.gammal.WT, JK28, P116, P116.c139, A3, JX17, D1.1, I9.2, I2.1); myelomonocytic leukemia cells (for example, MV-4-11); lymphoma cells (for example, HT, BC-3, CA46, Raji, Daudi, GA-10-Clone-4, HH, H9); Non-Hodgkin's lymphoma cells (such as, for example, SU-DHL-1, SU-DHL-2, SU-DHL-4, SU-DHL-5, SU-DHL-6, SU-DHL-8, SU-DHL-10, SU-DHL-16, NU-DUL-1, NCEB-1, EJ-1, BCP-1, TUR, U-937); Burkitt Lymphoma cells (for example, Ramos/RA 1, Ramos.2G6.4C10, P3HR-1, Daudi, ST486, Raji, CA46, Human gammaherpesvirus 4/HHV-4 cheek tumor from Burkitt Lymphoma Patient, DG-75, GA-10, NAMALWA, HS-Sultan, Jiyoye, NC-37, 20-B8, EB2, 1G2, EB1, EB3, 2B8, GA-10 clone 20, HKB-11/Kidney-B cell Hybrid); diffuse large B cell lymphoma cells (for example, Toledo, Pfeiffer); Mantle Cell Lymphoma cells (for example, JeKo-1, JMP-1, PF-1, JVM-2, REC-1, Z-138, Mino, MAVER-1); AML cells (for example, AML-193, BDCM, KG-1, KG-1a, Kasumi-6, HL-60/S4); CML cells (for example, K562, K562-r, K562-s, LAMA84-r, LAMA84-s, AR230-r, AR230-s); ALL cells (for example, N6/ADR, RS4;11, NALM6 clone G5, Loucy, SUP-B15, CCRF-SB); erythroleukemia cells (for example, IDH2-mutant-TF-1 Isogenic cell line); myelomonoblastic leukemia cells (for example, GDM-1); malignant Non-Hodgkin's NK lymphoma cells (for example, NK-92, NK-92MI); myeloma/plasmocytoma cells (for example, U266B1/U266, HAA1, SA13, RPMI8226, NCI-H929, MC/CAR); multiple myeloma cells (for example, MM.1R, IM-9, MM.1S); and macrophage cell lines (for example, MD, SC, WBC264-9C).

Commercial allogeneic cell lines include: mesenchymal stem cells, such as, for example, APCETH-201, APCETH-301 (APCETH), Cx601 (TIGENIX), TEMCELL, MSC-100-IV, Prochymal (MESOBLAST); induced pluripotent stem cells (iPSC), such as, for example, ToleraCyte (Fate Therapeutics); fibroblast cells, for example, CCD-16Lu, WI-38; tumor-associated fibroblasts, for example, Malme-3M, COLO 829, HT-144, Hs 895.T, hTERT PF179T CAF, etc.; endothelial cells, for example, HUVEC, HUVEC/TERT 2, TIME; embryonic epithelial cells, for example, HEK-293, HEK-293 STF, 293T/17, 293T/17 SF, HEK-293.2sus; embryonic stem cells, for example, hESC BG01V; and epithelial cells, for example, NuLi-1, ARPE-19, VK2/

E6E7, Ect1/E6E7, RWPE-2, WPE-stem, End1/E6E7, WPMY-1, NL20, NL20-TA, WT 9-7, WPE1-NB26, WPE-int, RWPE2-W99, BEAS-2B. In embodiments of the compositions and methods provided herein, the carrier cells are not of embryonic origin, e.g., embryonic epithelial cells, embryonic stem cells, fetal cells, etc.

Autologous or allogeneic whole tumor cell vaccines include GM-CSF secreting whole tumor cell vaccines (GVAX), such as, for example, GVAX Prostate (PC3/LN-CaP-based); GVAX Pancreas; GVAX Lung; and GVAX Renal Cell, etc., from Cell Genesys/BioSante/Aduro Biotech.

Allogeneic human tumor cell lines include, for example, NCI-60 panel (BT549, HS 578T, MCF7, MDA-MB-231, MDA-MB-468, T-47D, SF268, SF295, SF539, SNB-19, SNB-75, U251, Colo205, HCC 2998, HCT-116, HCT-15, HT29, KM12, SW620, 786-0, A498, ACHN, CAKI, RXF 393, SN12C, TK-10, UO-31, CCRF-CEM, HL-60, K562, MOLT-4, RPMI-8226, SR, A549, EKVX, HOP-62, HOP-92, NCI-H226, NCI-H23, NCI-H322M, NCI-H460, NCI-H522, LOX IMVI, M14, MALME-3M, MDA-MB-435, SK-MEL-2, SK-MEL-28, SK-MEL-5, UACC-257, UACC-62, IGROV1, OVCAR-3, OVCAR-4, OVCAR-5, OVCAR-8, SK-OV-3, NCI-ADR-RES, DU145, PC-3). Other allogeneic human tumor cell lines include, for example, fibrosarcoma cell lines (HT-1080); hepatocarcinoma cell lines (Hih-7); prostate cancer cell lines (LAPC4, LAPC9, VCaP, LuCaP, MDA PCa 2a/2b, C4, C4-2, PTEN-CaP8, PTEN-P8); breast cancer cell lines (HCC1599, HCC1937, HCC1143, MDA-MB-468, HCC38, HCC70, HCC1806, HCC1187, DU4475, BT-549, Hs 578T, MBA-MB-231, MDA-MB-436, MDA-MB-157, MDA-MB-453, HCC1599, HCC1937, HCC1143, MDA-MB-468, HCC38, HCC70, HCC1806, HCC1187, DU4475, BT-549, Hs 578T, MDA-MB-231, MDA-MB-436, MDA-MB-157, MDA-MB-453, BT-20, HCC1395, MDA-MB-361, EMT6, T-47D, HCC1954); head and neck cancer cell lines (A-253, SCC-15, SCC-25, SCC-9, FaDu, Detroit 562); lung cancer cell lines (NCI-H2126, NCI-H1299, NCI-H1437, NCI-H1563, NCI-H1573, NCI-H1975, NCI-H661, Calu-3, NCI-H441); pancreatic cancer cell lines (Capan-2, Panc 10.05, CFPAC-1, HPAF-II, SW 1990, BxPC-3, AsPC-1, MIA PaCa-2, Hs 766T, Panc 05.04, PL45); ovarian cancer cell lines (PA-1, Caov-3, SW 626, SK-OV-3); bone cancer cell lines (HOS, A-673, SK-PN-DW, U-2 OS, Saos-2); colon cancer cell lines (SNU-C1, SK-CO-1, SW1116, SW948, T84, LS123, LoVo, SW837, SNU-C1, SW48, RKO, COLO 205, SW1417, LS411N, NCI-H508, HT-29, Caco-2, DLD-1); gastric cancer cell lines (KATOIII, NCI-N87, SNU-16, SNU-5, AGS, SNU-1); gynecological cancer cell lines (SK-LMS-1, HT-3, ME-180, Caov-3, SW626, IVIES-SA, SK-UT-1, KLE, AN3-CA, HeLa); sarcoma cell lines (SW684, HT-1080, SW982, RD, GCT, SW872, SJSA-1, MES-SA/MX2, MES-SA, SK-ES-1, SU-CCS-1, A-673, VA-ES-BJ, Hs 822.T, RD-ES, HS 132.T, Hs 737.T, Hs 863.T, Hs 127.T, Hs 324.T, Hs 821.T, Hs 706.T, Hs 707(B).Ep, LL 86/LeSa, Hs 57.T, Hs 925.T, GCT, KHOS-312H, KHOS/NP R-970-5, SK-LMS-1, HOS); melanoma cell lines (SK-MEL-1, A375, G-361, SK-MEL-3, SH-4, SK-MEL-24, RPMI-7951, CHL-1, Hs 695T, A2058, VMM18, A375.S2, Hs 294T, VMM39, A375-P, VMM917, VMM5A, VMM15, VMM425, VMM17, VMM1, A375-MA1, A375-MA2, SK-MEL-5, Hs 852.T, LM-MEL-57, A101D, LM-MEL-41, LM-MEL-42, MeWo, LM-MEL-53, MDA-MB-435S, C32, SK-MEL-28, SK-MEL-2, MP38, MP41, C32TG, NM2C5, LM-MEL-1a, A7/M2A7); squamous cell carcinoma cell lines (SiHa, NCI-H520, SCC-15, NCI-H226, HCC1806, SCC-25, FaDu, SW 954, NCI-H2170, SCC-4, SW 900, NCI-H2286, NCI-H2066, SCC-9, SCaBER, SW579, SK-MES-1, 2A3, UPCI:SCC090, UPCI:SCC152, CAL 27, RPMI 2650, UPCI:SCC154, SW756, NCI-H1703, ME-180, SW962); hepatocellular carcinoma cell lines (Hep G2, Hep 3B2.1-7/Hep 3B, C3A, Hep G2/2.2.1, SNU-449, SNU-398, SNU-475, SNU-387, SNU-182, SNU-423, PLC/PRF/5); bladder cancer cell lines (5637, HT-1197, HT-1376, RT4, SW780, T-24, TCCSUP, UM-UC-3); renal cell carcinoma cell lines (ACHN, 786-O/786-0, 769-P, A-498, Hs 891.T, Caki-2, Caki-1); embryonal carcinoma/testicular teratoma cell lines (NTERA-2 cl.D1, NCCIT, Tera-2, Tera-1, Cates-1B); glioblastoma cell lines (LN-229, U-87 MG, T98G, LN-18, U-118 MG, M059K, M059J, U-138 MG, A-172); astrocytoma cell lines (SW 1088, CCF-STTG1, SW 1783, CHLA-03-AA); brain cancer cell lines (PFSK-1, Daoy); thyroid carcinoma cell lines (TT, MDA-T68, MDA-T32, MDA-T120, MDA-T85, MDA-T41) and mesothelioma cell lines (NCI-H28, NCI-H226, NCI-H2452, NCI-H2052, MSTO-211H).

2. Selection of Viruses

The carrier cells selected and/or modified according to the methods provided herein, can be used for virotherapy with any virus identified as having oncolytic properties. As discussed herein, in some examples of the methods provided herein for the selection of a carrier cell that is a match for a particular subject and/or cancer type to be treated, the carrier cell also can also be selected based on its ability to promote amplification of the oncolytic virus to be used for treatment. The carrier cell-virus combination selected according to the methods provided herein for identifying a subject and/or cancer-specific match can be used in the methods of treatment provided herein. Exemplary oncolytic viruses that can be used in the methods, combinations and compositions provided herein are as follows:

Types of Viruses

Oncolytic viruses are characterized by their largely tumor cell specific replication, resulting in tumor cell lysis and efficient tumor regression. Oncolytic viruses effect treatment by colonizing or accumulating in tumor cells, including metastatic tumor cells such as circulating tumor cells, and replicating therein. The invention described herein can be used with any anti-cancer vaccine or virus. For example, the oncolytic virus can be any naturally occurring or engineered recombinant virus such as, but not limited to, vaccinia virus, poxvirus, herpes simplex virus, adenovirus, adeno-associated virus, measles virus, reovirus, vesicular stomatitis virus (VSV), coxsackie virus, Semliki Forest Virus, Seneca Valley Virus, Newcastle Disease Virus, Sendai Virus Dengue Virus, picornavirus, poliovirus, parvovirus, retrovirus, lentivirus, alphavirus, flavivirus, rhabdovirus, papillomavirus, influenza virus, mumps virus, gibbon ape leukemia virus, and Sindbis virus, among others. In many cases, tumor selectivity is an inherent property of the virus, such as vaccinia viruses and other oncolytic viruses. Generally oncolytic viruses effect treatment by replicating in tumors or tumor cells resulting in lysis.

In some embodiments, an attenuated strain derived from a pathogenic virus is used for the manufacturing of a live vaccine. Non-limiting examples of vaccinia viruses include, but are not limited to, Lister (also known as Elstree), New York City Board of Health (NYCBH), Dairen, Ikeda, LC16M8, Western Reserve (WR), Copenhagen (Cop), Tashkent, Tian Tan, Wyeth, Dryvax, IHD-J, IHD-W, Brighton, Ankara, Modified Vaccinia Ankara (MVA), Dairen I, LIPV, LC16M0, LIVP, WR 65-16, EM63, Bern, Paris, CVA382, NYVAC, ACAM2000 and Connaught strains. The viruses can be clonal strains of an oncolytic virus. The sequence of nucleotides encoding a chromophore-producing enzyme can be inserted into, or in place of, a nonessential gene or region in the genome of an unmodified oncolytic virus, or is inserted into or in place of nucleic acid encoding a heterologous gene product in the genome of an unmodified oncolytic virus.

In some embodiments, the vaccinia virus utilized in the methods disclosed herein is an attenuated New York City Board of Health (NYCBOH) strain. In some embodiments, the NYCBOH strain of vaccinia virus can be ATCC VR-118 or CJ-MVB-SPX.

In some embodiments, the vaccinia virus is selected from Dryvax, ACAM1000, ACAM2000, Lister, EM63, LIVP, Tian Tan, Copenhagen, Western Reserve, or Modified Vaccinia Ankara (MVA). In some embodiments, the oncolytic virus is not deficient in any genes present in one or more of these strains.

In some embodiments, the virus or vaccine is a replication competent virus. In some embodiments, the virus or vaccine is replication deficient.

In some embodiments, the virus or vaccine is non-attenuated.

Other unmodified oncolytic viruses include any known to those of skill in the art, including those selected from among viruses designated GLV-1h68, JX-594, JX-954, ColoAd1, MV-CEA, MV-NIS, ONYX-015, B18R, H101, OncoVEX GM-CSF, Reolysin, NTX-010, CCTG-102, Cavatak, Oncorine, and TNFerade.

Oncolytic viruses for use in the methods provided herein include several well-known to one of skill in the art and include, for example, vesicular stomatitis virus, see, e.g., U.S. Pat. Nos. 7,731,974, 7,153,510, 6,653,103 and U.S. Pat. Pub. Nos. 2010/0178684, 2010/0172877, 2010/0113567, 2007/0098743, 20050260601, 20050220818 and EP Pat. Nos. 1385466, 1606411 and 1520175; herpes simplex virus, see, e.g., U.S. Pat. Nos. 7,897,146, 7,731,952, 7,550,296, 7,537,924, 6,723,316, 6,428,968 and U.S. Pat. Pub. Nos. 2011/0177032, 2011/0158948, 2010/0092515, 2009/0274728, 2009/0285860, 2009/0215147, 2009/0010889, 2007/0110720, 2006/0039894 and 20040009604; retroviruses, see, e.g., U.S. Pat. Nos. 6,689,871, 6,635,472, 6,639,139, 5,851,529, 5,716,826, 5,716,613 and U.S. Pat. Pub. No. 20110212530; and adeno-associated viruses, see, e.g., U.S. Pat. Nos. 8,007,780, 7,968,340, 7,943,374, 7,906,111, 7,927,585, 7,811,814, 7,662,627, 7,241,447, 7,238,526, 7,172,893, 7,033,826, 7,001,765, 6,897,045, and 6,632,670.

Newcastle Disease Virus

Newcastle Disease Virus (NDV) is an avian paramyxovirus with a single-stranded RNA genome of negative polarity that infects poultry and is generally nonpathogenic to humans, but can cause flu-like symptoms (Tayeb et al. (2015) Oncolytic Virotherapy 4:49-62; Cheng et al. (2016) J. Virol. 90:5343-5352). Due to its cytoplasmic replication, lack of host genome integration and recombination and high genomic stability, NDV and other paramyxoviruses provide safer and more attractive alternatives to other oncolytic viruses, such as retroviruses or some DNA viruses (Matveeva et al. (2015) Molecular Therapy—Oncolytics 2, 150017). NDV has been shown to demonstrate tumor selectivity, with 10,000 times greater replication in tumor cells than normal cells, resulting in oncolysis due to direct cytopathic effects and induction of immune responses (Tayeb et al. (2015; Lam et al. (2011) Journal of Biomedicine and Biotechnology, Article ID 718710). Though the mechanism of NDV's tumor selectivity is not entirely clear, defective interferon production and responses to IFN signaling in tumor cells allow the virus to replicate and spread (Cheng et al. (2016); Ginting et al. (2017) Oncolytic Virotherapy 6:21-30). The high affinity of paramyxoviruses towards cancer cells can also be due to overexpression of viral receptors on cancer cell surfaces, including sialic acid (Cheng et al. (2016); Matveeva et al. (2015); Tayeb et al. (2015)).

Non-engineered NDV strains are classified as lentogenic (avirulent), mesogenic (intermediate), or velogenic (virulent), based on their pathogenicity in chickens, with velogenic and mesogenic strains being capable of replication in (and lysis of) multiple human cancer cell lines, but not lentogenic strains (Cheng et al. (2016); Matveeva et al. (2015)). NDV strains also are categorized as lytic or non-lytic, with only the lytic strains being able to produce viable and infectious progeny (Ginting et al. (2017); Matveeva et al. (2015)). On the other hand, the oncolytic effects of non-lytic strains stems mainly from their ability to stimulate immune responses that result in antitumor activity (Ginting et al. (2017) Oncolytic Virotherapy 6:21-30). Mesogenic lytic strains commonly utilized in oncotherapy include PV701 (MK107), MTH-68/H and 73-T, and lentogenic non-lytic strains commonly utilized include HUJ, Ulster and Hitchner-B1 (Tayeb et al. (2015); Lam et al. (2011); Freeman et al. (2006) Mol. Ther. 13(1):221-228).

The use of NDV as an oncolytic virus was first reported in the early 1950s, when adenovirus and NDV were injected directly into a uterine carcinoma, resulting in partial necrosis. However, tumor regrowth was observed, likely due to suppression of oncolytic activity by the production of neutralizing antibodies against the virus (Lam et al. (2011) Journal of Biomedicine and Biotechnology, Article ID 718710). More recently, NDV strain PV701 displayed promising activity against colorectal cancer in a phase 1 trial (Laurie et al. (2006) Clin. Cancer Res. 12(8):2555-2562), while NDV strain 73-T demonstrated in vitro oncolytic activity against various human cancer cell lines, including fibrosarcoma, osteosarcoma, neuroblastoma and cervical carcinoma, as well as in vivo therapeutic effects in mice bearing human neuroblastomas, fibrosarcoma xenografts and several carcinoma xenografts, including colon, lung, breast and prostate cancer xenografts (Lam et al. (2011)). NDV strain MTH-68/H resulted in significant regression of tumor cell lines, including PC12, MCF7, HCT116, DU-145, HT-29, A431, HELA, and PC3 cells, and demonstrated favorable responses in patients with advanced cancers when administered by inhalation (Lam et al. (2011)). The non-lytic strain Ulster demonstrated cytotoxic effects against colon carcinoma, while the lytic strain Italien effectively killed human melanomas (Lam et al. (2011)). Lentogenic NDV strain HUJ demonstrated oncolytic activity against recurrent glioblastoma multiforme when administered intravenously to patients, while lentogenic strain LaSota prolonged survival in colorectal cancer patients (Lam et al. (2011); Freeman et al. (2006) Mol. Ther. 13(1):221-228) and was capable of infecting and killing non-small cell lung carcinoma (A549), glioblastoma (U87MG and T98G), mammary gland adenocarcinoma (MCF7 and MDA-MB-453) and hepatocellular carcinoma (Huh7) cell lines (Ginting et al. (2017) Oncolytic Virotherapy 6:21-30).

Genetically engineered NDV strains also have been evaluated for oncolytic therapy. For example, the influenza NS1 gene, an IFN antagonist, was introduced into the genome of NDV strain Hitchner-B1, resulting in an enhanced oncolytic effect in a variety of human tumor cell lines and a mouse model of B16 melanoma (Tayeb et al. (2015)). The antitumor/immunostimulatory effects of NDV have been augmented by introduction of IL-2 or GM-CSF genes into the viral genome (Lam et al. (2011)).

In addition to the use of free virus, studies have evaluated the use of NDV oncolysates, NDV-infected cell-based vehicles, and combination therapies with other noncancer agents for cancer therapy. In several clinical trials, NDV oncolysates demonstrated oncolytic activity against malignant melanomas (Lam et al. (2011)). The use of NDV-infected cell-based carriers also has been demonstrated successfully. Autologous tumor cell lines infected with NDV were successfully utilized against colorectal, breast, ovarian, kidney, head and neck cancers and glioblastomas (Lam et al. (2011)). MSCs derived from bone marrow, adipose and umbilical cord that were infected with NDV strain MTH-68/H delivered the virus to co-cultured A172 and U87 glioma cells and glioma stem cells, resulting in dose-dependent cell death in glioma cells, a low level of apoptosis and inhibition of self-renewal in glioma stem cells, and higher levels of apoptosis than direct infection with naked virus (Kazimirsky et al. (2016) *Stem Cell Research & Therapy* 7:149). Combination therapy, utilizing intratumoral NDV injection with systemic CTLA-4 antibody administration resulted in the efficient rejection of pre-established distant tumors (Matveeva et al. (2015)).

Parvovirus

H-1 parvovirus (H-1PV) is a small, non-enveloped single-stranded DNA virus belonging to the family Parvoviridae, whose natural host is the rat (Angelova et al. (2017) *Front. Oncol.* 7:93; Angelova et al. (2015) *Frontiers in Bioengineering and Biotechnology* 3:55). H-1PV is nonpathogenic to humans, and is attractive as an oncolytic virus due to its favorable safety profile, the absence of preexisting H-1PV immunity in humans and their lack of host cell genome integration (Angelova et al. (2015)). H-1PV has demonstrated broad oncosuppressive potential against both solid tumors, including preclinical modes of breast, gastric, cervical, brain, pancreatic and colorectal cancer, as well as hematological malignancies, including lymphoma and leukemia Angelova et al. (2017)). H-1PV stimulates anti-tumor responses via the increased presentation of tumor-associated antigens, maturation of dendritic cells and the release of pro-inflammatory cytokines (Moehler et al. (2014) *Frontiers in Oncology* 4:92). H-1PV also displays tumor selectivity, which is thought to be due to the availability of cellular replication and transcription factors, the overexpression of cellular proteins that interact with the NS1 parvoviral protein, and the activation of metabolic pathways involved in the functional regulation of NS1 in tumor cells, but not normal cells (Angelova et al. (2015) *Frontiers in Bioengineering and Biotechnology* 3:55). Due to the innocuous nature of H-1PV, the wild type strain is often utilized, negating the need for attenuation by genetic engineering (Angelova et al. (2015)).

Studies have shown that oncolytic H-1PV infection of human glioma cells resulted in efficient cell killing, and high-grade glioma stem cell models were also permissive to lytic H-1PV infection. Enhanced killing of glioma cells has been observed when the virus was applied shortly after tumor cell irradiation, indicating that this protocol can be useful in non-resectable recurrent glioblastoma (Angelova et al. (2017)). Intracerebral or systemic H-1PV injection led to regression of gliomas without toxic side effects in immunocompetent rats with orthotopic RG-2 tumors, as well as immunodeficient animals implanted with human U87 gliomas (Angelova et al. (2015)). Del H-1PV, a fitness variant with higher infectivity and spreading in human transformed cell lines, demonstrated oncolytic effects in vivo in pancreatic cancer and cervix carcinoma xenograft models (Geiss et al. (2017) Viruses 9, 301). H-1PV also demonstrated oncolytic activity against a panel of five human osteosarcoma cell lines (CAL 72, H-OS, MG-63, SaOS-2, U-20S) (Geiss et al. (2017) Viruses 9, 301) and against human melanoma cells (SK29-Mel-1, SK29-Mel-1.22) (Moehler et al. (2014) *Frontiers in Oncology* 4:92). In another study, nude rats bearing cervical carcinoma xenografts demonstrated dose-dependent tumor growth arrest and regression following treatment with H-1PV (Angelova et al. (2015)). The intratumoral and intravenous administration of H-1PV also demonstrated significant growth suppression in human mammary carcinoma xenografts in immunocompromised mice (Angelova et al. (2015)). Intratumoral H-1PV injection in human gastric carcinoma or human Burkitt lymphoma-bearing mice resulted in tumor regression and growth suppression (Angelova et al. (2015)).

The first phase I/IIa clinical trial of an oncolytic H-1PV (ParvOryx01) in recurrent glioblastoma multiforme patients was completed in 2015 (clinical trial NCT01301430), and demonstrated favorable progression-free survival, clinical safety and patient tolerability with intratumoral or intravenous injection (Angelova et al. (2017); Geiss et al. (2017) Viruses 9, 301; Geletneky et al. (2017)*Mol. Ther.* 25(12): 2620-2634). This trial demonstrated the ability of H-1PV to cross the blood-brain barrier in a dose-dependent manner and to establish an immunogenic anti-tumor response, characterized by leukocytic infiltration, predominantly by CD8+ and CD4+T lymphocytes, and the detection in locally treated tumors of several markers of immune cell activation, including perform, granzyme B, IFNγ, IL-2, CD25 and CD40L (Geletneky et al. (2017) *Mol. Ther.* 25(12):2620-2634).

H-1PV also has demonstrated efficient killing of highly aggressive pancreatic ductal adenocarcinoma (PDAC) cells in vitro, including those resistant to gemcitabine, and intratumoral injection of H-1PV resulted in tumor regression and prolonged animal survival in an orthotopic rat model of PDAC (Angelova et al. (2017); Angelova et al. (2015)). Similar results, including selective tumor targeting and absence of toxicity, were observed in an immunodeficient nude rat PDAC model (Angelova et al. (2015)). The combination of H-1PV and cytostatic (cisplatin, vincristine) or targeted (sunitinib) drugs results in the synergistic induction of apoptosis in human melanoma cells (Moehler et al. (2014)). The combination of H-1PV and valproic acid, an HDAC inhibitor, resulted in synergistic cytotoxicity towards cervical and pancreatic cells (Angelova et al. (2017)), while the therapeutic efficiency of gemcitabine was significantly improved when combined with H-1PV in a two-step protocol (Angelova et al. (2015)). As with other viruses, H-1PV can also be engineered to express anti-cancer molecules. For example, studies have shown that a parvovirus-H1-derived vector expressing Apoptin had a greater capacity to induce apoptosis than wild-type H-1PV (Geiss et al. (2017)).

As with other oncolytic viruses, the therapeutic potential of parvoviruses is limited by nonspecific uptake due to the ubiquitous expression of cell surface receptors that recognize them, and due to the development of neutralizing antibodies following repeated administration. However, H-1PV has demonstrated successful anti-tumor effects when combined with cell-based vehicles, circumventing these potential issues. In one study, autologous MI-13924A rat hepatoma cells were successfully used for the targeted delivery of H-1PV and suppression of metastases formed by the same cells (Raykov et al. (2004) *Int. J. Cancer* 109:742-749). The hepatoma cells were inactivated by γ-radiation 24 h following infection with H-1PV, which only reduced progeny virus yields by 2-fold or less. In comparison to direct virus injection, the vehicle cell-based therapy results in improved suppression of metastases and the generation of fewer neutralizing antibodies, supporting the use of carrier cells to deliver oncolytic parvoviruses systemically (Raykov et al. (2004)).

Measles Virus

Measles virus (MV) is an enveloped, single-stranded RNA virus with a negative-sense genome that belongs to the family of Paramyxoviruses (Aref et al. (2016) *Viruses* 8:294; Hutzen et al. (2015) *Oncolytic Virotherapy* 4:109-118). Its non-segmented genome is stable, with a low risk of mutating and reverting to its pathogenic form, and due to its replication in the cytoplasm, poses no risk of insertional DNA mutagenesis in infected cells (Aref et al. (2016); Hutzen et al. (2015)). MV was first isolated from a patient called Edmonston in 1954, and developed into a live vaccine with an excellent safety profile, that has successfully protected over a billion individuals worldwide for 50 years, by attenuation following multiple in vitro passages (Aref et al. (2016) *Viruses* 8:294; Hutzen et al. (2015) *Oncolytic Virotherapy* 4:109-118). Derivatives of this strain, denoted as MV-Edm, are the most commonly utilized MV strains in oncolytic therapy studies. However, the Schwarz/Moraten measles vaccine strain is more attenuated and immunogenic than Edm derivatives, which makes them safer and more immunomodulatory (Veinalde et al. (2017) *Oncoimmunology* 6(4):e1285992). The oncolytic effects of wildtype MV were documented in the 1970s, with reports of improvements in patients with acute lymphoblastic leukemia, Burkitt's lymphoma and Hodgkin's lymphoma (Aref et al. (2016)).

MV utilizes three main receptors for entry into target cells: CD46, nectin-4 and signaling lymphocyte activation molecule (SLAM) (Aref et al. (2016); Hutzen et al. (2015)). Whereas SLAM, which is expressed on activated B and T cells, immature thymocytes, monocytes and dendritic cells, is the main receptor for wildtype strains, attenuated and tumor-selective MV-Edm strains primarily target the CD46 receptor, a regulator of complement activation that is overexpressed in many tumor cells (Aref et al. (2016); Hutzen et al. (2015); Jacobson et al. (2017) *Oncotarget* 8(38):63096-63109; Msaouel et al. (2013) *Expert Opin. Biol. Ther.* 13(4)). Nectin-4, which is predominantly expressed in the respiratory epithelium, is utilized by both wildtype and attenuated MV strains (Aref et al. (2016); Msaouel et al. (2013) *Expert Opin. Biol. Ther.* 13(4)). As with other oncolytic viruses, defects in the IFN antiviral response of tumor cells also facilitates the tumor-selectivity of MV (Aref et al. (2016); Jacobson et al. (2017) *Oncotarget* 8(38):63096-63109). There are currently several clinical trials investigating the potential of MV in the treatment of several cancers, including multiple myeloma (NCT02192775, NCT00450814), head and neck cancer (NCT01846091), mesothelioma (NCT01503177), and ovarian cancer (NCT00408590, NCT02364713).

MV has been genetically engineered to express immune-stimulating and immunomodulatory genes, including those encoding IL-13, INF-beta, GM-CSF and Heliobacter *pylori* neutrophil-activating protein (NAP), for example (Aref et al. (2016), Hutzen et al. (2015); Msaouel et al. (2013) *Expert Opin. Biol. Ther.* 13(4)). Combination therapies utilizing oncolytic MV with anti-CTLA4 and anti-PD-L1 antibodies have proven successful in melanoma mouse models (Aref et al. (2016); Hutzen et al. (2015)). Due to widespread vaccination or previous natural infection, most patients have prior immunity to MV, which hinders its therapeutic potential. To circumvent this, MV has been delivered to tumors in carrier cells, such as mesenchymal stromal cells, effectively evading the host neutralizing antibodies and proving effective in pre-clinical models of acute lymphoblastic leukemia, hepatocellular carcinoma and ovarian carcinoma (Aref et al. (2016)). Several other cell carriers have demonstrated promising results for the delivery of MV, including the U-937 monocytic cell line, immature and mature primary dendritic cells, PMBCs, activated T cells, primary CD14+ cells, the multiple myeloma MM1 cell line and blood outgrowth endothelial cells (Msaouel et al. (2013) *Expert Opin. Biol. Ther.* 13(4)). Currently, a clinical trial (NCT02068794) is studying the use of oncolytic MV infected mesenchymal stem cells in the treatment of patients with recurrent ovarian cancer. Another strategy to overcome pre-existing immunity involves the combination of MV therapy with immunosuppressive agents such as cyclophosphamide (Hutzen et al. (2015)).

MV-CEA

MV-CEA, which is genetically engineered to express the tumor marker carcinoembryonic antigen (CEA), results in the release of CEA into the blood stream of patients following infection of cancer cells, allowing the detection of CEA levels and thus, the tracking of in vivo viral infection (Aref et al. (2016); Hutzen et al. (2015)). The therapeutic potential of MV-CEA has been demonstrated pre-clinically, and is currently being investigated in Phase I clinical trials for the treatment of ovarian cancer (NCT00408590).

MV-NIS

MV-NIS is another trackable oncolytic MV of the Edmonston vaccine lineage, engineering to express the sodium iodide symporter (NIS), which displays superior viral proliferation compared to MV-CEA, due to the positioning of the NIS transgene downstream of the hemagglutinin (H) gene of the MV genome, instead of upstream of the nucleocapsid (N) gene, as in the MV-CEA construct (Aref et al. (2016); Galanis et al. (2015) *Cancer Res.* 75(1):22-30). Radioisotopes such as 123I, 124I, 125I, 131I and $^{99m}$Tc are transported via NIS, which is expressed on MV-NIS infected cells, allowing for non-invasive imaging using, for example, PET, SPECT/CT, and γcamera (Msaouel et al. (2013) *Expert Opin. Biol. Ther.* 13(4)). The expression of NIS also can improve the efficacy of oncolytic MV by facilitating the entry of beta-emitting radioisotopes, such as I-131, into tumor cells for radiovirotherapy, and has demonstrated promising results pre-clinically in multiple myeloma, glioblastoma multiforme, head and neck cancer, anaplastic thyroid cancer and prostate cancer models (Aref et al. (2016); Hutzen et al. (2015); Msaouel et al. (2013)). Several Phase VII clinical trials are currently investigating the use of MV-NIS in multiple myeloma (NCT00450814, NCT02192775), mesothelioma (NCT01503177), head and neck cancer (NCT01846091) and in ovarian cancer using virus-infected MSCs (NCT02068794).

Reovirus

Respiratory Enteric Orphan virus, commonly known as Reovirus, is a non-enveloped double-stranded RNA virus of the Reoviridae family that is nonpathogenic to humans. Wild-type reovirus is ubiquitous throughout the environment, resulting in a 70-100% seropositivity in the general population (Gong et al. (2016) *World J. Methodol.* 6(1):25-42). There are three serotypes of reovirus, which include type 1 Lang, type 2 Jones, type 3 Abney and type 3 Dearing (T3D). T3D is the most commonly utilized naturally occurring oncolytic reovirus serotype in pre-clinical and clinical studies.

Oncolytic reovirus is believed to be tumor-selective due to activated Ras signaling that is characteristic of cancer cells (Gong et al. (2016)); Zhao et al. (2016) *Mol. Cancer Ther.* 15(5):767-773). Activation of the Ras signaling pathway disrupts the cell's anti-viral responses, by inhibiting the phosphorylation of dsRNA-dependent protein kinase (PKR), a protein that is normally responsible for preventing viral protein synthesis (Zhao et al. (2016)). Ras activation also enhances viral un-coating and disassembly, results in enhanced viral progeny generation and infectivity, and accelerates the release of progeny through enhanced apoptosis (Zhao et al. (2016)). It is estimated that approximately 30% of all human tumors display aberrant Ras signaling (Zhao et al. (2016)). For example, the majority of malignant gliomas possess activated Ras signaling pathways, with reovirus demonstrating antitumor activity in 83% of malignant glioma cells in vitro, as well as in vivo in human malignant glioma models, and in 100% of glioma specimens ex vivo (Gong et al. (2016) *World J. Methodol.* 6(1):25-42). Additionally, pancreatic adenocarcinomas display a very high incidence of Ras mutations (approximately 90%), and reovirus has shown potent cytotoxicity in 100% of pancreatic cell lines tested in vitro and induced regression in 100% of subcutaneous tumor mouse models in vivo. (Gong et al. (2016)).

Reovirus has demonstrated broad anticancer activity preclinically across a spectrum of malignancies including colon, breast, ovarian, lung, skin (melanoma), neurological, hematological, prostate, bladder, and head and neck cancer (Gong et al. (2016)). Reovirus therapy is currently being tested in combination with radiotherapy, chemotherapy, immunotherapy, and surgery. The combination of reovirus and radiation therapy has proven beneficial in the treatment of head and neck, colorectal and breast cancer cell lines in vitro, as well as colorectal cancer and melanoma models in vivo (Gong et al. (2016)). The combination of reovirus and gemcitabine, as well as reovirus, paclitaxel and cisplatin, have proven successful in mouse tumor models (Zhao et al. (2016)). Preclinical studies in B16 melanoma mouse models have shown that the combination of oncolytic reovirus and anti-PD-1 therapy demonstrated improved anticancer efficacy in comparison to reovirus alone (Gong et al. (2016); Zhao et al. (2016); Kemp et al. (2015) Viruses 8, 4).

The promising pre-clinical results demonstrated by reovirus have led to many clinical trials. Reolysin®, developed by the Canadian company Oncolytics Biotech Inc., is the only therapeutic wild-type reovirus in clinical development, and has demonstrated anticancer activity in many malignancies alone, and in combination with other therapeutics. For example, a phase I clinical study of Reolysin® in the treatment of recurrent malignant gliomas (NCT00528684) found that the reovirus was well tolerated, while a phase I/II trial found that Reolysin® is able to kill tumor cells without damaging normal cells in patients with ovarian epithelial cancer, primary peritoneal cancer, or fallopian tube cancer that did not respond to platinum chemotherapy (NCT00602277). A phase II clinical trial of Reolysin® found that it was safe and effective in the treatment of patients with bone and soft tissue sarcomas metastatic to the lung (NCT00503295). A phase I clinical trial of Reolysin® in combination with FOLFIRI and bevacizumab in currently active in patients with metastatic colorectal cancer (NCT01274624). A phase II clinical trial of Reolysin® in combination with the chemotherapeutic gemcitabine was carried out in patients with advanced pancreatic adenocarcinoma (NCT00998322), a phase II clinical study investigated the therapeutic potential of Reolysin® in combination with docetaxel in metastatic castration resistant prostate cancer (NCT01619813), and a phase II clinical trial investigated the combination of Reolysin® with paclitaxel in patients with advanced/metastatic breast cancer (NCT01656538). A phase III clinical trial investigated the efficacy of Reolysin® in combination with paclitaxel and carboplatin in platinum-refractory head and neck cancers (NCT01166542), while phase II clinical studies employing this combination therapy were carried out in patients with non-small cell lung cancer (NCT00861627) and metastatic melanoma (NCT00984464). A phase I clinical trial of Reolysin® in combination with carfilzomib and dexamethasone in patients with relapsed or refractory multiple myeloma is ongoing (NCT02101944).

Due to the presence of neutralizing antibodies in the majority of the population, systemic administration of reovirus has limited therapeutic potential, which can be overcome with the co-administration of reovirus with immunosuppressive agents, such as cyclosporin A or cyclophosphamide (Gong et al. (2016)). The administration of GM-CSF prior to IV administration of reovirus resulted in significant reduction of B16 melanoma tumors and prolonged survival in mice (Kemp et al. (2015) Viruses 8, 4). Carrier cells also have demonstrated success in shielding the virus from pre-existing immunity. For example, lymphokine-activated killer cells (LAKs) and DCs were utilized as cell carriers for reovirus in a model of ovarian cancer, and successfully protected the virus from neutralizing antibodies (Zhao et al. (2016)). PMBCs, including NK cells, have been shown to not only successfully transport reovirus, but were also stimulated by reovirus to kill the tumor targets (Zhao et al. (2016)). Another study showed that both DCs and T cells were effective carriers of reovirus in vitro in the absence of human serum, but only DCs successfully delivered the virus to melanoma cells in the presence of neutralizing serum (Ilett et al. (2011) *Clin. Cancer Res.* 17(9):2767-2776). DCs also were capable of delivering reovirus in mice bearing lymph node B16tk melanoma metastases, whereas neat reovirus was completely ineffective (Ilett et al. (2009) *Gene Ther.* 16(5):689-699).

Vesicular Stomatitis Virus (VSV)

Vesicular stomatitis virus (VSV) is a member of the *Vesiculovirus* genus within the Rhabdoviridae family. Its genome, which consists of a single-stranded RNA with negative-sense polarity, consists of 11,161 nucleotides and encodes for five genes: nucleocapsid protein (N), phosphoprotein (P), matrix protein (M), glycoprotein (G), and large polymerase protein (L) (Bishnoi et al. (2018) *Viruses* 10(2), 90). VSV is transmitted by insect vectors and disease is limited to its natural hosts, including horses, cattle and pigs, with mild and asymptomatic infection in humans (Bishnoi et al. (2018) *Viruses* 10(2), 90). VSV is a potent and rapid inducer of apoptosis in infected cells, and has been shown to sensitize chemotherapy-resistant tumor cells. VSV has been shown to infect tumor vasculature, resulting in a loss of blood flow to the tumor, blood-coagulation and lysis of neovasculature. This virus also is capable of replication and induction of cytopathic effects and cell lysis in hypoxic tissues. In addition, WT VSV grows to high titers in a variety of tissue culture cells lines, facilitating large-scale virus production, it has a small and easy to manipulate genome, and it replicates in the cytoplasm without risk of host cell transformation (Bishnoi et al. (2018); Felt and Grdzelishvili (2017) *Journal of General Virology* 98:2895-2911). These factors, together with the fact that it is not pathogenic to humans and there is generally no pre-existing human immunity to VSV, make it a good candidate for viral oncotherapy.

Although VSV can attach to ubiquitously expressed cell-surface molecules, making it "pantropic," WT VSV is sensitive to type I IFN responses and thus displays oncoselectivity based on the defective or inhibited type I IFN signaling of tumors (Felt and Grdzelishvili (2017)). However, due to its infectivity of normal cells, VSV can cause neuropathogenecity, but can be attenuated by modifying its matrix protein and/or glycoprotein. For example, the matrix protein can be deleted or the methionine residue at position 51 of the matrix protein can be deleted or substituted with arginine (Bishnoi et al. (2018); Felt and Grdzelishvili (2017)). Another approach replaces the glycoprotein of VSV with that of lymphocytic choriomeningitis virus (LCMV) (rVSV-GP) (Bishnoi et al. (2018); Felt and Grdzelishvili (2017)). VSV also can be genetically modified to include suicide genes, such as herpes virus thymidine kinase (TK), or to express immune-stimulatory cytokines such as IL-4, IL-12, IFNβ, or costimulatory agents such as granulocyte-macrophage-colony-stimulating factor 1 (GM-CSF1), to enhance oncolytic activity (Bishnoi et al. (2018). VSV-IFNβ-sodium iodide symporter (VSV-IFNβ-NIS), which encodes NIS and IFNβ, is currently being tested in the USA in several phase I clinical trials (see details at ClinicalTrials.gov for trials NCT02923466, NCT03120624 and NCT03017820).

Vesicular stomatitis virus (VSV) is an effective oncolytic therapeutic when administered intravenously (IV) in a variety of murine cancer models. In one study, VSV-GP was successful in the intratumoral treatment of subcutaneously engrafted G62 human glioblastoma cells, as well as the intravenous treatment of orthotopic U87 human glioma cells, in immune-deficient mouse models. Intratumoral injection of VSV-GP also was effective against intracranial CT2A murine glioma cells (Muik et al. (2014) *Cancer Res.* 74(13):3567-3578). It was found that VSV-GP did not elicit a detectable neutralizing antibody response, and that this genetically modified oncolytic virus was insensitive to human complement, remaining stable over the length of the experiment (Muik et al. (2014)). In another example, intratumoral administration of VSV-GP was found to effectively infect and kill human A375 malignant melanoma cells transplanted in a mouse model, as well as the murine B16 melanoma cell line (Kimpel et al. (2018) Viruses 10, 108). However, intravenous injection of the oncolytic virus was not successful, and even in the intratumorally-administered groups, the tumors all eventually grew, due to type I IFN responses (Kimpel et al. (2018)). In another study, a subcutaneous xenograft mouse model with A2780 human ovarian cancer cells was treated with intratumoral injection of VSV-GP, and although tumor remission was initially observed with no neurotoxicity, remission was temporary and the tumors recurred. This was found to be due to type I IFN responses, with an observed reversal of the antiviral state by combining VSV-GP with the JAK1/2 inhibitor ruxolitinib. (Dold et al. (2016) *Molecular Therapy—Oncolytics* 3, 16021). However, inhibition of type I IFN responses often is not be possible for attenuated variants of wild type VSV in vivo due to safety concerns, giving rise to the need for an alternative solution.

Studies have shown that humoral immunity, giving rise to anti-virus antibodies, limits the therapeutic potential of VSV. It was found that repeated administration of VSV in carrier cells to animals bearing metastatic tumors resulted in a much higher therapeutic efficacy in comparison to the injection of naked virions (Power et al. (2007) *Molecular Therapy* 15(1):123-130), demonstrating the ability for carrier cells to evade the circulating antibodies. Syngeneic CT26 murine colon carcinoma cells were readily infected with VSV, and following intravenous administration, accumulated rapidly in lung tumors, but not in surrounding normal lung tissue, where they remained until releasing virus and undergoing lysis within 24h (Power et al. (2007) at the delivery of VSV to infect lung tumors in mice. Systemic cell-mediated delivery also was obtained using xenogeneic A549 cells as carrier cells, illustrating that cell-mediated delivery of VSV can be achieved using immunologically compatible syngeneic CT26 cells as well as immunologically incompatible xenogeneic A549 cells (Power et al. (2007)). L1210 murine leukemia cells also successfully delivered VSV to lung tumors, as well as subcutaneous tumors located in the hind flank of the mice (Power et al. (2007)). When these VSV infected leukemia cells were administered to mice without tumors, there was no detectable virus replication in normal tissues, indicating tumor selectivity.

In another study, VSV-651, which lacks the methionine 51 of the matrix protein and thus cannot block the nuclear export of IFN-encoding mRNAs, was loaded onto OT-I CD8+ T cells expressing a transgenic T cell receptor specifically for the SIINFEKL epitope of ovalbumin antigen, which is expressed by B16ova tumors (Qiao et al. (2008) *Gene Ther.* 15(8):604-616). This oncolytic virus/cell-based vehicle combination was used against B16ova tumors in the lungs of immune-competent C57B1/6 mice, and resulted in significant increases in therapeutic efficacy when compared to the use of virus or T cells alone. There was no detectable replication of VSV within the OT-I cells, but virus was released and effectively infected, replicated in, and killed tumor cells following co-culture of infected T cells with B16ova cells. The loading of VSV onto the T cells was shown to increase T-cell activation in vitro and increase trafficking of the T cells to the tumors in vivo (Qiao et al. (2008)).

Adenovirus

Adenoviruses (Ads) are non-enveloped ds-DNA viruses with a linear genome that were first discovered in 1953 by Wallace Rowe and colleagues, and were tested for the treatment of cervical cancer as early as 1956 (Choi et al. (2015) *J Control. Release* 10(219):181-191). Human Ads are ubiquitous in the environment and are classified into 57 serotypes (Ad1-Ad57), based on cross-susceptibility, and 7 subgroups (A-G), based on virulence and tissue tropism. Adenovirus serotype 5 (Ad5) is the most commonly utilized adenovirus for oncolytic virotherapy. Infections in humans are mild and result in cold-like symptoms (Yokoda et al. (2018) *Biomedicines* 6, 33) and systemic administration results in liver tropism and can lead to hepatotoxicity (Yamamoto et al. (2017) *Cancer Sci.* 108:831-837), but Ads are considered safe for therapeutic purposes. Ads enter cells by attaching to the coxsackievirus and adenovirus receptor (CAR), followed by interaction between the $\alpha v\beta 3$ and $\alpha v\beta 5$ integrins on the cell surface and the Arg-Gly-Asp tripeptide motif (RGD) at the adenoviral penton base (Jiang et al. (2015) *Curr. Opin. Virol.* 13:33-39). CAR is expressed on the surfaces of most normal cells, but expression is highly variable across cancer cell types. On the other hand, RGD-related integrins are highly expressed by cancer cells, but are expressed at much lower levels in normal cells (Jiang et al. (2015)). As a result, Ads are often targeted to cancer cells via the RGD motif.

Ads are attractive as oncolytic viruses due to their high transduction efficiency in transformed cells, their lack of integration into the host genome/lack of insertional mutagenesis, their genomic stability, the ability to insert large therapeutic genes into their genomes, and their capacity for tumor selectivity via genetic manipulation, such as the substitution of viral promoters with cancer tissue-selective promoters (Yokoda et al. (2018) *Biomedicines* 6, 33; Choi et al. (2015) *J. Control. Release* 10(219):181-191).

Examples of oncolytic Ads with tumor-specific promoters include CV706 for prostate cancer treatment, with the adenovirus early region 1A (E1A) gene under control of the prostate specific antigen promoter, and OBP-301, which utilizes the telomerase reverse transcriptase (TERT) promoter for regulation of E1A gene expression (Yamamoto et al. (2017) *Cancer Sci.* 108:831-837). Another method for inducing tumor selectivity is the introduction of mutations in the E1 region of the Ad genome, where the missing genes are functionally complemented by genetic mutations commonly found in tumor cells, such as abnormalities in the retinoblastoma (Rb) pathway or p53 mutations (Yamamoto et al. (2017) *Cancer Sci.* 108:831-837). For example, the oncolytic Ads ONYX-015 and H101 have deletions in the E1B55K gene, which inactivates p53. These mutants cannot block the normal apoptotic defense pathway, resulting in tumor selectivity via the infection of neoplastic cells with defective p53 tumor suppressor pathways (Yamamoto et al. (2017) *Cancer Sci.* 108:831-837; Uusi-Kerttula et al. (2015) *Viruses* 7:6009-6042). E1AΔ24 is an oncolytic Ad that contains a 24-bp mutation in the E1A gene, disrupting the Rb-binding domain and promoting viral replication in cancer cells with Rb pathway mutations. ICOVIR-5 is an oncolytic Ad that combines E1A transcriptional control by the E2F promoter, the 424 mutation of E1A and an RGD-4C insertion into the adenoviral fiber (Yamamoto et al. (2017) *Cancer Sci.* 108:831-837; Uusi-Kerttula et al. (2015)). Delta-24-RGD, or DNX-2401, is an oncolytic Ad in which the 424 backbone is modified by insertion of the RGD motif, that demonstrated enhanced oncolytic effects in vitro and in vivo (Jiang et al. (2015)).

An alternative strategy for improving tumor selectivity involves overcoming the physical barrier in solid tumors by targeting the extracellular matrix (ECM). For example, VCN-01, an oncolytic Ad that expresses hyaluronidase, that has shown promise in murine cancer models. Ads also have been engineered to express relaxin to disrupt the ECM (Yamamoto et al. (2017) *Cancer Sci.* 108:831-837; Shaw and Suzuki (2015) *Curr. Opin. Virol.* 21:9-15). Ads expressing suicide genes, such as cytosine deaminase (CD) and HSV-1 thymidine kinase (TK) have shown enhanced antitumor efficacy in vivo, have Ads expressing immunostimulatory cytokines, such as ONCOS-102, which expresses GM-CSF (Yamamoto et al. (2017) *Cancer Sci.* 108:831-837; Shaw and Suzuki (2015) *Curr. Opin. Virol.* 21:9-15). A 424-based oncolytic Ad expressing an anti-CTLA4 antibody has shown promise in preclinical studies (Jiang et al. (2015)).

The adenovirus H101 (Oncorine®) was the first oncolytic Ad approved for clinical use in China in combination with chemotherapy, for treating patients with advanced nasopharyngeal cancer in 2005. Due to the promise shown in preclinical studies, many clinical trials have investigated the use of oncolytic adenoviruses for the treatment of a wide variety of cancers. For example, ongoing and past clinical trials include studies involving Ad5 encoding IL-12 in patients with metastatic pancreatic cancer (NCT03281382); an immunostimulatory Ad5 (LOAd703) expressing TMX-CD40L and 41BBL in patients with pancreatic adenocarcinoma, ovarian cancer, biliary carcinoma and colorectal cancer (NCT03225989); LOAd703 in combination with gemcitabine and nab-paclitaxel in patients with pancreatic cancer (NCT02705196); an oncolytic adenovirus encoding human PH20 hyaluronidase (VCN-01) in combination with gemcitabine and Abraxane® in patients with advanced solid tumors, including pancreatic adenocarcinoma (NCT02045602; NCT02045589); Telomelysin® (OBP-301), an oncolytic Ad with tumor selectivity, containing the human telomerase reverse transcriptase (hTERT) promoter, in patients with hepatocellular carcinoma (NCT02293850); an E1B gene deleted Ad5 in combination with transarterial chemoembolization (TACE) in patients with hepatocellular carcinoma (NCT01869088); CG0070, an oncolytic Ad that expresses GM-CSF and contains the cancer-specific E2F-1 promoter to drive expression of E1A, in patients with bladder cancer (NCT02365818; NCT01438112); Enadenotucirev (Colo-Ad1), an Ad11p/Ad3 chimeric Group B oncolytic virus, in patients with colon cancer, non-small cell lung cancer, bladder cancer and renal cell carcinoma (NCT02053220); and DNX-2401 (Ad5 E1AΔ24RGD) in combination with Temozolomide (NCT01956734), or in combination with IFNγ (NCT02197169) in patients with glioblastoma.

As with other oncolytic viruses, Ads suffer from a low therapeutic efficacy when systemically administered due to the development of neutralizing antibodies, and due to their high seroprevalence, it is estimated that as much as 90% of some populations possess prior immunity to Ads (Uusi-Kerttula et al. (2015) *Viruses* 7:6009-6042). Additionally, nonspecific liver sequestration of the Ads results in hepatotoxicity (Choi et al. (2015)). Polymers, such as PEG, positively charged arginine-grafted bioreducible polymer (ABP), PAMAMGS, and other nanomaterials can be utilized to mask the viral capsid protein, mitigating the anti-viral immune response and nonspecific liver accumulation, and increasing tumor accumulation (Choi et al. (2015)). Other approaches to evade the immune system involve the use of carrier vehicle cells to deliver oncolytic Ads. For example, T-cells were used to deliver Delta24-RGD Ad to glioblastoma cells in vitro and in vivo in an orthotopic glioma stem cell (GSC)-based xenograft murine model (Balvers et al. (2014) *Viruses* 6:3080-3096). Systemic administration of virus-loaded T-cells resulted in intratumoral viral delivery (Balvers et al. (2014)). Clinical trials investigating the delivery of Ad with carrier/vehicle cells include the use of neural stem cells loaded with oncolytic Ad for the treatment of malignant gliomas (NCT03072134); autologous dendritic cells infected with Ad expressing Her2 in patients with metastatic breast cancer (NCT00197522); and autologous mesenchymal stem cells (MSCs) infected with ICOVIR5 in children and adults with metastatic and refractory solid tumors (NCT01844661).

Poliovirus

Poliovirus (PV) belongs to the genus Enterovirus in the family Picornaviridae and has a positive-sense single-stranded RNA genome. PV infection results in severe neurological syndrome poliomyelitis, due to the tropism of PV for spinal cord and motor neurons (Brown and Gromeier (2015) *Discov. Med.* 19(106):359-365). PVs are useful in clinical application due to their retention of a robust replicative capacity and cytotoxicity in the presence of an active antiviral IFN response, allowing for several rounds of viral replication to amplify the immune-stimulating viral cytotoxic effects (Brown and Gromeier (2015) *Discov. Med.* 19(106):359-365). PVs also do not integrate into the host cell genome (Yla-Pelto et al. (2016) Viruses 8, 57).

PV host cell entry is mediated by the Ig-superfamily cell adhesion molecule CD155, also known as PV receptor (PVR) and Nectin-like molecule 5 (Nec15), which is widely overexpressed in solid neoplasias, such as glioblastoma (Brown and Gromeier (2015) *Curr. Opin. Virol.* 13:81-85). CD155 also is expressed in colorectal carcinoma, lung adenocarcinoma, breast cancers and melanoma, and is expressed in antigen presenting cells (APCs) such as macrophages and dendritic cells (Brown et al. (2014) *Cancer* 120(21):3277-3286).

The internal ribosomal entry site (IRES) of PV is responsible for driving translation initiation of the PV RNA genome, and is implicated in the neuropathogenicity of PV. The live-attenuated PV vaccines, which are derived from the Sabin serotypes, carry critical attenuating point mutations in the IRES (Brown and Gromeier (2015) *Curr. Opin. Virol.* 13:81-85). The highly attenuated polio-/rhinovirus recombinant PVSRIPO, a type 1 (Sabin) live-attenuated PV vaccine in which the cognate PV IRES is replaced with that of the human rhinovirus 2 (HRV2), exhibits no neurovirulence/ neuropathogenicity in comparison to the parent PV, but retains cancer cell cytotoxicity and specificity towards GBM cells. (Brown and Gromeier (2015) *Curr. Opin. Virol.* 13:81-85; Brown and Gromeier (2015) *Discov. Med.* 19(106):359-365). PVSRIPO causes tumor regression by eliciting an antitumor immune response, rather than the direct lysis of bulk tumor, and has shown promise in clinical trials for the treatment of recurrent glioblastoma (GBM) (NCT01491893) (Brown and Gromeier (2015) *Curr. Opin. Virol.* 13:81-85; Brown and Gromeier (2015) *Discov. Med.* 19(106):359-365). Currently, a Phase 1b clinical trial is investigating the use of PVSRIPO for treatment of recurrent malignant glioma in children (NCT03043391) and a Phase 2 clinical trial is investigating the use of PVSRIPO alone, or in combination with the chemotherapy drug lomustine in adult patients with recurrent malignant glioma (NCT02986178).

Herpes Simplex Virus

Herpes simplex virus (HSV) belongs to the family Herpesviridae and has a large linear double-stranded DNA genome, including many genes that are nonessential for viral replication, making it an ideal candidate for genetic manipulation. Other advantages include its ability to infect a broad range of cell types, its sensitivity to antivirals such as aciclovir and ganciclovir, and its lack of insertional mutagenesis (Sokolowski et al. (2015) *Oncolytic Virotherapy* 4:207-219; Yin et al. (2017) *Front. Oncol.* 7:136). There are two types of HSV, HSV type I (HSV-1) and type II (HSV-2), with the majority of oncolytic HSVs being derived from HSV-1. In humans, HSV-1 causes fever blister disease and infects epithelial cells, neurons, and immune cells by binding to nectins, glycoproteins, and the herpesvirus entry mediator (HVEM) on the cell surface (Kohlhapp and Kaufman (2016) *Clin. Cancer Res.* 22(5):1048-1054).

Many different oncolytic HSV-1 viruses have been generated to date. For example, HSV-1 has been engineered to express the anti-HER-2 antibody trastuzumab, targeting tumors that overexpress HER-2, such as breast and ovarian cancers, gastric carcinomas and glioblastomas. The gene encoding trastuzumab was inserted into two regions within the HSV-1 gD glycoprotein gene, generating two oncolytic HSVs, R-LM113 and R-LM249. R-LM113 and R-LM249 demonstrated preclinical activity against human breast and ovarian cancers, and against a murine model of HER2+ glioblastoma. R-LM249 has been administered systemically using mesenchymal stromal cells (MSCs) as carrier cells, exerting therapeutic effects against lung and brain metastases of ovarian and breast cancer in a murine model (Campadelli-Fiume et al. (2016) *Viruses* 8, 63). Another oncolytic HSV-1, dlsptk HSV-1, contains a deletion in the unique long 23 (UL23) gene, which encodes the viral homologue of thymidine kinase (TK), while the hrR3 HSV-1 mutant contains a LacZ insertion mutation of the large subunit of ribonucleotide reductase (RR), also known as ICP6, encoded by the gene UL39. As a result, dlsptk and hrR3 HSV-1 mutants can only replicate in cancer cells that overexpress TK and RR, respectively (Sokolowski et al. (2015) *Oncolytic Virotherapy* 4:207-219).

HF10 is a spontaneously mutated oncolytic HSV-1 that lacks the genes encoding UL43, UL49.5, UL55, UL56 and latency-associated transcripts, and overexpresses UL53 and UL54. HF10 has shown promising results in preclinical studies and demonstrated high tumor selectivity, high viral replication, potent antitumor activity and a favorable safety profile (Eissa et al. (2017) *Front. Oncol.* 7:149). Clinical trials investigating HF10 include: a phase I study in patients with refractory head and neck cancer, squamous cell carcinoma of the skin, carcinoma of the breast and malignant melanoma (NCT01017185) and a Phase I study of HF10 in combination with chemotherapy (gemcitabine, Nab-paclitaxel, TS-1) in patients with unresectable pancreatic cancer (NCT03252808). HF10 also has been combined with the anti-CTLA-4 antibody ipilimumab, resulting in improved therapeutic efficacy in patients with stage IIIb, IIIc or IV unresectable or metastatic melanoma (NCT03153085). A phase II clinical study is currently investigating the combination of HF10 with the anti-PD-1 antibody Nivolumab in patients with resectable stage IIIb, IIIc and IV melanoma (NCT03259425) and in combination with ipilimumab in patients with unresectable or metastatic melanoma (NCT02272855). Paclitaxel and HF10 combination therapy resulted in superior survival rates in peritoneal colorectal cancer models compared with either treatment alone, while combination treatment with HF10 and erlotinib resulted in improved activity against pancreatic xenografts in vitro and in vivo than either HF10 or erlotinib alone (Eissa et al. (2017) *Front. Oncol.* 7:149).

Talimogene laherparepvec (Imlygic®, T-VEC), previously known as OncoVEX$^{GM-CSF}$ is an FDA-approved oncolytic herpes simplex virus for the treatment of advanced melanoma, that was generated from the JS1 strain of HSV-1 and genetically engineered to express granulocyte macrophage stimulating factor (GM-CSF) (Aref et al. (2016) *Viruses* 8:294). In T-VEC, GM-CSF expression enhances the antitumor cytotoxic immune response, while deletion of both copies of the infected cell protein 34.5 (ICP34.5) gene suppresses replication in normal tissues, and deletion of the ICP47 gene increases expression of MHC class I molecules, allowing for antigen presentation on infected cells (Eissa et al. (2017)). T-VEC exhibits tumor selectivity by binding to nectins on the surface of cancer cells and preferentially replicates in tumor cells by exploiting disrupted oncogenic and antiviral signaling pathways, particularly the protein kinase R (PKR) and type I IFN pathways. In normal cells, PKR is activated by viral infection, which then phosphorylates the eukaryotic initiation factor-2A protein (eIF-2A), inactivating it and in turn, inhibiting cellular protein synthesis, blocking cell proliferation and preventing viral replication. Wild-type HSV escapes the antiviral response due to expression of the ICP34.5 protein, which activates a phosphatase that dephosphorylates eIF-2A, restoring protein synthesis in the infected cells. Thus, deletion of ICP34.5 precludes viral replication of T-VEC in normal cells. The PKR-eIF-2A pathway in cancer cells, however, is disrupted, permitting continuous cell growth and uninhibited viral replication (Kohlhapp and Kaufman (2016) *Clin. Cancer Res.* 22(5):1048-1054; Yin et al. (2017) *Front. Oncol.* 7:136). The expression of GM-CSF improves the immunogenicity of T-VEC by causing dendritic cell accumulation, promoting antigen-presentation and priming T-cell responses (Kohlhapp and Kaufman (2016) *Clin. Cancer Res.* 22(5):1048-1054).

T-VEC has shown preferential replication in a variety of different cancer cell lines, including breast cancer, colorectal adenocarcinoma, melanoma, prostate cancer, and glioblastoma. Clinical trials include, for example, those investigating T-VEC in pancreatic cancer (NCT03086642, NCT00402025), recurrent breast cancer (NCT02658812), advanced non-CNS tumors in children (NCT02756845), non-melanoma skin cancer (NCT03458117), non-muscle invasive bladder transitional cell carcinoma (NCT03430687), and malignant melanoma (NCT03064763), as well as T-VEC in combination with atezolizumab in patients with metastatic triple negative breast cancer and metastatic colorectal cancer with liver metastases (NCT03256344), in combination with paclitaxel in patients with triple negative breast cancer (NCT02779855), in combination with nivolumab in patients with refractory lymphomas or advanced/refractory non-melanoma skin cancers (NCT02978625), in combination with cisplatin and radiotherapy in patients with advanced head and neck cancer (NCT01161498), and in combination with pembrolizumab in patients with liver tumors (NCT02509507), carcinoma of the head and neck (NCT02626000), sarcoma (NCT03069378) and melanoma (NCT02965716, NCT02263508).

In addition to GM-CSF, numerous other immune stimulating genes have been inserted into oncolytic HSVs, including those encoding IL-12, IL-15, IL-18, TNFα, IFNα/β and fms-like tyrosine kinase 3 ligand, resulting in increased therapeutic efficacy (Sokolowski et al. (2015); Yin et al. (2017)).

Another oncolytic HSV-1, R3616 contains deletions in both copies of the RL1 (also known as $\gamma_1 34.5$) gene, which encodes ICP34.5, targeting cancer cells with disrupted PKR pathways. NV1020 (or R7020) is an HSV-1 mutant that contains deletions in the UL55, UL56, ICP4, RL1 and RL2 genes, resulting in reduced neurovirulence and cancer selectivity. NV1020 displayed promising results in murine models of head and neck squamous cell carcinoma, epidermoid carcinoma and prostate adenocarcinoma (Sokolowski et al. (2015)). Additionally, clinical trials have investigated the safety and efficacy of NV1020 in colorectal cancer metastatic to the liver (NCT00149396 and NCT00012155).

G207 (or MGH-1) is another HSV-1 mutant with an RL1 ($\gamma_1 34.5$) deletion and a LacZ inactivating insertion in the UL39 neurovirulence gene. Clinical studies utilizing G207 include the investigation of G207 administration alone or with a single radiation dose in children with progressive or recurrent supratentorial brain tumors (NCT02457845), the investigation of the safety and efficacy of G207 in patients with recurrent brain cancer (glioma, astrocytoma, glioblastoma) (NCT00028158), and the investigation of the effects of G207 administration followed by radiation therapy in patients with malignant glioma (NCT00157703).

G207 was used to generate G474, which contains a further deletion in the gene encoding ICP47. Other HSV-1 derived oncolytic viruses include HSV1716, which contains deletions in RL1, but has an intact UL39 gene and replicates selectively in actively dividing cells, and the KM100 mutant, which has insertions in the UL48 and RL2 genes, resulting in a loss of expression of immediate early viral genes and cancer cell selectivity (Sokolowski et al. (2015); Yin et al. (2017) *Front. Oncol.* 7:136).

Since the majority of the population possesses preexisting immunity to HSV-1, the use of carrier cells to deliver oncolytic HSVs can improve their therapeutic potential. For example, human peritoneal mesothelial cells (MCs) were used as carrier cells for HF10, leading to the efficient killing of ovarian cancer cells in vitro, as well as in a mouse xenograft model of ovarian cancer (Fujiwara et al. (2011) *Cancer Gene Therapy* 18:77-86).

Oncolytic viruses also have been derived from HSV-2. For example, FusOn-H2 is an HSV-2 oncolytic virus with a deletion of the N-terminal region of the ICP 10 gene that encodes a serine/threonine protein kinase (PK) domain. This PK is responsible for phosphorylating GTPase-activating protein Ras-FAP, which activates the Ras/MEK/MAPK mitogenic pathway and induces and stabilizes c-Fos, which is required for efficient HSV-2 replication. Normal cells usually have an inactivated Ras signaling pathway. Thus, FusOn-H2 exhibits tumor selectivity by replicating only in tumor cells with activated Ras signaling pathways (Fu et al. (2006) *Clin. Cancer Res.* 12(10):3152-3157). FusOn-H2 has demonstrated activity against pancreatic cancer xenografts (Fu et al. (2006) *Clin. Cancer Res.* 12(10):3152-3157), against Lewis lung carcinoma xenografts in combination with cyclophosphamide, and against syngeneic murine mammary tumors and neuroblastoma (Li et al. (2007) *Cancer Res.* 67:7850-7855).

Poxvirus

Vaccinia Virus

Examples of vaccinia viruses include, but are not limited to, Lister (also known as Elstree), New York City Board of Health (NYCBH), Dairen, Ikeda, LC16M8, Western Reserve (WR), Copenhagen (Cop), Tashkent, Tian Tan, Wyeth, Dryvax, IHD-J, IHD-W, Brighton, Ankara, Modified Vaccinia Ankara (MVA), Dairen I, LIPV, LC16M0, LIVP, WR 65-16, EM63, Bern, Paris, CVA382, NYVAC, ACAM2000 and Connaught strains. Vaccinia viruses are oncolytic viruses that possess a variety of features that make them particularly suitable for use in wound and cancer gene therapy. For example, vaccinia is a cytoplasmic virus, thus, it does not insert its genome into the host genome during its life cycle. Unlike many other viruses that require the host's transcription machinery, vaccinia virus can support its own gene expression in the host cell cytoplasm using enzymes encoded in the viral genome. Vaccinia viruses also have a broad host and cell type range. In particular, vaccinia viruses can accumulate in immunoprivileged cells or immunoprivileged tissues, including tumors and/or metastases, and also including wounded tissues and cells. Yet, unlike other oncolytic viruses, vaccinia virus can typically be cleared from the subject to whom the viruses are administered by activity of the subject's immune system, and hence are less toxic than other viruses such as adenoviruses. Thus, while the viruses can typically be cleared from the subject to whom the viruses are administered by activity of the subject's immune system, viruses can nevertheless accumulate, survive and proliferate in immunoprivileged cells and tissues such as tumors, because such immunoprivileged areas are isolated from the host's immune system.

Vaccinia viruses also can be easily modified by insertion of heterologous genes. This can result in the attenuation of the virus and/or permit delivery of therapeutic proteins. For example, the vaccinia virus genome has a large carrying capacity for foreign genes, where up to 25 kb of exogenous DNA fragments (approximately 12% of the vaccinia genome size) can be inserted. The genomes of several of the vaccinia strains have been completely sequenced, and many essential and nonessential genes identified. Due to high sequence homology among different strains, genomic information from one vaccinia strain can be used for designing and generating modified viruses in other strains. Finally, the techniques for production of modified vaccinia strains by genetic engineering are well established (Moss (1993) *Curr. Opin. Genet. Dev.* 3:86-90; Broder and Earl, (1999) *Mol. Biotechnol.* 13:223-245; Timiryasova et al. (2001) *Biotechniques* 31:534-540).

Various vaccinia viruses have been demonstrated to exhibit antitumor activities. In one study, for example, nude mice bearing non-metastatic colon adenocarcinoma cells were systemically injected with a WR strain of vaccinia virus modified by having a vaccinia growth factor deletion and an enhanced green fluorescence protein inserted into the thymidine kinase locus. The virus was observed to have antitumor effects, including one complete response, despite a lack of exogenous therapeutic genes in the modified virus (McCart et al. (2001) *Cancer Res.* 1:8751-8757). In another study, vaccinia melanoma oncolysate (VMO) was injected into sites near melanoma positive lymph nodes in a Phase III clinical trial of melanoma patients. As a control, a New York City Board of Health strain vaccinia virus (VV) was administered to melanoma patients. The melanoma patients treated with VMO had a survival rate better than that for untreated patients, but similar to patients treated with the VV control (Kim et al. (2001) *Surgical Oncol.* 10:53-59).

LIVP strains of vaccinia virus also have been used for the diagnosis and therapy of tumors, and for the treatment of wounded and inflamed tissues and cells (see e.g., Lin et al. (2007) *Surgery* 142:976-983; Lin et al. (2008) *J. Clin. Endocrinol. Metab.* 93:4403-7; Kelly et al. (2008) *Hum. Gene Ther.* 19:774-782; Yu et al. (2009) *Mol. Cancer Ther.* 8:141-151; Yu et al. (2009) *Mol. Cancer* 8:45; U.S. Pat. Nos. 7,588,767; 8,052,968; and U.S. Publication No. U.S. 2004/0234455). For example, when intravenously administered, LIVP strains have been demonstrated to accumulate in internal tumors at various loci in vivo, and have been demonstrated to effectively treat human tumors of various tissue origin, including, but not limited to, breast tumors, thyroid tumors, pancreatic tumors, metastatic tumors of pleural mesothelioma, squamous cell carcinoma, lung carcinoma and ovarian tumors. LIVP strains of vaccinia, including attenuated forms thereof, exhibit less toxicity than WR strains of vaccinia virus, and result in increased and longer survival of treated tumor-bearing animal models (see, e.g., U.S. Publication No. U.S. 2011/0293527).

Vaccinia is a cytoplasmic virus, thus, it does not insert its genome into the host genome during its life cycle. Vaccinia virus has a linear, double-stranded DNA genome of approximately 180,000 base pairs in length that is made up of a single continuous polynucleotide chain (Baroudy et al. (1982) *Cell* 28:315-324). The structure is due to the presence of 10,000 base pair inverted terminal repeats (ITRs). The ITRs are involved in genome replication. Genome replication is believed to involve self-priming, leading to the formation of high molecular weight concatemers (isolated from infected cells) which are subsequently cleaved and repaired to make virus genomes (see, e.g., Traktman, P., Chapter 27, Poxvirus DNA Replication, pp. 775-798, in DNA Replication in Eukaryotic Cells, Cold Spring Harbor Laboratory Press (1996)). The genome contains approximately 250 genes. In general, the non-segmented, non-infectious genome is arranged such that centrally located genes are essential for virus replication (and are thus conserved), while genes near the two termini effect more peripheral functions such as host range and virulence. Vaccinia viruses practice differential gene expression by utilizing open reading frames (ORFs) arranged in sets that, as a general principle, do not overlap.

Vaccinia virus possesses a variety of features for use in cancer gene therapy and vaccination including broad host and cell type range, and low toxicity. For example, while most oncolytic viruses are natural pathogens, vaccinia virus has a unique history in its widespread application as a smallpox vaccine that has resulted in an established track record of safety in humans. Toxicities related to vaccinia administration occur in less than 0.1% of cases, and can be effectively addressed with immunoglobulin administration. In addition, vaccinia virus possesses a large carrying capacity for foreign genes (up to 25 kb of exogenous DNA fragments, approximately 12% of the vaccinia genome size, can be inserted into the vaccinia genome) and high sequence homology among different strains for designing and generating modified viruses in other strains. Techniques for production of modified vaccinia strains by genetic engineering are well established (Moss (1993) *Curr. Opin. Genet. Dev.* 3: 86-90; Broder and Earl (1999) *Mol. Biotechnol.* 13: 223-245; Timiryasova et al. (2001) *Biotechniques* 31: 534-540). Vaccinia virus strains have been shown to specifically colonize solid tumors, while not infecting other organs (see, e.g., Zhang et al. (2007) *Cancer Res.* 67:10038-10046; Yu et al. (2004) *Nat. Biotech.* 22:313-320; Heo et al. (2011) *Mol. Ther.* 19:1170-1179; Liu et al. (2008) *Mol. Ther.* 16:1637-1642; Park et al. (2008) *Lancet Oncol.* 9:533-542).

Coxsackie Virus

Coxsackie virus (CV) belongs to the genus Enterovirus and the family Picornaviridae and has a positive-sense single-stranded RNA genome that does not integrate into the host cell genome. CVs are classified into groups A and B, based on their effects in mice, and can cause mild upper respiratory tract infections in humans (Bradley et al. (2014) *Oncolytic Virotherapy* 3:47-55). Commonly investigated coxsackie viruses for oncolytic virotherapy include attenuated coxsackie virus B3 (CV-B3), CV-B4, CV-A9 and CV-A21 (Yla-Pelto et al. (2016) *Viruses* 8, 57). CV-A21 infects cells via the ICAM-1 (or CD54) and DAF (or CD55) receptors, which are expressed at much higher levels in tumor cells, including melanoma, breast, colon, endometrial, head and neck, pancreatic and lung cancers, as well as in multiple myeloma and malignant glioma. CV-A21 has shown promising preclinical anticancer activity in vitro against malignant myeloma, melanoma, prostate, lung, head and neck, and breast cancer cells lines, and in vivo in mice bearing human melanoma xenografts, and against primary breast cancer tumors as well as their metastases in mice (Yla-Pelto et al. (2016); Bradley et al. (2014)). A derivative of CV-A21, CV-A21-DAFv, also known as CAVATAK™, was generated from the wildtype Kuykendall strain by serial passage of CV-A21 on DAF-expressing, ICAM-1—negative rhabdomyosarcoma (RD) cells and was found to possess enhanced oncolytic properties in comparison to the parent strain. CAVATAK™ binds only to the DAF receptor, which can contribute to its enhanced tropism towards cancer cells (Yla-Pelto et al. (2016)).

CV-A21 also has been studied in combination with doxorubicin hydrochloride, exhibiting enhanced oncolytic efficiency compared to either treatment alone against human breast, colorectal and pancreatic cancer cell lines, as well as in a xenograft mouse model of human breast cancer (Yla-Pelto et al. (2016)). Since a significant portion of the population has already developed neutralizing antibodies against CV, CV-A21 therapy has been combined with immunosuppressants such as cyclophosphamide (Bradley et al. (2014)) and is a good candidate for delivery via vehicle cells.

Clinical trials have investigated the use of CAVATAK™ in patients with stage IIIc or IV malignant melanoma (NCT01636882; NCT00438009; NCT01227551), and CAVATAK™ alone or in combination with low dose mitomycin C in patients with non-muscle invasive bladder cancer (NCT02316171). Clinical trials also have studied the effects of intravenous administration of CV-A21 in the treatment of solid tumors including melanoma, breast and prostate cancer (NCT00636558). Ongoing clinical trials include the investigation of CAVATAK™ alone or in combination with pembrolizumab for treatment of patients with non-small cell lung cancer (NCT02824965, NCT02043665) and bladder cancer (NCT02043665); CAVATAK™ in combination with ipilimumab in patients with uveal melanoma and liver metastases (NCT03408587) and in patients with advanced melanoma (NCT02307149); and CAVATAK™ in combination with pembrolizumab in patients with advanced melanoma (NCT02565992).

Seneca Valley Virus

Seneca Valley Virus (SVV) is a member of the *Senecavirus* genus within the family Picornaviridae, that has a positive-sense single-stranded RNA genome and is selective for neuroendocrine cancers including neuroblastoma, rhabdomyosarcoma, medulloblastoma, Wilms tumor, glioblastoma and small-cell lung cancer (Miles et al. (2017) *J. Clin. Invest.* 127(8):2957-2967; Qian et al. (2017) *J. Virol.* 91(16): e00823-17; Burke, M. J. (2016) *Oncolytic Virotherapy* 5:81-89). Studies have identified the anthrax toxin receptor 1 (ANTXR1) as the receptor for SVV, which is frequently expressed on the surface of tumor cells in comparison to normal cells, but prior studies also have indicated that sialic acid can be a component of the SVV receptor in pediatric glioma models (Miles et al. (2017)). SVV isolate 001 (SVV-001) is a potent oncolytic virus that can target and penetrate solid tumors following intravenous administration and is attractive due to its lack of insertional mutagenesis as well as its selective tropism for cancer cells and its non-pathogenicity in humans and animals. Additionally, previous exposure in humans is rare, resulting in low rates of preexisting immunity (Burke, M. J. (2016) *Oncolytic Virotherapy* 5:81-89).

SVV-001 has shown promising in vitro activity against small-cell lung cancer, adrenal gland cortical carcinoma, neuroblastoma, rhabdomyosarcoma, and Ewing sarcoma cell lines, and in vivo activity in orthotopic xenograft mouse models of pediatric GBM, medulloblastoma, retinoblastoma, rhambdomyosarcoma and neuroblastoma (Burke (2016)). NTX-010, an oncolytic SVV-001 developed by Neotropix®, has proven feasible and tolerable for the treatment of pediatric patients with relapsed/refractory solid tumors alone or in combination with cyclophosphamide, but was limited in its therapeutic efficacy due to the development of neutralizing antibodies (Burke et al. (2015) *Pediatr. Blood Cancer* 62(5):743-750). Clinical trials include studies utilizing SV-001 in patients with solid tumors with neuroendocrine features (NCT00314925), NTX-010/SVV-001 in combination with cyclophosphamide in patients with relapsed or refractory neuroblastoma, rhabdomyosarcoma, Wilms tumor, retinoblastoma, adenocortical carcinoma or carcinoid tumors (NCT01048892), and NTX-010/SVV-001 in patients with small cell lung cancer after chemotherapy (NCT01017601).

C. ASSAYS FOR MATCHING CELL VEHICLES AND VIRUSES WITH SUBJECTS

To facilitate viral therapy, cells that serve as viral delivery vehicles are selected based on their ability to exhibit certain characteristics in vivo, such as promoting amplification of the virus, thereby increasing infection of the tumor/cancer and the subsequent potential for oncolysis; and overcoming innate (e.g., NK cell mediated) and adaptive (e.g., T cell mediated) immune barriers, and/or mixed innate/adaptive immune barriers (e.g., γδ T cell mediated). T cells are subdivided into two major populations distinguished by their surface expression of αβ and γδ T cell receptors (TCR). The gamma delta (γδ) T cells are the prototype of 'unconventional' T cells and represent a relatively small subset of T cells (For an overview, see Wu et al., *Int. J. Biol. Sci.,* 10(2):119-135 (2014); Moser and Eberl, *Immunol. Reviews,* 215(1):89-102 (2007), the contents of which are incorporated by reference herein). They are defined by expression of heterodimeric T-cell receptors (TCRs) composed of γ and δ chains. This sets them apart from the more prevalent CD4+ helper T cells and CD8+ cytotoxic T cells that express αβ TCRs. The majority of γδ T cells are activated in an MHC-independent manner, in contrast to the MHC-restricted αβ T cells. γδ T cells can recognize a variety of structurally different ligands that vary in size, composition and molecular structure, including but not limited to non-peptidic antigens, MHC and non-MHC cell surface molecules, soluble proteins, sulfatide and the like. γδ T cells can recognize MHC molecules such as group 1(CD1a, b, c) and group 2 (CD1d) CD1 molecules (adaptive immunity). However, NKG2D (associated with NK cell-mediated immunity), which is expressed on Vγ9Vδ2 T cells (a γδ T cell population), also plays a role in the ligand recognition by γδ T cells (innate immunity). NKG2D ligands are not expressed by most normal tissues but are upregulated by many tumor-cell types, which are required for tumor cell-recognition by Vγ9Vδ2 T cells. Some soluble proteins also are involved in the recognition by γδ T cells, for example, bacterial proteins including the unrelated staphylococcal enterotoxinA (SEA) and the toxin listeriolysin O (LLO). γδ T cells also can recognize heat shock proteins (HSPs), which does not need antigen processing and can occur in the absence of any antigen presenting cells (APCs). Non-peptide antigens can be important targets for T-cell recognition, such as those occurring during infections with fungus, bacteria, or protozoa. Butyrophilin (BTN3A1) has been identified as phosphorylated antigen-presenting molecule (APM) to Vγ9Vδ2 T cells, which belongs to a family of immunoglobulin-like molecules with immunomodulatory functions. It plays an important role in Vγ9Vδ2 TCR recognition of prenyl pyrophosphates and can function as a sensor for the intracellular levels of phosphorylated antigens.

While autologous cells can be used as vehicles, their availability can be limiting and obtaining the cells from the subject can sometimes be onerous and/or expensive. Certain cell vehicles, such as mesenchymal stem cells (MSCs), have been shown to promote viral amplification and overcome innate/adaptive immune barriers even in allogeneic settings, in part due to their immunosuppressive properties. For example, it is shown herein that adipose-derived stem cells (ADSCs) can eradicate even resistant tumor cells through their combined properties of facilitating potent viral amplification and sensitizing the tumor cells to viral infection. The ability to use "off the shelf" allogeneic cell lines, including allogeneic mesenchymal stem cells such as ADSCs as delivery vehicles, however can be restricted by subject-specific differences that sometimes lead to a "mismatch" (insufficient viral amplification; insufficient evasion of the subject's immune system and/or insufficient immunosuppression, including transient or local immunosuppression), in part due to anti-cell vehicle cytotoxic IFNγ-mediated responses. These innate and/or adaptive immune responses can compromise therapeutic efficacy, e.g., by eliminating the cell vehicles or inducing an anti-viral state. Other studies also have shown that MHC-mismatched MSCs sometimes are not immune privileged (Berglund et al. (2017) *Stem Cell Research & Therapy,* 8:288). Accordingly, there is a need for tests that screen for cell vehicles that are matched with a particular subject for virotherapy and permits the use of "off the shelf" allogeneic cell-based delivery platforms. Provided herein are assays that identify subject-specific specific "matched" cell vehicles for administering virotherapy to the subject. Also provided herein are modified cell vehicles that are sensitized and/or engineered in one or more ways for improved cell delivery (see, e.g., Section D below). Any of the cell vehicles provided herein, including the modified cell vehicles (sensitized and/or engineered), can be tested using the assays provided herein for their matching compatibility with a subject to be administered virotherapy through cell vehicle-based delivery.

Overview

Provided herein are assays ("matching" assays), one or a combination of which can be used to identify a cell vehicle as being "matched" with a subject for delivery of an oncolytic virus to the subject. The assays provided herein measure subject-specific responses to cell vehicle-mediated delivery of a virus, thereby identifying whether a cell vehicle is suitable for administering a virus to the specific subject, i.e., whether it is "matched" to the subject. Any one of the assays A-F, summarized below and then elucidated in greater detail herein, or any combination thereof, can be used to identify a cell vehicle that is matched with a subject of interest. One or more of the assays A-F can be used to screen a single cell vehicle of interest for its suitability as a match for a subject, or more than one or a plurality/panel of cell vehicles can be screened and ranked according to their desirability as a match for a subject, in general #1 being the highest rank and subsequent numbers (2, 3, 4, . . . etc.) indicating lower ranks, although any suitable ranking system to identify suitable match(es) can be used. The ranking can be based on a single assay, if only one of the assays A-F is performed, or can be a combined ranking based on the performance of the cell vehicles in more than one assay. An overview of each of the Matching Assays, A-F is provided below:

A. Haplotype Analysis (a) Overview of Haplotypes

A haplotype is a set of DNA variations or polymorphisms that are inherited together, and can refer to a group of alleles or a set of single nucleotide polymorphisms (SNPs) located on the same chromosome.

Major Histocompatibility Complex (MHC)

The major histocompatibility complex (MEW) on chromosome 6 comprises the human leukocyte antigen (HLA) genes, which encode a set of cell surface proteins essential for antigen presentation for the adaptive immune system. MHC molecules bind antigens derived from pathogens and display them on the cell surface for recognition by the appropriate T-cells, thus mediating the interactions of immune cells with each other and with other cells. The MEW determines compatibility of donors for organ transplant, as well as one's susceptibility to an autoimmune disease via cross-reacting immunization.

The MEW gene family is divided into three subgroups: class I, class II, and class III. MHC class I molecules bind peptides in the rough endoplasmic reticulum that are derived from intracellular proteins. They are found on all nucleated cells and interact with CD8 receptors on the surfaces of cytotoxic T lymphocytes (CTLs), mediating cellular immunity. MEW class I comprises three α-chain genes: HLA-A, HLA-B and HLA-C. MHC class II molecules, which bind peptides from phagocytized proteins, are expressed by antigen-presenting cells (APCs), including macrophages and dendritic cells (DCs), and interact with CD4 receptors on the surfaces of helper T cells, mediating adaptive immunity. MEW class II comprises three pairs of α- and β-chain genes: HLA-DP, HLA-DQ and HLA-DR, with the HLA-DR cluster containing an extra β-chain that can pair with the DRα chain, resulting in four types of MEW class II molecules. The combination of HLA alleles that is present on a single chromosome is called the HLA haplotype. HLA loci are among the most polymorphic in the human genome, with more than 12,000 alleles for class I and more than 4,000 alleles for class II. It is thus unlikely for two individuals to possess the same HLA haplotype (Meyer et al. (2018) *Immunogenetics* 70:5-27).

MHC Class I

MHC class I comprises HLA-A, HLA-B and HLA-C molecules. Individual loci are designated by upper-case letters, for example, HLA-A, and alleles are designated by numbers following an asterisk, for example HLA-A*0201. Since MHC alleles are co-dominantly expressed and each person carries 2 alleles of each of the 3 MHC class I genes, there are six possible different types of MHC class I (Janeway C A Jr., et al., "Immunobiology: The Immune System in Health and Disease." 5th edition. *New York: Garland Science;* 2001. The major histocompatibility complex and its functions. Available from ncbi.nlm.nih.gov/books/NBK27156/).

MHC class I molecules are expressed by most cell types and bind peptides derived from intracellular proteins, after they have been degraded by the proteasome and translocated to the endoplasmic reticulum, then traffic the peptides to the cell surface, and present them to cytotoxic CD8 T cells. These peptides are short and are typically 8-11 amino acids long (Kaczmarek et al. (2017) *Arch. Immunol. Ther. Exp.* 65:201-214; Reeves and James (2016) *Immunology* 150:16-24).

MHC Class II

MHC class II comprises the HLA-DP, HLA-DQ and HLA-DR isotypes, each containing an alpha and a beta chain that are highly polymorphic, with the exception of the DR alpha chain. Every individual inherits a pair of HLA-DP genes, a pair of HLA-DQ genes, one HLA-DRA gene and one or more HLA-DRB genes from their parents, such that a heterozygote can have 8 different MHC class II molecules on their cells. Different combinations of α and β chains, encoded by different chromosomes, can give rise to an even larger number of different MHC class II molecules (Janeway C A Jr., et al., "Immunobiology: The Immune System in Health and Disease." 5th edition. New York: Garland Science; 2001. The major histocompatibility complex and its functions. Available from ncbi.nlm.nih.gov/books/NBK27156/).

MHC class II molecules are expressed by antigen-presenting cells, including DCs, B cells and monocytes/macrophages, and bind to peptides from proteins derived from phagocytosed pathogens after they have been degraded by lysosomes, then traffic them to the cell surface, and present them to helper T cells. These peptides are longer than the peptides presented by MHC class I molecules, and are usually 14-20 amino acid residues long (Kaczmarek et al. (2017) *Arch. Immunol. Ther. Exp.* 65:201-214).

MHC Class IB (including MIC, HLA-E)

In addition to the classical MHC class I and class II genes, there are genes encoding MHC class I-type molecules that show little polymorphism, known as MHC class IB genes, which include members of the MIC gene family, HLA-G and HLA-E. Only two of the five MIC genes, MICA and MICB, are expressed, particularly in epithelial cells and fibroblasts, and play a role in innate immunity. The MIC receptor, which is expressed by NK cells and T cells, such as γδ T cells, is comprised of an NKG2D chain (an activating member of the NKG2 family of NK cell receptors), and a signaling protein called DAP10. HLA-E complexes with a specific subset of peptides derived from the leader peptides of other HLA class I molecules, and the peptide:HLA-E complex binds to the inhibitory NKG2A receptor on NK cells, resulting in the inhibition of NK cell cytotoxic activity (Janeway C A Jr., et al., "Immunobiology: The Immune System in Health and Disease." 5th edition. New York: Garland Science; 2001. The major histocompatibility complex and its functions. Available from ncbi.nlm.nih.gov/books/NBK27156/).

CD1 Family

The CD1 family, which is expressed mainly on antigen-presenting cells and thymocytes and presents antigens to $CD4^+$ T cells, $CD8^+$ T cells, double negative T cells, γδ T cells, iNKT cells and NKT cells, is a family of MHC class I-like genes that lie outside the MHC region. Unlike MHC class I and class II molecules, CD1 molecules are capable of binding and presenting lipid antigens. There are five CD1 proteins, CD1a-e, with CD1a-d displaying lipid antigens on the cell surface. CD1a-c, which are expressed mostly by antigen-presenting cells, present antigens to clonally diverse T cells that mediate adaptive immunity, while CD1d molecules are expressed by several cell types, including DCs, B cells, monocytes, macrophages, keratinocytes and gastrointestinal epithelial cells, and present antigens to NKT cells (Kaczmarek et al. (2017) *Arch. Immunol. Ther. Exp.* 65:201-214).

KIRs and KIR Ligands

NK cells express killer Ig-like receptors (KIRs) that recognize and bind to MHC class I molecules (KIR ligands). There are 17 KIR genes, found on chromosome 19 in the leukocyte receptor complex, and most of these genes have multiple alleles. The nomenclature of KIR genes is based on the number of extracellular immunoglobulin-like domains (2D or 3D), the length (L=long, S=short) of the cytoplasmic tail, and if the gene is a pseudogene (P). Whereas most KIRs are inhibitory, NK cells also possess activating KIRs. The binding of inhibitory KIRs to their ligands inactivates the NK cells. In infected or neoplastic cells, the expression of classical class I loci may decrease, reducing the availability of ligands for KIR molecules and activating NK-mediated cell lysis (Benson Jr. and Caligiuri (2014) *Cancer Immunol Res.* 2(2):99-104).

KIR molecules are highly polymorphic and the KIR gene clusters lead to two distinct haplotypes, known as group A and group B haplotypes. Group A haplotypes consist of a fixed number of genes and have only inhibitory KIRs, while group B haplotypes have a variable set of genes and include both inhibitory and activating KIRs (Benson Jr. and Caligiuri (2014) *Cancer Immunol Res.* 2(2):99-104).

While KIR molecules and their ligands (MHC class I molecules) are inherited independently, the inheritance of specific KIR/HLA combinations have been associated with susceptibility or resistance to viral infection, autoimmunity and cancer. For example, inhibitory KIR/HLA interactions prevent the lysis of cancer cells, but KIR-ligand mismatch leads to increased tumor cell lysis in patients receiving allogeneic donor NK cells (Benson Jr. and Caligiuri (2014) *Cancer Immunol Res.* 2(2):99-104).

(b) Haplotype Matching Analysis

A haplotype matching analysis can be conducted as follows:

i. Obtain whole blood or an alternate source of DNA (e.g., soft tissue samples, semen, saliva, skin cells, hair roots, etc.) from the subject.

ii. Extract gDNA from the whole blood or other source.

iii. Analyze subject-specific genetic polymorphisms (using, e.g., Next Generation sequencing) at one or more of the following loci:
  a. Classic MHC I/II Haplotypes
  b. KIR Haplotype and Ligands
  c. Non-classic MHC Haplotypes (e.g., HLA-E, CD1a/b/c/d; MIC-AB)

iv. The genetic polymorphism profile of the subject, as identified in iii above, is compared with the genetic polymorphism profiles of a cell vehicle or more than one cell vehicle or a panel of cell vehicles. Cell vehicles that have at least 10%, 20%, 30%, 35%, 40%, 45%, 50%, 55%, 60%, 65%, 70%, 75%, 80%, 85%, 90%, 95% or more matching loci with the subject can be identified as matches for delivery of a virus to the subject. In some examples, the genetic polymorphism profile of the cell vehicle at one or more of the loci indicated in iii matches 100% with the genetic polymorphism profile of the subject. In other examples, the genetic polymorphism profile of the cell vehicle at one or more of the loci indicated in iii matches at least 50%, 55%, 60%, 65%, 70%, 75%, 80%, 85%, 90%, 95% with the genetic polymorphism profile of the subject, or is a match of between at or about 50% to at or about 99% with the genetic polymorphism profile of the subject, to be identified as a matching cell vehicle for the subject.

v. When more than one cell vehicles is analyzed for haplotype matching, the cell vehicle with the maximum number of matching loci is identified as most compatible, with a 100% match being best.

vi. In some embodiments, an in silico software algorithm/program can be used to identify the loci that are predictive of compatibility and guide the identification of the most compatible matches.

B. Ability to Recruit/Sensitize Resistant Tumor Cells and/or Promote Viral Amplification In this matching assay, migration assays are performed to measure the ability of the cell vehicle(s) to recruit/sensitize tumor/cancer cells to viral infection and/or promote viral amplification. The migration assays can be set up in standard transwell, bio-gel (hydrogel, Matrigel) or extracellular matrix (collagen/fibronectin)-coated surface systems, where each of the components of the assay (e.g., solid tumor biopsy and Cell Vehicles) are deposited in separate chambers (separated by semi-permeable membrane, e.g.) or at adjacent locations, depending on the type of system. The method is performed as follows:

i. Obtain a tumor biopsy from the subject, which can include a surgical section, fine needle aspirate, needle core biopsy or primary tumor cells/tumor organoids derived after tissue processing (enzymatic digestion with Collagenase, Dispase, DNase, etc.). Culture the solid biopsy/organoids/tumor cells in the appropriate transwell/bio-gel/extracellular matrix-coated surface system.

ii. Perform a migration assay using the tumor biopsy and one or more cell vehicles, or a panel of cell vehicles, each type of Cell Vehicle (if more than one is screened) being labelled with a unique detectable marker (e.g., fluorescent marker). The percent of labelled cells (for each type of Cell Vehicle) that accumulates in/migrates towards/clusters around the solid tumor biopsy, the primary tumor cells, or the tumor organoids is the cell vehicle-to-tumor migration score (CTMS), with 100% being the best and 0% being the worst, with CTMS scores of at least or about 10%, 15%, 20%, 25%, 30%, 35%, 40%, 45% or 50% to be considered a match. In some examples, a CTMS score of at least 20% for a cell vehicle is considered a match between the cell vehicle and the subject (or the type of tumor/cancer being treated). In other examples, obtaining a CTMS score of between about 20% to about 60% for a cell vehicle is considered a match between the cell vehicle and the subject (or the type of tumor/cancer being treated).

iii. Label the tumor biopsy or biopsy-derived primary tumor cells/organoids (e.g., using a fluorescent marker) and perform a migration assay using the labelled tumor biopsy and each of the Cell Vehicles of the sub-panel of Step 2 above, or of the entire panel if a pre-screen is not performed. The percent of labelled tumor cells, or tumor-associated stromal cells, migrating out of the solid tumor and towards the Cell Vehicles is the tumor-to-cell vehicle migration score (TCMS), with 100% being the best and 0% being the worst, with TCMS scores of at least or about 10%, 15%, 20%, 25%, 30%, 35%, 40%, 45% or 50% to be considered a match. In some examples, a TCMS score of at least 20% for a cell vehicle is considered a match between the cell vehicle and the subject (or the type of tumor/cancer being treated). In other examples, obtaining a TCMS score of between about 20% to about 60% for a cell vehicle is considered a match between the cell vehicle and the subject (or the type of tumor/cancer being treated).

iv. Prepare samples as in ii. and iii. above, except perform the migration assay in the presence of different viruses to test if some viruses interfere with the migration of the tumor or carrier cells. Virus can be added directly to the co-culture or pre-loaded onto the carrier cells prior to their co-culture with the biopsy specimens. Compute the virus-corrected CTMS (VCTMS) and TCMS (VTCMS) as above, reflecting the ability of viruses to interfere with cell migration and viability.

v. A cumulative mean Migration/Recruitment Score (MRS) can be computed for each subject tumor biopsy/Cell Vehicle/Virus combination as follows:

MRS (Biopsy, Cell Vehicle, Virus combination)= [VCTMS (Biopsy, Cell Vehicle, Virus)+VTCMS (Biopsy, Cell Vehicle, Virus)]/2; or MRS (Biopsy, Cell Vehicle combination)=[CTMS (Biopsy, Cell Vehicle)+TCMS (Biopsy, Cell Vehicle)]/2.

MRS scores of at least or about 10%, 15%, 20%, 25%, 30%, 35%, 40%, 45% or 50% for a cell vehicle can be considered a match between the cell vehicle and the subject (or type of tumor/cancer being treated). In some examples, a MRS score of at least 20% for a cell vehicle is considered a match between the cell vehicle and the subject (or the type of tumor/cancer being treated). In other examples, obtaining a MRS score of between about 20% to about 60% for a cell vehicle is considered a match between the cell vehicle and the subject (or the type of tumor/cancer being treated). This matching assay identifies Cell Vehicles/Virus-associated Cell Vehicles that have the potential to successfully home towards the tumor mass or attract/recruit migrating tumor cells, thus facilitating virus spread and infection. MRS scores can be used to rank viruses based on their ability not to interfere with the proper migration of particular cell vehicles, or alternatively to rank cell vehicles based on their resistance to virus-mediated suppression of cell migration, thus permitting identification of an optimal subject-specific combination of virus and carrier vehicle.

One or more of the scores set forth in ii-v can be measured, to identify a good match.

C. Ability of Subject-Derived Immune Cells to Promote Viral Amplification

This matching assay measures cell vehicle-mediated viral amplification in the presence of subject-derived immune cells. The assay is performed as follows:

i. Obtain subject-derived immune cells (e.g., whole blood, PBMCs)

ii. Co-culture the PMBCs with Cell Vehicle and Virus. The order of addition can be:

Simultaneous, or

First incubate Cell Vehicle+Virus (range of at or about 15 min. to at or about 48 hours; in some embodiments the range is between at or about 1 hours to at or about 5 hours; in particular embodiments the incubation time is at or about 2 hours), then add to PBMCs Incubate the resulting co-culture for at or about 24 hours to at or about 1 week (in embodiments, range of at or about 15 minutes to at or about 70 hours; in some embodiments the range is between at or about 20 hours to at or about 60 hours; in particular embodiments the incubation time is at or about 48 hours)

iii. Measure virus amplification (e.g., by fluorescence imaging or viral plaque assay (VPA)), compare against control under equivalent conditions except for the absence of PBMCs.

iv. If virus amplification in the presence of PBMCs is under 10% of the value obtained in the absence of PBMCs, the cell vehicle is considered to be incompatible or not a match with the subject. If virus amplification in the presence of PBMCs is at least or about 10%-30% of the value obtained in the absence of PBMCs the match can be considered adequate, if virus amplification in the presence of PBMCs is at least or about 30%-80% of the value obtained in the absence of PBMCs the match can be considered moderate, if virus amplification in the presence of PBMCs is at least or about 80% or greater of the value obtained in the absence of PBMCs the match can be considered good.

v. An immunological virus amplification score (IVAS) can be computed for each subject, cell vehicle, virus combination using the formula:

IVAS=(pfu (or fluorescence) of virus from Cell Vehicle+PBMC co-cultures/pfu of virus from Cell Vehicle alone). Ratio of 0.1 or more can be considered compatible, with degrees of matching as described in iv. above (10% or more of the value obtained in the absence of PBMCs, with a ratio of 1.0 being the highest).

vi. The IVAS score optionally can be corrected for the effect of serum (Subject/Patient Serum Resistance Screen). The IVAS score only takes into account cellular immunity; if the subject's serum significantly suppresses viral amplification, then even if the IVAS score is acceptable (e.g., 0.1 or greater), there nonetheless may not be a good match. The correction can be performed as follows:

Add serum from the subject to the co-culture of ii. above in the amount of 10-50% of the co-culture volume.

The Patient (Subject) Serum Resistance Score can be computed using the formula:

PSRS=(pfu without serum−pfu with serum)/pfu without serum (×100, to convert ratio to percent value). The higher the serum resistance score, the more the serum is interfering with viral amplification.

IVAS (PSRS corrected)=IVAS×(1-PSRS)(×100, to convert ratio to percent value).

D. Measurement of Immunological Compatibility with the Subject

In this matching assay, i. and ii. is performed as in part C. above iii. In the co-cultures, measure one or more of the markers below (e.g., by flow cytometry using fluorescently labelled antibodies against the markers; specific markers are listed in the detailed outline)

Add fluorescently labelled antibodies against the marker(s) of interest, measure up-regulation (if any) in the presence of the Cell Vehicle (control: PBMC alone; sample: PBMC+Cell Vehicle)
   a. IFNγ
   b. Markers associated with T/NK/NKT cell-mediated cytotoxicity
   c. Markers associated with T/NK/NKT cell expression of activator/effector function markers iv. Measure (by flow cytometry) fluorescence in the sample and in the control.

v. Compute an Immunological Compatibility Score (ICS): Ratio of (fluorescence in sample/fluorescence in control). If more than one marker is measured, a mean ICS score can be computed as an average of the measured ICS scores, or some of the scores can be weighted, e.g., based on their established association with decreased virus amplification.

vi. Ratio of 1-1.05 or less means the Cell Vehicle has no effect on the subject's immune response, i.e., a good match
   Ratio of 1.05-1.5 indicative of moderately compatible Cell Vehicle
   Ratio of 1.5-2 indicative of an adequately compatible Cell Vehicle
   Ratio greater than 2 indicates an immunologically incompatible match E. Measurement of Cell Vehicle-Mediated Suppression of Anti-Viral Immunity Perform i.-iv. as in part D. above, except in addition to the controls: PBMC alone and PBMC+Cell Vehicle, also include the following samples: PBMCs+Virus; PBMC+Cell Vehicle+Virus v. Compute an Immunological Suppression Score (ISS) for one or more marker: Ratio of

[(Marker level in PBMC+Virus co-culture+Marker level in PBMC+Cell Vehicle co-culture)−Marker level in PBMC+Virus+Cell Vehicle co-culture]/(Marker level in PBMC+Virus co-culture+Marker level in PBMC+Cell Vehicle co-culture)(×100, for % immunosuppression).

vi. ISS % scores of higher than 0% are considered favorable, i.e., indicative of the Cell Vehicle's ability to suppress anti-viral immunity and permit the virus to infect the tumor cells. If more than one marker is measured, a mean ISS score can be computed as an average of the measured ISS scores.

F. Measurement of Immunomodulative Effects of Cell Vehicles by Analyzing Supernatants The measurements described in sections D. and E. above also could be performed with the supernatants of the co-cultures by, e.g., ELISA or Luminex Assay. Although the specific responding cell population cannot be identified (since the cells/virus in the co-cultures are not being analyzed directly, the ISS and ICS scores measured in the supernatants also can be informative regarding compatibility; these scores are determined as described above in sections D. and E.

In some embodiments of the methods provided herein the cell vehicle or vehicles can be subjected, optionally, to a pre-screen to determine the ability of the cell vehicle to promote viral amplification in the absence of subject-specific cells. For a given viral therapy of choice (e.g., Vaccinia virus), the cell vehicle(s) or panel of available Cell Vehicles (Autologous/Allogeneic/Original/Sensitized/Engineered) can be screened for their ability to promote viral amplification. The rate of viral amplification (pfu/cell) for each type of Cell Vehicle, normalized against the number of infected cells, under equivalent multiplicity of infection (MOI in the range of 0.001 to 1) and co-culture conditions is determined (e.g., using VPA—virus plaque assay). An optimal read out time point for each type of virus used (e.g., between at or about 1 day and at or about 5 days). The pfu/cell for each type of cell vehicle is calculated and used as a virus amplification score (VAS) of the cell vehicle.

In the pre-screen, Cell Vehicles that produce pfu/cell of at least 10 can be selected for further screening by matching to the subject according to any of the methods summarized in A-F and described further herein (10-100 is good, 100-1000 is very good, greater than 1000 is excellent). The sub-panel (or selected cell vehicle or vehicles) can be screened for optimal matching with the subject.

In the methods provided herein, a match between a cell vehicle and a subject can be identified using one or more of the assays A-F as summarized above. In some embodiments, more than one cell vehicle, or a plurality or panel of cell vehicles are analyzed according to one or more of the matching assays A-F. The cell vehicles are then ranked according to their compatibility with the subject, ranging from "best match" (e.g., Rank 1) to worst match (e.g., a higher number rank). For each cell vehicle, a cumulative rank is computed, depending on the number of assays performed:

Cumulative Rank=Rank (VAS)+Rank (IVAS)+Rank (ICS)+Rank (ISS)+Rank (MRS)/5 (if all these scores are obtained; one could obtain fewer than 5 scores). The cell vehicles are then ranked in order of their suitability as a match. Haplotype analysis also can be considered in ranking the cell vehicles.

Detailed Methods for the Matching Assays a. General Methods for Measurements Performed in the Assays The following are general methods used to measure certain parameters in the matching assays provided herein:

Virus Plaque Assays (VPAs)

Virus Plaque Assay (VPA) is used to measure the virus titer, or the concentration of viruses in a sample. For example, VPA can be used to quantify virus particle amplification under different conditions and with different combinations of patient-derived immune cells and cell-based delivery vehicles.

Virus containing samples are stored at −80° C. and subjected to a three-fold freeze (−80° C.)/thaw (+37° C.) cycle followed by sonication on ice-cold water for three 1 min intervals, one min apart. Sonicated samples are serially diluted in vaccinia virus infection medium (DMEM supplemented with 2% FBS, L-Glutamine and Penicillin/Streptomycin). Plaque assays are performed in 24-well plates in duplicate wells. Briefly, 200,000 CV-1 monkey kidney cells are plated in 1 mL D10 medium per well, overnight. Supernatants are aspirated and 10-fold serial dilutions of the virus-containing sample are applied to the CV-1 monolayer at 200 µL/well. Plates are incubated for 1 h at 37° C. (incubator) with manual shaking every 20 min. 1 mL CMC medium is layered gently on top of the cells and plates are incubated for 48 h. CMC overlay medium is prepared by autoclaving 15 g Carboxymethylcellulose sodium salt (Sigma-Aldrich, C4888) and re-suspending with overnight stirring at RT in 1 L DMEM, supplemented with Penicillin/ Streptomycin, L-Glutamine, and 5% FBS, with short-term storage at 4° C. Plaques are counted after fixing the cells by toping the wells with Crystal Violet solution (1.3% Crystal violet (Sigma-Aldrich, C6158), 5% Ethanol (Pure Ethanol, Molecular Biology Grade, VWR, 71006-012), 30% Formaldehyde (37% v/v formaldehyde, Fisher, cat #F79-9), and double distilled water) for 3-5 h at room temperature, followed by washing the plates in tap water and drying overnight. The virus tier is calculated in plaque-forming units (PFU) per sample.

Flow Cytometry

Flow cytometry can be utilized for cell counting, cell sorting and biomarker/cell surface antigen detection. For example, flow cytometry can be performed using gating parameters to identify specific immune cell populations including T cells (such as, but not limited to, CD3, CD4, CD8), γδ T cells (e.g., $CD3^+$ $NKp46^+$ and $CD3^+$ $NKp46^-$ populations of cells and others), NK cells (such as, but not limited to, NKp46 (CD335), CD16, CD56) and NKT cells (such as, but not limited to, CD3, CD16, CD56, NKp46, aGalCer-CD1d tetramers). Immune responses, for example, are evaluated by analyzing various activation/effector function parameters using flow cytometry, including, but not limited to: CD69, CD25, CD71, CD27 (CD70L), CD154 (CD40L), CD137 (4-1BB), CD44, CD45RA, CD45RO, CD278 (ICOS), CD127 (IL-7RA), CD183 (CXCR3), CD197 (CCR7), CD39, CD73, CD314 (NKG2D), PD-1, CTLA-4, IFNα/β, IFNγ, TNFα, IL-2, IL-4, IL-5, IL-9, IL-10, IL-12, IL-13, IL-15, IL-18, IL-21, IL-22, IL-23, IL-25, GM-CSF, IL-17, IL-6, CD107a, CD107b, TGFβ, Perforin, Granzyme B, IL-1a/IL-1b, G-CSF, RANTES, EXOTAXIN, MIP-1b, MCP-1, EGF, HGF, VEGF, IL-1RA, IL-7, IP-10, IL-2R, MIG and IL-8, among others. Flow cytometry also is used to detect eGFP expression by genetically engineered ADSCs, and to measure the percentages of cells infected with L14 VV (TK-inserted Turbo-FP635 engineered LIVP strain of vaccinia virus), for example.

If the biomarker/antigen to be detected is on the cell surface, such as CD markers, surface staining is used. However, if intracellular proteins such as cytokines or transcription factors are to be detected, then additional fixation and permeabilization steps are required prior to antibody staining.

Surface Staining

For flow cytometry analysis of co-cultures, for example, co-cultures of PBMCs and stem cells are recovered by pipetting, transferred to V-bottom plates, and washed with FACS Buffer (1×PBS with 1% FBS). The cells are then surface stained for 30 min at 4° C. in FACS Buffer supplemented with the appropriate antibody cocktail. For example, for detection of CD3 on the surface of T cells or NKT cells, anti-human CD3-PerCP/Cy5.5 (BioLegend, cat #300328, at 1:50) is used; for detection of CD335/NKp46 on the surface of NK cells, for example, anti-human CD335/NKp46-PE (BioLegend, cat #331908, at 1:50) is used; and for detection of CD69 on the surface of T cells, NK cells and NKT cells, for example, anti-human CD69-APC (BioLegend, cat #310910, at 1:50) is used. The FACS buffer also can contain a viability probe (ThermoFisher Scientific, LIVE/DEAD Fixable Violet Dead Cell Stain Kit, for 405 nm excitation, cat #L34964, at 1:1000). After staining, the cells are washed twice with FACS Buffer, fixed in 2% PFA in 1×PBS for 15 min at RT, washed again with FACS Buffer to remove PFA, and then analyzed on a BD FACSAria II flow cytometer (BD Biosciences, San Jose, Calif.).

For the evaluation of cytotoxic functions, for example, by detection of CD107a on the surface of immune cells, anti-human CD107a-AlexaFluor 488 (BioLegend, cat. #328610) is added directly to the co-cultures at 1:20 (10 μl/well), 5 hours prior to recovery and surface staining, followed by the addition of Monensin (BioLegend, cat. #420701-BL, 1000×) at 1:1000 an hour later for an additional 4h incubation at 37° C.

Intracellular Staining

To evaluate IFNγ production in activated NK, NKT and T cells, including γδ T cells, for example, intracellular staining is required. Brefeldin A solution (BioLegend, cat. #420601-BL, 1000×) is added at 1:1000 an hour after stimulation, or 4 h prior to recovery and surface staining. If cells are to be evaluated for both IFNγ production and CD107a surface exposure, Monensin (BioLegend, cat. #420701-BL, 1000×) and Brefeldin A are added together. Following standard surface and viability staining, cells are processed using the eBioscience Intracellular Staining Buffer Set (ThermoFisher, cat. #00-5523). Briefly, following surface staining with or without anti-CD107a-AlexaFluor 488, cells are fixed for 30 min with 1 part Fixation/Permeabilization Concentrate (ThermoFisher, cat. #00-5123) and 3 parts of Fixation/Permeabilization Diluent (ThermoFisher, cat. #00-5223), washed twice with 200 μl/well Permeabilization Buffer 10× (ThermoFisher, cat. #00-8333) diluted 1:10 in double distilled water, and stained with anti-human IFNγ-APC antibody (BioLegend, cat. #502512, at 1:50) in Permeabilization Buffer for 1 h at room temperature. Cells are then washed twice in Permeabilization Buffer, fixed in 2% PFA in 1×PBS for 15 min at room temperature, washed again with FACS Buffer to remove PFA, and analyzed on a BD FACSAria II flow cytometer (BD Biosciences, San Jose, Calif.).

ELISPOT

Enzyme-Linked ImmunoSpot (ELISPOT) is an immunoassay that is widely utilized for monitoring cellular immune responses, based on its sensitive and accurate identification and quantification of rare antigen-specific and cytokine-producing immune cells, and its ability to detect single positive cells within a population of PBMCs. As with flow cytometry, ELISPOT can be used to analyze immune activation and immunosuppression, based on a panel of markers identifying specific immune cell populations such as T cells, including γδ T cells (such as, but not limited to, CD3, CD4, CD8), NK cells, including γδ T cells (such as, but not limited to, NKp46 (CD335), CD16, CD56) and NKT cells (such as, but not limited to, CD3, CD16, CD56, NKp46, aGalCer-CD1d tetramers), as well as a panel of activation/effector function markers, including, but not limited to: CD69, CD25, CD71, CD27 (CD70L), CD154 (CD40L), CD137 (4-1BB), CD44, CD45RA, CD45RO, CD278 (ICOS), CD127 (IL-7RA), CD183 (CXCR3), CD197 (CCR7), CD39, CD73, CD314 (NKG2D), PD-1, CTLA-4, IFNα/β, IFNγ, TNFα, IL-2, IL-4, IL-5, IL-9, IL-10, IL-12, IL-13, IL-15, IL-18, IL-21, IL-22, IL-23, IL-25, GM-CSF, IL-17, IL-6, CD107a, CD107b, TGFβ, Perforin, Granzyme B, IL-1a/IL-1b, G-CSF, RANTES, EXOTAXIN, MIP-1b, MCP-1, EGF, HGF, VEGF, IL-1RA, IL-7, IP-10, IL-2R, MIG and IL-8, among others.

ELISPOT assays are very similar in technique to sandwich enzyme-linked immunosorbent assays (ELISAs). In a typical protocol, first, the PVDF membranes are prepared in 96-well plates by incubating in 35% ethanol for 30s, followed by washing with 200 μl/well phosphate buffered saline (PBS) 3 times to remove ethanol. The plates are then coated with capture antibody (diluted in PBS to approximately 2-15 μg/ml, 100 μl/well), specific for the analyte of interest, and incubated overnight at 4° C. The wells are then emptied and washed 3 times with 200 µl/well PBS to remove unbound capture antibody, and the membranes are blocked, for example, using 100 µl/well 2% dry skim milk or 200 µl/well 1% BSA in PBS, and incubated for 2 h at room temperature, to prevent non-specific binding to the membrane. The plates are then washed with 200 µl/well PBS 3 times and air dried, then used in the next step or stored at 4° C. with desiccant, for up to 2 weeks. The cells, for example, PBMCs, are diluted and pipetted into the wells, typically with $2 \times 10^4$ to $5 \times 10^5$ PBMCs per well, the appropriate culture medium is added and the plates are placed in a humidified 37° C. $CO_2$ incubator for a specified period of time, usually 24-72 h, for example, 24 h for IFNγ, IL-2 and TNFα, and 48 h for IL-4, IL-5 and IL-10. Cytokines, such as IFNγ, that are secreted by activated cells bind the immobilized antibody on the PVDF membrane. The wells are washed 3 times with 200 µl/well PBS, then 3 times with 200 µl/well PBS/0.1% Tween-20 to wash away cells and unbound analyte, and a biotinylated detection antibody, specific for the analyte of interest, diluted to approximately 0.25-2 µg/well in PBS/1% BSA (100 µl/well) is added and incubated for 1-2 h at room temperature, or at 4° C. overnight. The plates are then washed 3-4 times with 200 µl/well PBS 0.1% Tween-20 to remove any unbound biotinylated, and streptavidin conjugated to an enzyme, such as horseradish peroxidase (HRP) or alkaline phosphatase (AP) (100 µl/well, diluted to 1:500-1:2000 in PBS-Tween-BSA), is added to each well and the plates are incubated at room temperature for 1-2 h. Alternatively, the detection antibody can be directly conjugated to the enzyme. Unbound enzyme is washed away (3×200 µl/well PBS/0.1% Tween-20 and 3×200 µA/well PBS) and a precipitating substrate solution (e.g., AEC for HRP or BCIP/NBT for AP) is added. A colored precipitate forms, which is red for HRP, or blackish blue for AP, and each colored spot typically represents an individual cytokine-secreting cell. The reaction is stopped by gently washing with distilled water, the plates/membranes are dried at room temperature, and the spots can be counted manually (e.g., with a dissecting or stereomicroscope) or with an automated ELISPOT reader. If multiple cytokines are to be measured in the same assay, fluorescently-labeled anti-cytokine antibodies are used and the modified assay is known as a FluoroSpot assay.

b. Selection of Subject-Derived Immune Cells

1. PBMCs—Can be isolated using, e.g., Ficoll-Paque Centrifugation.
2. Whole Blood—whole heparinized blood includes blood cell types other than PBMCs, e.g., neutrophils.
3. Whole Blood with RBC lysis—Removes high number of erythrocytes and can achieve higher concentration of lymphocytes and myeloid cells. Washing steps following this lysis optionally can be performed to remove subject serum/plasma, as during Ficoll-Paque PBMC isolation
4. PBMCs/Whole Blood with RBC lysis supplemented with Autologous Subject Plasma/Serum—Subject plasma can be isolated from heparinized human blood after high speed centrifugation, serum can be isolated after high speed centrifugation of non-heparinized and coagulated blood from the subject. The PBMC or whole blood cells after RBC lysis can then be incubated with 10% to 50% autologous subject serum or plasma added as a supplement. In some conditions of the assay the complement in the serum/plasma optionally can further be inactivated thermally or pharmacologically, as needed.
5. Specific immune cell populations, sub-populations and combinations thereof c. Matching Cell Vehicle with Virus This analysis can be performed prior to culturing with the subject-derived immune cells. A Cell Vehicle/Virus compatibility screen is performed by analysis of co-cultures one or more Cell Vehicles and viruses to be analyzed; when more than one cell vehicle/virus combination is assessed, the methods are performed under assay equivalent conditions.

For each of the co-cultures, the ability of the cell vehicle to promote Viral Amplification is measured by methods known to those of skill in the art using cell vehicles/virus that are engineered to express detectably labeled proteins, e.g., fluorescently labeled proteins. Methods known to those of skill in the art can be used including, for example:

1. Virus Plaque Assay (VPA)
2. qPCR
3. Fluorescence Imaging (detectable label or engineered to express fluorescent protein)
4. ELISA (e.g., measuring virus-encoded ß-galactosidase)
5. Bioluminescence (e.g., virus engineered to express reporter gene luciferase)
6. Fluorescence Microscopy (imaging software to measure fluorescence intensity)/Fluorescence Plate Reader to monitor time course of virus infection (e.g., follow Cell Vehicles on green channel (GFP), Virus on red channel (TurboFP635)).

The rates of virus amplification are measured for each cell vehicle analyzed, using MOI (0.01-10) and co-culture periods of about 24 hours-1 week under equivalent assay conditions. The measured rate is normalized against the number of infected Cell Vehicles: Pfu per Cell Vehicle of 1-10 can be considered limited potency (as a Cell Vehicle for a given virus); Pfu per Cell Vehicle of 10-100 considered good potency; Pfu Cell Vehicle of 100-1000 considered very good potency; Pfu per Cell Vehicle of more than 1000 considered extremely high potency. Combinations of Cell Vehicles and viruses demonstrating pfu/Cell Vehicle of at least 10 can be considered for testing in the matching assays using cells derived from the subject. Alternately, the normalized pfu per Cell Vehicle values measured under equivalent assay conditions can be used as a virus amplification score (VAS) that contributes toward ranking of a Cell Vehicle+virus combination as a match (or not) for therapy.

d. Matching Cell Vehicle/Virus Combination with Subject

1. Subject Haplotyping data can be predictive for the patient's compatibility with a particular Cell Vehicle based on closer or more distant matching. HLA loci matching (HLA-A, HLA-DP) and KIR haplotype matching often is suggestive of broad permissivity of a subject towards multiple allogeneic Cell Vehicles, but not conclusive. The predictive value of the data however can be augmented by accumulating subject matching/compatibility data into a database and using development algorithms to predict compatibility based on assay-validated correlations. The haplotyping method can be performed as follows:

i. Isolate patient blood or other DNA source
ii. Extract gDNA, using methods known in the art
iii. Analyze of relevant loci of patient-specific genetic polymorphisms using next generation sequencing or equivalent method known in the art
    Classical MHC I/II Haplotype
    KIR Haplotype and Ligands
    Non-classical MHC Haplotype (e.g., HLA-E; CD1a, b, c, d; MICA/B)

iv. Compare the genetic polymorphism profile of each patient with the profile of the available Cell Vehicle(s).

Identify MHC mismatches between the patient and the Cell Vehicles

Identify KIR and KIR ligand mismatches between the patient and the Cell Vehicles Identify mismatches at non-classical MHC loci between the patient and the Cell Vehicles Compare all available Cell Vehicles to identify which Cell Vehicles are most compatible with the patient based on minimal number of mismatches; or if only a single Cell Vehicle is used, ascertain the percent mismatches to see if there is at least a 10%, 15%, 20%, 25%, 30%, 35%, 40%, 45%, 50% or greater match.

An in silico software algorithm/program can be used to predict the most compatible matches based on accumulating assay data iteratively and showing that mismatches at particular loci are not favorable and result in failure of the Cell Vehicles to amplify virus. The in silico compatibility prediction algorithm can iteratively be updated with new subject and Cell Vehicle compatibility screening data, and can be adjust in silico to predict Cell Vehicle compatibility for various oncolytic viruses (e.g., other than Vaccinia virus).

2. Measurement of the Ability to Recruit/Sensitize otherwise Resistant Tumor Cells: Cell Vehicle+Live Tumor Biopsy+/−Virus The Subject-Derived Immune Cells, Cell Vehicles and Viruses can be co-cultured simultaneously, or the Cell Vehicle+Virus can first be incubated (e.g., 15 min. to 48 h), then added to Subject-derived Immune Cells. After incubation times of, e.g., 24 hours to 1 week, in some embodiments, 48 hours), the following measurements are performed:

a. Fluorescence Imaging to Visualize and Quantitate "Tumor-directed migration" of labeled Cell Vehicles b. Fluorescence Imaging to Visualize and Quantitate Cell Vehicle-directed migration of unlabeled or labelled tumor-biopsy-derived cancer or stromal cells (e.g., cancer associated fibroblasts, immune cells, etc.)

c. Fluorescence Imaging to Visualize and Quantitate the Synergistic Effect of Cell Vehicle-enhanced colonization and virus amplification of the subject tumor biopsy, i.e., viral amplification in the subject tumor biopsy+cell vehicles is either:

5% or more greater than the sum of viral amplification in the tumor biopsy alone under equivalent conditions+viral amplification in the cell vehicles alone under equivalent conditions;

or is at least 5% or more greater than viral amplification in the tumor biopsy alone under equivalent conditions.

d. Methods:

live solid tumor biopsies freshly isolated from subjects can be split into equivalent size/mass/volume replicate pieces.

migration assays can be set up using standard transwell, bio-gel (hydrogel), or extracellular matrix (Collagen/Fibronectin)-coated surface systems, where the two components (solid tumor biopsy and cell vehicles) will be deposited in separate chambers or at adjacent locations, respectively.

equivalent replicate pieces of fresh and live subject tumor biopsies are co-cultured with cell vehicles labelled with fluorescent markers like CF SE, GFP, RFP, etc., for a period of 15 min to one week.

if a tumor biopsy is co-cultured with more than one type of cell vehicle, the cell vehicles can be labeled with different fluorescent markers to allow identification and quantification of which type of cell vehicle preferentially is recruited to the subject's tumor biopsy.

the % of fluorescently labeled Cell Vehicle cells accumulating in the solid tumor biopsy can be used as a measure of the efficiency of cell vehicle recruitment, with 100% recruitment being the best and 0% recruitment being the worst, and this % can be used as a cell vehicle-to-tumor migration score (CTMS).

alternatively, the fresh tumor biopsy can be fluorescently labeled with non-toxic tracer dyes like CFSE, CYTO-ID Green/Red (Enzo), CellTracker (Thermofisher Scientific) or alternative, in order to track the cell vehicle-directed migration of tumor or tumor associated stromal cells out of the solid tumor biopsy and towards the cell vehicles.

the % of fluorescently labeled tumor or tumor-associated stromal cells migrating out of the tumor and towards the cell vehicles can be used as a measure of the efficiency of tumor/stromal cell recruitment by the cell vehicles, with 100% recruitment being the best and 0% recruitment being the worst, and this % can be used as a tumor-to-cell vehicle migration score (TCMS).

in parallel, some of the replicate co-cultures of tumor cell biopsies alone, tumor cell biopsies with cell vehicles, or cell vehicles alone can be infected with a fluorescent marker-engineered oncolytic virus (such as TurboFP635) to allow visualization and fluorescence intensity-based quantification of the extent of virus amplification in the tumor biopsy versus the fluorescently labeled cell vehicles that remain outside of the tumor biopsy;

the extent of virus amplification in the tumor biopsy+/−cell vehicles or in the cell vehicles alone can be evaluated using the fluorescent intensity of the virus-engineered marker as well as by the standard VPA (virus plaque assay).

can also use the migration assay in the presence of different viruses to test if some viruses significantly interfere with the migration of the tumor or carrier cells. Virus can be added directly to the co-culture or pre-loaded onto the carrier cells prior to their co-culture with the biopsy specimens. Compute virus-corrected CTMS (VCTMS) and TCMS (VTCMS) as above, reflecting the ability of viruses to interfere with cell migration and viability Cumulative mean migration/recruitment score (MRS) for each subject tumor biopsy-Cell Vehicle-virus combination can be computed using the formula: MRS (Biopsy, Cell Vehicle, Virus combination)=[VCTMS (Biopsy, Cell Vehicle, Virus)+VTCMS (Biopsy, Cell Vehicle, Virus)]/2; or MRS (Biopsy, Cell Vehicle combination)=[CTMS (Biopsy, Cell Vehicle)+TCMS (Biopsy, Cell Vehicle)]/2

The cell vehicles subsequently can be ranked for each subject and virus combination based on the mean MRS scores.

3. Analysis of Co-Cultures for Subject/Cell Vehicle Match, i.e., subject permissivity to Cell Vehicle-mediated virotherapy: Subject-derived PBMCs+Cell Vehicle+Virus (a)—Measurement of Viral Amplification (see assays as known to those in the art and as provided herein)

Compatible match if virus amplification in the co-cultures of Cell Vehicle and patient PBMC is in excess of 80% of the virus amplification when the same Cell Vehicle is infected in the absence of PBMC.

Moderately compatible match if virus amplification in the co-cultures of Cell Vehicle and patient PBMC is in the range of 30-80% of the virus amplification when the same Cell Vehicle is infected in the absence of PBMC.

Adequately compatible match if virus amplification in the co-cultures of Cell Vehicle and patient PBMC is in the range of 10-30% of the virus amplification when the same Cell Vehicle is infected in the absence of PBMC.

Incompatible match if virus amplification in the co-cultures of Cell Vehicle and patient PBMC is less than 10% of the virus amplification when the same Cell Vehicle is infected in the absence of PBMC.

The % compatibility can be used to rank Cell Vehicles from the least to the most compatible Cell Vehicles for each individual patient and for each particular virus.

The % compatibility also can be computed as an immunological virus amplification score (IVAS) for each combination of patient, cell vehicle and oncolytic virus using the formula:

IVAS (%, patient, cell vehicle, virus)=(pfu of virus from cell vehicle+subject PBMC co-cultures/pfu of virus from cell vehicle alone)×100.

IVAS scores of e.g., 10% or higher, 20% and higher, 30% and higher or between 10%-30% and higher can be considered adequate for consideration.

When more than one type of cell vehicle is screened, this IVAS score (higher the percent, higher the compatibility) can be used to rank the cell vehicles from the least to the most compatible cell vehicles for each patient and for each virus.

The IVAS score optionally can further be corrected by taking into account the effect of complement and neutralizing antibodies in the serum of the subject (Optional Subject Serum Resistance Screen):

Evaluate % suppression of virus amplification by the Cell Vehicles in the presence of subject derived serum with or without PBMC on a scale from 0 to 100% suppression and compute a patient serum resistance score (PSRS), using the formula:

PSRS=(pfu with no serum−pfu with serum and without complement inactivation/pfu with no serum)×100.

PSRS scores of more than 95% would indicate strong serum-mediated suppression, suggesting that the virus might not be compatible with the subject despite demonstrating an acceptable IVAS score because the latter (IVAS score) takes into account only the subject's cellular immunity.

Rate the viruses used in the Cell Vehicle compatibility test using a corrected IVAS score: IVAS (PSRS-corrected)=IVAS×(100−PSRS)/100

The contribution of complement to suppression of viral amplification can be evaluated using the % suppression of virus amplification by the Cell Vehicles in the presence of subject-derived serum with or without subject PBMC and with or without thermal or pharmacological serum inactivation on a scale from 0 to 100% using the formula:

% complement suppression=(pfu with serum and with complement inactivation−pfu with serum and without complement inactivation/pfu with no serum)×100.

this % complement suppression can be used as a subject/patient complement resistance score (PCRS) and will be indicative of subjects having broader resistance to multiple oncolytic viruses that is independent of the presence of pre-existing exposure/immunity associated with virus-specific neutralizing antibodies.

(b)—Measurement of Immunological Compatibility (Immune Privilege/Immunosuppressive Effects)

(i)—Measure Up Regulation of Virus/Cell Vehicle-Mediated Interferon (e.g., IFNγ) Production (for acceptable parameter range see ICS score description in section (I) below)

IFNγ ELISPOT

Flow Cytometry
labeled antibody used is an anti-human IFNγ, e.g., anti-human IFNγ-APC (ii)—Measure Up Regulation of Markers associated with T cell, including γδ T cell, NK cell and NKT cell-mediated Cytotoxicity Granzyme B ELISPOT Flow Cytometry
labeled antibodies used is an anti-human CD107a/CD107b (e.g., anti-human CD107a-AlexaFluor 488)

(iii)—Measure Up Regulation of Other Markers associated with T cell, including γδ T cell, NK cell and NKT cell—mediated Activation/Effector Functions (for acceptable parameter range see ICS score description in section (I) below)

fluorescently-labeled antibodies can be used to measure the level of surface or intracellular expression of various activation/effector function markers on/in the immune cells, e.g.:

Activator/Effector Function Markers
CD69 (e.g., anti-human CD69-APC)
CD25
CD71
ICOS
CD314 (NKG2D)
PD-1
CTLA-4
IFNα/β
IFNγ
TNFα
IL-2
IL-4
IL-5
IL-6
IL-8
IL-9
IL-10
IL-12
IL-13
IL-15
IL-17
IL-18
IL-21
IL-22
IL-23
IL-25
GM-CSF
CD107a
CD107b
TGFβ
Perforin
Granzyme B
CD27 (CD70L)
CD154 (CD40L)
CD137 (4-1BB)
CD44

CD45RA
CD45RO
CD278 (ICOS)
CD127 (IL-7RA)
CD183 (CXCR3)
CD197 (CCR7)
CD39
CD73
IL-1a/IL-1b
G-CSF
RANTES
EXOTAXIN
MIP-1b
MCP-1
EGF
HGF
VEGF
IL-IRA
IL-7
IP-10
IL-2R
MIG (iv)—Labeled antibodies (e.g., fluorescent) can be used to identify specific immune cell populations expressing various characteristic markers, e.g.:

T-Cells/γδ T Cells:
CD3 (e.g., anti-human CD3-PerCP/Cy5.5)
CD69 (e.g., anti-human CD69-APC)
CD4
CD8
NK Cells/γδ T Cells:
CD107a/CD107b (e.g., anti-human CD107a-AlexaFluor 488)
CD335 (e.g., anti-human CD335 or NKp46-PE)
CD16
CD56
NKT Cells:
CD335 (e.g., anti-human CD335 or NKp46-PE)
CD3
CD16
CD56
aGalCer-CD1d tetramers (v)—Analysis of ELISPOT/Flow Cytometry data from co-cultures for best Match can be determined by the following scores:

(I) Immunological Compatibility Score (ICS)

When ratio of activation/effector function parameters (at least one of the above) in the co-culture relative to PBMC alone is around 1-1.05 or lower, indicative the Cell Vehicle has no effect on immune response or reduces the response, i.e., it is an immunologically compatible match.

Moderately immunologically compatible match is when ratio is within the range of 1.05 to 1.5.

Minimally immunologically compatible match is when ratio is in the range of 1.5 to 2.

Immunologically incompatible match is when the ratio is greater than 2.

The activation/effector parameters can be weighted based on their established association with decreased virus amplification, e.g., IFNγ and CD107a considered significant in their influence on viral amplification, and iteratively updating the significance level/weight as data from other activation/effector parameters become available (see In Silico Analysis Section).

The immune cell populations responding to the allogeneic Cell Vehicles also can be weighted based on their established association with decreased virus amplification, e.g., NK, NKT and T cell, including γδ T cell subpopulations considered significant, and iteratively updating the significance level/weight subpopulations as new data of associations with other populations/subpopulations become available (see In Silico Analysis Section).

Calculate cumulative ICS score based on the mean of the ICS ratios of selected immune cell subpopulations and activation/effector parameters (p1, 2, 3, etc.) for each patient-Cell Vehicle combination, as follows:

$$NK\text{ cells: }ICS(NK)=[ICS(p1)+ICS(p2)+ICS(p3)+\ldots ICS(pn)]/n$$

$$T\text{ cells: }ICS(T)=[ICS(p1)+ICS(p2)+ICS(p3)+\ldots ICS(pn)]/n$$

$$NKT\text{ cells: }ICS(NKT)=[ICS(p1)+ICS(p2)+ICS(p3)+\ldots ICS(pn)]/n$$

where "n" is the total number of relevant activation/effector function parameters under consideration (e.g., n=2 if only IFNγ and CD107a are being evaluated).

Cumulative mean ICS score for each patient-Cell Vehicle combination and combining all relevant effector populations can be computed using the formula:

$$ICS[NK(1)+T(2)+NKT(3)+\ldots E(n)]=[ICS(NK,1)+ICS(T,2)+ICS(NKT,3)+\ldots ICS(E,n)]/n,$$

where "n" is the total number of relevant effector immune cell populations/subpopulations under consideration (e.g., n=3 if only NK, T, and NKT cells are being evaluated, n=4 if other populations, e.g., gd (γδ) T cells also are considered, etc.).

(II) Immunological Suppression Score (ISS)

Cell Vehicle-mediated suppression of anti-viral immunity can be evaluated for each combination of patient and Cell Vehicle and for each immune cell subtype and effector parameter to compute an immunological suppression score (ISS; % suppression of anti-viral cellular immunity) using the formula:

ISS=(% activated effectors in PBMC+virus co-cultures+% activated effectors in PBMC+Cell Vehicle co-cultures−% activated effectors in PBMC+virus+Cell vehicle co-cultures/% activated effectors in PBMC+virus co-cultures+% activated effectors in PBMC+Cell Vehicle co-cultures)×100, where the % activated effectors are first normalized by subtracting the background or % activated effectors in the PBMC alone controls.

ISS of 0% or higher is favorable. Although ISS of 0% indicates absence of immunosuppression, or negative ISS values might indicate cell vehicles stimulate rather than suppress antiviral immunity, such conclusions are not definitive as they might simply reflect the ability of the Cell Vehicle to amplify the virus and thus could be expected downstream to augment rather than suppress antiviral immunity.

Negative % values are inconclusive.

Higher ISS values indicate higher ability of the cell vehicles to suppress anti-viral immunity and improved ability of the virus to spread to the tumor cells. Overall significance, however, also depends on other scoring criteria such as IVAS and ICS, as higher IVAS and lower ICS scores correlate with higher virus amplification and might make suppression of anti-viral responses more challenging.

Calculate cumulative ISS score based on the mean of the ISS % suppression for every responding immune cell subpopulation and key activation/effector parameters (p1, 2, 3, etc.) for each patient-Cell Vehicle combination, as follows:

$NK$ cells: $ISS(NK)=[ISS(p1)+ISS(p2)+ISS(p3)+ \ldots ISS(pn)]/n$ $T$ cells: $ISS(T)=[ISS(p1)+ISS(p2)+ISS(p3)+ \ldots ISS(pn)]/n$ $NKT$ cells: $ICS(NKT)=[ISS(p1)+ISS(p2)+ISS(p3)+ \ldots ISS(pn)]/n$, where "n" is the total number of relevant activation/effector function parameters under consideration (e.g., n=2 if only IFNγ and CD107a are being evaluated).

Cumulative mean ISS score for each patient-Cell Vehicle combination and combining all relevant effector populations can be computed using the formula:

$ISS[NK(1)+T(2)+NKT(3)+ \ldots E(n)]=[ISS(NK,1)+ISS(T,2)+ISS(NKT,3)+ \ldots ISS(E,n)]/n$, where "n" is the total number of relevant effector immune cell populations/subpopulations under consideration (e.g., n=3 if only NK, T, and NKT cells are being evaluated, n=4 if other populations, e.g., gd (γδ) T cells also are considered, etc.).

(c)—Measurement of Immunomodulation (Immune Privilege/Immunosuppressive Effects) by Analyzing Supernatants of Co-Cultures Methods known in the art, e.g., ELISA and Luminex Assay can be used to measure the following activator/effector function parameters in the supernatants of the co-cultures:

IFNα/β
IFNγ
TNFα,
IL-2
IL-4
IL-5
IL-9
IL-10
IL-12
IL-13
IL-15
IL-18
IL-21
IL-22
IL-23
IL-25
GM-CSF
IL-17
IL-6
TGFβ
Perforin
Granzyme B
IL-1a/IL-1b
G-CSF
RANTES
EXOTAXIN
MIP-1b
MCP-1
EGF
HGF
VEGF
IL-IRA
IL-7
IP-10
IL-2R
MIG
IL-8

While these measurements (supernatants) cannot identify the cell of origin, one can still measure cumulative ICS (and/or ISS) scores in the manner described for the co-cultures.

Confirm flow cytometry results or make corrections to cumulative scores for patients where minimal increases in Cell Vehicle-induced activated/effector immune cells are associated with significant increases in the production of effector cytokines/chemokines. This accounts not only for the frequency of immune effectors but also for the magnitude of their activity.

(d)—Selection of Cell Vehicle for Viral Therapy Based on Subject-Specific Compatibility A cell vehicle selected as being matched with a subject according to the methods provided herein possess at least one, two, three, four, five or six of the following characteristics:

(1) Maximum virus amplification in the absence of subject-derived cells (VAS score);

(2) Maximum virus amplification in the presence of subject-derived cells (IVAS score);

(3) Minimum induction of anti-Cell Vehicle immunological responses (ICS score);

(4) Maximum ability to suppress the induction of anti-viral immunological responses (ISS score);

(5) Maximum ability to migrate towards tumors and recruit tumor and/or tumor-associated stromal cells (when such cells/tumors can be accessed; MRS score); and/or (6) Minimal haplotype mismatches at certain loci as provided herein.

When more than one or a panel of cell vehicles is screened for matching with a subject, the cell vehicle choices can be ranked based on the number of haplotype mismatches, one of the scores set forth in (1)-(5) above, or a combination of two or more of any of the scores set forth in (1)-(5) above, if more than one type of matching assay is performed, can be used to obtain a cumulative rank. The cell vehicles can be ranked, for example, according to best combination of two or more of the VAS, IVAS, ICS, ISS and MRS scores Cumulative RANK score=[RANK(VAS)+RANK(IVAS)+RANK(ICS)+RANK(ISS)+(optional) RANK(MRS)]/5(if all 5 scores are obtained; 2, 3 or 4 if fewer scores are obtained)

Each of these scores could be subject to additional weighting factors in an in silico analysis, when a sufficient amount of matching data is gathered from these assays.

(e)—in Silico Analysis can be Performed as Follows:

Each subject and cell vehicle is analyzed for their typing characteristic, e.g.,
  Classical MHC I/II Haplotype;
  KIR Haplotype and Ligands;
  Non-classical MHC Haplotype (HLA-E; CD1a, b, c, d; MICA/B).

Data is collected from each co-culture assay of subject immune cells (PBMC/immune cells/blood) with a particular virus/cell vehicle pair to establish a databank.

The matching compatibility scores (IVAS, ICS, ISS) established in each assay in the databank is correlated to the degree of matching between the cell vehicle and the subject's haplotype to establish negative correlations between a mismatch/mismatches at particular locus/loci and a significant negative impact on one or all of the matching compatibility scores (IVAS, ICS, ISS).

Such correlations, when found to be statistically significant, can be used to "In Silico" pre-screen and exclude inappropriate cell vehicles based on the presence of undesirable mismatches with the subject (associated with poor matching compatibility scores).

Additionally, the matching compatibility scores established for every combination of cell vehicle and virus chosen and used to treat subjects is collected in the database and further correlated with the virus amplification data obtained from the blood or tumor of the treated subjects, within the first 48 hours of treatment (range of, e.g., 24 hours to 3 days), which can be used as a measure of the actual therapeutic efficacy in vivo.

A correlative analysis between the matching compatibility scores and the actual therapeutic efficacy in vivo can be used to adjust/improve the cumulative RANK score formula used to select optimal cell vehicles by assigning higher weighting factors to the IVAS, ICS, or ISS scores that are more closely associated/predictive of therapeutic efficacy in vivo.

D. MODIFIED CELL VEHICLES WITH IMPROVED DELIVERY AND/OR MATCHING CAPABILITIES

Also provided herein are cell vehicles (carrier cells) whose properties are modified to facilitate delivery of an oncolytic virus to a subject and/or provide improved matching with a subject. Any of the cell vehicles provided herein (e.g., stem cells, immune cells, cancer cells) can be so modified. Such properties can include, but are not limited to, improved facilitation of viral amplification in the cell delivery vehicle, an improved ability to evade immune responses directed against the cell vehicle and/or the virus and/or improved immunosuppression. In embodiments, the immunomodulatory capabilities (e.g., evading immune responses, suppressing immune responses) can be local and/or transient, being present to the extent needed to facilitate delivery, accumulation and infection of the virus in the tumor or other cancerous cells.

In some embodiments, a modified cell vehicle provided herein can be screened using the matching assay provided herein (Section C) to ascertain its suitability as a cell vehicle for delivery of an oncolytic virus to a particular subject and/or a particular cancer/tumor type. In embodiments, a plurality/panel of modified cell vehicles can be screened by the matching assay provided herein and ranked in order of their matching capability. In some examples, the panel of cell vehicles can include unmodified cell vehicles.

The modified cell vehicles provided herein can contain one or more of the modifications set forth in this section and elsewhere herein, as described:

(i) Sensitized/Protected Cell Vehicles for Improved Viral Amplification and/or Immunomodulation Provided herein are cell vehicles that are modified for improved viral amplification and/or immunomodulation to facilitate viral delivery and/or improved matching with the subject being treated with viral therapy. The modifications can include one or more of the following embodiments: In embodiments, the cell vehicles can be sensitized to enhance their virus amplification ability by pre-treating/loading the cell vehicles with one or more of: IL-10, TGFβ, VEGF, FGF-2, PDGF, HGF, IL-6, GM-CSF, Growth factors, RTK/mTOR agonists, wnt protein ligands and GSK3 inhibitors/antagonists (e.g., Tideglusib, Valproic acid). In other embodiments, the cell vehicles can be sensitized to block induction of the anti-viral state, for example, by pre-treating/loading the cell vehicles with small molecule or protein inhibitors that interfere with IFN Type I/Type II receptors and/or interfere with downstream signaling including, but not limited to, IFNAR1/IFNAR2 signaling, IFNGR1/IFNGR2 signaling, STAT1/2 signaling, Jakl signaling (e.g., Tofacitinib, Ruxolitinib, Baricitinib), Jak2 signaling (e.g., SAR302503, LY2784544, CYT387, NS-018, BMS-911543, AT9283), IRF3 signaling, IRF7 signaling, IRF9 signaling, TYK2 signaling (e.g., BMS-986165), TBK1 signaling (e.g., BX795, CYT387, AZ13102909).

In some embodiments, the cell vehicles can be pre-treated/loaded with HDAC inhibitors for interfering with/deregulating IFN signaling/responsiveness; such inhibitors can include, but are not limited to, Vorinostat, Romidepsin, Chidamide, Panobinostat, Belinostat, Valproic acid, Mocetinostat, Abexinostat, Entinostat, SB939, Resminostat, Givinostat, Quisinostat, HBI-8000, Kevetrin, CUDC-101, AR-42, CHR-2845, CHR-3996, 4SC-202, CG200745, ACY-1215, ME-344, Sulforaphane and/or Trichostatin. In other embodiments, the cell vehicles can be pre-treated/loaded with antagonists of virus sensing and/or anti-virus defense pathways mediated by STING, PKR, RIG-1, MDA-5, OAS-1/2/3, AIM2, MAVS, RIP-1/3, DAI (ZBP1); such antagonists can include, but are not limited to, one or more of K1, E3L, K3L proteins (Vaccinia), NS1/NS2 proteins (Influenza), NS3-4A (Hepatitis C), NP and Z proteins (Arenavirus), VP35 (Ebola virus), US11, ICP34.5, ICP0 (HSV), M45 (MCMV) and X protein (BDV: Borna Disease Virus). In embodiments, the cell vehicles can be protected against allogeneic inactivation/rejection determinants, such as by pre-treating/loading the cells with MEW antagonists of viral origin, e.g., one or more of A40R MHCI antagonist (Vaccinia), Nef and TAT (HIV), E3-19K (Adenovirus), ICP47 (HSV-1/2), CPXV012 and CPXV203 (Cowpox), ORF66 (VZV), EBNA1, BNLF2a, BGLF5, BILF1 (EBV), US2/gp24, US3/gp23, US6/gp21, US10, US11/gp33 (hCMV), Rh178/VIHCE (RhCMV), U21 (HHV-6/7), LANA1, ORF37/SOX, kK3/MIR1, kK5/MIR2 (KSHV), mK3 (MHV-68), UL41/vhs (a-herpesvirus, HSV, BHV-1, PRV), UL49.5 (Varicellovirus, BHV-1, EHV-1/4, PRV) and m4/gp34, m6/gp48, m27, m152/gp40 (mCMV).

In embodiments, the modified cell vehicles provided herein can be pre-treated/loaded with B2M antagonists of viral origin, e.g., UL18 (HCMV). In other embodiments, the cell vehicles can be pre-treated/loaded with antagonists of MIC-A and MIC-B (NKG2D ligands), e.g., kK5 (KHSV). In some embodiments, the cell vehicles can be pre-treated/loaded with one or more immunosuppressing factors of viral origin including, but not limited to, inhibitors of immune FAS/TNF/Granzyme B-induced apoptosis (e.g., Ectromelia/Vaccinia virus SP1-2/CrmA), IL-1/NFkB/IRF3 antagonists (e.g., Vaccinia virus-encoded N1), IL-1 and TLR antagonists (e.g., IL-18 binding protein, A46R, A52R), IL-1β antagonists (e.g., B15R/B16R), TNFα blockers (e.g., Vaccinia virus CmrC/CmrE), IFNα/β blockers (e.g., Vaccinia virus B18R/B19R) and IFNγ blockers (e.g., Vaccinia virus B8R). In embodiments, the cell vehicles can be pre-treated/loaded with small molecule inhibitors of TAP1/2 and/or tapasin.

In embodiments, the modified cell vehicles provided herein can be protected against complement by, e.g., pre-treating/loading the cell vehicles with small molecule inhibitors of complement factors (e.g., C1, C2, C3, C4, C5, MBL); such inhibitors can include, but are not limited to, one or more of VCP (Vaccinia virus complement control protein), B5R (Vaccinia virus complement inhibitor), scFv anti-CD1q/CD1r/CD1s, anti-C3, anti-C5 (e.g., Eculizumab), peptidic C3 inhibitors of the compstatin family (e.g., Cp40), Human soluble membrane (s/m) proteins (e.g., s/mCR1

(CD35), s/mCR2 (CD21), s/mCD55, s/mCD59), Human Factor H and derivatives, Cobra venom factors and derivatives with complement inhibitory activity.

The sensitized cell vehicles can be generated by methods known in the art. For example, the cell vehicles can be pre-treated with the sensitizing agents, e.g., proteins or small molecule agonists/antagonists by incubation for between 10 minutes to 48 or more hours prior to cell banking, virus infection or administration to the subject, e.g., about or at least for 10, 15, 20, 25, 30, 35, 40, 45, 50, 55 or 60 minutes or about or at least 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 or more hours prior to cell banking, virus infection or administration to subject. To enhance the loading of proteins/lipid insoluble small molecules into the cells, lipofectamine or alternative protein transfection reagents can be used, such as, for example, Xfect (Takara), Pierce Pro-Ject (ThermoFisher), Pro-DeliverIN (OZ Biosciences), TurboFect (Fermentas), or alternative.

(ii) Sensitized for Resistance to Virus-Mediated Killing (for Extended Survival and Improved Local Immunosuppression)

The modified cell vehicles provided herein can, in some embodiments, be pre-treated/loaded with one or more agents that render the cell vehicles resistant to virus-mediated killing. For example, in some embodiments, the cell vehicles can be pretreated with Type I and/or Type II interferons. In other embodiments, the cell vehicles can be pretreated with agonists/inducers of anti-viral state (e.g., STING, PKR, RIG-I, MDA-5). To generate such "protected" cell vehicles, any autologous or allogeneic cell vehicles can be treated with Interferon Type I (e.g., IFNα/β) and/or Type II (e.g., IFNγ) and/or agonists of STING, PKR, RIG-I, MDA-5, OAS-1/2/3, AIM-2, MAVS, RIP-1/3, DAI (ZBP1) pathways for between 30 minutes to up to 48 or more hours, e.g., about or at least 30 minutes or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 or more hours without or prior to virus infection.

These "protected" cell vehicles can be administered as a separate composition concurrently with a matched/sensitized/engineered cell vehicle that is not so protected and includes the virus; the protected cell vehicles can provide extended survival and/or improved local immunosuppression. In some embodiments, the protected cell vehicles can be administered within, for example, about or at least 10, 15, 20, 24, 25, 26, 27, 28, 29, 30, 31, 32, 33, 34, 35, 36, 37, 38, 39, 40, 41, 42, 43, 44, 45, 46, 47 or 48 hours or 1, 2, 3, 4 or 5 days prior to or after administering the matched/sensitized/engineered cell vehicle that is not so protected and includes the virus.

(iii) Engineered Cell Vehicles for Improved Viral Amplification and/or Immunomodulation Also provided herein are modified cell vehicles that are engineered for transient or permanent expression or suppression of genes to facilitate improved viral amplification and/or immunomodulation. The cell vehicles can be engineered in one or more of the following embodiments. Any of the cell vehicles provided herein can be modified using one or a combination of the embodiments for sensitizing, protecting and/or engineering the cell vehicles as provided herein.

In some embodiments, the cell vehicles can be engineered to be unresponsive to an interferon (IFN)-induced antiviral state. For example, the cell vehicles can be engineered for transient or permanent (excising the gene locus, e.g.) suppression of IFN Type I/Type II receptors and/or downstream signaling such as, for example, suppression of one or more of Type I/Type II interferon receptor expression; IFN α/β, IFNγ receptor expression; IFNAR1/IFNAR2 receptor expression; IFNGR1/IFNGR2 receptor expression; STAT1/2 receptor expression; Jak1/2 receptor expression; IRF3 receptor expression; IRF7 receptor expression; IRF9 receptor expression; TYK2 kinase expression and TBK1 kinase expression.

In embodiments, the cell vehicles can be engineered for transient or permanent suppression of elements of the cytosolic viral DNA/RNA-sensing and anti-viral defense machinery including, but not limited to, one or more of PKR, RIG-I, MDA-5, cGAS, STING, TBK1, IRF3, OAS-1/2/3, AIM2, MAVS, RIP-1/3 and DAI (ZBP1). In other embodiments, the cell vehicle can be engineered for transient or permanent expression of antagonists of virus-sensing and anti-viral defense pathways mediated by, e.g., STING, PKR, RIG-1, MDA-5, OAS-1/2/3, AIM2, MAVS, RIP-1/3, DAI (ZBP1); these can include, but are not limited to, one or more of K1, E3L, K3L (Vaccinia); NS1/NS2 (Influenza A); NS3-4A (Hepatitis C); NP, Z protein (Arenavirus); VP35 (Ebola virus); US11, ICP34.5, ICP0 (HSV); M45 (MCMV); and X protein (BDV: Borna Disease Virus).

In some embodiments, the modified cell vehicles provided herein can be engineered to evade allogeneic recognition by one or more of T and NKT cells, and the adaptive immune response(s) of γδ T cells. For example, the cell vehicles can be engineered for transient or permanent suppression of expression of one or more of: MEW Class I molecules (HLA-A, B, C); MHC Class II molecules (HLA-DP, DQ, DR); MHC-like molecules (CD1a/b/c/d); or regulators of transcription or expression of MEW Class I, MHC Class II, MHC-like molecules (e.g., TAP1/2, Tapasin, Beta-2 microglobulin, CIITA, RFXANK, RFX5 and RFXAP). In other examples, the cell vehicles can be engineered for transient or permanent expression of one or more of: B2M Antagonists of Viral Origin (e.g., UL18 (HCMV); and/or MEW Antagonists of Viral Origin (e.g., one or more of A40R MHCI (Vaccinia); Nef, TAT (HIV); E3-19K (Adenovirus); ICP47 (HSV-1/2); CPXV012, CPXV203 (Cowpox); EBNA1, BNLF2a, BGLF5, BILF1 (EBV); ORF66 (VZV); US2/gp24, US3/gp23, US6/gp21, US10, US11/gp33 (hCMV); rh178/VIHCE (RhCMV); U21 (HHV-6/7); LANA1, ORF37/SOX, kK3/MIR1, kK5/MIR2 (KHSV); mK3 (MHV-68); UL41/vhs (a-herpesvirus, HSV, BHV-1, PRV); UL49.5 (Varicellovirus, BHV-1, EHV-1/4, PRV); and m4/gp34, m6/gp48, m27, m152/gp40 (mCMV)).

In embodiments, the cell vehicles can be engineered to evade allogeneic recognition by NK Cells and/or the innate immune response(s) of γδ T cells. For example, the cell vehicles can be engineered for transient or permanent suppression of expression of one or more of: Membrane-Bound MICA/B (NKG2D Ligands); Membrane-Bound PVR (DNAM-1 Ligand); Membrane-Bound Nectin-2 (DNAM-1 Ligand). In other examples, the cell vehicles can be engineered for transient or permanent expression of one or more of:

antagonists of MIC-A and MIC-B (NKG2D ligands) (e.g., kK5 (KHSV)); antagonists of the NKG2D receptor (e.g., Cowpox OMCP); antagonists of NCR—targeting NKp30, NKp44, NKp46 receptors (e.g., HA (hemagglutinin—in vaccinia and other viruses)); ligands for the NK inhibitory receptors (KIR) (e.g., HLA-Bw4; HLA-C2); ligands for the NK inhibitory receptors (NKG2a/CD94) (e.g., HLA-E and derivatives alone or combined with 21M HLA-B ligands to generate HLA-E binding peptides and stabilize HLA-E surface expression).

In certain embodiments, the cell vehicles can be engineered to express immunosuppressive factors of human or viral origin (e.g., to prevent/inhibit allogeneic anti-cell vehicle or anti-viral immune responses). Factors of human origin include, but are not limited to, IDO, Arginase, TRAIL, iNOS, VEGF, FGF-2, PDGF, HGF, IL-6, sMICA, sMICB, sHLA-G, HLA-E, PD-L1, FAS-L, B7-H4 and single-chain antibodies (scFv) that target or deplete NK and/or NKT and/or γδ T cells. Factors of viral origin include, but are not limited to, Ectromelia/Vaccinia virus SPI-2/CrmA (inhibitor of immune FAS/TNF/Granzyme B induced apoptosis); Vaccinia Virus encoded N1 (IL-1/NFkB/IRF3 antagonist); HA (NCR antagonists targeting NKp30, NKp44, NKp46); IL-18 binding protein; A40R; A46R; A52R; B15R/B16R; TNFα blockers (e.g., Vaccinia virus CmrC/CmrE); IFN α/β blockers (e.g., Vaccinia virus B18R/B19R); IFNγ blockers (e.g., Vaccinia virus B8R) and other IL-1/IL-1β/NFκB/IRF3/NCR/MHCI/TLR/NKG2D antagonists.

In some embodiments, the cell vehicles can be engineered to express cancer or stem cell-derived factors that facilitate viral infection of otherwise impermissive cell vehicles and/or tumor cells. For example, the cell vehicles can be engineered to express one or more of: cancer associated antigens (e.g., cancer testis antigens (MAGE-A1, MAGE-A3, MAGE-A4, NY-ESO-1, PRAME, CT83, SSX2, BAGE family, CAGE family); oncofetal antigens (AFP, CEA); oncogene/tumor suppressors (myc, Rb, Ras, p53, Telomerase); differentiation antigens (MELAN, Tyrosinase, TRP-1/2, gp100, CA-125, MUC-1, ETA); GM-CSF; IL-10; TGFβ; VEGF; FGF-2; PDGF; HGF; IL-6; growth factors; RTK/mTOR agonists and wnt protein ligands.

In embodiments, the modified cell vehicles can be engineered to express factors that interfere with the function of complement and/or neutralizing antibodies, including, but not limited to, one or more of: protein Antagonists of complement factors (C1, C2, C3, C4, C5, MBL); Vaccinia virus complement control protein (VCP); Vaccinia virus complement inhibitor (B 5R); scFv anti-CD1q/CD1r/CD1s; anti-C3; anti-CS (e.g., Eculizumab); peptidic C3 inhibitors of the compstatin family (e.g., Cp40); human soluble membrane (s/m) proteins (e.g., s/mCR1 (CD35), s/mCR2 (CD21), s/mCD55, s/mCD59); Human Factor H and derivatives and cobra venom factors and derivatives with complement inhibitory activity.

A number of methods of engineering cells, such as for making the engineered cell vehicles provided herein, are known in the art. Such methods include, but are not limited to:

(a) CRISPR-CAS9 Targeted Suppression (Permanent Gene/Locus Deletion)

Cell vehicles can be transfected with a DNA plasmid that expresses both the CAS9 protein a guide RNA (gRNA) specific for the gene of interest. The gRNA-CAS9-mediated cut in the genome can be repaired using a donor DNA plasmid, which causes specific deletion of the targeted gene and permanent and total loss of the gene-encoded protein. Loss of protein expression can be validated using PCR (DNA level), Northern Blot/FISH (RNA level), or any Protein assay such as, for example western blot or flow cytometry.

(b) CRISPR-CAS9 Targeted Expression (Permanent Gene/Locus Insertion)

This method can be used to insert the gene of interest into a specific location of the cell vehicle genome. Cell vehicles can be transfected with a DNA plasmid that expresses both the CAS9 protein a guide RNA (gRNA) specific for the specific insertion location. The gRNA-CAS9-mediated cut in the genome can be repaired using a donor DNA plasmid, which has the inserted gene of interest flanked by sequences of the cell vehicle genome on both sides of the location of the DNA cut/double stranded break, causing homologous recombination-mediated insertion of the gene of interest in the specific genome location rather than randomly. Successful insertion and protein expression can be validated using PCR (DNA level), Northern Blot/FISH (RNA level), or any Protein assay such as, for example, western blot or flow cytometry.

(c) RNA Interference (Retroviral/Lentiviral/Transposon-Mediated Transduction of shRNA/microRNA) (Permanent Gene Suppression)

shRNA/microRNA targeting the specific gene/protein of interest can be designed and cloned into a retroviral/lentiviral/transposon vector for stable integration into the cell vehicle genome. Cell vehicles can be transduced with the vector and successfully transduced cells can be selected using the vector encoded selection markers. shRNA-mediated suppression of the gene of interested can be evaluated using, e.g., Northern Blot and Protein assays.

(d) Lentivirus/γ-Retrovirus-Mediated Random/Multiple Copy Gene Insertion

The specific gene/protein of interest can be designed and/or cloned into a retroviral or lentiviral vector for stable random integration into the cell vehicle genome. Cell vehicles can be transduced with the viral vector and successfully transduced cells can be selected using the vector encoded selection markers. shRNA-mediated suppression of the gene of interested will be evaluated using Northern Blot and any Protein assays, such as western blot, flow cytometry, etc.

(e) Transposon-Mediated Random/Multiple Copy Gene Insertion

The specific gene/protein of interest can be designed and/or cloned into a mammalian transposon vector system such as the PiggyBac (SBI System Biosciences) or equivalent. Cell vehicles can be co-transfected with the transposon vector with the gene (cDNA) of interest flanked by the inverted terminal repeat (ITR) sequences and the Transposase vector. The Transposase enzyme can mediate transfer of a gene of interest into TTAA chromosomal integration sites. Successfully transduced cells optionally can be selected using vector encoded selection markers. Successful insertion and protein expression can be validated using PCR (DNA level), Northern Blot/FISH (RNA level), or any Protein assay such as, for example western blot or flow cytometry.

(f) Transient gene suppression of the expression of a protein of interest can be achieved, e.g., through RNA interference. siRNA/MicroRNA can be transfected into the cell vehicles by any of the established methodologies known in the art, e.g.: calcium chloride transfection; lipofection; Xfect; electroporation; sonoporation and cell squeezing (e.g., to introduce siRNA).

(g) Transient gene expression can be achieved, e.g., by cloning the gene of interest into an appropriate mammalian plasmid expression vector that can be transfected into cell vehicles with plasmid DNA encoding the desired product. Alternatively, mRNA encoding the gene/protein of interest can be transfected directly into the cell vehicles. Transfection can be performed using any of the established methodologies, e.g.: calcium chloride transfection; lipofection; Xfect; electroporation; sonoporation and cell squeezing (e.g., to introduce siRNA).

Exemplary Modifications of Cell Vehicles

1. Suppress Induction of the Antiviral State

Untransformed stem cells and several tumor cells often have intact anti-viral mechanisms that compromise the ability to use them as cell vehicles/carrier cells for oncolytic viruses. Type I and Type II interferons are potent inducers of the anti-viral state in stem cells as well as in some tumor cells, which can interfere with the ability of these cells to get infected and support virus amplification. Therefore, in some embodiments, the cell vehicles provided herein and used in the methods provided herein are loaded with or engineered to express one or more inhibitors of interferon signaling that blocks the detection of viral infection and/or initiation of an anti-viral state/immune response. For example, Ruxolitinib, an interferon signaling small molecule inhibitor of Jak1/Jak2, can successfully be used as to augment the therapeutic potential of various stem as well as tumor cells to function as carriers of oncolytic viruses by sensitizing them (making them susceptible to) to virus infection, amplification and spread (see, e.g., Example 6).

2. Protect the Cell Vehicles Against Complement

Human serum can have deleterious effects on carrier cells, including directly attacking and killing virus-infected carrier cells before viral amplification has initiated and/or reached its peak, or by neutralizing naked virus particles released from the carrier cells, thus limiting the spread of the virus into the target tumor cells. Therefore, in some embodiments, the cell vehicles provided herein and used in the methods provided herein are loaded with or engineered to express one or more complement blocking factors. For example, compstatin, a peptidic inhibitor of complement C3 activation, or a neutralizing anti-human C3a/C3a(desArg)/C3 antibody can be used to increase virus payload in the carrier cells and also obtain enhanced virus amplification and spread in the target tumor (see, e.g., Example 7).

3. Evade Allogeneic Recognition/Rejection

As demonstrated herein, stem cell carriers (cell vehicles) can successfully amplify and deliver oncolytic vaccinia virus against allogeneic barriers due to their ability to avoid allogeneic recognition and actively immunosuppress NK cells, T cells, gd (γδ) T cells and/or a population of "NKT" cells expressing both NK (NKp46) and T cell (CD3) markers. However, in a subset of "incompatible/resistant" recipients, the stem cell carriers sometimes are unable to avoid allogeneic recognition, which resulted in the mounting of fast and potent allogeneic immune responses against the carrier stem cells even in the absence of virus. These fast allogeneic responses can be associated with the development of anti-stem cell cytotoxicity and the induction of a interferon (e.g., IFNγ)-mediated antiviral state, resulting in significantly inhibited ability to amplify vaccinia virus due to a combination of carrier cell killing and induction of the anti-viral response. Therefore, in some embodiments, the cell vehicles provided herein and used in the methods provided herein, the cell vehicles are loaded with inhibitory factors or engineered for suppression/elimination/blockade of allogeneic rejection determinants. Such allogeneic rejection determinants can include, but are not limited to, the highly polymorphic and patient-specific MEW Class I and Class II molecules recognized by CD8 and CD4 T cells, or a broad spectrum of less polymorphic determinants recognized by various innate or mixed innate/adaptive T cell subpopulations such as NKT, iNKT, γδ (gd) T cells, which include the MHC-like MICA and CD1a, b, c, d molecules as well as various other stress-related or stress-sensing molecules like butyrophilins and Annexin A2.

For example, elimination/blockade of allogeneic MHC I, molecules can suppress the allogeneic immune responses against the carrier stem and tumor cells, particularly those of the CD8 T cells responsible for recognizing and responding to allogeneic MHC I mismatches. A pan-HLA blocking antibody (anti-human HLA-A, B, C Antibody) (see Example 8) can be used to suppress allogeneic anti-carrier cell responses of various innate and adaptive immune cell populations, whose numbers can be identified, for example, by multi-parameter flow cytometry analysis using CD69 as an activation marker and a set of cell type specific markers as follows: γδ T cells (CD3$^+$, γδ TCR$^+$), iNKT/NKT Type 1 cells (CD3$^+$, Va24Ja18$^+$), general NKT (CD3$^+$CD56$^+$ cells; γδ and iNKT excluded), classical CD4 (CD3$^+$CD4$^+$; γδ and iNKT excluded), classical CD8 T cells (CD3$^+$CD8$^+$; γδ and iNKT excluded), general NK cells (CD3$^-$CD56$^+$), and the NK subpopulations CD56$^{high}$CD16$^-$ (cytokine producing) and CD56$^{low}$CD16$^+$ (cytotoxic). It is demonstrated herein that transient or permanent blockade or elimination of allogeneic rejection determinants such as HLA (MEW Class I) and others can be used as an effective strategy to generate stem- or tumor cell-based carriers (cell vehicles) with enhanced immune evasive potential and the ability to more effectively deliver oncolytic viruses by blocking the induction of allogeneic immune responses and/or the secretion of effector cytokines such as IFNγ that can induce an anti-viral state and block the delivery and spread of the virus payload.

Immunologic responses and rejection of allogeneic and virus-infected stem or tumor carrier cells can be enhanced by engagement of various other non-MHC markers that typically are up-regulated on the surface of virally infected or transformed tumor cells and serve as immune co-stimulatory molecules. Such markers can compromise the ability of the carrier cells (e.g., tumor cells or stem cells infected with virus and used for delivery of the virus) to evade immunological rejection. For example, NKG2D molecules recognize MHC Class I-related proteins, such as human MIC A and MIC B, that are known to function as co-stimulatory molecules involved in the recognition and rejection of virus-infected and transformed tumor cells. Example 9 demonstrates that activation of the NKG2D signaling pathway using, e.g., an NKG2D-specific antibody provides a potent co-stimulatory signal that enhances and contributes to immune recognition and activation of the cellular immune response. Therefore, in some embodiments of the cell vehicles provided herein and used in the methods provided herein, the cell vehicles are loaded with inhibitory factors or engineered for suppression/elimination/blockade of co-stimulatory signals of the NKG2D signaling pathway. For example, the carrier cells can be engineered for transient or permanent suppression of expression of MIC A and/or MIC B, or can be loaded with or engineered for the transient or permanent expression of: Kaposi's sarcoma-associated herpesvirus (KSHV) protein K5 (aka kK5 or MIR2), which targets the degradation of MICA/MICB, UL16 (HCMV), which binds MICB and prevents expression of the ligand on the cell surface (causes intracellular retention of MICB), HCMV US18 and US20, which target MICA for lysosomal degradation (US20 also downregulates MICA and MICB), HCMV UL142, which downregulates MICA by retention at the cis-golgi apparatus, Human Herpesvirus-7 (HHV-7) U21 protein, which suppresses cell surface expression of MICA and MICB, EBV protein LMP2A, which leads to downregulation of MICA, Adenovirus E3/19K protein, which prevents cell surface transport of MICA/B, inhibiting recognition by CD8 T cells and NK cells, and the like.

4. Secrete Immunosuppressive Factors

Stem cells and tumor cells are known to use various strategies for immune suppression and evasion including IDO expression and IL-10 secretion. When they are used as carrier cells/cell vehicles for viruses, however, the viral amplification in the carrier cells causes gradual loss of viability and immunosuppressive potential. Therefore, in some embodiments of the cell vehicles provided herein and used in the methods provided herein, the cell vehicles are loaded with or engineered to transiently or permanently express an immunosuppressive molecule or cytokine, e.g., IL-10, to partially or completely reverse virus-mediated loss of immunosuppressive properties and improve the ability of virus infected carrier cells to avoid allogeneic responses and/or early immune recognition (see, e.g., Example 10).

5. Modifying the Cell Vehicles; Administration for Therapy

The carrier cells/cell vehicles modified to evade immune recognition and/or suppress anti-viral and/or allogeneic immune responses, as described above and elsewhere herein, can be obtained by pretreating/loading the carrier cells with the immune response modifying agent of interest (e.g., Ruxolitinib, peptidic inhibitor of C3 activation, IL-10, inhibitors of MIC A/MIC B, etc.) or by transient or permanent modification of the carrier cells for expression/suppression of expression of the immune response modifying agent of interest, using methods known to those of skill in the art and described herein. In embodiments, the load/expression can be local and/or transient, being present to the extent needed to facilitate infection by the virus, amplification of the virus, delivery of the virus to a tumor or other cancerous cells, and spread of the virus within the tumor or other cancer. In embodiments, the modification is by transient expression using a plasmid or other vector as known to those of skill in the art. In embodiments, the plasmid is engineered so that expression of the exogenous gene that is expressed is under the control of a viral promoter (e.g., immediate-early, early, intermediate, late promoters of a number of viruses such as adenovirus, vaccinia virus, CMV, RSV long terminal repeat promoter, adenoviral E1A promoter, and the like), thereby reducing or eliminating shutdown of exogenous gene expression by the virus that is subsequently loaded into the carrier cell. The modified carrier cells can be loaded with virus as described herein and administered parenterally, systemically, intratumorally or other routes as provided herein. For systemic administration, the carrier cell should evade immune recognition and/or suppress viral or allogeneic cellular immune responses long enough to deliver the virus to the target tumor/cancer site and facilitate its amplification and spread. For intratumoral administration, the carrier cell should evade immune recognition and/or suppress viral or allogeneic cellular immune responses long enough to penetrate deep into the tumor. The time for delivery can be anywhere from several hours, e.g., between 10-20 hours, such as 10, 15, 16, 17, 18, 19 or 20 hours to several days, e.g., 24 hours, 30 hours, 36 hours, 40 hours, 48 hours, to 3, 4, 5 or more days, depending on the carrier cell/virus composition. In general, sustained immunosuppression is not desirable once the viral delivery and spread at the target delivery site (e.g., tumor) has been achieved because it can prevent tumor-specific immune responses (directed against the tumor) from taking effect.

E. MODES OF ADMINISTRATION OF CELL VEHICLE/VIRUS FOR THERAPY

The carrier cells/viruses provided herein can be administered to a subject, including a subject having a tumor or having neoplastic cells, for therapy. An administered carrier cell and virus can be a carrier cell and virus provided herein or any other carrier cell and virus generated using the methods provided herein. In some examples, the carrier cells are autologous cells (i.e., derived from the patient) or allogeneic cells (i.e., not derived from the patient) that are stem cells, immune cells, or cancer cells. The carrier cells can be sensitized, for example, to enhance virus amplification ability, to block induction of the anti-viral state, to protect against allogeneic inactivation/rejection determinants, and to protect against complement, or the carrier cells can be engineered, for example, to be unresponsive to an interferon-induced antiviral state, to evade allogeneic recognition by T cells, including γδ T cells, NK cells and NKT cells, to express immunosuppressive factors of human or viral origin, to express cancer- or stem cell-derived factors sensitizing poorly permissive tumor cells to oncolytic virus infection, and to express factors interfering with the function of complement and neutralizing antibodies. In some examples, the virus administered is a virus containing a characteristic such as attenuated pathogenicity, low toxicity, preferential accumulation in tumor, ability to activate an immune response against tumor cells, high immunogenicity, replication competence and ability to express exogenous proteins, and combinations thereof.

a. Administration of Irradiated or Non-Irradiated Virus-Infected Carrier Cells

Carrier cells can be irradiated prior to, or following, infection with oncolytic virus. In order to use transformed cells as cell carriers for oncolytic virotherapy, uninfected cells must be prevented from establishing new metastatic growth following administration. This can be accomplished by γ-irradiation of carrier cells before or after viral infection, prior to administration, which ablates tumorigenicity, but preserves metabolic activity and does not affect viral production/amplification and release. For example, carrier cells can be irradiated up to 24 hours before viral infection, or up to 24 hours after viral infection.

The amount of radiation can be selected by one skilled in the art according to any of a variety of factors, including the nature of the carrier cell and virus. The radiation amount can be sufficient to inactivate the carrier cells and prevent tumorigenesis without affecting viral infection, amplification and release. For example, the amount of radiation can be about 5 Gy, 10 Gy, 15 Gy, 20 Gy, 25 Gy, 30 Gy, 35 Gy, 40 Gy, 45 Gy 50 Gy, 100 Gy, 120 Gy, 150 Gy, 200 Gy, 250 Gy, 500 Gy or more.

b. Routes of Administration

The carrier cell/virus combination can be delivered or administered to a subject locally or systemically. For example, modes of administration include, but are not limited to, systemic, parenteral, intravenous, intraperitoneal, subcutaneous, intramuscular, transdermal, intradermal, intra-arterial (e.g., hepatic artery infusion), intravesicular perfusion, intrapleural, intraarticular, topical, intratumoral, intralesional, endoscopic, multipuncture (e.g., as used with smallpox vaccines), by inhalation, percutaneous, subcutaneous, intranasal, intratracheal, oral, intracavity (e.g., administering to the bladder via a catheter, administering to the gut by suppository or enema), vaginal, rectal, intracranial, intraprostatic, intravitreal, aural, ocular or topical administration.

One skilled in the art can select any mode of administration compatible with the subject and the carrier cell/virus combination, and that also is likely to result in the carrier cell/virus reaching and entering the target cell-type or tissue, e.g., tumors and/or metastases. The route of administration can be selected by one skilled in the art according to any of a variety of factors, including the nature of the disease, the properties of the target cell or tissue (e.g., the kind of tumor), and the particular cell vehicle/virus to be administered. Administration to the target site can be performed, for example, by ballistic delivery, as a colloidal dispersion system, or systemic administration can be performed by injection into an artery.

c. Devices

Any of a variety of devices known in the art for administering medications, pharmaceutical compositions and vaccines can be used for administering the carrier cell/virus combinations. Exemplary devices include, but are not limited to, a hypodermic needle, an intravenous needle, a catheter, a needle-less injection device, an inhaler and a liquid dispenser, such as an eyedropper. For example, the Qaudra-Fuse™ multi-pronged injection needle (Rex Medical, Conshohocken, Pa.) can be used.

Typically, the device for administering a carrier cell/virus combination will be compatible with the carrier cell/virus combination; for example, a needle-less injection device such as a high-pressure injection device can be used with carrier cells/viruses not damaged by high-pressure injection, but is typically not used with carrier cells/viruses damaged by high-pressure injection. Also provided herein are devices for administering an additional agent or compound to a subject. Any of a variety of devices known in the art for administering medications to a subject can be used. Exemplary devices include, but are not limited to, a hypodermic needle, an intravenous needle, a catheter, a needle-less injection device, an inhaler and a liquid dispenser, such as an eyedropper. Typically the device for administering the compound will be compatible with the desired method of administration of the compound. For example, a compound to be delivered systemically or subcutaneously can be administered with a hypodermic needle and syringe.

d. Dosages of Administration

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular cell carrier and virus to be administered, duration and route of administration, the kind and stage of the disease, for example, tumor size, and other treatments or compounds, such as chemotherapeutic drugs, being administered concurrently. In addition to the above factors, such levels can be affected by the infectivity and amplification potential of the virus, and the nature of the carrier cell and/or virus, as can be determined by one skilled in the art.

In the present methods, appropriate minimum dosage levels and dosage regimes of cell carriers and viruses can be levels sufficient for the carrier cells to deliver virus to the target site and for the virus to survive, grow and replicate in a tumor or metastasis. Generally, 100,000 to 1 billion unmodified, sensitized, protected or genetically engineered allogeneic or autologous carrier cells are infected ex vivo with any suitable oncolytic virus, including an oncolytic virus chosen based on the co-culture screen and analysis methods provided herein, at a multiplicity of infection (MOI) of 0.1 and higher. Cell carriers that produce a pfu/cell of at least 10 are selected. For example, cell carriers that produce a pfu/cell of at least or at least about 10, at least or at least about 100, at least or at least about 1,000 or higher are selected. Generally, the virus is administered in an amount that is at least or about or $1\times10^5$ pfu at least one time over a cycle of administration. Exemplary minimum levels for administering a virus to a 65 kg human can include at least about $1\times10^5$ plaque forming units (pfu), at least about $5\times10^5$ pfu, at least about $1\times10^6$ pfu, at least about $5\times10^6$ pfu, at least about $1\times10^7$ pfu, at least about $1\times10^8$ pfu, at least about $1\times10^9$ pfu, or at least about $1\times10^{10}$ pfu. For example, the virus is administered in an amount that is at least or about or is $1\times10^5$ pfu, $1\times10^6$ pfu, $1\times10^7$ pfu, $1\times10^8$ pfu, $1\times10^9$ pfu, $1\times10^{10}$ pfu, $1\times10^{11}$ pfu, $1\times10^{12}$ pfu, $1\times10^{13}$ pfu, or $1\times10^{14}$ pfu at least one time over a cycle of administration.

e. Regimens

In the dosage regimen, the amount of carrier cell and virus can be administered as a single administration or multiple times over the cycle of administration. Hence, the methods provided herein can include a single administration of a cell carrier/virus combination to a subject or multiple administrations of a cell carrier/virus combination to a subject. In some examples, a single administration is sufficient to deliver and establish a virus in a tumor, where the virus can proliferate and can cause or enhance an anti-tumor response in the subject; such methods do not require additional administrations of a carrier cell/virus combination in order to cause or enhance an anti-tumor response in a subject, which can result, for example in inhibition of tumor growth, inhibition of metastasis growth or formation, reduction in tumor size, elimination of a tumor or metastasis, inhibition or prevention of recurrence of a neoplastic disease or new tumor formation, or other cancer therapeutic effects.

In other examples, a cell carrier/virus combination can be administered on different occasions, separated in time typically by at least one day. For example, a carrier cell/virus combination can be administered two times, three time, four times, five times, or six times or more, with one day or more, two days or more, one week or more, or one month or more time between administrations. Separate administrations can increase the likelihood of delivering a virus to a tumor or metastasis, where a previous administration has been ineffective in delivering a virus to a tumor or metastasis. Separate administrations can increase the locations on a tumor or metastasis where virus proliferation can occur or can otherwise increase the titer of virus accumulated in the tumor, which can increase the scale of release of antigens or other compounds from the tumor in eliciting or enhancing a host's anti-tumor immune response, and also can, optionally, increase the level of virus-based tumor lysis or tumor cell death. Separate administrations of a virus can further extend a subject's immune response against viral antigens, which can extend the host's immune response to tumors or metastases in which viruses have accumulated, and can increase the likelihood of a host mounting an anti-tumor immune response.

When separate administrations are performed, each administration can be a dosage amount that is the same or different relative to other administration dosage amounts. In one example, all administration dosage amounts are the same. In other examples, a first dosage amount can be a larger dosage amount than one or more subsequent dosage amounts, for example, at least 10× larger, at least 100× larger, or at least 1000× larger than subsequent dosage amounts. In one example of a method of separate administrations in which the first dosage amount is greater than one or more subsequent dosage amounts, all subsequent dosage amounts can be the same, or smaller amount relative to the first administration.

Separate administrations can include any number of two or more administrations, including two, three, four, five or six administrations. One skilled in the art can readily determine the number of administrations to perform or the desirability of performing one or more additional administrations according to methods known in the art for monitoring therapeutic methods and other monitoring methods provided herein. Accordingly, the methods provided herein include methods of providing to the subject one or more administrations of a carrier cell/virus combination, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, indication of tumor growth or inhibition of tumor growth, appearance of new metastases or inhibition of metastasis, the subject's anti-virus antibody titer, the subject's anti-tumor antibody titer, the overall health of the subject, the weight of the subject, the presence of virus solely in tumor and/or metastases, and the presence of virus in normal tissues or organs.

The time period between administrations can be any of a variety of time periods. The time period between administrations can be a function of any of a variety of factors, including monitoring steps, as described in relation to the number of administrations, the time period for a subject to mount an immune response, the time period for a subject to clear the virus from normal tissue, or the time period for virus proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the virus from normal tissue; for example, the time period can be more than the time period for a subject to clear the virus from normal tissue, such as more than about a day, more than about two days, more than about three days, more than about five days, or more than about a week. In another example, the time period can be a function of the time period for virus proliferation in the tumor or metastasis; for example, the time period can be more than the amount of time for a detectable signal to arise in a tumor or metastasis after administration of a virus expressing a detectable marker, such as about 3 days, about 5 days, about a week, about ten days, about two weeks, or about a month.

For example, an amount of carrier cell/virus combination is administered two times, three times, four times, five times, six times or seven times over a cycle of administration. The amount of virus can be administered on the first day of the cycle, the first and second day of the cycle, each of the first three consecutive days of the cycle, each of the first four consecutive days of the cycle, each of the first five consecutive days of the cycle, each of the first six consecutive days of the cycle, or each of the first seven consecutive days of the cycle. Generally, the cycle of administration is 7 days, 14 days, 21 days or 28 days. Depending on the responsiveness or prognosis of the patient, the cycle of administration is repeated over the course of several months or years.

Generally, appropriate maximum dosage levels or dosage regimens of carrier cells/viruses are levels that are not toxic to the host, levels that do not cause splenomegaly of 3 times or more, levels that do not result in viral colonies or plaques in normal tissues or organs after about 1 day or after about 3 days or after about 7 days.

F. TREATMENT METHODS AND MONITORING COORDINATED WITH TREATMENT

Provided herein are methods of treatment by administering an oncolytic virus, in combination with a cell vehicle as provided herein to facilitate delivery of the virus, to treat a subject having proliferative or inflammatory disease or condition. In particular, the condition is associated with immunoprivileged cells or tissues. A disease or condition associated with immunoprivileged cells or tissues includes, for example, proliferative disorders or conditions, including the treatment (such as inhibition) of cancerous cells, neoplasms, tumors, metastases, cancer stem cells, and other immunoprivileged cells or tissues, such as wounds and wounded or inflamed tissues. In particular, examples of such methods, combinations provided herein are administered by intravenous administration for systemic delivery. In other examples, the combinations provided herein are administered by intratumoral injection. In embodiments, the subject has cancer. Any of the cell vehicles provided herein can be used to provide virotherapy to subjects in need thereof including, sensitized cell vehicles, protected cell vehicles, engineered cell vehicles and matched cell vehicles which can include sensitized/engineered cell vehicles that additionally are screened by the matching assay provided herein.

In some embodiments of the methods provided herein, the subject, in addition to being treated with the combination of the cell vehicle and the virus, additionally is treated with a separate composition containing a protected cell vehicle, e.g., pretreated with IFNγ, to provide extended survival and/or local immunosuppression. The separate composition containing the protected cell vehicle can be administered concurrently with the cell vehicle/virus combination or can be administered between 10 hours to 3 or more days prior to or after administering the combination. In some embodiments, the protected cell vehicle is administered 24 hours prior to, or 24 hours after, administering the combination.

The combinations provided herein can be administered by a single injection, by multiple injections, or continuously. For example, the compositions can be administered by slow infusion including using an intravenous pump, syringe pump, intravenous drip or slow injection. For example, continuous administration of the compositions can occur over the course of minutes to hours, such as between or about between 1 minute to 1 hour, such as between 20 and 60 minutes.

Cancers amenable to the treatment and detection methods described herein also include cancers that metastasize. It is understood by those in the art that metastasis is the spread of cells from a primary tumor to a noncontiguous site, usually via the bloodstream or lymphatics, which results in the establishment of a secondary tumor growth. Examples of cancers contemplated for treatment include, but are not limited to melanoma, including choroidal and cutaneous melanoma; bladder, non-small cell lung, small cell lung, lung, head, neck, breast, pancreatic, gum, tongue, prostate, renal, bone, testicular, ovarian, cervical, gastrointestinal lymphoma, brain, or colon cancer; hepatocarcinoma; retinoblastoma; mesothelioma; astrocytoma; glioblastoma; neuroblastoma; and any other tumors or neoplasms that are metastasized or at risk of metastasis.

The subject of the methods provided herein can be any subject, such as an animal or plant subject, including mammal or avian species. For example, the animal subject can be a human or non-human animal including, but not limited to, domesticated and farm animals, such as a pig, cow, a goat, sheep, horse, cat, or dog. In particular examples, the animal subject is a human subject.

The methods provided herein can further include one or more steps of monitoring the subject, monitoring the tumor, and/or monitoring the virus administered to the subject. Any of a variety of monitoring steps can be included in the methods provided herein, including, but not limited to, monitoring tumor size, monitoring anti-(tumor antigen) antibody titer, monitoring the presence and/or size of metastases, monitoring the subject's lymph nodes, monitoring the subject's weight or other health indicators including blood or urine markers, monitoring anti-(viral antigen) antibody titer, monitoring viral expression of a detectable gene product, and directly monitoring viral titer in a tumor, tissue or organ of a subject.

The purpose of the monitoring can be for assessing the health state of the subject or the progress of therapeutic treatment of the subject, or can be for determining whether or not further administration of the same or a different virus is warranted, or for determining when or whether or not to administer a compound to the subject where the compound can act to increase the efficacy of the therapeutic method, or the compound can act to decrease the pathogenicity of the virus administered to the subject.

Tumor and or metastasis size can be monitored by any of a variety of methods known in the art, including external assessment methods or tomographic or magnetic imaging methods, such as the detection methods described herein. In addition, methods provided herein, for example, monitoring gene expression (e.g., viral gene expression), can be used for monitoring tumor and/or metastasis size.

Monitoring size over several time points can provide information regarding the efficacy of the therapeutic methods provided herein. In addition, monitoring the increase or decrease in size of a tumor or metastasis can also provide information regarding the presence (i.e., detection and/or diagnosis) of additional tumors and/or metastases in the subject. Monitoring tumor size over several time points can provide information regarding the development of a neoplastic disease in a subject, including the efficacy of treatments of a neoplastic disease in a subject, such as the treatments provided herein.

The methods provided herein also can include monitoring the antibody titer in a subject, including antibodies produced in response to administration of a cell vehicle delivering a virus to a subject. For example, the viruses administered in the methods provided herein can elicit an immune response to endogenous viral antigens. The viruses administered in the methods provided herein also can elicit an immune response to exogenous genes expressed by a virus. The viruses administered in the methods provided herein also can elicit an immune response to tumor antigens. Monitoring antibody titer against viral antigens, viral expressed exogenous gene products, or tumor antigens can be used in methods of monitoring the toxicity of a virus, monitoring the efficacy of treatment methods, or monitoring the level of gene product or antibodies for production and/or harvesting.

In one example, monitoring antibody titer can be used to monitor the toxicity of a virus. Antibody titer against a virus can vary over the time period after administration of the virus to the subject, where at some particular time points, a low anti-(viral antigen) antibody titer can indicate a higher toxicity, while at other time points a high anti-(viral antigen) antibody titer can indicate a higher toxicity. The viruses used in the methods provided herein can be immunogenic, and can therefore elicit an immune response soon after administering the virus to the subject.

Generally, a virus against which a subject's immune system can quickly mount a strong immune response can be a virus that has low toxicity when the subject's immune system can remove the virus from all normal organs or tissues. Thus, in some examples, a high antibody titer against viral antigens soon after administering the virus to a subject can indicate low toxicity of a virus. In contrast, a virus that is not highly immunogenic can infect a host organism without eliciting a strong immune response, which can result in a higher toxicity of the virus to the host. Accordingly, in some examples, a high antibody titer against viral antigens soon after administering the virus to a subject can indicate low toxicity of a virus.

In other examples, monitoring antibody titer can be used to monitor the efficacy of treatment methods. In the methods provided herein, antibody titer, such as anti-(tumor antigen) antibody titer, can indicate the efficacy of a therapeutic method such as a therapeutic method to treat neoplastic disease. Therapeutic methods provided herein can include causing or enhancing an immune response against a tumor and/or metastasis. Thus, by monitoring the anti-(tumor antigen) antibody titer, it is possible to monitor the efficacy of a therapeutic method in causing or enhancing an immune response against a tumor and/or metastasis.

The therapeutic methods provided herein also can include administering to a subject a cell vehicle containing a virus that can accumulate in a tumor and can cause or enhance an anti-virus or anti-cell vehicle immune response. Accordingly, it is possible to monitor the ability of a host to mount an immune response against viruses or cell vehicles accumulated in a tumor or metastasis, which can indicate that a subject has also mounted an anti-tumor immune response, or can indicate that a subject is likely to mount an anti-tumor immune response, or can indicate that a subject is capable of mounting an anti-tumor immune response.

The methods provided herein also can include methods of monitoring the health of a subject. Some of the methods provided herein are therapeutic methods, including neoplastic disease therapeutic methods. Monitoring the health of a subject can be used to determine the efficacy of the therapeutic method, as is known in the art. The methods provided herein also can include a step of administering to a subject a combination of a cell vehicle as provided herein, and a virus. Monitoring the health of a subject can be used to determine the pathogenicity of a virus in the combination, when administered to a subject. Any of a variety of health diagnostic methods for monitoring disease such as neoplastic disease, infectious disease, or immune-related disease can be monitored, as is known in the art. For example, the weight, blood pressure, pulse, breathing, color, temperature or other observable state of a subject can indicate the health of a subject. In addition, the presence or absence or level of one or more components in a sample from a subject can indicate the health of a subject. Typical samples can include blood and urine samples, where the presence or absence or level of one or more components can be determined by performing, for example, a blood panel or a urine panel diagnostic test. Exemplary components indicative of a subject's health include, but are not limited to, white blood cell count, hematocrit, or reactive protein concentration.

G. PHARMACEUTICAL COMPOSITIONS, COMBINATIONS AND KITS

Provided herein are pharmaceutical compositions, combinations and kits containing carrier cells and oncolytic viruses provided herein. Pharmaceutical compositions can include a matched carrier cell identified by the methods provided herein and a pharmaceutical carrier. The matched carrier cells can include sensitized cells, engineered cells or primed cells (e.g., "protected" carrier cells pre-treated with IFNγ), prepared by any of the methods provided herein. Pharmaceutical compositions can include an oncolytic virus provided herein and a pharmaceutical carrier. Combinations can include, for example, a carrier cell and an oncolytic virus; a matched carrier cell and an oncolytic virus; a sensitized carrier cell and an oncolytic virus; an engineered carrier cell and an oncolytic virus; any carrier cell, including sensitized and engineered cells, an oncolytic virus and a primed (protected) carrier cell; an oncolytic virus, a primed (protected) carrier cell and an unprotected carrier cell that is matched or modified as provided herein. Combinations can include any of the carrier cells provided herein, an oncolytic virus and a detectable compound; any carrier cell, an oncolytic virus and a therapeutic compound; any carrier cell, an oncolytic virus and a viral expression modulating compound, or any combination thereof. Kits can include one or more pharmaceutical compositions or combinations provided herein, and one or more components, such as instructions for use, a device for administering the pharmaceutical composition or combination to a subject, a device for administering a therapeutic or diagnostic compound to a subject or a device for detecting a virus in a subject.

A carrier cell contained in a pharmaceutical composition, combination or kit can include any carrier cell provided herein. An oncolytic virus contained in a pharmaceutical composition, combination or kit can include any virus provided herein.

1. Pharmaceutical Compositions

Provided herein are pharmaceutical compositions containing a carrier cell, a primed (protected) carrier cell, a sensitized carrier cell, an engineered carrier cell, an oncolytic virus, or any carrier cell and oncolytic virus provided herein, and a suitable pharmaceutical carrier. A pharmaceutically acceptable carrier includes a solid, semi-solid or liquid material that acts as a vehicle carrier or medium for the virus. Pharmaceutical compositions provided herein can be formulated in various forms, for example in solid, semi-solid, aqueous, liquid, powder or lyophilized form. Exemplary pharmaceutical compositions containing any carrier cell (including primed, sensitized, engineered cells) or an oncolytic virus provided herein include, but are not limited to, sterile injectable solutions, sterile packaged powders, eye drops, tablets, pills, powders, lozenges, sachets, cachets, elixirs, suspensions, emulsions, solutions, syrups, aerosols (as a solid or in a liquid medium), ointments, soft and hard gelatin capsules, and suppositories.

Examples of suitable pharmaceutical carriers are known in the art and include, but are not limited to, water, buffers, saline solutions, phosphate buffered saline solutions, various types of wetting agents, sterile solutions, alcohols, gum arabic, vegetable oils, benzyl alcohols, gelatin, glycerin, carbohydrates, such as lactose, sucrose, dextrose, amylose or starch, sorbitol, mannitol, magnesium stearate, talc, silicic acid, viscous paraffin, perfume oil, fatty acid monoglycerides and diglycerides, pentaerythritol fatty acid esters, hydroxy methylcellulose, and powders, among others. Pharmaceutical compositions provided herein can contain other additives including, for example, antioxidants, preserving agents, analgesic agents, binders, disintegrants, coloring, diluents, excipients, extenders, glidants, solubilizers, stabilizers, tonicity agents, vehicles, viscosity agents, flavoring agents, sweetening agents, emulsions, such as oil/water emulsions, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxypropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients, such as, but not limited to, crystalline cellulose, microcrystalline cellulose, citric acid, dextrin, liquid glucose, lactic acid, lactose, magnesium chloride, potassium metaphosphate, starch, among others. Such carriers and/or additives can be formulated by conventional methods and can be administered to the subject at a suitable dose. Stabilizing agents such as lipids, nuclease inhibitors, polymers, and chelating agents can preserve the compositions from degradation within the body. Other suitable formulations for use in a pharmaceutical composition can be found, for example, in *Remington: The Science and Practice of Pharmacy* (2005, Twenty-first edition, Gennaro & Gennaro, eds., Lippencott Williams and Wilkins).

Pharmaceutical formulations that include a carrier cell and/or oncolytic virus provided herein for injection or mucosal delivery typically include aqueous solutions of the virus provided in a suitable buffer for injection or mucosal administration or lyophilized forms of the virus for reconstitution in a suitable buffer for injection or mucosal administration. Such formulations optionally can contain one or more pharmaceutically acceptable carriers and/or additives as described herein or known in the art. Liquid compositions for oral administration generally include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Pharmaceutical compositions provided herein can be formulated to provide quick, sustained or delayed released of a carrier cell and/or virus as described herein by employing procedures known in the art. For preparing solid compositions such as tablets, a carrier cell and/or virus provided herein is mixed with a pharmaceutical carrier to form a solid composition. Optionally, tablets or pills are coated or otherwise compounded to provide a dosage form affording the advantage of prolonged action in the subject. For example, a tablet or pill contains an inner dosage and an outer dosage component, the latter being in the form of an envelope over the former. The two components can be separated by an enteric layer, for example, which serves to resist disintegration in the stomach and permit the inner component to pass intact into the duodenum or to be delayed in release. A variety of materials are used for such enteric layers or coatings, including, for example, a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. These liquid or solid compositions optionally can contain suitable pharmaceutically acceptable excipients and/or additives as described herein or known in the art. Such compositions are administered, for example, by the oral or nasal respiratory route for local or systemic effect. Compositions in pharmaceutically acceptable solvents are nebulized by use of inert gases. Nebulized solutions are inhaled, for example, directly from the nebulizing device, from an attached face mask tent, or from an intermittent positive pressure breathing machine. Solution, suspension, or powder compositions are administered, orally or nasally, for example, from devices which deliver the formulation in an appropriate manner such as, for example, use of an inhaler.

Pharmaceutical compositions provided herein can be formulated for transdermal delivery via a transdermal delivery devices ("patches"). Such transdermal patches are used to provide continuous or discontinuous infusion of a virus provided herein. The construction and use of transdermal patches for the delivery of pharmaceutical agents are performed according to methods known in the art (see, for example, U.S. Pat. No. 5,023,252). Such patches are constructed for continuous, pulsatile, or on-demand delivery of a carrier cell and/or virus provided herein.

Colloidal dispersion systems that can be used for delivery of viruses include macromolecule complexes, nanocapsules, microspheres, beads and lipid-based systems including oil-in-water emulsions (mixed), micelles, liposomes and lipoplexes. An exemplary colloidal system is a liposome. Organ-specific or cell-specific liposomes can be used in order to achieve delivery only to the desired tissue. The targeting of liposomes can be carried out by the person skilled in the art by applying commonly known methods. This targeting includes passive targeting (utilizing the natural tendency of the liposomes to distribute to cells of the reticuloendothelial system (RES) in organs which contain sinusoidal capillaries) or active targeting (for example, by coupling the liposome to a specific ligand, for example, an antibody, a receptor, sugar, glycolipid and protein, by methods known to those of skill in the art). Monoclonal antibodies can be used to target liposomes to specific tissues, for example, tumor tissues, via specific cell-surface ligands.

2. Combinations

Provided are combinations of a carrier cell and an oncolytic virus; a sensitized carrier cell and an oncolytic virus; an engineered carrier cell and an oncolytic virus; or any carrier cell, including sensitized and engineered cells, an oncolytic virus and a primed (protected) carrier cell (e.g., a carrier cell pretreated with IFNγ), which combination optionally can include an unprotected carrier cell that is matched or modified according to the methods provided herein. A combination can include a third or fourth agent, such as a second virus or other therapeutic or diagnostic agent. A combination can include a virus provided herein with one or more additional viruses, including, for example, one or more additional diagnostic or therapeutic viruses. A combination can contain pharmaceutical compositions containing a virus provided herein; or a carrier cell (including sensitized and engineered cells) and a virus; or a carrier cell (including sensitized and engineered cells), a virus and a primed cell, as described herein. A combination also can include any reagent for effecting treatment or diagnosis in accord with the methods provided herein such as, for example, an antiviral or chemotherapeutic agent. Combinations also can contain a compound used for the modulation of gene expression from endogenous or heterologous genes encoded by the virus.

Combinations provided herein can contain a carrier cell, virus and a therapeutic compound. Therapeutic compounds for the compositions provided herein can be, for example, an anti-cancer or chemotherapeutic compound. Exemplary therapeutic compounds include, for example, cytokines, growth factors, photosensitizing agents, radionuclides, toxins, siRNA molecules, enzyme/pro E drug pairs, anti-metabolites, signaling modulators, anti-cancer antibiotics, anti-cancer antibodies, angiogenesis inhibitors, chemotherapeutic compounds, antimetastatic compounds or a combination of any thereof.

Carrier cells and viruses provided herein can be combined with an anti-cancer compound, such as a platinum coordination complex. Exemplary platinum coordination complexes include, for example, cisplatin, carboplatin, oxaliplatin, DWA2114R, NK121, IS3 295, and 254-S. Exemplary chemotherapeutic agents also include, but are not limited to, methotrexate, vincristine, adriamycin, non-sugar containing chloroethylnitrosoureas, 5-fluorouracil, mitomycin C, bleomycin, doxorubicin, dacarbazine, taxol, fragyline, Meglamine GLA, valrubicin, carmustine, polifeprosan, MM1270, BAY 12-9566, RAS farnesyl transferase inhibitor, farnesyl transferase inhibitor, MMP, MTA/LY231514, lometrexol/LY264618, Glamolec, CI-994, TNP-470, Hycamtin/topotecan, PKC412, Valspodar/PSC833, Novantrone/mitoxantrone, Metaret/suramin, BB-94/batimastat, E7070, BCH-4556, CS-682, 9-AC, AG3340, AG3433, Incel/VX-710, VX-853, ZD0101, IS1641, ODN 698, TA 2516/marimastat, BB2516/marimastat, CDP 845, D2163, PD183805, DX8951f, Lemonal DP 2202, FK 317, picibanil/OK-432, valrubicin/AD 32, strontium-89/Metastron, Temodal/temozolomide, Yewtaxan/paclitaxel, Taxol/paclitaxel, Paxex/paclitaxel, Cyclopax/oral paclitaxel, Xeloda/capecitabine, Furtulon/doxifluridine, oral taxoids, SPU-077/cisplatin, HMR 1275/flavopiridol, CP-358 (774)/EGFR, CP-609 (754)/RAS oncogene inhibitor, BMS-182751/oral platinum, UFT(Tegafur/Uracil), Ergamisol/levamisole, Campto/levamisole, Eniluracil/776C85/5FU enhancer, Camptosar/irinotecan, Tomudex/raltitrexed, Leustatin/cladribine, Caelyx/liposomal doxorubicin, Myocet/liposomal doxorubicin, Doxil/liposomal doxorubicin, Evacet/liposomal doxorubicin, Fludara/fludarabine, Pharmorubicin/epirubicin, DepoCyt, ZD1839, LU 79553/Bis-Naphthalimide, LU 103793/Dolastatin, Gemzar/gemcitabine, ZD 0473/AnorMED, YM 116, Iodine seeds, CDK4 and CDK2 inhibitors, PARP inhibitors, D4809/dexifosfamide, Ifex/Mesnex/ifosfamide, Vumon/teniposide, Paraplatin/carboplatin, Platinol/cisplatin, VePesid/Eposin/Etopophos/etoposide, ZD 9331, Taxotere/docetaxel, prodrugs of guanine arabinoside, taxane analogs, nitrosoureas, alkylating agents such as melphalan and cyclophosphamide, aminoglutethimide, asparaginase, busulfan, carboplatin, chlorambucil, cytarabine HCl, dactinomycin, daunorubicin HCl, estramustine phosphate sodium, etoposide (VP16-213), floxuridine, fluorouracil (5-FU), flutamide, hydroxyurea (hydroxycarbamide), ifosfamide, interferon alfa-2a, interferon alfa-2b, leuprolide acetate (LHRH-releasing factor analogue), lomustine (CCNU), mechlorethamine HCl (nitrogen mustard), mercaptopurine, mesna, mitotane (o,p'-DDD), mitoxantrone HCl, octreotide, plicamycin, procarbazine HCl, streptozocin, tamoxifen citrate, thioguanine, thiotepa, vinblastine sulfate, amsacrine (m-AMSA), azacitidine, erythropoietin, hexamethylmelamine (HMM), interleukin 2, mitoguazone (methyl-GAG; methyl glyoxal bis-guanylhydrazone; MGBG), pentostatin (2'deoxycoformycin), semustine (methyl-CCNU), teniposide (VM-26) and vindesine sulfate. Additional exemplary therapeutic compounds for use in pharmaceutical compositions and combinations provided herein can be found elsewhere herein (see e.g., Section H for exemplary cytokines, growth factors, photosensitizing agents, radionuclides, toxins, siRNA molecules, enzyme/pro-drug pairs, anti-metabolites, signaling modulators, anti-cancer antibiotics, anticancer antibodies, angiogenesis inhibitors, and chemotherapeutic compounds).

In some examples, the combination can include additional therapeutic compounds such as, for example, compounds that are substrates for enzymes encoded and expressed by the virus, or other therapeutic compounds provided herein or known in the art to act in concert with a virus. For example, the virus can express an enzyme that converts a prodrug into an active chemotherapy drug for killing the cancer cell. Hence, combinations provided herein can contain a therapeutic compound, such as a prodrug. An exemplary virus/therapeutic compound combination can include a virus encoding Herpes simplex virus thymidine kinase with the prodrug ganciclovir. Additional exemplary enzyme/pro-drug pairs, for the use in combinations provided include, but are not limited to, varicella zoster thymidine kinase/ganciclovir, cytosine deaminase/5-fluorouracil, purine nucleoside phosphorylase/6-methylpurine deoxyriboside, beta lactamase/cephalosporin-doxorubicin, carboxypeptidase G2/4-[(2-chloroethyl)(2-mesyloxyethyl)amino]benzoyl-L-glutamic acid, cytochrome P450/acetaminophen, horseradish peroxidase/indole-3-acetic acid, nitroreductase/CB1954, rabbit carboxylesterase/7-ethyl-10-[4-(1-piperidino)-1-piperidino] carbonyloxycamptothecin (CPT-11), mushroom tyrosinase/bis-(2-chloroethyl)amino-4-hydroxyphenylaminomethanone 28, beta galactosidase/1-chloromethyl-5-hydroxy-1,2-dihydro-3H-benz[e]indole, beta glucuronidase/epirubicin-glucuronide, thymidine phosphorylase/5'-deoxy-5-fluorouridine, deoxycytidine kinase/cytosine arabinoside, beta-lactamase and linamerase/linamarin. Additional exemplary prodrugs, for the use in combinations can also be found elsewhere herein (see e.g., Section H). Any of a variety of known combinations provided herein or otherwise known in the art can be included in the combinations provided herein.

In some examples, the combination can include compounds that can kill or inhibit viral growth or toxicity. Such compounds can be used to alleviate one or more adverse side effects that can result from viral infection (see, e.g., U.S. Patent Pub. No. US 2009-016228-A1). Combinations provided herein can contain antibiotic, antifungal, anti-parasitic or antiviral compounds for treatment of infections. In some examples, the antiviral compound is a chemotherapeutic agent that inhibits viral growth or toxicity.

Exemplary antibiotics which can be included in a combination with a carrier cell and virus provided herein include, but are not limited to, ceftazidime, cefepime, imipenem, aminoglycoside, vancomycin and antipseudomonal β-lactam. Exemplary antifungal agents which can be included in a combination with a carrier cell and virus provided herein include, but are not limited to, amphotericin B, dapsone, fluconazole, flucytosine, griseofulvin, itraconazole, ketoconazole, miconazole, clotrimazole, nystatin, and combinations thereof. Exemplary antiviral agents which can be included in a combination with a carrier cell and virus provided herein include, but are not limited to, cidofovir, alkoxyalkyl esters of cidofovir (CDV), cyclic CDV, and (S)-9-(3-hydroxy-2 phosphonylmethoxypropyl)adenine, 5-(dimethoxymethyl)-2'-deoxyuridine, isatin-beta-thiosemicarbazone, N-methanocarbathymidine, brivudine, 7-deazaneplanocin A, ST-246, Gleevec, 2'-beta-fluoro-2',3'-dideoxyadenosine, indinavir, nelfinavir, ritonavir, nevirapine, AZT, ddI, ddC, and combinations thereof. Typically, combinations with an antiviral agent contain an antiviral agent known to be effective against the virus of the combination. For example, combinations can contain a vaccinia virus with an antiviral compound, such as cidofovir, alkoxyalkyl esters of cidofovir, ganciclovir, acyclovir, ST-246, Gleevec, and derivatives thereof.

In some examples, the combination can include a detectable compound. A detectable compound can include, for example, a ligand, substrate or other compound that can interact with and/or bind specifically to a protein or RNA encoded and expressed by the virus or carrier cell, and can provide a detectable signal, such as a signal detectable by tomographic, spectroscopic, magnetic resonance, or other known techniques. In some examples, the protein or RNA is an exogenous protein or RNA. In some examples, the protein or RNA expressed by the virus or carrier cell modifies the detectable compound where the modified compound emits a detectable signal. Exemplary detectable compounds can be, or can contain, an imaging agent such as a magnetic resonance, ultrasound or tomographic imaging agent, including a radionuclide. The detectable compound can include any of a variety of compounds as provided elsewhere herein or are otherwise known in the art. Exemplary proteins that can be expressed by the virus or carrier cell and a detectable compound combinations employed for detection include, but are not limited to luciferase and luciferin, β-galactosidase and (4,7,10-tri(acetic acid)-1-(2-β-galactopyranosylethoxy)-1,4,7,10-tetraazacyclododecane) gadolinium (Egad), and other combinations known in the art.

In some examples, the combination can include a gene expression modulating compound that regulates expression of one or more genes encoded by the virus or carrier cell. Compounds that modulate gene expression are known in the art, and include, but are not limited to, transcriptional activators, inducers, transcriptional suppressors, RNA polymerase inhibitors and RNA binding compounds such as siRNA or ribozymes. Any of a variety of gene expression modulating compounds known in the art can be included in the combinations provided herein. Typically, the gene expression modulating compound included with a virus in the combinations provided herein will be a compound that can bind, inhibit or react with one or more compounds, active in gene expression such as a transcription factor or RNA of the virus or carrier cell of the combination. An exemplary virus or carrier cell/expression modulator combination can be a virus or carrier cell encoding a chimeric transcription factor complex having a mutant human progesterone receptor fused to a yeast GAL4 DNA-binding domain an activation domain of the herpes simplex virus protein VP16 and also containing a synthetic promoter containing a series of GAL4 recognition sequences upstream of the adenovirus major late E1B TATA box, where the compound can be RU486 (see, e.g., Yu et al. (2002) Mol Genet Genomics 268:169-178). A variety of other virus or carrier cell/expression modulator combinations known in the art also can be included in the combinations provided herein.

In some examples, the combination can contain nanoparticles. Nanoparticles can be designed such that they carry one or more therapeutic agents provided herein. Additionally, nanoparticles can be designed to carry a molecule that targets the nanoparticle to the tumor cells. In one non-limiting example, nanoparticles can be coated with a radionuclide and, optionally, an antibody immunoreactive with a tumor-associated antigen.

In some examples, the combination can contain one or more additional therapeutic and/or diagnostic viruses or other therapeutic and/or diagnostic microorganism (e.g., therapeutic and/or diagnostic bacteria) for diagnosis or treatment. Exemplary therapeutic and/or diagnostic viruses are known in the art and include, but are not limited to, therapeutic and/or diagnostic poxviruses, herpesviruses, adenoviruses, adeno-associated viruses, and reoviruses. Exemplary oncolytic viruses are described herein above.

3. Kits

The carrier cells, viruses, pharmaceutical compositions or combinations provided herein can be packaged as kits. Kits can optionally include one or more components such as instructions for use, devices and additional reagents, and components, such as tubes, containers and syringes for practice of the methods. Exemplary kits can include a carrier cell and a virus provided herein, or a protected carrier cell, an unprotected carrier cell and a virus; and can optionally include instructions for use, a device for detecting a carrier cell and/or virus in a subject, a device for administering the carrier cell and virus to a subject, or a device for administering an additional agent or compound to a subject.

In one example, a kit can contain instructions. Instructions typically include a tangible expression describing the carrier cell and virus and, optionally, other components included in the kit, and methods for administration, including methods for determining the proper state of the subject, the proper dosage amount, and the proper administration method, for administering the carrier cell and virus. Instructions also can include guidance for monitoring the subject over the duration of the treatment time.

In another example, a kit can contain a device for detecting a carrier cell and/or virus in a subject. Devices for detecting a carrier cell and/or virus in a subject can include a low light imaging device for detecting light, for example, emitted from luciferase, or fluoresced from a fluorescent protein, such as a green or red fluorescent protein, a magnetic resonance measuring device such as an MRI or NMR device, a tomographic scanner, such as a PET, CT, CAT, SPECT or other related scanner, an ultrasound device, or other device that can be used to detect a protein expressed by the carrier cell and/or virus within the subject. Typically, the device of the kit will be able to detect one or more proteins expressed by the carrier cell and/or virus of the kit. Any of a variety of kits containing carrier cells, viruses and detection devices can be included in the kits provided herein, for example, a carrier cell or virus expressing luciferase and a low light imager or a carrier cell or virus expressing a fluorescent protein, such as a green or red fluorescent protein, and a low light imager.

Kits provided herein also can include a device for administering a carrier cell and virus to a subject. Any of a variety of devices known in the art for administering medications, pharmaceutical compositions and vaccines can be included in the kits provided herein. Exemplary devices include, but are not limited to, a hypodermic needle, an intravenous needle, a catheter, a needle-less injection device, an inhaler and a liquid dispenser, such as an eyedropper. For example, a carrier cell and virus combination to be delivered systemically, for example, by intravenous injection, can be included in a kit with a hypodermic needle and syringe. Typically, the device for administering a carrier cell and virus of the kit will be compatible with the carrier cell and virus of the kit; for example, a needle-less injection device such as a high pressure injection device can be included in kits with carrier cells and viruses not damaged by high pressure injection, but is typically not included in kits with carrier cells and viruses damaged by high pressure injection.

Kits provided herein also can include a device for administering an additional agent or compound to a subject. Any of a variety of devices known in the art for administering medications to a subject can be included in the kits provided herein. Exemplary devices include, but are not limited to, a hypodermic needle, an intravenous needle, a catheter, a needle-less injection device, an inhaler and a liquid dispenser, such as an eyedropper. Typically the device for administering the compound of the kit will be compatible with the desired method of administration of the compound. For example, a compound to be delivered systemically or subcutaneously can be included in a kit with a hypodermic needle and syringe.

The kits provided herein also can include any device for applying energy to a subject, such as electromagnetic energy. Such devices include, but are not limited to, a laser, light-emitting diodes, fluorescent lamps, dichroic lamps, and a light box. Kits also can include devices to effect internal exposure of energy to a subject, such as an endoscope or fiber optic catheter.

H. ADDITIONAL THERAPIES ADMINISTERED WITH CELL VEHICLE+VIRUS TREATMENT

Virotherapy using the combinations, compositions or kits provided herein containing an oncolytic virus and a cell vehicle as provided herein for delivery of the oncolytic virus to a subject in need of virotherapy, can be used alone or in further combination with other therapies or treatments. The combinations or compositions provided herein can further be co-formulated or co-administered together with, prior to, intermittently with, or subsequent to, other therapeutic or pharmacologic agents or treatments, such as procedures. For example, such agents include, but are not limited to, other biologics, anti-cancer agents, small molecule compounds, dispersing agents, anesthetics, checkpoint inhibitors, vasoconstrictors, surgery, radiation, a chemotherapeutic agent, a biological agent, a polypeptide, an antibody, a peptide, a small molecule, a gene therapy vector, a virus and DNA and combinations thereof. Such agents also can include one or more agents to ameliorate, reduce or prevent side effects. In some cases, the combination therapy can be used in combination with one or more cancer treatments that remove the primary tumor or that immunosuppress the subject prior to treatment. For example, additional chemotherapy or radiation therapy can be used in addition to the combination therapy provided herein. Such additional therapy can have the effect of weakening a subject's immune system. In other examples, surgical removal and/or immune-system weakening therapy may not be necessary. Exemplary other methods that can be combined therein include administering a compound that decreases the rate of proliferation of the tumor or neoplastic cells without weakening the immune system (e.g., by administering tumor suppressor compounds or by administering tumor cell-specific compounds) or administering an angiogenesis-inhibiting compound.

A preparation of a second agent or agents or treatment or treatments can be administered at once, or can be divided into a number of smaller doses to be administered at intervals of time. Selected agent/treatment preparations can be administered in one or more doses over the course of a treatment time for example over several hours, days, weeks, or months. In some cases, continuous administration is useful. It is understood that the precise dosage and course of administration depends on the indication and patient's tolerability. Generally, dosing regimens for second agents/treatments herein are known to one of skill in the art.

For example, the combination therapy provided herein can be used in further combination with one or more of the following including, but not limited to, immune co-stimulation agonists, (e.g., B7 Family (CD28, ICOS); TNFR family (4-1BB, OX40, GITR, CD40, CD30, CD27); LIGHT, LTα); BiTEs; CAR-T cells and TCR transgenic T cell targeting tumor-specific antigens; Checkpoint Inhibitors (Targets include PD-1, PD-2, PD-L1, PD-L2, CTLA-4, IDO 1 and 2, CTNNB1 (β-catenin), SIRPα, VISTA, LIGHT, HVEM, LAG3, TIM3, TIGIT, Galectin-9, KIR, GITR, TIM1, TIM4, CEACAM1, CD27, CD40/CD40L, CD48, CD70, CD80, CD86, CD112, CD137 (4-1BB), CD155, CD160, CD200, CD226, CD244 (2B4), CD272 (BTLA), B7-H2, B7-H3, B7-H4, B7-H6, ICOS, A2aR, A2bR, HHLA2, ILT-2, ILT-4, gp49B, PIR-B, HLA-G, ILT-2/4 and OX40/OX-40L, MDR1, Arginasel, iNOs, IL-10, TGF-β, pGE2, STAT3, VEGF, KSP, HER2, Ras, EZH2, NIPP1, PP1, TAK1 and PLK1a); and chemotherapeutic compounds and antibodies.

Exemplary chemotherapeutic compounds and antibodies for administering in addition to the virotherapy provided herein can include Cytokines, Chemokines, Growth Factors, Photosensitizing Agents, Toxins, Anti-Cancer Antibiotics, Chemotherapeutic Compounds, Radionuclides, Angiogenesis Inhibitors, Signaling Modulators, Antimetabolites, Anti-cancer Vaccines, Anti-cancer Oligopeptides, Mitosis Inhibitor Proteins, Antimitotic Oligopeptides, Anti-cancer Antibodies, Anti-cancer Antibiotics and Immunotherapeutic Agents.

Exemplary anti-cancer agents that can be administered after, coincident with or before administration of the combination therapy herein, include, but are not limited to Acivicins; Avicin; Aclarubicins; Acodazoles; Acronines; Adozelesins; Aldesleukins; Alemtuzumabs; Alitretinoins (9-Cis-Retinoic Acids); Allopurinols; Altretamines; Alvocidibs; Ambazones; Ambomycins; Ametantrones; Amifostines; Aminoglutethimides; Amsacrines; Anastrozoles; Anaxirones; Ancitabines; Anthramycins; Apaziquones; Argimesnas; Arsenic Trioxides; Asparaginases; Asperlins; Atrimustines; Azacitidines; Azetepas; Azotomycins; Banoxantrones; Batabulins; Batimastats; BCG Live; Benaxibines; Bendamustines; Benzodepas; Bexarotenes; Bevacizumab; Bicalutamides; Bietaserpines; Biricodars; Bisantrenes; Bisantrenes; Bisnafide Dimesylates; Bizelesins; Bleomycins; Bortezomibs; Brequinars; Bropirimines; Budotitanes; Busulfans; Cactinomycins; Calusterones; Canertinibs; Capecitabines; Caracemides; Carbetimers; Carboplatins; Carboquones; Carmofurs; Carmustines with Polifeprosans; Carmustines; Carubicins; Carzelesins; Cedefingols; Celecoxibs; Cemadotins; Chlorambucils; Cioteronels; Cirolemycins; Cisplatins; Cladribines; Clanfenurs; Clofarabines; Crisnatols; Cyclophosphamides; Cytarabine liposomals; Cytarabines; Dacarbazines; Dactinomycins; Darbepoetin Alfas; Daunorubicin liposomals; Daunorubicins/Daunomycins; Daunorubicins; Decitabines; Denileukin Diftitoxes; Dexniguldipines; Dexonnaplatins; Dexrazoxanes; Dezaguanines; Diaziquones; Dibrospidiums; Dienogests; Dinalins; Disermolides; Docetaxels; Dofequidars; Doxifluridines; Doxorubicin liposomals; Doxorubicin HCL; Doxorubicin HCL liposome injection; Doxorubicins; Droloxifenes; Dromostanolone Propionates; Duazomycins; Ecomustines; Edatrexates; Edotecarins; Eflornithines; Elacridars; Elinafides; Elliott's B Solutions; Elsamitrucins; Emitefurs; Enloplatins; Enpromates; Enzastaurins; Epipropidines; Epirubicins; Epoetin alfas; Eptaloprosts; Erbulozoles; Esorubicins; Estramustines; Etanidazoles; Etoglucids; Etoposide phosphates; Etoposide VP-16s; Etoposides; Etoprines; Exemestanes; Exisulinds; Fadrozoles; Fazarabines; Fenretinides; Filgrastims; Floxuridines; Fludarabines; Fluorouracils; 5-fluorouracils; Fluoxymesterones; Flurocitabines; Fosquidones; Fostriecins; Fostriecins; Fotretamines; Fulvestrants; Galarubicins; Galocitabines; Gemcitabines; Gemtuzumabs/Ozogamicins; Geroquinols; Gimatecans; Gimeracils; Gloxazones; Glufosfamides; Goserelin acetates; Hydroxyureas; Ibritumomabs/Tiuxetans; Idarubicins; Ifosfamides; Ilmofosines; Ilomastats; Imatinib mesylates; Imexons; Improsulfans; Indisulams; Inproquones; Interferon alfa-2as; Interferon alfa-2bs; Interferon Alfas; Interferon Betas; Interferon Gammas; Interferons; Interleukin-2s and other Interleukins (including recombinant Interleukins); Intoplicines; Iobenguanes [131-I]; Iproplatins; Irinotecans; Irsogladines; Ixabepilones; Ketotrexates; L-Alanosines; Lanreotides; Lapatinibs; Ledoxantrones; Letrozoles; Leucovorins; Leuprolides; Leuprorelins (Leuprorelides); Levamisoles; Lexacalcitols; Liarozoles; Lobaplatins; Lometrexols; Lomustines/CCNUs; Lomustines; Lonafarnibs; Losoxantrones; Lurtotecans; Mafosfamides; Mannosulfans; Marimastats; Masoprocols; Maytansines; Mechlorethamines; Mechlorethamines/Nitrogen mustards; Megestrol acetates; Megestrols; Melengestrols; Melphalans; MelphalanslL-PAMs; Menogarils; Mepitiostanes; Mercaptopurines; 6-Mercaptopurine; Mesnas; Metesinds; Methotrexates; Methoxsalens; Metomidates; Metoprines; Meturedepas; Miboplatins; Miproxifenes; Misonidazoles; Mitindomides; Mitocarcins; Mitocromins; Mitoflaxones; Mitogillins; Mitoguazones; Mitomalcins; Mitomycin Cs; Mitomycins; Mitonafides; Mitoquidones; Mitospers; Mitotanes; Mitoxantrones; Mitozolomides; Mivobulins; Mizoribines; Mofarotenes; Mopidamols; Mubritinibs; Mycophenolic Acids; Nandrolone Phenpropionates; Nedaplatins; Nelzarabines; Nemorubicins; Nitracrines; Nocodazoles; Nofetumomabs; Nogalamycins; Nolatrexeds; Nortopixantrones; Octreotides; Oprelvekins; Ormaplatins; Ortataxels; Oteracils; Oxaliplatins; Oxisurans; Oxophenarsines; Paclitaxels; Pamidronates; Patubilones; Pegademases; Pegaspargases; Pegfilgrastims; Peldesines; Peliomycins; Pelitrexols; Pemetrexeds; Pentamustines; Pentostatins; Peplomycins; Perfosfamides; Perifosines; Picoplatins; Pinafides; Pipobromans; Piposulfans; Pirfenidones; Piroxantrones; Pixantrones; Plevitrexeds; Plicamycid Mithramycins; Plicamycins; Plomestanes; Plomestanes; Porfimer sodiums; Porfimers; Porfiromycins; Prednimustines; Procarbazines; Propamidines; Prospidiums; Pumitepas; Puromycins; Pyrazofurins; Quinacrines; Ranimustines; Rasburicases; Riboprines; Ritrosulfans; Rituximabs; Rogletimides; Roquinimexs; Rufocromomycins; Sabarubicins; Safingols; Sargramostims; Satraplatins; Sebriplatins; Semustines; Simtrazenes; Sizofirans; Sobuzoxanes; Sorafenibs; Sparfosates; Sparfosic Acids; Sparsomycins; Spirogermaniums; Spiromustines; Spiroplatins; Spiroplatins; Squalamines; Streptonigrins; Streptovarycins; Streptozocins; Sufosfamides; Sulofenurs; Sunitinib Malate; 6-thioguanine (6-TG); Tacedinalines; Talcs; Talisomycins; Tallimustines; Tamoxifens; Tariquidars; Tauromustines; Tecogalans; Tegafurs; Teloxantrones; Temoporfins; Temozolomides; Teniposides/VM-26s; Teniposides; Teroxirones; Testolactones; Thiamiprines; Thioguanines; Thiotepas; Tiamiprines; Tiazofurins; Tilomisoles; Tilorones; Timcodars; Timonacics; Tirapazamines; Topixantrones; Topotecans; Toremifenes; Tositumomabs; Trabectedins (Ecteinascidin 743); Trastuzumabs; Trestolones; Tretinoins/ATRA; Triciribines; Trilostanes; Trimetrexates; Triplatin Tetranitrates; Triptorelins; Trofosfamides; Tubulozoles; Ubenimexs; Uracil Mustards; Uredepas; Valrubicins; Valspodars; Vapreotides; Verteporfins; Vinblastines; Vincristines; Vindesines; Vinepidines; Vinflunines; Vinformides; Vinglycinates; Vinleucinols; Vinleurosines; Vinorelbines; Vinrosidines; Vintriptols; Vinzolidines; Vorozoles; Xanthomycin As (Guamecyclines); Zeniplatins; Zilascorbs [2-H]; Zinostatins; Zoledronate; Zorubicins; and Zosuquidars, for example:

Aldesleukins (e.g. PROLEUKIN®); Alemtuzumabs (e.g. CAMPATH®); Alitretinoins (e.g. PANRETIN®); Allopurinols (e.g. ZYLOPRIM®); Altretamines (e.g. HEXALEN®); Amifostines (e.g. ETHYOL®); Anastrozoles (e.g. ARIMIDEX®); Arsenic Trioxides (e.g. TRISENOX®); Asparaginases (e.g. ELSPAR®); BCG Live (e.g. TICE® BCG); Bexarotenes (e.g. TARGRETIN®); Bevacizumab (AVASTIN®); Bleomycins (e.g. BLENOXANE®); Busulfan intravenous (e.g. BUSULFEX®); Busulfan orals (e.g. MYLERAN®); Calusterones (e.g. METHOSARB®); Capecitabines (e.g. XELODA®); Carboplatins (e.g. PARAPLATIN®); Carmustines (e.g. BCNU®, BiCNU®); Carmustines with Polifeprosans (e.g. GLIADEL® Wafer); Celecoxibs (e.g. CELEBREX®); Chlorambucils (e.g. LEUKERAN®); Cisplatins (e.g. PLATINOL®); Cladribines (e.g. LEUSTATIN®, 2-CdA®); Cyclophosphamides (e.g. CYTOXAN®, NEOSAR®); Cytarabines (e.g. CYTOSAR-U®); Cytarabine liposomals (e.g. DepoCyt®); Dacarbazines (e.g. DTIC-Dome): Dactinomycins (e.g. COSMEGEN®); Darbepoetin Alfas (e.g. ARANESP®); Daunorubicin liposomals (e.g. DANUOXOME®); Daunorubicins/Daunomycins (e.g. CERUBIDINE®); Denileukin Diftitoxes (e.g. ONTAK®); Dexrazoxanes (e.g. ZINECARD®); Docetaxels (e.g. TAXOTERE®); Doxorubicins (e.g. ADRIAMYCIN®, RUBEX®); Doxorubicin liposomals, including Doxorubicin HCL liposome injections (e.g. DOXIL®); Dromostanolone propionates (e.g. DROMOSTANOLONE® and MASTERONE® Injection); Elliott's B Solutions (e.g. Elliott's B Solution®); Epirubicins (e.g. ELLENCE®); Epoetin alfas (e.g. EPOGEN®); Estramustines (e.g. EMCYT®); Etoposide phosphates (e.g. ETOPOPHOS®); Etoposide VP-16s (e.g. VEPESID®); Exemestanes (e.g. AROMASIN®); Filgrastims (e.g. NEUPOGEN®); Floxuridines (e.g. FUDR®); Fludarabines (e.g. FLUDARA®); Fluorouracils incl. 5-FUs (e.g. ADRUCIL®); Fulvestrants (e.g. FASLODEX®); Gemcitabines (e.g. GEMZAR®); Gemtuzumabs/Ozogamicins (e.g. MYLOTARG®); Goserelin acetates (e.g. ZOLADEX®); Hydroxyureas (e.g. HYDREA®); Ibritumomabs/Tiuxetans (e.g. ZEVALIN®); Idarubicins (e.g. IDAMYCIN®); Ifosfamides (e.g. IFEX®); Imatinib mesylates (e.g. GLEEVEC®); Interferon alfa-2as (e.g. ROFERON-A®); Interferon alfa-2bs (e.g. INTRON A®); Irinotecans (e.g. CAMPTOSAR®); Letrozoles (e.g. FEMARA®); Leucovorins (e.g. WELLCOVORIN®, LEUCOVORIN®); Levamisoles (e.g. ERGAMISOL®); Lomustines/CCNUs (e.g. CeeBU®); Mechlorethamines/Nitrogen mustards (e.g. MUSTARGEN®); Megestrol acetates (e.g. MEGACE®); Melphalans/L-PAMs (e.g. ALKERAN®); Mercaptopurine, including 6-mercaptopurines (6-MPs; e.g. PURINETHOL®); Mesnas (e.g. MESNEX®); Methotrexates; Methoxsalens (e.g. UVADEX®); Mitomycin Cs (e.g. MUTAMYCIN®, MITOZYTREX®); Mitotanes (e.g. LYSODREN®); Mitoxantrones (e.g. NOVANTRONE®); Nandrolone Phenpropionates (e.g. DURABOLIN-50®); Nofetumomabs (e.g. VERLUMA®); Oprelvekins (e.g. NEUMEGA®); Oxaliplatins (e.g. ELOXATIN®); Paclitaxels (e.g. PAXENE®, TAXOL®); Pamidronates (e.g. AREDIA®); Pegademases (e.g. ADAGEN®); Pegaspargases (e.g. ONCASPAR®); Pegfilgrastims (e.g. NEULASTA®); Pentostatins (e.g. NIPENT®); Pipobromans (e.g. VERCYTE®); Plicamycin/Mithramycins (e.g. MITHRACIN®); Porfimer sodiums (e.g. PHOTOFRIN®); Procarbazines (e.g. MATULANE®); Quinacrines (e.g. ATABRINE®); Rasburicases (e.g. ELITEK®); Rituximabs (e.g. RITUXAN®); Sargramostims (e.g. PROKINE®); Streptozocins (e.g. ZANOSAR®); Sunitinib Malates (e.g. SUTENT®); Talcs (e.g. SCLEROSOL®); Tamoxifens (e.g. NOLVADEX®); Temozolomides (e.g. TEMODAR®); Teniposides/VM-26s (e.g. VUMON®); Testolactones (e.g. TESLAC®); Thioguanines including, 6-thioguanine (6-TG); Thiotepas (e.g. THIOPLEX®); Topotecans (e.g. HYCAMTIN®); Toremifenes (e.g. FARESTON®); Tositumomabs (e.g. BEXXAR®); Trastuzumabs (e.g. HERCEPTIN®); Tretinoins/ATRA (e.g. VESANOID®); Uracil Mustards; Valrubicins (e.g. VALSTAR®); Vinblastines (e.g. VELBAN®); Vincristines (e.g. ONCOVIN®); Vinorelbines (e.g. NAVELBINE®); and Zoledronates (e.g. ZOMETA®).

Exemplary checkpoint inhibitors include, but are not limited to, anti-CTLA4 agents, anti-PD-1 agents and others, exemplary of which are the following:

| Exemplary inhibitory immune checkpoint target proteins and inhibitors | | | |
|---|---|---|---|
| Target | Target Function | Antibody/fusion protein | Synonyms and Code Names |
| CTLA4 | Inhibitory receptor | Ipilimumab | (MDX-CTLA-4; BMS-734016; MDX-010) |
|  |  | Tremelimumab | (ticilimumab; CP-675,206) |
| PD-1 | Inhibitory receptor | MK-3475 | (Pembrolizumab; Lambrolizumab; SCH 900475) |
|  |  | AMP-224 | (anti-PD-1 fusion protein AMP-224) |
|  |  | Nivolumab | (BMS-936558; MDX-1106; ONO-4538) |
|  |  | Pidilizumab | (CT-011) |
| PD-L1 | Ligand for PD-1 | MDX-1105 | (RG7446) |
|  |  | BMS-936559 |  |
|  |  | MED14736 |  |
|  |  | MPDL33280A |  |
| LAG3 | Inhibitory receptor | IMP321 | ImmuFact |
| B7-H3 | Inhibitory ligand | MGA271 |  |
| B7-H4 | Inhibitory ligand |  |  |
| TIM3 | Inhibitory receptor |  |  |
| CD25 | inhibitory receptor subunit |  |  |
| CD137 | stimulatory receptor |  |  |

-continued

Exemplary inhibitory immune checkpoint target proteins and inhibitors

| Target | Target Function | Antibody/fusion protein | Synonyms and Code Names |
|---|---|---|---|
| OX40 | stimulatory receptor | | |
| 4-1BB | co-stimulatory receptor | Aptamer ligand | |
| IDO | immunosuppressive enzyme | | |

The additional treatments administered with the combinations for virotherapy provided herein can include one or more immunosuppressive drugs, for example, Glucocorticoids (e.g., prednisone, dexamethasone, hydrocortisone); Calcineurin Inhibitors (e.g., cyclosporin, tacrolimus); mTOR Inhibitors (e.g., sirolimus, everolimus); Methotrexate; Lenalidomide; Azathioprine; Mercaptopurine; Fluorouracil; Cyclophosphamide; TNFα blocking antibodies (e.g., infliximab/Remicade, etanercept/Enbrel, adalimumab/Humira) and Fludarabine.

I. TYPES OF CANCERS TO BE TREATED

The methods disclosed herein can be used to treat any type of cancer or metastases, including solid tumors and hematologic malignancies. Tumors that can be treated by the methods disclosed herein include, but are not limited to a bladder tumor, breast tumor, prostate tumor, carcinoma, basal cell carcinoma, biliary tract cancer, bladder cancer, bone cancer, brain cancer, CNS cancer, glioma tumor, cervical cancer, choriocarcinoma, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, lung cancer, lymphoma, Hodgkin's lymphoma, Non-Hodgkin's lymphoma, melanoma, myeloma, neuroblastoma, oral cavity cancer, ovarian cancer, pancreatic cancer, retinoblastoma, rhabdomyosarcoma, rectal cancer, renal cancer, cancer of the respiratory system, sarcoma, skin cancer, stomach cancer, testicular cancer, thyroid cancer, uterine cancer, and cancer of the urinary system, such as lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, small cell lung cancer, non-small cell lung cancers, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumor, testicular tumor, seminoma, Sertoli cell tumor, hemangiopericytoma, histiocytoma, chloroma, granulocytic sarcoma, corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma, cystadenoma, follicular lymphoma, intestinal lymphosarcoma, fibrosarcoma, and pulmonary squamous cell carcinoma, leukemia, hemangiopericytoma, ocular neoplasia, preputial fibrosarcoma, ulcerative squamous cell carcinoma, preputial carcinoma, connective tissue neoplasia, mastocytoma, hepatocellular carcinoma, lymphoma, pulmonary adenomatosis, pulmonary sarcoma, Rous sarcoma, reticulo-endotheliosis, fibrosarcoma, nephroblastoma, B-cell lymphoma, lymphoid leukosis, retinoblastoma, hepatic neoplasia, lymphosarcoma, plasmacytoid leukemia, swimbladder sarcoma (in fish), caseous lumphadenitis, lung carcinoma, insulinoma, lymphoma, sarcoma, salivary gland tumors, neuroma, pancreatic islet cell tumor, gastric MALT lymphoma and gastric adenocarcinoma.

In some embodiments, the tumor is selected from metastatic melanoma; esophageal and gastric adenocarcinoma; cholangiocarcinoma (any stage); pancreatic adenocarcinoma (any stage); gallbladder cancer (any stage); high-grade mucinous appendix cancer (any stage); high-grade gastrointestinal neuroendocrine cancer (any stage); mesothelioma (any stage); soft tissue sarcoma; prostate cancer; renal cell carcinoma; lung small cell carcinoma; lung non-small cell carcinoma; head and neck squamous cell carcinoma; colorectal cancer; ovarian carcinoma; hepatocellular carcinoma; and glioblastoma.

In some embodiments, the tumor is selected from: glioblastoma, breast carcinoma, lung carcinoma, prostate carcinoma, colon carcinoma, ovarian carcinoma, neuroblastoma, central nervous system tumor, and melanoma.

J. EXAMPLES

The following examples are included for illustrative purposes only and are not intended to limit the scope of the subject matter.

Example 1

Cell Isolation and Culture

A. Adipose-derived Stem Cells (ADSCs)
    i. Retrieval and Preparation of Adipose Stromal Vascular Fraction Local anesthesia, containing 0.5% lidocaine 0.5% with 1:400,000 epinephrine and 8.4% $HCO_3$ titrated to a pH of 7.4 (generally, 5 cc of $HCO_3$ in a total volume of 60 cc), is administered to the subject. The subject then undergoes a liposuction procedure utilizing the cell harvesting and closed system harvesting and processing system available under the trademark Time-Machine® device from the Cell Surgical Network, Beverly Hills, Calif., USA (CSN), which includes a fat processing unit (an airtight syringe for liposuction) and 2.5-3 mm cannula. Bacitracin ointment and a band aid are secured over the wound along with a compressive bandage.

Expanded adipose stem cells derived from supra advential adipose stromal cells were used in the examples provided herein. The stromal vascular fraction (SVF) containing the ADSCs is prepared in a closed system according to the following protocol:

a. A closed system for harvesting and processing adipose stem cells, such as the CSN TimeMachine® (available from CSN) extracts the harvest of fat into a 60 cc TP-101 syringe (single use sterile airtight fat processing syringe)
b. Centrifuge at 2800 rpm for 3 min
c. Remove free fatty acids and debris (local/blood) via TP-109 closed system
d. Transfer 25 cc of condensed fat to TP-102 syringe (SVF processing syringe)
e. Add pre-warmed (38° C.) 25 cc of Roche T-MAX® Time Machine Accelerator (GMP grade collagenase) containing 12.5 Wunsch units of enzyme (1 Wunsch unit=1000 collagen degrading units (CDU))
f. Incubate at 38° C. for 30-45 minutes
g. Centrifuge at 200 g for 4 minutes
h. Remove supernatant fluid except for bottom 3-10 cc
i. Add 50 cc D5LR (Lactated Ringer's and 5% dextrose) as a washing solution to remove collagenase residue and centrifuge at 200 g for 4 minutes
j. Repeat 2 more times for a total of 3 washings
k. Remove all supernatant fluid, leaving 3-10 cc of pellet collection—this is the Stromal Vascular Fraction
l. Transfer SVF to labeled 20 cc syringe through 100-micron filters
m. SVF sample is collected and identified for number of cells, viability and to confirm no clumping or debris.
n. Aliquots of each cell suspension are set aside for cell sorting, endotoxin testing and sterility staining. The SVF is released for injection after confirming endotoxin unit level (EU) less than or equal to 5 EU/kg/hr and negative gram stain results
o. The cells are resuspended in 20 ml of Isolyte. Cell suspensions are drawn into a syringe through an 18-gauge needle for injection; up to 100 million viable cells are used for injection
p. The syringe is then placed in a sealed specimen bag labeled with the subject's name and medical record number.

ii. Cell Culture

Non-cancer donor Stromal Vascular Fractions (SVFs) were obtained as part of an IRB-approved protocol after informed written consent (International Cell Surgical Society; IRB #ICSS-2016-024), as described above. Fresh SVFs were plated to attach overnight and were washed the next day to remove unattached cells and debris. Media was changed every 3-4 days until the mesenchymal stem cells (MSCs) started to grow and reached 80% confluency. Cells were expanded to 80% confluency and passaged every 3-4 days using TrypLE™ Express (Life Technologies, (1×), no phenol red, Cat #12604021, 3 min, 37° C. incubator) for up to 10 passages. Adipose-derived stem cells (ADSCs) were expanded and maintained in 5% Human Platelet Extract (Cook Regentec, Stemmulate, PL-SP-100) in DMEM supplemented with L-Glutamine and Penicillin/Streptomycin. ADSCs were isolated from 6 donors and labeled RM20, RM35, RM47, RM48, RM58 and BH21.

iii. Generation of Adipose-Derived Stem Cells Constitutively Expressing eGFP (Enhanced Green Fluorescent Protein)

RM20 adipose-derived stem cells at passage 0 were engineered to express eGFP (Clontech, Palo Alto, Calif.) under the control of a CMV promoter (UniProtKB—C5MKY7 (C5MKY7_HCMV)). A Lentiviral vector (VectorBuilder available from VectorBuilder Inc., Santa Clara, Calif.) containing eGFP was used to introduce eGFP into the ADSCs for constitutive expression. 10,000 eGFP-positive cells were sorted at passage 1 and subsequently at passage 2 using the BioRAD S3 Cell Sorter. eGFP expression was confirmed by flow cytometry and fluorescence microscopy using the Keyence All-in-one Fluorescence Microscope BZ-X700 Series.

B. Cancer Cells

B16 F10 melanoma, A549 lung carcinoma and K562 cells were propagated in DMEM (B16, A549) (Gibco, Cat. #: 11960069) or RPMI 1640 (K562) (Gibco, Cat. #: 21870092), supplemented with 10% Fetal Bovine Serum (Omega Scientific, FB-02, USDA certified, heat inactivated), 2 mM L-Glutamine (ThermoFisher Scientific, 25030081, 100×) and Penicillin/Streptomycin (Life Technologies, 15140122, 100×).

C. Peripheral Blood Mononuclear Cells (PBMCs)

PBMCs were obtained as part of an IRB-approved protocol after informed written consent (International Cell Surgical Society; IRB #ICSS-2016-024). PBMCs were isolated using a standard Ficoll protocol (Ficoll-Paque Plus, GE Healthcare, cat. #95021-205). PBMCs were isolated from 8 donors and labeled BH62, RM20, RM47, RM48, RM52, RM53, SIBD01 and SIBD02.

D. Co-Cultures

Co-cultures can include a patient's immune cells, such as PBMCs or whole blood, together with the cell-based delivery vehicle/carrier cells, including stem cells or tumor cells, and with or without the oncolytic virus to be tested, for example, vaccinia virus, herpes simplex virus and adenovirus, among others.

After isolating the patient's blood and processing it to isolate PBMCs and serum, the patient's PBMCs are co-cultured with different carrier cells, with or without oncolytic virus, to determine carrier cell compatibility. Co-cultures, including controls, to be tested include, for example: PBMCs alone+/−virus; carrier cells alone+/−virus; PBMCs+carrier cells+/−virus; carrier cells alone+virus+/−serum (10-50%)+/−heat or pharmacological (cobra venom factor or equivalent) inactivation of complement (for a patient serum resistance screen); PBMCs+carrier cells+virus+/−serum (10-50%)+/−heat or pharmacological (cobra venom factor or equivalent) inactivation of complement (for a patient serum resistance screen); and heparinized whole blood instead of PBMCs as above (for a native environment test).

The co-cultures (including cells and/or supernatants) are then analyzed to determine the levels of virus amplification and infection, as well as immunosuppressive/immunostimulatory effects, using various assays and tests, including, but not limited to: surface and intracellular multiparameter flow cytometry or equivalents like Cytometry by Time of Flight (CyTOF), for example; enzyme-linked immunosorbent assay (ELISA); enzyme-linked immunospot (ELISPOT) assay; virus plaque assays (VPAs); quantitative PCR (qPCR); bioluminescence assays; fluorescence microscopy; and intracellular staining.

Flow cytometry is performed, for example, using gating parameters to identify specific immune cell populations including T cells (such as, but not limited to, CD3, CD4, CD8), NK cells (such as, but not limited to, NKp46, CD16, CD56) and NKT cells (such as, but not limited to, CD3, CD16, CD56, NKp46, aGalCer-CD1d tetramers). Immune responses are evaluated by analyzing various activation/effector function parameters including, but not limited to: CD69, CD25, CD71, CD27 (CD70L), CD154 (CD40L), CD137 (4-1BB), CD44, CD45RA, CD45RO, CD278 (ICOS), CD127 (IL-7RA), CD183 (CXCR3), CD197 (CCR7), CD39, CD73, CD314 (NKG2D), PD-1, CTLA-4, IFNα/β, IFNγ, TNFα, IL-2, IL-4, IL-5, IL-9, IL-10, IL-12, IL-13, IL-15, IL-18, IL-21, IL-22, IL-23, IL-25, GM-CSF, IL-17, IL-6, CD107a, CD107b, TGFβ, Perforin, Granzyme B, IL-1a/IL-1b, G-CSF, RANTES, EXOTAXIN, MIP-1b, MCP-1, EGF, HGF, VEGF, IL-1RA, IL-7, IP-10, IL-2R, MIG and IL-8, among others.

For example, PBMCs are co-cultured (100 μl) with ADSCs (50 μl) with or without vaccinia virus (50 μl) for 48 h on 96-well flat-bottom plates and in a total of 200 μl R10 medium (RPMI 1640 supplemented with 10% FBS, L-Glutamine and Pen/Strep). In some experiments, the virus (50 μl) and ADSCs (50 μl) are premixed and agitated on an orbital shaker at 37° C. (incubator) for 1 h, and then (100 μl of the mix) is added to the PBMCs without additional washing of any unbound virus. At the end of the 48 h incubation period, the cells are recovered for staining and flow cytometry analysis directly, or after an additional 4-5 hour stimulation with K562 cells or PMA/Ionomycin (50 μl) with Monensin/Brefeldin A (50 μl), as needed.

Example 2

Effect of Adipose Derived Stem Cells (ADSCs) on Virus Amplification and Infection in the Presence and Absence of Immune Cells (Peripheral Blood Mononuclear Cells (PBMCs)) from a Subject For particular viruses, carrier cells that amplify the virus are identified as candidates for delivery of the virus to a subject for virotherapy. This example evaluates the effect of immune cells derived from the subject on the ability of the carrier cell to facilitate viral amplification and infection. PBMCs are used for this purpose. Factors that affect virus infection and amplification by carrier cells include, for example, the presence or absence of interferons (IFNs) and/or the presence or absence of PBMCs, are evaluated using appropriate assays that measure the amount of virus present. Such assays include, for example, virus plaque assays (VPAs), qPCR (or any alternative assays that measure the amount of viral DNA genomes present), ELISAs (to measure virus-encoded or engineered reporter proteins or enzymes, such as, but not limited to, β-galactosidase), and bioluminescence assays (to measure virus-encoded luminescent reporter proteins such as, but not limited to, luciferase). Viral infection of carrier cells, PBMCs and tumor cells can be monitored using, for example, flow cytometry and fluorescence microscopy.

A. Virus Plaque Assays (VPAs)

Co-cultures as described in Example 1 can be stored and subsequently analyzed using VPA to quantify virus particle amplification under different conditions and with different combinations of patient-derived immune cells and cell-based delivery vehicles.

Virus-containing samples are stored at −80° C. and subjected to a three-fold freeze (−80° C.)/thaw (+37° C.) cycle followed by sonication on ice-cold water for three 1 min intervals, one min apart. Sonicated samples are serially diluted in vaccinia virus infection medium (DMEM supplemented with 2% FBS, L-Glutamine and Penicillin/Streptomycin). Plaque assays are performed in 24-well plates in duplicate wells. 200,000 CV-1 monkey kidney cells are plated in 1 mL D10 medium per well, overnight. Supernatants are aspirated and 10-fold serial dilutions of the virus-containing sample are applied to the CV-1 monolayer at 200 μL/well. Plates are incubated for 1 h at 37° C. (incubator) with manual shaking every 20 min. 1 mL CMC medium is layered gently on top of the cells and plates are incubated for 48 h. Plaques are counted after fixing the cells by toping the wells with Crystal Violet solution (1.3% Crystal violet (Sigma-Aldrich, C6158), 5% Ethanol (Pure Ethanol, Molecular Biology Grade, VWR, 71006-012), 30% Formaldehyde (37% v/v formaldehyde, Fisher, cat. #F79-9), and double distilled water) for 3-5 h at room temperature, followed by washing the plates in tap water and drying overnight. CMC overlay medium is prepared by autoclaving 15 g carboxymethylcellulose sodium salt (Sigma-Aldrich, cat. #C4888) and re-suspending with overnight stirring at room temperature in 1 L DMEM, supplemented with Penicillin/Streptomycin, L-Glutamine, and 5% FBS, with short-term storage at 4° C.

B. Fluorescence Microscopy

Virus infection is monitored using fluorescently labeled cells, such as eGFP-labeled ADSCs (Example 1), and fluorescently labeled oncolytic viruses, such as, for example, a TurboFP635-engineered L14 virus, which is a TK-inserted Turbo-FP635 engineered LIVP strain of vaccinia obtained from StemVac GmbH, Bernried, Germany. Time course microscopic observations of virus infection are performed using fluorescence microscopy, on a Keyence All-in-one Fluorescence Microscope BZ-X700 Series. For example, ADSCs engineered to express eGFP are followed on the GFP channel (1 second exposure), while virus infection with the TurboFP635-engineered LIVP virus is monitored on the TRITC channel (3 second exposure). Images at 4× or 10× magnification are collected and overlaid with bright field (phase contrast, 1/50 second exposure).

C. Evaluation of Vaccinia Virus Amplification by ADSCs (Adipose-Derived Stem Cells) in the Presence and Absence of Interferons (IFNs)

The ability of ADSCs to amplify vaccinia virus and to respond to the protective anti-viral effects of interferons was evaluated using L14 vaccinia virus (VV) (TK-inserted Turbo-FP635 engineered LIVP strain). Vaccinia viruses (L14 VV) were obtained from StemVac GmbH, Bernried, Germany. 50,000 RM35 ADSCs were infected in a 12-well plate with 10,000 pfu (plaque forming units) L14 VV, in the presence of increasing doses (0.08 ng/mL, 0.3 ng/mL, 1.3 ng/mL, 5 ng/mL and 20 ng/mL) of IFNγ (Peprotech, cat. #AF3000220UG, 20 mg lyophilized, diluted to 20 μg/mL from approximately 1000× stock in 1×PBS, supplemented with 0.1% FBS, stored at −80° C.) or IFNβ (Peprotech, cat #AF30002B5UG, 5 μg lyophilized, diluted to 5 μg/mL from approximately 1000× stock in 1×PBS, supplemented with 0.1% FBS, stored at −80° C.), added at the time of infection, or 24 h earlier (IFNβ/γ 24 h). Fluorescence imaging and plaque assays were performed at 48 h post infection.

The results of plaque assay analysis are shown in Table 1. Fluorescence imaging and plaque assays at 48 h post infection show that type I and type II interferons protect the ADSCs against vaccinia virus (VV) infection in a dose-dependent manner. This is consistent with these cells being untransformed and having functional anti-viral interferon responses. Protection from viral infection was less efficient when interferons were added concurrently, rather than 24 h prior, to virus exposure.

To assess whether the combination of type I and II interferons results in increased protection against VV infection, 50,000 RM35 ADSCs were pretreated for 24 h with increasing doses (0.02, 0.08, 0.3, 1.3, 5, 20 and 80 ng/mL) of IFNγ and IFNβ alone or in combination, before infection with 10,000 pfu L14 VV. Plaque assay results (Table 2) show that the combination of type I and II interferons does not further enhance protection.

The stability of the IFNγ-induced anti-viral state was then determined. 100,000 RM20-eGFP ADSCs (see, Example 1)

were infected in a 12-well plate with 100,000 pfu L14 VV and incubated for up to 4 days. The ADSCs were either untreated ((−) IFNγ control), or pre-treated with 20 ng/mL of IFNγ for 24 h. The IFNγ was administered 1, 2, or 3 days prior to virus infection. Time course fluorescence image analysis was used to visualize the progression of virus infection, with images taken at 24 h, 48 h, 72 h and 96 h post infection. Fluorescence imaging of ADSCs infected with virus in the absence of IFNγ ((−) IFNγ control) show uninfected (eGFP+/green) ADSCs, infected dead ADSCs (TurboFP635/red), and infected live ADSCs (yellow), with an increasing number of infected and dead cells from 24-96 h, demonstrating successful infection of ADSCs with virus in the absence of interferons. Fluorescence imaging of ADSCs infected with virus after 24 h exposure to IFNγ revealed no red or yellow cells, indicating that pretreatment with interferons prevents viral infection.

Plaque analysis was performed as described above, with a virus alone (no ADSCs) control and a (−)IFNγ control. As shown in Table 3, only the (−)IFNγ control showed virus amplification. ADSCs were highly permissive to vaccinia virus infection. The results of plaque analysis show that the ability of the ADSCs to amplify the virus was abrogated by interferon pretreatment, as compared to the no interferon control group. The anti-viral state induced by interferon treatment was stable, lasting for several days after a transient 24 h exposure to IFNγ. Thus, type I and type II interferon responses, while protecting the ADSCs against virus infection and potentially improving their immunosuppressive abilities, have the effect of also compromising their ability to deliver and amplify vaccinia virus in vivo.

TABLE 1

Plaque Assay Results

| IFNγ Treatment | Average pfu/sample | IFNβ Treatment | Average pfu/sample |
|---|---|---|---|
| (−) IFNγ CTRL | $3.40 \times 10^7$ | (−) IFNβ CTRL | $1.90 \times 10^7$ |
| 20 ng/ml IFNγ | $1.75 \times 10^5$ | 20 ng/ml IFNβ | $4.10 \times 10^5$ |
| 20 ng/ml IFNγ 24 h | $1.50 \times 10^3$ | 20 ng/ml IFNβ 24 h | $4.40 \times 10^3$ |
| 5 ng/ml IFNγ | $2.50 \times 10^5$ | 5 ng/ml IFNβ | $1.80 \times 10^6$ |
| 5 ng/ml IFNγ 24 h | $1.60 \times 10^3$ | 5 ng/ml IFNβ 24 h | $4.20 \times 10^4$ |
| 1.3 ng/ml IFNγ | $5.55 \times 10^5$ | 1.3 ng/ml IFNβ | $5.90 \times 10^6$ |
| 1.3 ng/ml IFNγ 24 h | $2.25 \times 10^3$ | 1.3 ng/ml IFNβ 24 h | $5.40 \times 10^5$ |
| 0.3 ng/ml IFNγ | $1.85 \times 10^6$ | 0.3 ng/ml IFNβ | $3.40 \times 10^7$ |
| 0.3 ng/ml IFNγ 24 h | $2.25 \times 10^3$ | 0.3 ng/ml IFNβ 24 h | $2.10 \times 10^6$ |
| 0.08 ng/ml IFNγ | $4.80 \times 10^6$ | 0.08 ng/ml IFNβ | $4.00 \times 10^7$ |
| 0.08 ng/ml IFNγ 24 h | $1.50 \times 10^4$ | 0.08 ng/ml IFNβ 24 h | $4.10 \times 10^6$ |

TABLE 2

Plaque Assay Results for IFNγ + IFNβ

| IFN Concentration | Average PFU/sample | | | |
|---|---|---|---|---|
| | (−) IFN CTRL | IFNγ | IFNβ | IFNγ + IFNβ |
| CTRL | $2.85 \times 10^6$ | — | — | — |
| 80 ng/ml | — | $1.90 \times 10^3$ | $5.10 \times 10^3$ | $5.25 \times 10^3$ |
| 20 ng/ml | — | $2.50 \times 10^3$ | $3.10 \times 10^3$ | $2.95 \times 10^3$ |
| 5 ng/ml | — | $2.30 \times 10^3$ | $3.15 \times 10^3$ | $2.55 \times 10^3$ |
| 1.3 ng/ml | — | $1.80 \times 10^3$ | $4.50 \times 10^3$ | $2.45 \times 10^3$ |
| 0.3 ng/ml | — | $2.75 \times 10^3$ | $4.95 \times 10^4$ | $2.45 \times 10^3$ |
| 0.08 ng/ml | — | $7.40 \times 10^3$ | $6.90 \times 10^4$ | $3.05 \times 10^3$ |
| 0.02 ng/ml | — | $4.55 \times 10^5$ | $7.00 \times 10^5$ | $3.15 \times 10^5$ |

TABLE 3

Stability of IFNγ-induced anti-viral state

| Treatment | Average PFU/sample |
|---|---|
| VIRUS INPUT | $3.80 \times 10^4$ |
| VIRUS ALONE | $1.30 \times 10^4$ |
| (−) IFNγ CTRL | $4.10 \times 10^5$ |
| IFNγ −1 Day | $1.02 \times 10^4$ |
| IFNγ −2 Days | $5.20 \times 10^3$ |
| IFNγ −3 Days | $9.55 \times 10^3$ |

D. Virus Amplification and Infection in Carrier Cell/PBMC Co-Cultures

To evaluate the amplification potential of vaccinia virus (VV) by ADSCs (carrier cells) in the presence of allogeneic PBMCs, 50,000 RM20-eGFP ADSCs were infected with 5,000 or 50,000 L14 VV alone, or in the presence of $1 \times 10^6$ allogeneic PBMCs (from the blood donor designated BH62) for up to 48 h. Overlay fluorescence imaging and a virus plaque assay were used to evaluate vaccinia virus infection and amplification, respectively, by comparing results from co-cultures of allogeneic ADSCs+PBMCs to ADSCs cultured alone and PBMCs cultured alone.

The results are shown in Table 4. ADSCs alone are permissive to VV infection and amplification, whereas PBMCs alone do not show VV infection or amplification. The co-cultures demonstrated that ADSCs can amplify vaccinia virus in the presence of allogeneic PBMCs and that, in the presence of the allogeneic PBMCs, the overall virus output was increased relative to the combined output of ADSCs and PBMCs when infected separately, indicating that the ADSCs sensitize PBMCs to vaccinia virus infection.

TABLE 4

Viral amplification and infection in ADSC + PBMC co-cultures

| | Average PFU/sample | |
|---|---|---|
| Cultures/Conditions | 5,000 pfu L14 VV | 50,000 pfu L14 VV |
| VIRUS INPUT | $3.60 \times 10^3$ | $5.00 \times 10^4$ |
| VIRUS ALONE | $2.70 \times 10^3$ | $3.00 \times 10^4$ |
| PBMCs alone | $2.00 \times 10^3$ | $2.65 \times 10^4$ |
| ADSCs alone | $2.90 \times 10^6$ | $4.00 \times 10^6$ |
| ADSC + PBMC co-culture | $4.05 \times 10^6$ | $5.85 \times 10^6$ |

Example 3

Virus Amplification and Infection in Carrier Cell+Tumor Cell Co-Cultures

The amplification and infection of oncolytic viruses in the presence of different tumor/cancer cell types is evaluated to determine whether a particular carrier cell and oncolytic virus combination is effective at tumor/cancer cell oncolysis. In this manner, tumors can be identified as resistant or permissive to viral infection, and any enhancement of viral delivery to the tumor cells by the carrier cells can be evaluated. Other factors, such as the role of IFNγ pretreatment, carrier cell dose and secretion of soluble factors by carrier cells, also can be evaluated. This example evaluates the effects of an exemplary carrier cell type, ADSCs, on the ability to deliver an exemplary virus, vaccinia virus, to an exemplary cancer cell line, B16 melanoma cells.

A. ADSC-Promoted Oncolysis of Resistant and Permissive Tumor Cell Lines

Fluorescence microscopy, plaque assay analysis and flow cytometry, for example, can be used to determine the effects of using ADSCs to enhance the delivery of vaccinia virus to tumor/cancer cells. The use of ADSCs to more effectively deliver virus to resistant B16 F10 melanoma cells was evaluated. A549 cells, which are highly permissive to virus infection, were included for comparison.

$1 \times 10^6$ B16 cells or A549 cells were co-cultured with $2 \times 10^5$ eGFP-labelled ADSCs from the RM20 donor (see, Example 1) in a 12-well plate and infected with $1 \times 10^5$ pfu L14 VV (MOI=0.1 to B16) and incubated for up to 72 h. No virus controls included B16 cells alone, A549 cells alone, eGFP-labelled ADSCs alone, or B16 cells co-cultured with eGFP ADSCs. Fluorescent images were captured after 24 h, 48 h and 72 h incubation periods. Comparisons between resistant B16 cells cultured alone and permissive A549 cells cultured alone showed dramatically higher levels of virus infection in the A549 cells, as indicated by the presence of red cells in the fluorescent images. Using eGFP-labeled ADSCs (green) to visualize and distinguish them from the unlabeled B16 cells (grey), it was observed that in confluent environments, ADSCs tended to cluster together and attract the unlabeled melanoma cells. In the absence of virus, green stem cell clusters were observed after 72 h. In the presence of virus, this attraction resulted in the formation of highly infected yellow ADSC clusters surrounded by intensively red-colored infected B16 cells. These effects were associated with dramatically improved oncolysis of the monolayer of resistant murine B16 melanoma cells.

These results indicate that human ADSCs promote the oncolysis of resistant B16 melanoma cells through augmented amplification of the L14 vaccinia virus. Improved targeting of the resistant B16 cells was also observed with ADSCs derived from another donor (RM35). $1 \times 10^6$ B16 cells were co-cultured with 200,000 RM35 ADSCs and infected with 100,000 pfu L14 VV for up to 4 days. Fluorescence imaging analysis revealed that human RM35 ADSCs also promoted the oncolysis of the resistant murine B16 melanoma cells in vitro.

Plaque assay analysis of vaccinia virus amplification was performed as described above on B16 cells alone, A549 lung carcinoma cells alone, B16+A549 co-cultures, ADSCs alone, and B16+ADSC co-cultures. The results are summarized in Table 5. The A549 lung carcinoma cells were used as a highly vaccinia virus permissive positive control and showed virus amplification levels similar to ADSCs alone. The viral titers recovered from the B16+A549 or B16+ADSC co-cultures exceeded the combined virus output from the individual cells infected in separation, showing that the highly permissive cancer cells and ADSCs can both sensitize the resistant melanoma cells to infection with vaccinia virus.

TABLE 5

Plaque Assay Results

| Cultures/Conditions | Average pfu/sample |
| --- | --- |
| INPUT Virus | $9.50 \times 10^4$ |
| B16 cells alone | $5.55 \times 10^6$ |
| A549 cells alone | $6.10 \times 10^8$ |
| B16 + A549 co-cultures | $1.69 \times 10^9$ |
| ADSCs alone | $8.55 \times 10^8$ |
| B16 + ADSC co-cultures | $1.27 \times 10^9$ |

B. Effects of IFNγ Pretreatment on ADSC-Promoted Oncolysis of Resistant Tumor Cell Lines The effects of IFNγ pretreatment of ADSCs on virus amplification was tested. 200,000 RM20-eGFP cells (0.2 M) were pretreated with 20 ng/mL IFNγ for 24 h, then co-cultured with 200,000 (0.2 M) RM20 ADSCs, A549 cells or B16 cells, and infected with L14 vaccinia virus as described above. Fluorescent images were captured after 24 h, 48 h and 72 h. The results showed that IFNγ pretreatment protects ADSCs from virus infection only in the presence of relatively resistant B16 cells, but not in the presence of the highly permissive A549 cells. Due to the protection of ADSCs from the virus, IFNγ pretreatment of the ADSCs compromised the oncolysis of the B16 monolayer, indicating that the observed antitumor potential primarily depends on amplification of the virus by the ADSCs.

C. Effects of Carrier Cell Number/Dose on the Oncolysis of B16 Cells

The effects of stem cell number/dose on the oncolysis of the B16 monolayer was evaluated. $1 \times 10^6$ B16 cells were co-cultured with either 200,000 (0.2 M) or 20,000 (0.02 M) RM20-eGFP ADSCs, and infected with L14 VV as described above, and fluorescent images were captured at 24 h, 48 h and 72 h. The results show that an insufficient number of ADSCs (2% or less) leads to incomplete oncolysis of the B16 monolayer, confirming that the observed antitumor potential depends on amplification of the virus by the ADSCs.

D. Effects of Soluble Factors Secreted by Carrier Cells on the Oncolysis of Resistant Murine B16 Tumor Cells and Human K562 Cancer Cells i. Sensitization of Resistant Tumor Cells

Successful oncolysis of resistant tumor cells can be attributed not only to virus amplification by the ADSCs, but also to the sensitization of the tumor cells to virus infection. To determine the role that sensitization plays in the oncolysis of resistant tumor cells, the effects of soluble factors secreted by ADSCs were evaluated by adding supernatants from the ADSCs instead of the ADSC cells. 10,000 B16 cells were infected in triplicate for 96 h in 96-well flat-bottom plates as described above with L14 VV at an MOI of 0.1. Supernatants from human RM20 ADSCs were added and the effects on the virus infection of B16 cells was analyzed using the TurboFP635 fluorescence and quantitated by plaque assays at 72 h post infection. Plaque assay results are shown in Table 6. The fluorescent images and plaque assay results show that the addition of supernatant from ADSCs results in virus amplification in the resistant B16 cells, indicating that ADSCs sensitize the resistant B16 tumor cells to virus infection.

TABLE 6

Plaque Assay Results

| Cultures/Conditions | Average pfu/sample |
| --- | --- |
| INPUT Virus | $8.80 \times 10^4$ |
| ADSC Supernatant alone | $7.55 \times 10^4$ |
| B16 cells alone | $2.82 \times 10^7$ |
| B16 cells + ADSC Supernatant | $5.23 \times 10^7$ |

In a similar experiment, supernatants from four different ADSC donors (RM20, RM35, BH21 and RM58) were added to B16 (10,000) and K562 (100,000) cells infected with L14 VV at an MOI of 0.1 for 96 h in 96-well flat-bottom plates. Fluorescence imaging analysis revealed that supernatants from different ADSC donors provided similar sensitization of the murine B16 cells and of the extremely resistant human K562 cancer cells.

ii. Comparing ADSC-Mediated Sensitization of B16 Cells to Infection by Two Different Vaccinia Virus Strains: L14 VV and WT1 VV WT1 (ACAM2000) is a wild type thymidine kinase (TK)-positive Wyeth strain of vaccinia virus with a higher amplification potential and greater ability to evade anti-viral immunity than L14 VV. The ADSC-mediated sensitization potential of resistant B16 cells to infection by L14 VV was compared to the sensitization potential of the cells to infection by WT1 VV. Supernatants from four ADSC donors (RM20, RM35, BH21 and RM58) were added to 10,000 B16 cells infected with either L14 VV or WT1 VV at an MOI of 0.1 for 96 h in 96-well flat-bottom plates. Plaque assay analysis of L14 and WT1 vaccinia virus amplification in B16 cells was performed as described previously. Cell viability was determined using an MTT assay. An MTT (a tetrazolium dye; 3-(4,5-dimethylthiazol-2-yl)-2,5-diphenyltetrazolium bromide) assay is a well-known colorimetric assay for assessing cell metabolic activity. NAD(P)H-dependent cellular oxidoreductase enzymes can, under defined conditions, reflect the number of viable cells present. The assay assesses reduction of the tetrazolium dye MTT to a purple formazan dye. MTT (ThermoFisher, cat. #M-6494, 5 mg/mL stock in 1×PBS, kept at −20° C.) was added to the cells (10 µL to 100 µL cells/well) in 96-well flat-bottom plates, at a final concentration of 5 µg/mL and incubated for 1-2 h at 37° C. (incubator). Following incubation, cells were lysed by adding 100 µL of isopropanol:1M HCl (24:1, supplemented with 10% Triton X100, Sigma-Aldrich, X100-100 ML) and vigorous pipetting to dissolve the formazan. Plates were read on a Tecan Infinite® 200 Pro and the MTT signal was measured within 1 h by subtracting the OD value at 650 nm from the OD value at 570 nm. Cells without MTT or blank/medium wells were included as controls to eliminate background signal.

Results of the plaque analysis, which are shown in Table 7, show an overall trend of increasing average pfu/sample in the presence of ADSC supernatants, indicating that the ADSC supernatants are able to sensitize B16 cells to L14 and to WT1 VV infection. The MTT assay results (Table 8) show the absence of a significant impact of ADSC supernatants alone on the survival of B16 cells infected with L14 or WT1 VV.

TABLE 7

Plaque Assay Results for B16 Cells Infected with L14 VV and WT1 VV

| | Average pfu/sample | |
|---|---|---|
| Supernatant Donor | L14 VV | WT1 VV |
| CTRL | $1.80 \times 10^4$ | $9.00 \times 10^1$ |
| RM20 | $1.70 \times 10^4$ | $2.70 \times 10^2$ |
| RM35 | $4.10 \times 10^4$ | $3.10 \times 10^2$ |
| BH21 | $3.30 \times 10^4$ | $4.25 \times 10^2$ |
| RM58 | $4.10 \times 10^4$ | $5.30 \times 10^2$ |

TABLE 8

B16 MTT Assay Results

| | Relative Viability (MTT) | | |
|---|---|---|---|
| Supernatant Donor | Control | L14 VV | WT1 VV |
| Norm. MTT | 1.00 | 0.50 | 0.71 |
| CTRL | 0.73 | 0.75 | 0.70 |
| RM20 | 0.78 | 0.79 | 0.62 |
| RM35 | 0.73 | 0.67 | 0.70 |
| BH21 | 0.89 | 0.80 | 0.72 |
| RM58 | 1.00 | 0.50 | 0.71 | iii. Viral Infection of K562 Cells in the Presence of ADSC Supernatants or ADSCs 100,000 K562 cells were infected with TurboFP635+ (fluorescently labeled) L14 VV at an MOI of 0.1 for 96 h in 96-well flat-bottom plates and supernatants from the four different ADSC donors (RM20, RM35, BH21 and RM58) were added. Flow cytometry analysis was performed and the percentage of K562 cells infected with L14 VV and the median fluorescence intensity (MFI) was recorded. Plaque analysis was used to determine viral titers, and the MTT assay was used to determine cell viability. Results showed slight increases in the frequency (percentage) of infected K562 cells (Table 9), TurboFP635+MFI (Table 10), and viral titers (Table 11), but showed no significant effect on the overall survival of the highly resistant K562 cells, as measured by the MTT assay, demonstrating an ADSC supernatant-potentiated infection of K562 cells.

The results show that ADSC supernatants alone can sensitize K562 cells to virus infection, but do not result in significant oncolysis. The effects of ADSCs were compared to those of the ADSC supernatants. 100,000 K562 cells were infected with L14 VV at an MOI of 0.1, but instead of ADSC supernatants, K562 cells were co-cultured with 5,000 or 20,000 RM20-eGFP ADSCs in triplicate. Fluorescence imaging and flow cytometry analysis show that the green fluorescent ADSCs attract the unlabeled/grey K562 cells and dramatically increase the percentage of infected K562 cells. Despite the potentiated infectivity of the highly resistant K562 cells (Table 12), the ADSCs ultimately failed to eradicate or significantly impact their overall survival (Table 13), consistent with the minimal ability of K562 cells to amplify vaccinia virus that is distinct from the ability of the ADSCs to potentiate infection.

The results indicate that ADSCs have the unique properties of both amplifying the virus (approx. 10,000-fold or 5,000 pfu/cell) and spreading it to tumor cells. This can be attributed to a higher local multiplicity of infection (MOI) as well as some form of chemo-attraction. This effect is at least in part due to the secretion of unidentified soluble factors present in the supernatants of ADSCs. The observed potentiating effects of ADSC supernatants on the frequency of infected B16 and K562 cells and virus amplification were relatively small (approximately 2-fold), indicating that successful therapy of resistant tumors requires the sensitization and the amplification properties of the ADSCs and their supernatants, as well as the ability of the ADSCs themselves to recruit murine and human tumor cells and potentiate infection of these cells.

TABLE 9

Frequency of Infected K562 Cells

| ADSC Supernatant Donors | % TurboFP635 + Infected K562 Cells |
| --- | --- |
| CTRL | 2.11 |
| RM20 | 2.69 |
| RM35 | 3.31 |
| BH21 | 3.43 |
| RM58 | 4.32 |

TABLE 10

MFI of TurboFP635 + Infected K562 Cells

| ADSC Supernatant Donors | Average MFI |
| --- | --- |
| CTRL | $8.30 \times 10^3$ |
| RM20 | $1.02 \times 10^4$ |
| RM35 | $1.11 \times 10^4$ |
| BH21 | $9.70 \times 10^3$ |
| RM58 | $1.26 \times 10^4$ |

TABLE 11

Plaque Assay Results

| ADSC Supernatant Donors | Average pfu/sample |
| --- | --- |
| CTRL | $1.00 \times 10^4$ |
| RM20 | $1.50 \times 10^4$ |
| RM35 | $1.85 \times 10^4$ |
| BH21 | $1.55 \times 10^4$ |
| RM58 | $1.70 \times 10^4$ |

TABLE 12

Effect of ADSCs on Infection of K562 Cells with L14VV

| Number of ADSCs | TurboFP635 + Infected K562 Average Cell Numbers |
| --- | --- |
| CTRL | 119 |
| 5k | 853 |
| 20k | 1700 |

TABLE 13

Effect of ADSCs on Eradication of K562 Cells

| ADSCs/Virus | # Live K562 Cells | # Live Infected K562 Cells | # Dead K562 Cells | # Dead Infected K562 Cells | Total # Cells |
| --- | --- | --- | --- | --- | --- |
| CTRL | 3854 ± 258 | 0.33 ± 0.58 | 7876 ± 1241 | 3.67 ± 1.53 | 11730 ± 1412 |
| 5k ADSCs | 5870 ± 2793 | 1.67 ± 2.89 | 6819 ± 2740 | 3.33 ± 1.15 | 12689 ± 5533 |
| 20k ADSCs | 10006 ± 1075 | 0.33 ± 0.58 | 5468 ± 2121 | 1.33 ± 0.58 | 15474 ± 2638 |
| L14 VV | 5451 ± 1230 | 119 ± 22 | 12477 ± 2436 | 45 ± 8 | 17928 ± 3665 |
| 5k ADSCs + L14 VV | 6363 ± 3103 | 853 ± 507 | 9749 ± 4714 | 259 ± 128 | 16113 ± 7811 |
| 20k ADSCs + L14 VV | 7025 ± 5137 | 1700 ± 1183 | 8637 ± 6448 | 394 ± 260 | 15663 ± 11577 |

Example 4

Analysis of Immune Parameters to Identify Oncolytic Virus/Carrier Cell Combinations for Treating a Subject As described herein, an optimal oncolytic virus/cell-based delivery vehicle combination facilitates viral amplification and oncolysis in the subject to be treated, while preventing immune activation and suppressing virus-induced immune activation during delivery of the virus to tumors. The previous examples demonstrate how to evaluate carrier cells, such as ADSCs, for their viral amplification potential, their ability to sensitize tumor/cancer cells to infection by the virus, and their ability to facilitate oncolysis by the virus (e.g., by recruiting remote tumor/cancer cells).

This example assesses subject-specific immune restrictions that can limit the therapeutic potential of off-the-shelf cell-based delivery vehicles for delivering oncolytic viruses to tumors/cancer cells. Such restrictions include, for example, virus-induced and/or allogeneic carrier cell-induced immune activation, such as, for example, IFNγ and cytotoxic responses. These responses originate from the innate (NK, NKT) and adaptive (T) immune cells of improperly matched subjects/recipients. This example demonstrates that carrier cells that generally meet the requirements of a good delivery vehicle for viral therapy when administered autologously or allogeneically, such as ADSCs (i.e., they promote viral amplification and demonstrate evasion and/or suppression of innate and/or adaptive immune responses to the virus and/or the carrier cell), nonetheless can sometimes be less efficient in certain allogeneic settings.

To evaluate the potential immune responses of subjects to carrier cells/oncolytic virus, carrier cells (autologous or allogeneic), oncolytic virus and subject-derived immune cells (e.g., PBMCs, PBMCs+plasma/serum, or whole blood with or without red blood cell lysis) are co-cultured. The immune induction effects of oncolytic virus/allogeneic cell-based delivery vehicle combinations, and the parallel allogeneic/autologous cell-based carrier-induced immunosuppression, is evaluated using, e.g., Enzyme-Linked ImmunoSpot (ELISPOT) or flow cytometry analysis (or equivalents such as CyTOF, for example), based on a panel of markers identifying different immune cell populations, including T cells (such as, but not limited to, CD3, CD4, CD8), NK cells (such as, but not limited to, NKp46, CD16, CD56) and NKT cells (such as, but not limited to, CD3, CD16, CD56, NKp46, aGalCer-CD1d tetramers), as well as a panel of activation/effector function markers including, but not limited to: CD69, CD25, CD71, CD27 (CD70L), CD154 (CD40L), CD137 (4-1BB), CD44, CD45RA, CD45RO, CD278 (ICOS), CD127 (IL-7RA), CD183 (CXCR3), CD197 (CCR7), CD39, CD73, CD314 (NKG2D), PD-1, CTLA-4, IFNα/β, IFNγ, TNFα, IL-2, IL-4, IL-5, IL-9, IL-10, IL-12, IL-13, IL-15, IL-18, IL-21, IL-22, IL-23, IL-25, GM-CSF, IL-17, IL-6, CD107a, CD107b, TGFβ, Perforin, Granzyme B, IL-1a/IL-1b, G-CSF, RANTES, EXOTAXIN, MIP-1b, MCP-1, EGF, HGF, VEGF, IL-1RA, IL-7, IP-10, IL-2R, MIG and IL-8, for example.

A. Immunosuppressive Properties of ADSCs in Autologous and Allogeneic Settings

To evaluate the potential of ADSCs to overcome immune barriers, their ability to suppress NK cells in the presence of autologous or allogeneic human PBMCs was tested. 250,000 freshly isolated RM20 PBMCs were co-cultured for 48 h with 10,000 or 100,000 autologous (RM20) or allogeneic (RM35) ADSCs. PBMCs were co-cultured (100 μL) with ADSCs (50 μL) for 48 h on 96-well flat-bottom plates and in a total of 200 μL R10 medium (RPMI 1640 supplemented with 10% FBS, L-Glutamine and Pen/Strep). At the end of the 48 h incubation period, the co-cultures were subjected to an additional 4 h stimulation of NK cells with 250,000 K562 cells or PMA/Ionomycin (50 μL) with Monensin/Brefeldin A (50 μL), as needed.

The frequency (percentages) of NK and T cells, and the degrees of NK cell activation and NK cytotoxic activity were evaluated using flow cytometry analysis on PBMCs alone, PBMCs+10,000 or +100,000 autologous ADSCs, and PBMCs+10,000 or +100,000 allogeneic ADSCs. For flow cytometry analysis, co-cultures of PBMCs and ADSCs were recovered by pipetting and transferred to V-bottom plates, where they were washed with FACS Buffer (1×PBS with 1% FBS) and surface stained for 30 min at 4° C. in FACS Buffer supplemented with the following antibody cocktail: anti-human CD3-PerCP/Cy5.5 (BioLegend, cat. #300328, at 1:50), anti-human CD335 or NKp46-PE (BioLegend, cat. #331908, at 1:50), anti-human CD69-APC (BioLegend, cat. #310910, at 1:50). The FACS buffer also contained a viability probe (ThermoFisher Scientific, LIVE/DEAD Fixable Violet Dead Cell Stain Kit, for 405 nm excitation, cat. #L34964, at 1:1000). After staining, the cells were washed twice with FACS Buffer, fixed in 2% PFA in 1×PBS for 15 min at RT, washed again with FACS Buffer to remove PFA and analyzed on BD FACSAria II. To evaluate cytotoxic functions, anti-human CD107a-AlexaFluor 488 (BioLegend, cat. #328610) was added directly to the co-cultures at 1:20 (10 μl/well) 5 hours prior to recovery and surface staining, followed by the addition of Monensin at 1:1000 an hour later, for an additional 4 h incubation at 37° C. (BioLegend, cat. #420701-BL, 1000×).

The percentages of NK and T cells were determined in the autologous and allogeneic co-cultures and compared to a PBMC alone control. The results are summarized in Table 14 below. It was found that autologous and in allogeneic settings, ADSC-mediated immunosuppression does not affect the frequency of NK and T cells.

TABLE 14

Effects of ADSC-mediated immunosuppression effects on frequency of NK and T cells

| | % NK Cells | | % T Cells | |
| --- | --- | --- | --- | --- |
| Cultures/Conditions | Autologous (RM20) ADSCs + RM20 PBMCs | Allogeneic (RM35) ADSCs + RM20 PBMCs | Autologous (RM20) ADSCs + RM20 PBMCs | Allogeneic (RM35) ADSCs + RM20 PBMCs |
| (−) ADSCs | 17.90 | 18.37 | 66.90 | 66.27 |
| 10k ADSCs | 21.40 | 21.77 | 63.80 | 62.57 |
| 100k ADSCs | 19.93 | 20.40 | 64.30 | 64.17 |
| (−) ADSCs (+) K562 | 12.33 | 14.03 | 68.50 | 65.97 |
| 10k ADSCs (+) K562 | 21.90 | 17.23 | 58.70 | 65.53 |

TABLE 14-continued

Effects of ADSC-mediated immunosuppression effects on frequency of NK and T cells

| | % NK Cells | | % T Cells | |
| --- | --- | --- | --- | --- |
| Cultures/Conditions | Autologous (RM20) ADSCs + RM20 PBMCs | Allogeneic (RM35) ADSCs + RM20 PBMCs | Autologous (RM20) ADSCs + RM20 PBMCs | Allogeneic (RM35) ADSCs + RM20 PBMCs |
| 100k ADSCs (+) K562 | 21.23 | 21.70 | 59.50 | 58.87 |
| (−) ADSCs (+) PMA + Iono | 2.57 | 2.29 | 74.65 | 75.35 |
| 10k ADSCs (+) PMA + Iono | 1.61 | 1.99 | 76.15 | 79.35 |
| 100k ADSCs (+) PMA + Iono | 1.18 | 1.05 | 75.10 | 75.95 |

Flow cytometry analysis of NK activation using CD69 upregulation on gated live CD3$^-$ NKp46$^+$ NK cells (Table 15) shows that CD69 was upregulated when PBMCs were co-cultured with autologous (RM20) or with allogeneic (RM35) ADSCs, following stimulation with K562 cells or PMA/Ionomycin. Flow cytometry analysis of NK cell cytotoxic functions using CD107a surface exposure (Table 15) show upregulation of CD107a in co-cultures of PBMCs with autologous and with allogeneic ADSCs.

Thus, PBMC co-cultures with ADSCs demonstrate significant dose-dependent immunosuppressive effects against the immune response of NK cells that was stimulated by exposure to K562 target cells. The immunosuppressive effect was observed in autologous and in allogeneic settings, demonstrating that ADSCs can suppress NK cells in autologous and in allogeneic settings.

TABLE 15

% CD69$^+$ and CD107a$^+$ NK Cells in autologous vs. allogeneic cultures

| | % CD69$^+$ NK Cells | | % CD107a$^+$ NK Cells | |
| --- | --- | --- | --- | --- |
| Cultures/Conditions | Autologous (RM20) ADSCs + RM20 PBMCs | Allogeneic (RM35) ADSCs + RM20 PBMCs | Autologous (RM20) ADSCs + RM20 PBMCs | Allogeneic (RM35) ADSCs + RM20 PBMCs |
| (−) ADSCs | 8.49 | 12.09 | 4.15 | 3.71 |
| 10k ADSCs | 5.02 | 7.90 | 1.58 | 1.55 |
| 100k ADSCs | 2.72 | 2.02 | 0.62 | 1.10 |
| (−) ADSCs (+) K562 | 81.57 | 85.00 | 55.68 | 53.70 |
| 10k ADSCs (+) K562 | 44.90 | 66.23 | 28.66 | 39.53 |
| 100k ADSCs (+) K562 | 29.47 | 42.60 | 11.16 | 25.14 |
| (−) ADSCs (+) PMA + Iono | 96.20 | 95.30 | 29.98 | 22.62 |
| 10k ADSCs (+) PMA + Iono | 86.20 | 94.30 | 41.04 | 42.95 |
| 100k ADSCs (+30) PMA + Iono | 64.05 | 77.60 | 48.61 | 46.56 |

B. Allogeneic Stem Cell Suppression of Virus-Induced T, NK and NKT Cell Responses The potential of allogeneic stem cells to overcome immune barriers correlates with their ability to suppress virus-induced T, NK and NKT-like cell responses. The ability of allogeneic ADSCs from the RM35 donor to specifically suppress virus-induced responses mediated by NK, T and NKT cells was tested in a new cohort of two PBMC donors, with to reveal possible patient-specific restrictions.

250,000 PBMCs (100 µL) from two different blood donors (RM47 and RM48) were co-cultured with 400; 2,000; 10,000 or 60,000 allogeneic RM35 ADSCs (50 µL) for 48 h on 96 well flat-bottom plates, in a total of 200 µL R10 medium (RPMI 1640 supplemented with 10% FBS, L-Glutamine and Pen/Strep), in the presence or absence of 10,000 pfu (50 µL) of WT1 VV (ACAM2000). Flow cytometry analysis of gated live T, NK, and NKT-like cells was performed to determine the percentage of CD69$^+$ activated cells from each immune cell type in PBMCs cultured alone (control), PBMCs cultured with WT1 VV (no ADSCs), PBMCs+allogeneic ADSC co-cultures without virus, and PBMC+allogeneic ADSC co-cultures with WT1 VV.

The results are summarized in Table 16 below. Flow cytometry analysis of gated live T, NK, and NKT-like cells show that the percentage of CD69$^+$ activated T cells, NK cells and NKT cells all decreased dramatically in the WT1 VV+PBMC+allogeneic ADSC co-cultures, in comparison to the WT1 VV+PBMCs cultured without ADSCs. These results demonstrate that allogeneic RM35 ADSCs can suppress vaccinia virus-induced innate and adaptive immune responses.

A 4 h stimulation with 250,000 K562 cells at the end of the 48 h co-culture period was used to evaluate the immunosuppressive potential of the allogeneic stem cells. Relative to T cells, NK cells were the major responding population, with the combination of virus and low doses of stem cells resulting in the activation of more than 80% of the NK cells. Lower doses of the stem cells were insufficient for immunosuppression and increased virus-induced immune responses, possibly reflecting significantly augmented virus amplification. Higher doses of ADSCs, however, provided potent suppression of the weaker vaccinia virus-induced T cell responses in a dose-dependent fashion, indicating that stem cell-mediated immunosuppression overcomes the immune-stimulatory effect of augmented virus amplification.

Suppression of anti-viral NK cell responses was evident only at the highest stem cell doses, and was not consistent across the two allogeneic blood donors tested. The NK cells from one of the blood donors (RM48) responded directly to the allogeneic ADSCs. Using a standard 4 h K562 NK stimulation assay at the end of the 48 h PBMC/ADSC/VV co-culture experiment, it was demonstrated that the inconsistent suppression of the anti-viral NK responses correlated with loss of the stem cells' immune-privileged status and immunosuppressive abilities. An NKp46$^+$CD3$^+$ NKT-like population of cells was identified that responded vigorously to virus infection, with upregulation of activation markers. This population of cells manifested the ability for rapid and selective expansion in response to vaccinia virus, consistent with the already established role of NKT cells in the control of viral infections.

TABLE 16

| | | NK, T and NKT Cell Responses | | | | | |
|---|---|---|---|---|---|---|---|
| RM35 ADSC | | % CD69$^+$ T Cells | | % CD69$^+$ NK Cells | | % CD69$^+$ NKT Cells | |
| | Cell Number | RM47 PBMCs | RM48 PBMCs | RM47 PBMCs | RM48 PBMCs | RM47 PBMCs | RM48 PBMCs |
| No virus (PBMCs alone) | CTRL | 0.77 | 1.34 | 3.57 | 3.90 | 16.40 | 2.94 |
| | 60k | 1.06 | 2.72 | 4.80 | 20.05 | 30.80 | 3.27 |
| | 10k | 1.26 | 1.29 | 3.65 | 6.77 | 24.70 | 3.17 |
| | 2k | 1.13 | 1.19 | 4.37 | 3.86 | 20.85 | 1.63 |
| | 0.4k | 0.82 | 1.52 | 3.30 | 3.58 | 15.40 | 2.79 |
| | CTRL + K562 | 3.47 | 2.31 | 83.70 | 73.35 | 51.25 | 8.54 |
| | 60k + K562 | 1.29 | 1.80 | 36.70 | 46.90 | 34.75 | 3.47 |
| | 10k + K562 | 1.53 | 1.20 | 62.50 | 46.40 | 33.75 | 2.28 |
| | 2k + K562 | 1.63 | 1.12 | 68.65 | 42.60 | 30.55 | 4.40 |
| | 0.4k + K562 | 2.28 | 0.92 | 75.70 | 47.90 | 24.05 | 6.49 |
| +WT1 VV | CTRL | 15.80 | 21.95 | 40.80 | 76.45 | 52.40 | 39.60 |
| | 60k | 1.05 | 2.43 | 14.39 | 47.55 | 36.00 | 10.43 |
| | 10k | 4.05 | 6.29 | 75.05 | 86.10 | 65.85 | 37.75 |
| | 2k | 13.80 | 10.65 | 74.20 | 75.00 | 82.70 | 35.85 |
| | 0.4k | 19.30 | 12.75 | 64.35 | 71.60 | 73.30 | 33.45 |
| | CTRL + K562 | 30.25 | 33.95 | 94.25 | 97.85 | 82.80 | 53.40 |
| | 60k + K562 | 1.28 | 6.09 | 46.70 | 90.10 | 40.05 | 28.50 |
| | 10k + K562 | 5.89 | 11.50 | 89.20 | 95.50 | 72.90 | 45.95 |
| | 2k + K562 | 20.10 | 15.25 | 94.10 | 94.85 | 84.60 | 42.60 |
| | 0.4k + K562 | 24.60 | 13.25 | 93.00 | 92.55 | 81.30 | 31.65 |

C. Determining Subject-Specific Responses to Allogeneic Stem Cells

The immunosuppressive and virus amplification abilities of the allogeneic ADSCs derived from the RM20 donor (Example 1) were evaluated and tested in a larger cohort of PBMC donors to determine patient-specific restrictions.

250,000 PBMCs from four different blood donors (SIBD01, SIBD02, RM52, RM53) were each co-cultured with 5,000; 10,000; 20,000; or 40,000 allogeneic RM20 ADSCs for 48 h, in the presence or absence of 5,000 pfu of WT1 VV. Flow cytometry analysis was performed as described above to determine the percentage of CD69$^+$ activated NK, T and NKT cells. PBMCs cultured without stem cells were used as a control. The results, shown in Tables 17-19, were consistent with the previous data, showing that the same RM20 ADSCs, when tested against a panel of 4 new allogeneic PBMC donors, can trigger direct NK, T, and NKT cell responses in a subject-specific manner. High inter-subject variability was observed in the NK, T and NKT cell responses to both the allogeneic stem cells and to the virus. Two of the blood donors showed contrasting results, with SIBD01 being the most resistant and SIBD02 being the most permissive to the allogeneic ADSCs.

TABLE 17

NK cell responses to allogeneic ADSCs

| | | % CD69+ NK Cells | | | |
|---|---|---|---|---|---|
| | | RM20 ADSCs | SIBD01 PBMCs | SIBD02 PBMCs | RM52 PBMCs | RM53 PBMCs |
| No virus | CTRL | 9.35 | 4.88 | 7.02 | 20.60 |
| | 40k | 47.15 | 8.77 | 12.20 | 32.00 |
| | 20k | 34.15 | 8.83 | 12.05 | 29.70 |
| | 10k | 31.15 | 13.81 | 9.51 | 30.30 |
| | 5k | 27.40 | 7.99 | 15.47 | 26.50 |
| + WT1 VV | CTRL | 63.30 | 32.70 | 82.95 | 32.15 |
| | 40k | 68.10 | 19.80 | 56.85 | 51.15 |
| | 20k | 80.15 | 33.00 | 75.25 | 56.10 |
| | 10k | 77.60 | 85.80 | 92.25 | 78.80 |
| | 5k | 81.20 | 87.75 | 90.90 | 66.15 |

TABLE 18

T cell responses to allogeneic ADSCs

| | | % CD69+ T Cells | | | |
|---|---|---|---|---|---|
| | | RM20 ADSCs | SIBD01 PBMCs | SIBD02 PBMCs | RM52 PBMCs | RM53 PBMCs |
| No virus | CTRL | 6.00 | 1.65 | 3.63 | 4.92 |
| | 40k | 14.25 | 3.45 | 6.18 | 6.06 |
| | 20k | 11.90 | 3.11 | 6.08 | 5.79 |
| | 10k | 9.16 | 2.48 | 5.59 | 4.86 |
| | 5k | 9.97 | 2.16 | 8.77 | 5.19 |
| + WT1 VV | CTRL | 28.80 | 6.84 | 39.35 | 6.97 |
| | 40k | 20.05 | 1.71 | 4.72 | 5.38 |
| | 20k | 25.90 | 1.97 | 5.52 | 5.24 |
| | 10k | 25.20 | 11.15 | 12.25 | 6.27 |
| | 5k | 26.80 | 10.09 | 18.60 | 9.15 |

TABLE 19

NKT cell responses to allogeneic ADSCs

| | | % CD69+ T Cells | | | |
|---|---|---|---|---|---|
| | | RM20 ADSCs | SIBD01 PBMCs | SIBD02 PBMCs | RM52 PBMCs | RM53 PBMCs |
| No virus | CTRL | 9.49 | 36.80 | 29.45 | 42.85 |
| | 40k | 37.00 | 68.95 | 26.20 | 57.05 |
| | 20k | 35.00 | 54.85 | 34.75 | 56.40 |
| | 10k | 27.30 | 50.10 | 40.50 | 73.10 |
| | 5k | 20.35 | 41.25 | 34.50 | 35.65 |
| + WT1 VV | CTRL | 49.25 | 54.90 | 76.70 | 43.45 |
| | 40k | 56.00 | 39.70 | 50.95 | 61.60 |
| | 20k | 66.85 | 28.75 | 57.65 | 49.50 |
| | 10k | 60.25 | 74.90 | 70.70 | 86.35 |
| | 5k | 61.85 | 76.45 | 82.80 | 68.45 |

A 4 h stimulation with 250,000 K562 cells at the end of the 48 h co-culture period was used to evaluate the extent of NK cell suppression by the allogeneic RM20 ADSCs, using NK cells from the SIBD01 and SIBD02 blood donors. PBMCs cultured alone were used as a control. Flow cytometry analysis was used to determine the percentage of CD69+ NK, T and NKT cells, and plaque analysis was used to quantify virus amplification by the allogeneic ADSCs in the presence of the resistant vs. permissive blood donor samples. Flow cytometry analysis (Table 20) revealed that the immunosuppressive properties of ADSCs fail in unfavorable allogeneic settings, where the stem cells lose their immune privileged status and activate NK and T cells directly, even in the absence of the virus.

These immunological differences have a significant impact on the stem cells' virus amplification potential. As shown in Table 21, plaque assay analysis of the 48h co-cultures demonstrated that RM20 ADSCs can amplify WT1 vaccinia virus only in the presence of allogeneic PBMCs from the permissive SIBD02 donor, but not the resistant SIBD01 donor. This demonstrates that improperly matched stem cells and blood donors representing potential MSC-recipients can completely abrogate the virus amplification potential of the allogeneic ADSCs, thus revealing critical patient-specific differences that can lead to "permissiveness" or "resistance" to the ADSCs.

TABLE 20

NK, T and NKT Cell Responses

| | RM20 ADSC Cell Number | % CD69+ NK Cells | | % CD69+ T Cells | | % CD69+ NKT Cells | |
|---|---|---|---|---|---|---|---|
| | | SIBD01 PBMCs | SIBD02 PBMCs | SIBD01 PBMCs | SIBD02 PBMCs | SIBD01 PBMCs | SIBD02 PBMCs |
| No virus | CTRL | 5.65 | 3.37 | 2.38 | 1.10 | 7.23 | 26.45 |
| | 40k | 57.05 | 5.88 | 10.41 | 3.14 | 33.90 | 36.00 |
| | 20k | 30.75 | 4.19 | 6.43 | 1.27 | 22.85 | 51.70 |
| | 10k | 15.85 | 4.70 | 4.70 | 1.00 | 13.55 | 40.85 |
| | 5k | 10.85 | 5.33 | 4.78 | 1.02 | 10.75 | 34.60 |
| | CTRL + K562 | 73.40 | 79.40 | 15.70 | 2.19 | 37.60 | 97.20 |
| | 40k + K562 | 82.80 | 60.10 | 13.25 | 2.03 | 33.40 | 53.40 |
| | 20k + K562 | 64.80 | 49.00 | 9.36 | 1.35 | 21.95 | 69.00 |
| | 10k + K562 | 70.65 | 46.35 | 9.73 | 1.38 | 20.65 | 60.35 |
| | 5k + K562 | 70.25 | 55.60 | 10.80 | 1.44 | 21.25 | 52.55 |
| +WT1 VV | CTRL | 65.10 | 33.40 | 19.10 | 6.46 | 46.50 | 47.20 |
| | 40k | 86.20 | 10.56 | 20.75 | 1.39 | 64.50 | 14.25 |
| | 20k | 84.30 | 8.23 | 21.05 | 1.35 | 64.50 | 19.20 |
| | 10k | 77.55 | 7.16 | 19.00 | 1.11 | 57.50 | 23.55 |
| | 5k | 71.75 | 53.70 | 16.90 | 5.44 | 51.40 | 73.10 |
| | CTRL + K562 | 92.60 | 87.55 | 27.45 | 4.06 | 57.30 | 85.75 |
| | 40k + K562 | 95.15 | 63.85 | 25.10 | 1.58 | 70.55 | 52.40 |
| | 20k + K562 | 96.60 | 53.50 | 29.65 | 1.41 | 69.75 | 51.35 |

TABLE 20-continued

NK, T and NKT Cell Responses

| RM20 ADSC Cell Number | % CD69+ NK Cells | | % CD69+ T Cells | | % CD69+ NKT Cells | |
|---|---|---|---|---|---|---|
| | SIBD01 PBMCs | SIBD02 PBMCs | SIBD01 PBMCs | SIBD02 PBMCs | SIBD01 PBMCs | SIBD02 PBMCs |
| 10k + K562 | 95.30 | 66.60 | 25.30 | 2.39 | 67.80 | 41.65 |
| 5k + K562 | 92.80 | 66.40 | 21.05 | 1.94 | 56.05 | 66.20 |

TABLE 21

Plaque Assay Results

| Cultures/ Conditions | Average pfu/sample | | |
|---|---|---|---|
| | RM20 ADSCs alone | RM20 ADSCs + SIBD01 PBMCs | RM20 ADSCs + SIBD02 PBMCs |
| INPUT Virus | $1.05 \times 10^4$ | — | — |
| PBMCs alone | $5.30 \times 10^3$ | $4.30 \times 10^3$ | $4.10 \times 10^3$ |
| 5k RM20 ADSCs | $3.25 \times 10^4$ | $3.90 \times 10^3$ | $4.45 \times 10^3$ |
| 10k RM20 ADSCs | $6.00 \times 10^4$ | $3.70 \times 10^3$ | $1.20 \times 10^5$ |
| 20k RM20 ADSCs | $1.65 \times 10^5$ | $3.90 \times 10^3$ | $2.00 \times 10^5$ |
| 40k RM20 ADSCs | $3.20 \times 10^5$ | $4.65 \times 10^3$ | $2.45 \times 10^5$ |

Correlative analysis of NK, T, and NKT cell responses (% CD69+ cells, normalized to untreated PBMC control) against the highest dose (40,000) of the allogeneic ADSCs was performed. The results of the correlative analysis, shown in Tables 22-24, show that vaccinia virus induces significantly coordinated NK, NKT and T cell responses. A similar correlation is evident for the NK and T cell responses against the allogeneic stem cells, but responsiveness to the virus versus the allogeneic ADSCs was discordant and likely independent of each other.

TABLE 22

Anti-WT1 Correlative Analysis

| PBMC Donor | NK | T | NKT |
|---|---|---|---|
| RM47 | 37.23 | 15.03 | 36.00 |
| RM48 | 72.56 | 20.61 | 36.67 |
| SIBD01 | 53.96 | 22.81 | 39.76 |
| SIBD02 | 27.82 | 5.19 | 18.10 |
| RM52 | 75.94 | 35.73 | 47.25 |
| RM53 | 11.55 | 2.05 | 0.60 |

TABLE 23

Anti-ADSC Correlative Analysis

| PBMC Donor | NK | T | NKT |
|---|---|---|---|
| RM47 | 1.23 | 0.29 | 14.40 |
| RM48 | 16.16 | 1.38 | 0.33 |
| SIBD01 | 37.82 | 8.26 | 27.51 |
| SIBD02 | 3.89 | 1.80 | 32.15 |
| RM52 | 5.19 | 2.55 | -3.25 |
| RM53 | 11.40 | 1.14 | 14.20 |

TABLE 24

Anti-ADSC + WT1 Correlative Analysis

| PBMC Donor | NK | T | NKT |
|---|---|---|---|
| RM47 | 10.82 | 0.28 | 19.60 |
| RM48 | 43.66 | 1.09 | 7.50 |
| SIBD01 | 58.76 | 14.06 | 46.51 |
| SIBD02 | 14.92 | 0.060 | 2.90 |
| RM52 | 49.84 | 1.10 | 21.50 |
| RM53 | 30.55 | 0.47 | 18.75 |

Thus, PBMC donors demonstrate variable responses to the allogeneic stem cells and the virus alone, or in combination. These subject-specific differences indicate that proper matching between the subject and the carrier cell can improve therapeutic efficacy.

D. Subject-Specific Immunological Barriers to the Survival of ADSCs

Having identified a pair of blood donors who were respectively significantly resistant (SIBD01) and significantly permissive (SIBD02) to the allogeneic RM20 ADSCs, these donors were used to further analyze the underlying mechanisms of subject-specific resistance to the ADSCs. 20,000 eGFP-labelled RM20 ADSCs were co-cultured with 20,000 pfu L14 VV (MOI of 1) for up to 48 h in the presence of 250,000 PBMCs from the resistant (SIBD01; "resistant PBMCs") or permissive (SIBD02; "permissive PBMCs") blood donors. The ADSCs were infected with virus at the time of co-culture with the PBMCs, or were pre-infected for 1 h in a 37° C. incubator with constant shaking and then added to the PBMCs without washing away any unbound virus.

After 24 h and 48 h, fluorescence images were captured of the following cell cultures: ADSCs alone, ADSCs+resistant PBMCs and ADSCs+permissive PBMCs. Virus infection was observed in the ADSCs alone and in the ADSC+permissive PBMC co-cultures, but not in the ADSC+resistant PBMC co-cultures. Comparative analysis of the survival and amplification potential of the allogeneic ADSCs in the case of permissive versus resistant PBMCs indicated that resistance was associated with the rapid loss of the stem cells in the presence of the resistant allogeneic PBMCs and in the absence of virus infection. These same stem cells remained intact when co-cultured with PBMCs from the permissive recipient. Pre-infection of the ADSCs with L14 VV did not affect infection in the resistant PBMCs, indicating that giving the virus an amplification "head start" in the carrier cell was not sufficient to overcome the immunological barriers of the resistant PBMCs.

To assess the effects of pre-infecting the ADSCs with L14 VV or WT1 VV on levels of virus infection, 2,500; 5,000; 10,000 or 20,000 ADSCs were pre-incubated with L14 VV or WT1 VV, for 1 h in a 37° C. incubator with constant shaking, and plaque analysis was performed on the supernatants. The results are shown in Table 25. It was determined that pre-infection was sufficient for approximately half of the virus (L14 VV or WT1 VV) to get into the cells when 20,000 ADSCs were used, and that at a higher MOI (fewer stem cells), most of the virus appeared to remain free and required a longer time to integrate.

virus infection of the stem cells an hour prior to co-culture with the allogeneic PBMCs. Thus, patient-specific immunological barriers to allogeneic ADSCs can limit the therapeutic potential of genetically attenuated and wild type vaccinia virus strains.

TABLE 26

Plaque Assay Results

| | | | Average pfu/sample | | | |
|---|---|---|---|---|---|---|
| ADSC Cell Number | | Control | Control + 1 h pre-infection | SIBD01 PBMCs | SIBD01 PBMCs + 1 h pre-infection | SIBD02 PBMCs | SIBD02 PBMCs + 1 h pre-infection |
| WT1 VV | 2.5k | $1.00 \times 10^4$ | $1.38 \times 10^4$ | $5.01 \times 10^3$ | $5.00 \times 10^3$ | $2.46 \times 10^4$ | $2.22 \times 10^4$ |
| | 5k | $3.34 \times 10^4$ | $3.87 \times 10^4$ | $3.91 \times 10^3$ | $5.13 \times 10^3$ | $6.00 \times 10^4$ | $4.84 \times 10^4$ |
| | 10k | $7.91 \times 10^4$ | $1.24 \times 10^5$ | $6.81 \times 10^3$ | $7.37 \times 10^3$ | $1.80 \times 10^5$ | $1.25 \times 10^5$ |
| | 20k | $4.50 \times 10^4$ | $1.10 \times 10^5$ | $7.10 \times 10^3$ | $1.94 \times 10^4$ | $2.73 \times 10^5$ | $2.82 \times 10^5$ |
| L14 VV | 2.5k | $1.06 \times 10^4$ | $1.29 \times 10^4$ | $3.06 \times 10^3$ | $3.62 \times 10^3$ | $4.01 \times 10^3$ | $5.39 \times 10^3$ |
| | 5k | $4.30 \times 10^4$ | $4.34 \times 10^4$ | $4.46 \times 10^3$ | $4.68 \times 10^3$ | $8.97 \times 10^3$ | $1.13 \times 10^4$ |
| | 10k | $1.22 \times 10^5$ | $1.07 \times 10^5$ | $4.09 \times 10^3$ | $5.10 \times 10^3$ | $2.66 \times 10^4$ | $2.83 \times 10^4$ |
| | 20k | $1.29 \times 10^5$ | $1.30 \times 10^5$ | $1.86 \times 10^3$ | $2.27 \times 10^3$ | $4.54 \times 10^4$ | $3.21 \times 10^5$ |

TABLE 25

Uptake of VV by ADSCs with 1 h Incubation

| | Average pfu/sample | |
|---|---|---|
| #ADSCs | WT1 VV | L14VV |
| INPUT Virus | 15500 ± 707 | 15500 ± 707 |
| 2.5k | 14900 ± 1344 | 13175 ± 460 |
| 5k | 15525 ± 1732 | 16600 ± 990 |
| 10k | 14975 ± 884 | 17525 ± 530 |
| 20k | 7300 ± 212 | 7050 ± 424 |

The effects of pre-infection of ADSCs with L14 VV or WT1 VV on virus amplification in ADSC/PBMC co-cultures was assessed. 2,500; 5,000; 10,000 and 20,000 ADSCs were co-cultured with resistant and permissive PBMCs as described above, with parallel infection with the genetically attenuated L14 vaccinia virus and with the wild type WT1 (ACAM2000) vaccinia virus. ADSCs were infected with the virus at the time of co-culture with the PBMCs, or were pre-infected for 1 h in a 37° C. incubator with constant shaking and then added to the PBMCs without washing away any unbound virus. Plaque analysis of vaccinia virus amplification was performed as described above. The results (Table 26) show that, despite potentially enhancing stem cell infection and accelerating virus amplification, the 1 h head start had a small overall effect on the amplification potential of the ADSCs in the presence of allogeneic PBMCs. The permissive SIBD02 PBMCs partially suppressed the amplification of the L14 VV, but not the WT1 VV. In contrast to the Lister-based Turbo-FP635-engineered L14 virus, which has the TK locus inactivated/removed, as in most genetically attenuated vaccinia virus strains, WT1/ACAM2000 is a wild type TK-positive Wyeth strain vaccinia virus with a demonstrated higher amplification potential and ability to overcome stronger allogeneic barriers. This is due to a possible faster amplification cycle and/or augmented ability to evade anti-viral immunity. These advantages of the WT1 virus were nevertheless insufficient to overcome the immunological barriers in the resistant recipient (SIBD01), and virus amplification was only marginally improved by initiating Example 5

Analysis of Subject-Specific Genetic Polymorphisms

This example provides a haplotype analysis to gain an understanding of factors that can contribute to the rejection of allogeneic carrier cells by subjects, and ways that this problem can be circumvented. Certain subject-specific genetic polymorphisms can result in an "immunological mismatch" between the subject and the allogeneic carrier cells. Relevant loci include, but are not limited to, for example, classical MHC I/II haplotypes, KIR haplotypes/ligands and non-classical MHC haplotypes (such as, for example, HLA-E, CD1a, b, c, d and MICA/B).

Analysis of the relevant loci of subject-specific genetic polymorphisms can be performed using, for example, next generation sequencing. The genetic polymorphism profile of each subject is then compared with the profiles of each of the available carrier cell types to identify mismatches between subject and carrier cells, including MHC mismatches, KIR and KIR ligand mismatches and mismatches at non-classical MHC loci, and "immunocompromising" mismatches identified. An "immunocompromising mismatch" is a mismatch between the subject and the carrier cells at a genetic polymorphism locus that is associated with a significant (e.g., 10% or more) reduction in the % compatibility as determined by the matching assay methods provided herein.

A. Resistance to Allogeneic ADSCs is Associated with HLA Mismatches

Resistance or permissiveness to different allogeneic ADSC lines was assessed. 250,000 PBMCs from the resistant (SIBD01) and permissive (SIBD02) blood donors were co-cultured for 48 hours with 40,000 or 5,000 allogeneic ADSCs from four different donors (RM20, RM35, BH21 and RM58) that were infected with 5,000 pfu of WT1 VV. ADSCs alone were used as a control, and plaque assays were performed as described above. The results (Table 27) show that SIBD01 and SIBD02 blood donors demonstrated broad resistance and permissiveness to the four allogeneic ADSC lines, respectively. The four allogeneic ADSC lines amplified vaccinia virus only in the presence of PBMCs from the permissive SIBD02 blood donor.

TABLE 27

Plaque Assay Results

| Conditions | ADSCs Alone | SIBD01 PBMCs | SIBD01 PBMCs |
|---|---|---|---|
| | | Average pfu/sample | |
| INPUT | $2.95 \times 10^3$ | — | — |
| Virus Alone | $1.80 \times 10^3$ | — | — |
| PBMCs Alone | — | $1.30 \times 10^3$ | $2.05 \times 10^3$ |
| RM20 40k | $2.50 \times 10^5$ | $1.60 \times 10^3$ | $1.00 \times 10^5$ |
| RM20 5k | $1.10 \times 10^4$ | $1.55 \times 10^3$ | $1.70 \times 10^4$ |
| RM35 40k | $5.90 \times 10^5$ | $1.65 \times 10^3$ | $1.65 \times 10^5$ |
| RM35 5k | $3.80 \times 10^4$ | $1.60 \times 10^3$ | $4.80 \times 10^4$ |
| BH21 40k | $3.45 \times 10^5$ | $1.30 \times 10^3$ | $4.55 \times 10^5$ |
| BH21 5k | $2.90 \times 10^4$ | $1.95 \times 10^3$ | $3.15 \times 10^4$ |
| RM58 40k | $8.10 \times 10^5$ | $1.45 \times 10^3$ | $6.75 \times 10^4$ |
| RM58 5k | $6.35 \times 10^4$ | $2.10 \times 10^3$ | $2.25 \times 10^5$ |

Rejection of closely HLA-matched cells can be explained by differences in the KIR Haplotype or in the balance of signaling through the NK cell inhibitory (KIR, NKG2A/CD94) or stimulatory (KIR, NKG2D) receptors. HLA and KIR/MIC typing analysis was done via NGS by ProImmune (Oxford, UK) and Scisco Genetics (Seattle, USA), respectively. The presence/absence of the known KIR ligands A3/A11 (HLA-A), Bw4 (HLA-B) and C1/C2 (HLA-C) epitopes in the HLA alleles of the PBMC (SIBD01, SIBD02) and ADSC (RM20, RM35, BH21 and RM58) donors was obtained from dorak.info/mhc/nkcell.html. The −21M/T (Methionine/Threonine) dimorphism at the anchor amino acid from the leader sequence that predicts strong/weak binding and presentation of HLA-B-derived leader peptides by HLA-E, which provides inhibitory signaling though the NKG2A/CD94 receptors on NK cells, was obtained from the Immuno Polymorphism Database (IPD) at ebi.ac.uk/ipd.

An analysis of KIR Haplotypes as well as the presence of known KIR ligands including the Bw4 epitope (HLA-B) and the weak/strong C1/C2 epitopes (HLA-C) was performed, including an analysis of the oligomorphic MICA/B molecules that serve as ligands for NKG2D activating receptors on NK cells. The distribution and copy number of long(L)-inhibitory and short(S)-activating KIR receptors, with the total number of inhibitory and activating receptors present also was analyzed.

The results show the absence of a clear correlation between permissiveness/resistance and KIR haplotype/KIR ligands, −21M/T dimorphism, and MICA/B oligomorphism. The RM58 stem cells showed a KIR ligand C1/C2 mismatch with the resistant SIBD01 and with the permissive SIBD02 blood donors, indicating that this mismatch alone is insufficient to confer resistance. Broader determinants of permissiveness versus resistance correlated with partial matching mostly at the HLA-A and HLA-DP loci, with the broadly permissive donor having the most common HLA-A*02:01 allele, and the resistant donor having the HLA-A*01:01 allele. The discordant HLA-A*01:01 case could be linked to a C2 KIR ligand mismatch which, in previous studies, has been associated with insufficient KIR inhibitory signaling and NK cell-mediated rejection of HLA-Haploidentical iPSC (Ichise et al. (2017) Stem Cell Reports 9:853-867). Thus, HLA typing data alone are insufficient to predict permissiveness versus resistance, as seen by the discordant case of HLA-A*01:01 RM58 ADSCs. These data indicate that a combined consideration of various loci is needed.

B. Resistance to Allogeneic ADSCs is Associated with the Rapid Induction of Anti-Stem Cell Cytotoxic and Interferon Responses Correlative flow cytometry was used to analyze the CD107a and IFNγ responses to WT1 VV and allogeneic ADSCs in gated live NK, NKT and T cells from the PBMC/ADSC/WT1 co-cultures of Part A. above. The results, shown in Tables 28-30, show that all four of the tested allogeneic stem cell lines induced much stronger CD107a and IFNγ responses in the NK and T cells from the resistant, but not the permissive, blood donor, even in the absence of the virus. The average percentages of CD107a or IFNγ single positive lymphocytes of each cell type was analyzed based on triplicate wells and normalized to respective background (untreated PBMC control). In the permissive blood donor, the four allogeneic stem cells suppressed spontaneous NK cell-mediated IFNγ responses below background (untreated PBMC control).

TABLE 28

Anti-WT1 Correlations (R: Resistant; P: Permissive)

| PBMC Donor | NK | T | NKT |
|---|---|---|---|
| R:SIBD01 | 0.0393 | 0.0099 | 0.200 |
| P:SIBD02 | 0.0433 | 0.0011 | 0 |

TABLE 29

Anti-ADSC Correlations (R: Resistant; P: Permissive)

| PBMC Donor | NK | T | NKT |
|---|---|---|---|
| R:RM20 | 0.0307 | 0.0507 | 0.1200 |
| R:RM35 | 0.0700 | 0.0600 | 0 |
| R:BH21 | 0.0640 | 0.0620 | 0.1933 |
| R:RM58 | 0.1813 | 0.1890 | 0.2867 |
| P:RM20 | −0.2305 | 0.0093 | 0 |
| P:RM35 | −0.1693 | 0.0089 | 0 |
| P:BH21 | −0.2148 | 0.0051 | 0 |
| P:RM58 | −0.2140 | 0.0114 | 0 |

TABLE 30

Anti-ADSC + WT1 Correlations (R: Resistant; P: Permissive)

| PBMC Donor | NK | T | NKT |
|---|---|---|---|
| R:RM20 | 0.1147 | 0.0950 | 0 |
| R:RM35 | 0.0963 | 0.0366 | 0 |
| R:BH21 | 0.0263 | 0.1357 | 0.0323 |
| R:RM58 | 0.1593 | 0.1857 | 0.1933 |
| P:RM20 | −0.2043 | 0.0205 | 1.7533 |
| P:RM35 | −0.1557 | 0.0059 | 0 |
| P:BH21 | −0.2180 | 0.0010 | 0 |
| P:RM58 | −0.2333 | 0.0024 | 0 |

Flow cytometry analysis also shows that treatment with vaccinia virus or allogeneic stem cells does not significantly affect the frequency of the gated lymphocyte populations. The exception was the CD3+ NKp46+ NKT-like cells from the resistant SIBD01 blood donor. These cells expanded in response to the allogeneic stem cells alone and further in the presence of vaccinia virus infection (Table 31). The broad resistance of the SIBD01 donor to several allogeneic stem cell lines can be associated with the unusually high frequency of CD3+ NKp46+ NKT-like cells, which was the only cell population that expanded in numbers in response to the virus and to the allogeneic stem cells.

TABLE 31

NKT Cell Percentages in Response to Allogeneic Stem Cells/Virus

Average NKT Cell %

| ADSC DONOR | SIBD01 PBMCs | SIBD01 + WT1 VV | SIBD02 PBMCs | SIBD02 + WT1 VV |
|---|---|---|---|---|
| CTRL | 0.3267 | 0.3233 | 0.0187 | 0.0210 |
| RM20 40k | 0.9867 | 1.6467 | 0.0215 | 0.0280 |
| RM20 5k | 0.400 | 0.8133 | 0.0200 | 0.0167 |
| RM35 40k | 0.9033 | 0.9150 | 0.0130 | 0.0267 |
| R1V135 5k | 0.5500 | 0.8233 | 0.0175 | 0.0275 |
| BH21 40k | 0.87 | 1.5933 | 0.0187 | 0.0180 |
| BH21 5k | 0.4833 | 0.78 | 0.019 | 0.0220 |
| RM58 40k | 0.9867 | 1.5867 | 0.0283 | 0.0287 |
| RM58 5k | 0.5267 | 1.3633 | 0.0157 | 0.0255 |

C. NKT-Like Cells are the Earliest Producers of IFNγ

To assess anti-virus and anti-stem cell induced immune responses, 2,000 or 10,000 RM20 ADSCs were co-cultured with 250,000 PBMCs from the resistant SIBD01 or permissive SIBD02 blood donors and 5,000 pfu WT1 VV. Gated live NK, NKT and T cells were analyzed by flow cytometry for activator (CD69 surface stain; Tables 32-34) and effector (intracellular stain for IFNγ; Tables 35-37) functions at 6h and 24 h time points. Significant background immune cell activation was evident at 6h and subsided by the 24 h time point. At 6 h, only T and NKT cells from the resistant donor demonstrated stem cell-induced CD69 upregulation, but not IFNγ responses. At 24 h, all three subsets responded to the allogeneic stem cells by upregulation of the CD69 activation marker, regardless of the presence or absence of virus. While the NK cell response was the most vigorous, only the NKT subset manifested statistically significant stem cell-induced IFNγ responses, indicating that NKT cells might be the first immune cell subtype mounting effector cytokine responses against the allogeneic stem cells. The NK, NKT and T cells from the permissive donor did not upregulate CD69 or produce IFNγ in response to the stem cells at any time point. At the 24 h time point, the allogeneic stem cells were even able to suppress IFNγ production by the permissive donor NK cells below background.

TABLE 32

Percent Activated NK Cells

% CD69+ NK Cells

| Conditions | SIBD01 PBMCs | SIBD01 + WT1 VV | SIBD02 PBMCs | SIBD02 + WT1 VV |
|---|---|---|---|---|
| CTRL 6 h | 32.20 | 35.67 | 48.33 | 46.17 |
| 10k ADSCs 6 h | 32.00 | 33.97 | 43.43 | 43.23 |
| 2k ADSCs 6 h | 31.43 | 36.57 | 45.10 | 45.70 |
| CTRL 24 h | 10.90 | 13.60 | 10.50 | 8.57 |
| 10k ADSCs 24 h | 52.43 | 86.83 | 15.50 | 20.30 |
| 2k ADSCs 24 h | 24.60 | 39.40 | 7.69 | 9.31 |

TABLE 33

Percent Activated T Cells

% CD69+ T Cells

| Conditions | SIBD01 PBMCs | SIBD01 + WT1 VV | SIBD02 PBMCs | SIBD02 + WT1 VV |
|---|---|---|---|---|
| CTRL 6 h | 3.81 | 3.66 | 2.15 | 2.05 |
| 10k ADSCs 6 h | 6.26 | 6.08 | 2.23 | 2.36 |
| 2k ADSCs 6 h | 3.62 | 3.73 | 2.67 | 1.97 |
| CTRL 24 h | 2.74 | 2.45 | 0.76 | 0.58 |
| 10k ADSCs 24 h | 8.60 | 23.63 | 1.39 | 1.36 |
| 2k ADSCs 24 h | 4.02 | 5.25 | 0.72 | 0.75 |

TABLE 34

Percent Activated NKT Cells

% CD69+ NKT Cells

| Conditions | SIBD01 PBMCs | SIBD01 + WT1 VV | SIBD02 PBMCs | SIBD02 + WT1 VV |
|---|---|---|---|---|
| CTRL 6 h | 7.35 | 7.82 | 18.77 | 23.43 |
| 10k ADSCs 6 h | 11.00 | 10.70 | 22.37 | 20.17 |
| 2k ADSCs 6 h | 7.44 | 7.91 | 23.87 | 17.47 |
| CTRL 24 h | 5.43 | 6.10 | 8.30 | 11.07 |
| 10k ADSCs 24 h | 23.00 | 48.33 | 17.37 | 16.60 |
| 2k ADSCs 24 h | 10.79 | 11.90 | 10.88 | 9.08 |

TABLE 35

Percent IFNγ+ NK Cells

% IFNγ+ NK Cells

| Conditions | SIBD01 PBMCs | SIBD01 + WT1 VV | SIBD02 PBMCs | SIBD02 + WT1 VV |
|---|---|---|---|---|
| CTRL 6 h | 0.37 | 0.34 | 0.60 | 0.68 |
| 10k ADSCs 6 h | 0.31 | 0.34 | 0.37 | 0.54 |
| 2k ADSCs 6 h | 0.24 | 0.36 | 0.56 | 0.62 |
| CTRL 24 h | 1.10 | 1.05 | 3.39 | 2.06 |
| 10k ADSCs 24 h | 0.54 | 0.80 | 1.02 | 0.42 |
| 2k ADSCs 24 h | 0.38 | 0.37 | 1.01 | 0.51 |

TABLE 36

Percent IFNγ+ T Cells

% IFNγ+ T Cells

| Conditions | SIBD01 PBMCs | SIBD01 + WT1 VV | SIBD02 PBMCs | SIBD02 + WT1 VV |
|---|---|---|---|---|
| CTRL 6 h | 0.10 | 0.12 | 0.05 | 0.05 |
| 10k ADSCs 6 h | 0.09 | 0.09 | 0.04 | 0.05 |
| 2k ADSCs 6 h | 0.08 | 0.10 | 0.04 | 0.06 |
| CTRL 24 h | 0.26 | 0.17 | 0.20 | 0.03 |
| 10k ADSCs 24 h | 0.54 | 0.53 | 0.23 | 0.02 |
| 2k ADSCs 24 h | 0.27 | 0.20 | 0.30 | 0.02 |

TABLE 37

Percent IFNγ+ NKT Cells

% IFNγ+ NKT Cells

| Conditions | SIBD01 PBMCs | SIBD01 + WT1 VV | SIBD02 PBMCs | SIBD02 + WT1 VV |
|---|---|---|---|---|
| CTRL 6 h | 1.46 | 1.17 | 4.96 | 10.67 |
| 10k ADSCs 6 h | 1.83 | 1.50 | 3.04 | 3.85 |

TABLE 37-continued

Percent IFNγ+ NKT Cells

| | % IFNγ+ NKT Cells | | | |
|---|---|---|---|---|
| Conditions | SIBD01 PBMCs | SIBD01 + WT1 VV | SIBD02 PBMCs | SIBD02 + WT1 VV |
| 2k ADSCs 6 h | 1.93 | 2.20 | 4.87 | 4.38 |
| CTRL 24 h | 1.00 | 0.60 | 2.99 | 1.28 |
| 10k ADSCs 24 h | 5.07 | 4.93 | 2.21 | 0.92 |
| 2k ADSCs 24 h | 0.78 | 0.70 | 3.07 | 0.90 |

D. Effects of IFNγ Pretreatment of ADSCs on Immune Cell Responses in Permissive vs. Resistant PBMCs To study the potential detrimental effects of IFNγ secretion on the interactions between the immune cells and the allogeneic stem cells that can occur in vivo, the stem cells were pretreated with IFNγ prior to co-culture with the PBMCs in the presence or absence of vaccinia virus. PBMCs of a resistant (SIBD01) and several permissive (SIBD02, RM52, RM53) blood donors were co-cultured with increasing numbers of allogeneic RM20 ADSCs (5,000; 10,000; 20,000 or 40,000) that were untreated or pre-treated with 20 ng/mL IFNγ for 48 h. Flow cytometry analysis of gated NK, NKT, and T cells was performed as described previously.

It was determined that IFNγ pre-treatment enhanced, rather than suppressed, NK and T cell responses in the permissive patients in the presence, but also in the absence, of WT1 vaccinia virus (Tables 38-43). The data also demonstrate that a later passage of the RM20 stem cells (p12) retain some T cell immunosuppression ability, but lose the ability to suppress NK cells. Stimulation of NK cells with the NK-specific stimulator cell line, K562, induce indirect activation of T and NKT cell responses, which is indicative of NK-NKT-T cell crosstalk (Tables 44-46).

Thus, while HLA or KIR matching can play a role in determining permissiveness vs. resistance toward a carrier cell, the ultimate therapeutic efficacy of a carrier cell type can be influenced by other subject-specific differences including innate and adaptive immune cell composition, activation status and sensitivity to virus/allogeneic cell mismatch. For example, it was found that regardless of the degree of partial HLA or KIR/KIR ligand match, the ability of the allogeneic ADSCs to efficiently amplify the virus was associated with the absence of significant anti-stem cell IFNγ and cytotoxic NK and T cell responses across all the four allogeneic ADSC lines tested. Analysis of the PBMCs from the significantly resistant SIBD01 recipient show that the improperly matched allogeneic stem cells induce a detectable IFNγ response even in the absence of virus infection. This response appears to originate from NK and from T cells. While T cells represent the bulk of early IFNγ-producing cells, NK cells demonstrate the highest proportional cytotoxic activity, indicative of the existence of cross talk between the innate and adaptive immune cell populations.

TABLE 38

Effect of IFNγ Pretreatment on NK Cell Activation in the Presence of WT1 VV

| | % CD69+ NK Cells | | |
|---|---|---|---|
| | ADSCs Alone | ADSCs + WT1 VV | IFNγ ADSCs + WT1 VV |
| SIBD01 PBMCs alone | 9.35 | 63.30 | — |
| SIBD01 + 40k RM20 | 47.15 | 68.10 | 81.25 |
| SIBD01 + 20k RM20 | 34.15 | 80.15 | 70.75 |
| SIBD01 + 10k RM20 | 31.15 | 77.60 | 46.65 |
| SIBD01 + 5k RM20 | 27.40 | 81.20 | 77.70 |
| SIBD02 PBMCs Alone | 4.88 | 32.70 | — |
| SIBD02 + 40k RM20 | 8.77 | 19.80 | 91.15 |
| SIBD02 + 20k RM20 | 8.83 | 33.00 | 92.50 |
| SIBD02 + 10k RM20 | 13.81 | 85.80 | 93.00 |
| SIBD02 + 5k RM | 7.99 | 87.75 | 92.25 |
| RM52 PBMCs Alone | 7.02 | 82.95 | — |
| RM52 + 40k RM20 | 12.20 | 56.85 | 92.70 |
| RM52 + 20k RM20 | 12.05 | 75.25 | 95.00 |
| RM52 + 10k RM20 | 9.51 | 92.25 | 81.35 |
| RM52 + 5k RM20 | 15.47 | 90.90 | 97.50 |
| RM53 PBMCs Alone | 20.60 | 32.15 | — |
| RM53 + 40k RM20 | 32.00 | 51.15 | 96.60 |
| RM53 + 20k RM20 | 29.70 | 56.10 | 97.30 |
| RM53 + 10k RM20 | 30.30 | 78.80 | 94.10 |
| RM53 + 5k RM20 | 26.50 | 66.15 | 92.15 |

TABLE 39

Effect of IFNγ Pretreatment on T Cell Activation in Presence of WT1 VV

| | % CD69+ T Cells | | |
|---|---|---|---|
| | ADSCs Alone | ADSCs + WT1 VV | IFNγ ADSCs + WT1 VV |
| SIBD01 PBMCs alone | 6.00 | 28.80 | — |
| SIBD01 + 40k RM20 | 14.25 | 20.05 | 27.80 |
| SIBD01 + 20k RM20 | 11.90 | 25.90 | 25.15 |
| SIBD01 + 10k RM20 | 9.16 | 25.20 | 10.47 |
| SIBD01 + 5k RM20 | 9.97 | 26.80 | 29.90 |
| SIBD02 PBMCs Alone | 1.65 | 6.84 | — |
| SIBD02 + 40k RM20 | 3.45 | 1.71 | 10.20 |
| SIBD02 + 20k RM20 | 3.11 | 1.97 | 11.55 |
| SIBD02 + 10k RM20 | 2.48 | 11.15 | 12.50 |
| SIBD02 + 5k RM20 | 2.16 | 10.09 | 11.80 |
| RM52 PBMCs Alone | 3.63 | 39.35 | — |
| RM52 + 40k RM20 | 6.18 | 4.72 | 8.51 |
| RM52 + 20k RM20 | 6.08 | 5.52 | 12.40 |
| RM52 + 10k RM20 | 5.59 | 12.25 | 15.90 |
| RM52 + 5k RM20 | 8.77 | 18.60 | 16.50 |
| RM53 PBMCs Alone | 4.92 | 6.97 | — |
| RM53 + 40k RM20 | 6.06 | 5.38 | 16.60 |
| RM53 + 20k RM20 | 5.79 | 5.24 | 18.10 |
| RM53 + 10k RM20 | 4.86 | 6.27 | 18.95 |
| RM53 + 5k RM20 | 5.19 | 9.15 | 13.55 |

TABLE 40

Effect of IFNγ Pretreatment on NKT Cell Activation in the Presence of WT1 VV

| | % CD69+ NKT Cells | | |
|---|---|---|---|
| | ADSCs Alone | ADSCs + WT1 VV | IFNγ ADSCs + WT1 VV |
| SIBD01 PBMCs alone | 9.49 | 49.25 | — |
| SIBD01 + 40k RM20 | 37.00 | 56.00 | 68.70 |
| SIBD01 + 20k RM20 | 35.00 | 66.85 | 65.20 |
| SIBD01 + 10k RM20 | 27.30 | 60.25 | 66.85 |
| SIBD01 + 5k RM20 | 20.35 | 61.85 | 72.65 |

TABLE 40-continued

Effect of IFNγ Pretreatment on NKT Cell Activation in the Presence of WT1 VV

| | % CD69+ NKT Cells | | |
|---|---|---|---|
| | ADSCs Alone | ADSCs + WT1 VV | IFNγ ADSCs + WT1 VV |
| SIBD02 PBMCs Alone | 36.80 | 54.90 | — |
| SIBD02 + 40k RM20 | 68.95 | 39.70 | 84.00 |
| SIBD02 + 20k RM20 | 54.85 | 28.75 | 78.95 |
| SIBD02 + 10k RM20 | 50.10 | 74.90 | 80.15 |
| SIBD02 + 5k RM20 | 41.25 | 76.45 | 76.80 |
| RM52 PBMCs Alone | 29.45 | 76.70 | — |
| RM52 + 40k RM20 | 26.20 | 50.95 | 60.80 |
| RM52 + 20k RM20 | 34.75 | 57.65 | 78.35 |
| RM52 + 10k RM20 | 40.50 | 70.70 | 68.55 |
| RM52 + 5k RM20 | 34.50 | 82.80 | 87.20 |
| RM53 PBMCs Alone | 42.85 | 43.45 | — |
| RM53 + 40k RM20 | 57.05 | 61.60 | 81.70 |
| RM53 + 20k RM20 | 56.40 | 49.50 | 87.05 |
| RM53 + 10k RM20 | 73.10 | 72.70 | 82.80 |
| RM53 + 5k RM20 | 35.65 | 68.45 | 87.20 |

TABLE 41

Effect of IFNγ Pretreatment on NK Cell Activation in Absence of WT1 VV

| | % CD69+ NK Cells | | | |
|---|---|---|---|---|
| | ADSCs Alone | IFNγ ADSCs | ADSCs + WT1 VV | IFNγ ADSCs + WT1 VV |
| SIBD01 PBMCs alone | 5.70 | — | 13.61 | — |
| SIBD01 + 40k RM20 | 54.10 | 54.25 | 86.40 | 85.35 |
| SIBD01 + 20k RM20 | 46.40 | 36.15 | 88.55 | 89.10 |
| SIBD01 + 10k RM20 | 37.45 | 28.75 | 86.15 | 86.95 |
| SIBD01 + 5k RM20 | 31.90 | 19.95 | 86.20 | 84.75 |
| SIBD02 PBMCs Alone | 4.38 | — | 71.80 | — |
| SIBD02 + 40k RM20 | 9.51 | 26.85 | 78.45 | 81.45 |
| SIBD02 + 20k RM20 | 9.67 | 15.25 | 86.15 | 86.50 |
| SIBD02 + 10k RM20 | 9.48 | 8.42 | 84.00 | 86.50 |
| SIBD02 + 5k RM20 | 7.59 | 6.90 | 81.65 | 84.85 |

TABLE 42

Effect of IFNγ Pretreatment on T Cell Activation in Absence of WT1 VV

| | % CD69+ T Cells | | | |
|---|---|---|---|---|
| | ADSCs Alone | IFNγ ADSCs | ADSCs + WT1 VV | IFNγ ADSCs + WT1 VV |
| SIBD01 PBMCs alone | 4.29 | — | 5.85 | — |
| SIBD01 + 40k RM20 | 14.95 | 14.80 | 33.75 | 34.85 |
| SIBD01 + 20k RM20 | 10.45 | 11.30 | 36.30 | 40.15 |
| SIBD01 + 10k RM20 | 10.34 | 10.35 | 32.15 | 38.75 |
| SIBD01 + 5k RM20 | 10.16 | 9.10 | 33.80 | 35.55 |
| SIBD02 PBMCs Alone | 3.46 | — | 41.80 | — |
| SIBD02 + 40k RM20 | 5.15 | 7.00 | 7.04 | 16.45 |
| SIBD02 + 20k RM20 | 3.55 | 4.50 | 9.92 | 15.80 |
| SIBD02 + 10k RM20 | 2.87 | 2.74 | 15.65 | 19.60 |
| SIBD02 + 5k RM20 | 2.55 | 3.42 | 17.15 | 27.25 |

TABLE 43

Effect of IFNγ Pretreatment on NKT Cell Activation in Absence of WT1 VV

| | % CD69+ NKT Cells | | | |
|---|---|---|---|---|
| | ADSCs Alone | IFNγ ADSCs | ADSCs + WT1 VV | IFNγ ADSCs + WT1 VV |
| SIBD01 PBMCs alone | 11.85 | — | 22.95 | — |
| SIBD01 + 40k RM20 | 41.80 | 48.05 | 79.35 | 82.65 |
| SIBD01 + 20k RM20 | 34.10 | 33.45 | 85.55 | 87.85 |
| SIBD01 + 10k RM20 | 24.80 | 21.85 | 87.35 | 83.75 |
| SIBD01 + 5k RM20 | 22.25 | 22.45 | 76.00 | 81.00 |
| SIBD02 PBMCs Alone | 45.75 | — | 70.00 | — |
| SIBD02 + 40k RM20 | 72.15 | 70.80 | 85.25 | 95.00 |
| SIBD02 + 20k RM20 | 67.60 | 63.25 | 93.10 | 90.15 |
| SIBD02 + 10k RM20 | 64.55 | 62.40 | 53.90 | 91.20 |
| SIBD02 + 5k RM20 | 39.30 | 50.00 | 95.25 | 92.95 |

TABLE 44

Effect of IFNγ Pretreatment on T-NK-NKT Crosstalk

| | % CD69+ NK Cells | |
|---|---|---|
| | Control | WT1 VV |
| SIBD01 PBMCs alone | 5.70 | 13.61 |
| SIBD01 + 40k RM20 | 54.10 | 86.40 |
| SIBD01 + 40k IFNγ RM20 | 54.25 | 85.35 |
| SIBD01 + K562 Cells | 84.85 | 93.40 |
| SIBD01 + 40k RM20 + K562 Cells | 88.40 | 98.10 |
| SIBD01 + 40k IFNγ RM20 + K562 Cells | 87.70 | 97.10 |
| SIBD02 PBMCs Alone | 4.38 | 71.80 |
| SIBD02 + 40k RM20 | 9.51 | 78.45 |
| SIBD02 + 40k IFNγ RM20 | 26.85 | 81.45 |
| SIBD02 + K562 Cells | 90.05 | 95.95 |
| SIBD02 + 40k RM20 + K562 Cells | 84.65 | 87.60 |
| SIBD02 + 40k IFNγ RM20 + K562 Cells | 89.65 | 97.45 |

TABLE 45

Effect of IFNγ Pretreatment on T-NK-NKT Crosstalk

| | % CD69+ T Cells | |
|---|---|---|
| | Control | WT1 VV |
| SIBD01 PBMCs alone | 4.29 | 5.85 |
| SIBD01 + 40k RM20 | 14.95 | 33.75 |
| SIBD01 + 40k IFNγ RM20 | 14.80 | 34.85 |
| SIBD01 + K562 Cells | 30.45 | 40.05 |
| SIBD01 + 40k RM20 + K562 Cells | 21.65 | 44.70 |
| SIBD01 + 40k IFNγ RM20 + K562 Cells | 18.20 | 38.75 |
| SIBD02 PBMCs Alone | 3.46 | 21.50 |
| SIBD02 + 40k RM20 | 5.15 | 7.04 |
| SIBD02 + 40k IFNγ RM20 | 7.00 | 16.45 |
| SIBD02 + K562 Cells | 8.26 | 14.50 |
| SIBD02 + 40k RM20 + K562 Cells | 8.85 | 8.30 |
| SIBD02 + 40k IFNγ RM20 + K562 Cells | 10.25 | 16.50 |

TABLE 46

Effect of IFNγ Pretreatment on T-NK-NKT Crosstalk

| | % CD69+ NKT Cells | |
|---|---|---|
| | Control | WT1 VV |
| SIBD01 PBMCs alone | 11.85 | 22.95 |
| SIBD01 + 40k RM20 | 41.80 | 79.35 |
| SIBD01 + 40k IFNγ RM20 | 48.05 | 82.65 |
| SIBD01 + K562 Cells | 78.65 | 77.85 |
| SIBD01 + 40k RM20 + K562 Cells | 59.30 | 89.45 |
| SIBD01 + 40k IFNγ RM20 + K562 Cells | 53.75 | 85.45 |
| SIBD02 PBMCs Alone | 45.75 | 70.00 |
| SIBD02 + 40k RM20 | 72.15 | 85.25 |
| SIBD02 + 40k IFNγ RM20 | 70.80 | 95.00 |
| SIBD02 + K562 Cells | 95.00 | 95.70 |
| SIBD02 + 40k RM20 + K562 Cells | 92.25 | 84.15 |
| SIBD02 + 40k IFNγ RM20 + K562 Cells | 95.55 | 90.50 |

Example 6

Suppressing the Induction of the IFN-Mediated Anti-Viral State Sensitizes Stem and Tumor Cells to Virus Infection and Amplification Many types of tumor cells exhibit compromised interferon signaling that renders them sensitive to oncolytic virotherapy. The intact anti-viral mechanisms in untransformed stem cells and certain types of tumor cells, which is mediated by various cellular viral sensors and interferons, can create a barrier to the ability of such cells to function as carrier cells for the delivery of oncolytic viruses. For example, type I and II interferons are potent inducers of the anti-viral state in stem cells and in some types of tumor cells. This interferes with the susceptibility of these cells to virus infection, and reduces their ability to support virus amplification.

It is demonstrated herein that blocking the detection of virus infection and/or blocking the induction of the anti-viral state in stem and tumor carrier cells can sensitize the carrier cells to virus infection, amplification and spreading. Blocking the detection of virus infection was effected using Ruxolitinib, a small molecule inhibitor of JAK1/JAK2 that inhibits interferon signaling. This improves the therapeutic potential of various stem and tumor cells as carriers of oncolytic viruses.

A. JAK1/2 Inhibition Enhances the Virus Infection and Amplification Potential of Stem Cell Carriers To determine whether interfering with interferon signaling, and thus, the induction of the anti-viral state, improves the therapeutic potential of stem cells as oncolytic virus carriers, the stem cells were cultured in the presence of Type I or Type II interferons, with or without the interferon signaling inhibitor Ruxolitinib, and virus infection, amplification and delivery to tumor cells was assessed. RM35 ADSC (passage 5) stem cells (referred to hereafter as ADSC-RM35 stem cells; derived from supra advential adipose stromal cells as described in Example 1 above) were infected with the L14 oncolytic vaccinia virus, engineered to express the TurboFP635 fluorescent protein, at an MOI of 0.1 for 2 hours. After washing away the free virus, the cells were immediately plated at a density of 10,000 cells per well in 96-well tissue culture plates, with the addition of 20 ng/mL IFNβ (a Type I interferon) or 20 ng/mL IFNγ (a Type II interferon) with or without 50 nM Ruxolitinib (LC Laboratories, Cat. No. R-6688) and were incubated for 48 hours at 37° C., 5% $CO_2$. Cells cultured without IFN were used as a control. After 48 hours of culturing the cells, virus infection and amplification was evaluated by time course fluorescence imaging, which was used to measure the fluorescence intensity of the TurboFP635 protein encoded by the virus. The results are summarized in Table 47 below, which shows the average fluorescence intensity density for control stem cells (no IFN); control stem cells+Ruxolitinib; stem cells+IFNβ; stem cells+IFNβ+Ruxolitinib; stem cells+IFNγ; and stem cells+IFNγ+Ruxolitinib.

Since IFNs were not added to the control cells, there was no induction of an anti-viral state, and the amount of virus infection and amplification, as measured by the intensity of TurboFP635 fluorescence, was the same with or without the addition of Ruxolitinib. Compared to the control cells, the addition of 20 ng/mL IFNβ or IFNγ to the cell cultures resulted in a 26.7% and 17.8% decrease in fluorescence, respectively. This indicates that exposure of the stem cells to IFNs following virus infection decreases the ability of the carrier cells to support virus amplification. These culture conditions mimic the exposure of infected carrier cells to type I and type II interferons, which can originate from other infected carrier cells or from the subject's immune cells in vivo, respectively.

Untransformed stem cells (and many tumor cells) can have intact intrinsic virus sensing and defense mechanisms against vaccinia virus and other oncolytic viruses. Therefore, to maintain their high amplification potential when they are used as carrier cells, it can be beneficial to prevent the induction of an IFN-mediated anti-viral state. As shown in Table 47, the addition of 50 nM Ruxolitinib to the stem cells exposed to IFNβ or IFNγ results in approximately the same amount of fluorescence as the control cells that were not exposed to IFNs. These results demonstrate that the addition of 50 nM Ruxolitinib effectively and completely reverses the induction of the anti-viral state by type I and type II interferons, and sensitizes the carrier cells to support virus infection and amplification.

TABLE 47

Interferon blockade by Ruxolitinib in virus-infected stem cells

| | Average Fluorescence Intensity Density | | |
|---|---|---|---|
| | Control cells (no IFN) | 20 ng/mL IFNβ | 20 ng/mL IFNγ |
| (−) Ruxolitinib | 0.073 | 0.0535 | 0.06 |
| (+) 50 nM Ruxolitinib | 0.074 | 0.0755 | 0.0735 |

B. JAK1/2 Inhibition Enhances the Virus Infection and Amplification Potential of Tumor Cells To determine whether the inhibition of IFN signaling also sensitizes tumor cells to vaccinia virus infection and amplification, 200,000 PC3 human prostate cancer cells were co-cultured with 20,000 ADSC-RM35 stem cells that were pre-infected with the L14 virus at an MOI of 0.1 for 2 hours. 20 ng/mL IFN Type I+20 ng/mL IFN Type II, with or without 5 nM or 50 nM Ruxolitinib, were added to the co-cultures, and the progression of virus infection and spreading was monitored by fluorescence imaging for up to 48 hours. Co-cultures without the addition of IFN or Ruxolitinib (Rux) were used as a control. The results are summarized in Table 48 below, which shows the average fluorescence intensity density (IntDen) for: control cells (no IFN/no Ruxolitinib); co-cultures+IFN I/II; co-cultures+IFN I/II+5 nM Ruxolitinib; and co-cultures+IFN I/II+50 nM Ruxolitinib. The percent reversal of IFN inhibition was calculated using the formula:

% Reversal of IFN inhibition=[(IntDen$_{Rux+IFN}$−IntDen$_{IFN}$)/(IntDen$_{control}$−IntDen$_{IFN}$)]×100.

The results show that, upon the addition of IFN, the infection of tumor cells with virus, as well as the amplification of the virus by the tumor cells, decreased significantly. The addition of 5 nM Ruxolitinib partially reversed the induction of the anti-viral state in the PC3 cells (by 40%), and increased the levels of virus infection and amplification, as evidenced by the increased virus-encoded TurboFP635 fluorescent signal. The addition of 50 nM Ruxolitinib was highly effective at reversing the induction of anti-viral state in PC3 cells (~91% reversal), and restored the levels of virus infection and amplification to slightly less than the control cells.

These results demonstrate that pharmacological and/or genetic interference with the intrinsic anti-viral defense mechanisms, such as the interferon signaling pathways, of stem and tumor cells, can be used to improve/maintain their virus infection/amplification potential. This renders the carrier cells resistant to the effects of interferons during virus loading or exposure in vivo, improving their potential as carriers for oncolytic viruses. Because interferons mediate the spread of the anti-viral state between infected and neighboring uninfected cells, an additional benefit of blocking the induction of the anti-viral state in the carrier cells is that the suppressed production of Type I interferons can minimize the initial spread of the anti-viral state and thus facilitate the spread of virus infection in vivo.

TABLE 48

Interferon blockade by Ruxolitinib in virus-infected stem cell and PC3 tumor cell co-cultures

| Conditions | Average Fluorescence Intensity Density | % Reversal of IFN Inhibition |
|---|---|---|
| Control cells (−) IFN/(−) Ruxolitinib) | 6.4 | — |
| (+) 20 ng/mL IFNβ/γ (−) Ruxolitinib | 2.1 | — |
| (+) 20 ng/mL IFNβ/γ (+) 5 nM Ruxolitinib | 3.8 | 40.2 |
| (+) 20 ng/mL IFNβ/γ (+) 50 nM Ruxolitinib | 6.0 | 90.7 |

Example 7

Complement Blockade Sensitizes Stem Cells and Tumor Cells to Virus Infection and Amplification Human serum can have deleterious effects on some carrier cells, including directly attacking and killing the virus-infected carrier cells before virus amplification, or neutralizing naked virus particles released from the carrier cells, thereby limiting the spread of the virus to the target tumor cells. To determine whether engineering carrier cells to express complement-blocking factors protects the cells and improves their therapeutic potency, the effects of adding the complement peptide inhibitor Compstatin, or a neutralizing anti-human C3a/C3a(desArg)/C3 antibody, on the ability of carrier cells to amplify and deliver the L14 oncolytic vaccinia virus, was evaluated.

A. Effects of Complement Blockade on Virus-Infected Carrier Stem Cells

ADSC-RM35 carrier stem cells were infected with the L14 vaccinia virus, which is engineered to express the TurboFP635 fluorescent protein, at an MOI of 0.1 for 2 hours. The effects of complement activity on the amplification and spread of virus to the uninfected 90% of carrier cells was evaluated by the addition of 10% human serum (from donor CBD2), and comparing the accumulation of L14 vaccinia virus-encoded TurboFP635 fluorescent signal to control cells that were not exposed to serum.

Time course fluorescence imaging over 72 hours shows that 10% human serum did not prevent the virus-infected carrier stem cells from amplifying the virus. To evaluate whether blocking complement improves the virus amplification and delivery capabilities of the carrier stem cells, virus-infected stem cells were incubated with human serum in the presence of compstatin, which binds complement C3 and inhibits its proteolytic cleavage by C3 convertase, or in the presence of a neutralizing anti-human C3a/C3a(desArg)/C3 antibody. ADSC-RM35 stem cells were infected with L14 vaccinia virus at an MOI of 0.1 for 2 hours, and 10% human serum (from donor CBD2) was added, in the presence of 20 μM compstatin (Cat. No. 2585; Tocris Bioscience, MN), 50 ng/mL isotype control (Cat. No. 400166; BioLegend, San Diego, Calif.), or 50 ng/mL anti-C3 antibody (Cat. No. 518104; BioLegend, San Diego, Calif.). Virus-infected stem cells, incubated with 10% human serum alone, were used as a control. Fluorescence imaging at 72 hours was used to compare virus infection and amplification (as measured by the average fluorescence intensity density) between control carrier cells (10% human serum alone); carrier cells+serum+compstatin; carrier cells+serum+isotype control; and carrier cells+serum+anti-C3 antibody.

The results, which are summarized in Table 49 below, show that the addition of 20 μM compstatin increases the fluorescent signal, and hence, the amount of virus amplification in the carrier stem cells, by 50% compared to the control cells. The addition of 50 ng/mL isotype control does not affect the intensity of the fluorescent signal compared to control cells, while the addition of 50 ng/mL anti-C3 antibody increases the fluorescent signal by 12.5% compared to control cells. These results indicate that the blockade of complement with the peptide inhibitor compstatin or an anti-C3 neutralizing antibody further increases virus amplification. Thus, blocking complement allows for the accumulation of higher viral payloads. This can be achieved by co-administering an agent that blocks complement, such as, pre-loading the virus-carrying cells with a peptide or small molecule inhibitor and/or engineering the cells to express an inhibitor of complement or by any other suitable manner.

TABLE 49

Effects of complement blockade on L14 infection/amplification in stem cells exposed to 10% human serum

| Conditions | Average Fluorescence Intensity Density | % Increase in Fluorescence |
|---|---|---|
| Control cells (10% serum only) | 0.06 | — |
| 10% serum + 20 μM Compstatin | 0.09 | 50 |
| 10% serum + 50 μg/mL isotype control | 0.057 | −5 |
| 10% serum + 50 μg/mL anti-C3 Antibody | 0.0675 | 12.5 |

The effects of complement blockade by compstatin and/or the anti-C3 antibody next were evaluated against 20% human serum from three different donors. ADSC-RM35 stem cells were infected with L14 vaccinia virus at an MOI of 0.1 for 2 hours, and 20% human serum from 3 different donors (CBD1, CBD2 and CBD3) was added, in the presence of 20 μM compstatin, 10 μg/mL anti-C3 antibody, or 50 μg/mL anti-C3 antibody. Virus-infected stem cells, incubated with 20% human serum from each of the three donors (without complement blockade), were used as a control. Fluorescence imaging at 48 hours post incubation was used to compare virus infection and amplification (as measured by the average fluorescence intensity density of virus-expressed TurboFP635) between the different cell cultures. The results, which are summarized in Table 50 below, show that the addition of 20 μM compstatin increases the fluorescence intensity by 27.7%, 8.1% and 18.7% compared to serum only control cells for donors CBD1, CBD2 and CBD3, respectively. In comparison to control cells, the addition of 10 μg/mL anti-C3 antibody increases the fluorescence intensity by 6.1% for donor CBD1 and 10.3% for donor CBD3, and decreases it by 0.8% for donor CBD2. The addition of 50 μg/mL anti-C3 antibody increases the fluorescence intensity by 20.9%, 1.6% and 10.3% compared to control cells for donors CBD1, CBD2 and CBD3, respectively. These results indicate that complement blockade by the small peptide inhibitor compstatin (at a concentration of 20 μM) or an anti-C3 antibody (at 10 μg/mL or 50 μg/mL) partially reversed the negative effects of human serum on virus-infected stem cells, and enhanced vaccinia virus spread and amplification across multiple human blood/serum donors.

TABLE 50

Effects of complement blockade on L14 infection/amplification in carrier cells exposed to 20% human serum from 3 different donors

| | Average Fluorescence Intensity Density | | | % Increase in Fluorescence | | |
|---|---|---|---|---|---|---|
| Conditions | Donor CBD1 | Donor CBD2 | Donor CBD3 | Donor CBD1 | Donor CBD2 | Donor CBD3 |
| Control cells (20% serum only) | 0.0740 | 0.0620 | 0.0775 | — | — | — |
| 20% Serum + 20 μM Compstatin | 0.0945 | 0.0670 | 0.0920 | 27.7 | 8.1 | 18.7 |
| 20% Serum + 10 μg/mL anti-C3 Antibody | 0.0785 | 0.0615 | 0.0855 | 6.1 | −0.8 | 10.3 |
| 20% Serum + 50 μg/mL anti-C3 Antibody | 0.0895 | 0.0630 | 0.0855 | 20.9 | 1.6 | 10.3 |

B. Effects of Complement Blockade on Virus Infection and Amplification in Tumor Cells To show that blocking complement also enhances the spreading of virus to target tumor cells, stem cells were infected with L14 virus and co-cultured with tumor cells in the presence of 20% human serum, with or without compstatin. 20,000 RM35 adipose-derived stem cell carriers were infected with L14 vaccinia virus at an MOI of 1 for 2 hours, and then seeded into overnight monolayers of 300,000 PC3 human prostate cancer cells. The spreading of virus infection from the stem cell carriers to the tumor cells was allowed to proceed for 48 hours in the presence of 20% human serum from donor CBD2, with or without the addition of 20 μM compstatin. Co-cultures of virus-infected stem cells and tumor cells, in the absence of serum or compstatin, were used as controls. Fluorescence imaging after 48 hours was used to determine the degree of infection of the tumor cells, as measured by the average fluorescence intensity density, i.e., the fluorescent signal from the TurboFP635 expressed by the L14 vaccinia virus.

The results are summarized in Table 51 below. The addition of 20% human serum partially reduced the spreading of the virus from the infected carrier stem cells to the tumor cells, as evidenced by the decrease in fluorescence intensity density from 41.1 to 34.5. The addition of 20 μM compstatin increased the fluorescence intensity density to 36.4. Thus, blocking complement using compstatin partially reverses the complement-mediated suppression of virus spreading, and increases the fluorescence intensity by 28.5%. These results indicate that sensitizing carrier cells for protection against complement enhances virus spreading to and amplification in the target PC3 tumor cells.

Overall, these data confirm that blocking complement, such as by using carrier cells engineered to deliver complement blocking agents, such as peptide inhibitors or complement neutralizing/antagonizing antibodies, protects the carrier cells, and the naked virus particles they release, against complement and neutralizing antibodies in human serum. This allows for the accumulation of higher virus payloads, thereby improving the ability of the carrier cells to amplify, deliver and spread the oncolytic virus to tumor cells.

TABLE 51

Effects of complement blockade on L14 infection of PC3 cells co-cultured with virus-infected carrier stem cells and 20% human serum

| Conditions | Average Fluorescence Intensity Density |
|---|---|
| Control (no serum, no compstatin) | 41.1 |
| 20% serum only | 34.5 |
| 20% serum + 20 μM compstatin | 36.4 |

Example 8

Evaluation of Allogeneic Rejection Determinants and their Suppression Using HLA-Blockade Example 4 demonstrates that stem cell carriers can amplify and deliver oncolytic vaccinia virus despite allogeneic barriers. This results from their ability to avoid allogeneic recognition and actively immunosuppress NK cells, T cells, and a population of "NKT" cells expressing NK (NKp46) and T cell (CD3) markers. In a subset of "incompatible/resistant" recipients, the stem cells were unable to avoid allogeneic recognition, which resulted in the mounting of rapid and potent allogeneic NK, T, and NKT cell responses against the carrier stem cells, even in the absence of virus. These rapid allogeneic responses developed within 48 h of co-culture, and were associated with the development of anti-stem cell cytotoxic responses and an IFNγ-mediated anti-viral state, inhibiting the stem cells' ability to amplify vaccinia virus. These results indicate that non-stem cell carriers, such as tumor cells, that are devoid of the potent stem-cell specific immunosuppressive and immunoevasive abilities, could be subject to similar or stronger allogeneic restrictions, limiting their potential for oncolytic virus amplification and delivery in a patient-specific manner. This, in turn, limits their off-the-shelf use and effectiveness.

Identification, suppression and elimination of factors responsible for allogeneic recognition and rejection can be used to increase the therapeutic potential of allogeneic stem or tumor cells as carrier cells for the delivery of oncolytic viruses in an off-the-shelf manner. Such allogeneic rejection determinants include the highly polymorphic and patient-specific MHC Class I and Class II molecules recognized by CD8 and CD4 T cells, as well as a broad spectrum of less polymorphic determinants, which include the MHC-like MICA and CD1a, b, c, d molecules, and various other stress-related or stress-sensing molecules, such as butyrophilins and Annexin A2, that are recognized by various innate T cell subpopulations, such as gd (gamma delta) T, iNKT, and NKT cells, among others.

Blockade of allogeneic MHC I molecules was assessed for its ability to suppress allogeneic immune responses against carrier stem and tumor cells, particularly the responses of CD8 T cells that are responsible for recognizing and responding to allogeneic MHC I mismatches.

A. Immune Cell Depletion by Uninfected and Vaccinia Virus-Infected Stem Cells and Tumor Cells The immunosuppressive properties and immune cell depleting potential of uninfected and vaccinia virus infected carrier stem and tumor cells that were co-cultured with PBMCs from compatible and incompatible donors, was assessed. 300,000 PBMCs from incompatible/resistant (CBD1) and compatible/permissive (CBD2) donors were co-cultured for 60 hours with 10,000 adipose-derived stem cells (RM35) or cancer cells (human prostate PC3) that were either uninfected control cells, or carrier cells infected with ACAM2000 vaccinia virus at an MOI of 10 for 2 hours. After the 60 hour co-culture, the numbers of different immune cell subtypes recovered from the co-cultures of vaccinia virus (VV) infected carrier stem and tumor cells with PBMCs from the incompatible/resistant (CBD1) and compatible/permissive (CBD2) recipients were analyzed. The numbers of different immune cell subtypes recovered from CBD1 or CBD2 PBMCs alone, and from CBD1 or CBD2 PBMCs co-cultured with uninfected carrier cells, were used as controls. The various immune cell subtypes were identified by multi-parameter flow cytometry analysis using CD69 as an activation marker and a set of cell type specific markers as follows: γδ (gd) T cells (CD3$^+$, γδ TCR$^+$); iNKT/NKT Type 1 cells (CD3$^+$, Vα24Jα18$^+$); general NKT-like cells (CD3$^+$CD56$^+$; gd and iNKT excluded); classical CD4 T cells (CD3$^+$CD4$^+$; gd and iNKT excluded); classical CD8 T cells (CD3$^+$CD8$^+$; gd and iNKT excluded); general NK cells (CD3$^-$CD56$^+$); and the NK subpopulations CD56$^{high}$CD16$^-$ (cytokine producing) and CD56$^{low}$CD16$^+$ (cytotoxic).

The results are summarized in Table 52 (for stem cells) and Table 53 (for PC3 cells, human prostate cancer cells), below. Table 54 compares the immunosuppressive and immune cell depleting properties of uninfected stem cells vs. tumor cells in terms of % suppression. The % suppression of the immune cell subtypes was calculated using the formula:

$$\% \text{ Suppression} = \frac{\left(1 - \left(\frac{\text{avg. immune cell number from carrier cell} + \text{PBMC co-culture}}{\text{avg. immune cell number from PBMCs alone}}\right)\right)}{} \times 100.$$

The co-cultures of PBMCs from the incompatible/resistant (CBD1) and from the compatible/permissive (CBD2) donors with uninfected RM35 ADSCs results in the reduction/depletion of all immune subtypes compared to the PBMCs alone (control). This confirms the potent immunosuppressive potential of adipose-derived stem cells (see, Table 52). This effect also was observed, but to a much lesser extent, upon co-culture of CBD1 and CBD2 PBMCs with PC3 tumor cells (see, Table 53), indicating the superior immunosuppressive properties of stem cells compared to tumor cells (see, Table 54). When the stem cells (Table 52) and tumor cells (Table 53) were pre-infected with vaccinia virus (RM35 ADSCs (stem cells)+VV, or PC3 cells (tumor cells)+VV) and used as carriers, however, their ability to deplete immune cells was lost, as evidenced by the increase in the numbers of all immune cell subtypes. These data are consistent with the carrier cells being gradually killed by the amplifying virus, and losing their immunosuppressive potential.

TABLE 52

Numbers of immune cell subtypes from co-cultures of infected and uninfected stem cells with PBMCs from incompatible and compatible recipients

| | Average Total Number of Immune Cells | | | | | |
|---|---|---|---|---|---|---|
| | CBD1 PBMCs | | | CBD2 PBMCs | | |
| Immune Cell Subtype | PBMCs alone | RM35 ADSCs | RM35 ADSCs + VV | PBMCs alone | RM35 ADSCs | RM35 ADSCs + VV |
| γδ T | 255.0 | 13.5 | 705.1 | 34.5 | 14.5 | 139.5 |
| iNKT | 97.0 | 5.0 | 381.1 | 87.0 | 17.5 | 400.0 |
| NKT | 689.0 | 26.0 | 1721.5 | 39.0 | 11.5 | 296.5 |
| CD4 T | 1293.5 | 74.0 | 4062.1 | 1539.5 | 261.5 | 7190.0 |
| CD8 T | 419.5 | 26.0 | 1546.3 | 104.5 | 34.5 | 1626.5 |
| NK | 298.0 | 21.5 | 758.6 | 215.5 | 60.5 | 1901.5 |
| CD56$^{high}$CD16$^-$ | 27.5 | 3.0 | 104.8 | 17.5 | 5.0 | 123.5 |
| CD56$^{low}$CD16$^+$ | 225.5 | 13.5 | 336.4 | 169.0 | 42.0 | 1081.5 |

TABLE 53

Numbers of immune cell subtypes from co-cultures of infected and uninfected PC3 cells with PBMCs from incompatible and compatible recipients

| | Average Total Number of Immune Cells | | | | | |
|---|---|---|---|---|---|---|
| | CBD1 PBMCs | | | CBD2 PBMCs | | |
| Immune Cell Subtype | PBMCs alone | PC3 cells | PC3 cells + VV | PBMCs alone | PC3 cells | PC3 cells + VV |
| γδ T | 344.0 | 127.0 | 973.5 | 38.0 | 19.5 | 212.0 |
| iNKT | 155.0 | 62.5 | 540.5 | 68.5 | 31.5 | 520.0 |
| NKT | 723.0 | 217.0 | 2484.0 | 33.0 | 18.0 | 281.0 |
| CD4 T | 1379.5 | 610.0 | 4978.0 | 915.0 | 546.0 | 8636.5 |
| CD8 T | 434.0 | 265.5 | 2644.5 | 71.0 | 39.0 | 1729.5 |
| NK | 426.5 | 111.5 | 910.5 | 205.0 | 136.0 | 1536.0 |
| $CD56^{high}CD16^-$ | 28.0 | 14.5 | 123.5 | 19.0 | 14.5 | 112.0 |
| $CD56^{low}CD16^+$ | 348.5 | 66.5 | 452.5 | 150.0 | 108.5 | 835.5 |

TABLE 54

% Suppression of immune cell subtypes from co-cultures of uninfected stem or tumor cells with PBMCs from incompatible and compatible donors

| | % Suppression | | | |
|---|---|---|---|---|
| | RM35 ADSCs | | PC3 Tumor Cells | |
| Immune Cell Subtype | CBD1 PBMCs | CBD2 PBMCs | CBD1 PBMCs | CBD2 PBMCs |
| γδ T | 94.71 | 57.97 | 63.08 | 48.68 |
| iNKT | 94.85 | 79.89 | 59.68 | 54.01 |
| NKT | 96.23 | 70.51 | 69.99 | 45.45 |
| CD4 T | 94.28 | 83.01 | 55.78 | 40.33 |
| CD8 T | 93.80 | 66.99 | 38.82 | 45.07 |
| NK | 92.79 | 71.93 | 73.86 | 33.66 |
| $CD56^{high}CD16^-$ | 89.09 | 71.43 | 48.21 | 23.68 |
| $CD56^{low}CD16^+$ | 94.01 | 75.15 | 80.92 | 27.67 |

B. Immune Subsets Responding to Allogeneic Carrier Cells and to Vaccinia Virus

Analysis of immune activation, using the fraction of $CD69^+$ cells in each immune subpopulation recovered from the PBMC+uninfected carrier cell co-cultures versus the PBMCs alone, identified the major population of immune cells responding to the allogeneic stem or tumor cell carriers. The results, which are summarized in Table 55, show that, upon addition of uninfected stem cells or tumor cells to incompatible PBMCs, the numbers of immune cells of all subtypes (with the exception of $CD56^{high}CD16^-$ NK cells in response to stem cells) increases. The largest changes in numbers were observed for γδ T, iNKT, NKT, general NK and cytotoxic NK ($CD56^{low}CD16^+$) cells. The increases in general NK and cytotoxic NK cell numbers were significantly larger in response to PC3 cells than to stem cells, confirming that stem cells possess superior immunosuppressive properties. When the uninfected carrier cells were co-cultured with the compatible PBMCs, the immune responses were generally smaller, with the numbers of some immune subtypes decreasing (e.g., γδ T, iNKT, NKT and CD4 T cells) in some cases. This indicates that the immune responses in the incompatible allogeneic co-cultures were greater than in the compatible allogeneic co-cultures, confirming the importance of donor-recipient compatibility in allogeneic settings.

Analysis of immune activation, using the fraction of $CD69^+$ cells in each immune subpopulation recovered from the PBMC+virus-infected carrier cell co-cultures versus the PBMC+uninfected carrier cell co-cultures, identified the major population of immune cells responding to the virus. These results are summarized in Table 56, which shows that the major immune cell subtypes responding to virus included γδ T, iNKT, general NKT-like ($CD3^+CD56^+$; γδ T and iNKT excluded), general NK, cytotoxic NK ($CD56^{low}CD16^+$) and cytokine-producing NK ($CD56^{high}CD16^-$) cells. The same populations of immune cells responded to the virus in both the compatible and incompatible recipient. The magnitude of the response of all T subpopulations was weaker or even negative (indicating complete suppression of anti-viral responses) in the compatible recipient setting with both the stem and tumor cell carriers, demonstrating that compatibility impacts the responses to the virus with either type of allogeneic cell carrier. In the case of NK cells, this was found to be true only for the responses of the cytokine-producing NK cells ($CD56^{high}CD16^-$) to the virus delivered by the stem cell carriers, which were completely suppressed in the compatible, but not in the incompatible, recipient settings. The responses of the cytokine-producing NK cells ($CD56^{high}CD16^-$) to the virus delivered by allogeneic tumor carrier cells were equally strong in both recipients. The cytotoxic NK ($CD56^{low}CD16^+$) cell responses to the virus were very high and similar in both recipients. The seemingly lower responses to the virus with allogeneic tumor cell carriers in the incompatible recipient reflect the extremely high activation of these NK cells to the carrier cells alone (see Table 55), even in the absence of virus, and are not indicative of lower anti-viral NK cell responses in this setting.

Example 4 demonstrates an important role for innate T cell populations expressing T cell ($CD3^+$) and NK cell ($NKp46^+$) markers in response to allogeneic cell carriers of oncolytic viruses. The data summarized in Tables 55 and 56 indicate that these innate T cell populations include γδ T cells, iNKT (NKT type I) cells and $CD56^+CD3^+$ NKT (NKT type II) cells.

TABLE 55

Immune Cell Subtypes Responding to Allogeneic Carrier Cells

| | Average Δ % $CD69^+$ Subtypes in PBMC + Carrier Cells vs. PBMCs Alone | | | |
|---|---|---|---|---|
| | CBD1 | CBD1 | CBD2 | CBD2 |
| | PBMCs + | PBMCs + | PBMCs + | PBMCs + |
| Immune Cell Subtype | RM35 ADSCs | PC3 Tumor Cells | RM35 ADSCs | PC3 Tumor Cells |
| γδ T | 20.6 | 20.1 | -6.9 | 3.9 |
| iNKT | 20.0 | 4.2 | 6.4 | -21.6 |
| NKT | 11.4 | 10.6 | -4.9 | -6.9 |
| CD4 T | 4.5 | 3.8 | 3.1 | -21.8 |
| CD8 T | 1.5 | 5.3 | 12.2 | 9.6 |
| NK | 12.8 | 52.5 | 10.6 | 4.6 |
| $CD56^{high}CD16^-$ | -2.7 | 18.2 | Below detection | 6.3 |
| $CD56^{low}CD16^+$ | 17.3 | 59.4 | 8.4 | 6.1 |

TABLE 56

Immune Cell Subtypes Responding to Vaccinia Virus

Average Δ % CD69$^+$ Subtypes in Infected vs. Uninfected Carrier Cells

| Immune Cell Subtype | CBD1 PBMCs + RM35 ADSCs + VV | CBD1 PBMCs + PC3 Tumor Cells + VV | CBD2 PBMCs + RM35 ADSCs + VV | CBD2 PBMCs + PC3 Tumor Cells + VV |
|---|---|---|---|---|
| γδ T | 26.4 | 49.9 | 6.8 | 17.0 |
| iNKT | −13.1 | 25.6 | −3.4 | 6.4 |
| NKT | 0.0 | 30.5 | −3.1 | 8.1 |
| CD4 T | −2.6 | 11.6 | −5.7 | −2.1 |
| CD8 T | 8.9 | 24.7 | −10.2 | 1.8 |
| NK | 48.1 | 28.1 | 51.5 | 65.9 |
| CD56$^{high}$CD16$^-$ | 37.2 | 39.0 | −15.2 | 43.8 |
| CD56$^{low}$CD16$^+$ | 59.8 | 28.3 | 52.4 | 66.8 |

C. Immune Responses to Allogeneic Carrier Cells in Incompatible Vs. Compatible PBMCs As shown in Tables 55 and 56, co-cultures with the incompatible PBMCs elicit significantly higher numbers of innate immune T cell subpopulations (γδ T cells and CD3$^+$CD56$^+$ NKT cells) compared with the compatible PBMCs, as well as the stronger responses against the virus-infected carriers. The number of CD69$^+$ activated immune cell subpopulations, as a percentage of all PBMCs, was determined and compared for the incompatible (CBD1) and compatible (CBD2) PBMCs that were co-cultured with vaccinia virus-infected stem or tumor carrier cells, and the results are summarized in Table 57. The number of CD69$^+$ activated immune cell subpopulations, as a percentage within each specific subpopulation, also was calculated for the incompatible vs. compatible PBMCs, and the results are summarized in Table 58. Table 57 shows the CD69$^+$ activated cells of each PBMC subpopulation as a fraction (%) of the total number of PBMCs. Table 58 shows the CD69$^+$ activated cells in each PBMC subpopulation as a fraction of the total number of cells within that particular subpopulation.

The major difference between the incompatible (CBD1) and compatible (CBD2) PBMCs was the significantly higher numbers of innate immune T cell subpopulations (γδ T cells and CD3$^+$CD56$^+$ NKT cells) observed with the incompatible PBMCs, and their much stronger responses against the virus-infected carriers. This is evident from the increased total numbers of cells of different subtypes (see, Tables 55 and 56), as well as the percentages of CD69$^+$ activated cells in all PBMCs (see, Table 57), or within the specific subpopulations (see, Table 58).

The results also show that, in general, the stem cells have superior immunosuppressive/immune evasive properties as carriers compared to tumor cells, with the latter stimulating more potent activation of all innate and adaptive immune subpopulations, except for the NK cells (see Tables 57 and 58, RM35 vs. PC3).

TABLE 57

% CD69$^+$ Immune Subpopulations of PBMCs in the presence of infected stem or tumor carrier cells

| | Average % CD69+ Immune Subtype in PBMCs | | | | Ratio of CBD1/CBD2 Response | |
|---|---|---|---|---|---|---|
| | CBD1 PBMCs | | CBD2 PBMCs | | | |
| Immune Cell Subtype | RM35 ADSCs + VV | PC3 Cells + VV | RM35 ADSCs + VV | PC3 Cells + VV | RM35 ADSCs + VV | PC3 Cells + VV |
| γδ T | 3.4 | 4.8 | 0.2 | 0.5 | 19.3 | 10.1 |
| iNKT | 0.3 | 1.2 | 0.2 | 0.5 | 1.6 | 2.3 |
| NKT | 1.9 | 6.6 | 0.3 | 0.4 | 7.0 | 14.7 |
| CD4 T | 1.9 | 5.9 | 0.5 | 3.6 | 3.9 | 1.6 |
| CD8 T | 1.5 | 5.3 | 0.8 | 1.4 | 2.0 | 3.8 |
| NK | 4.4 | 5.0 | 8.8 | 6.8 | 0.5 | 0.7 |
| CD56$^{high}$CD16$^-$ | 0.3 | 0.5 | 0.3 | 0.4 | 1.2 | 1.3 |
| CD56$^{low}$CD16$^+$ | 2.3 | 2.6 | 4.8 | 3.7 | 0.5 | 0.7 |

TABLE 58

% CD69$^+$ Immune Subpopulations in the presence of infected stem or tumor carrier cells

| | Average % CD69$^+$ in Subtype | | | | Ratio of CBD1/CBD2 Response | |
|---|---|---|---|---|---|---|
| | CBD1 PBMCs | | CBD2 PBMCs | | | |
| Immune Cell Subtype | RM35 ADSCs + VV | PC3 Cells + VV | RM35 ADSCs + VV | PC3 Cells + VV | RM35 ADSCs + VV | PC3 Cells + VV |
| γδ T | 59.7 | 80.2 | 19.7 | 39.6 | 3.0 | 2.0 |
| iNKT | 10.7 | 36.0 | 8.2 | 17.7 | 1.3 | 2.0 |
| NKT | 13.4 | 43.2 | 14.3 | 28.7 | 0.9 | 1.5 |
| CD4 T | 5.7 | 19.5 | 1.1 | 7.6 | 5.4 | 2.6 |
| CD8 T | 12.5 | 32.6 | 7.3 | 14.3 | 1.7 | 2.3 |

TABLE 58-continued

% CD69+ Immune Subpopulations in the presence of infected stem or tumor carrier cells

| | Average % CD69+ in Subtype | | | | Ratio of CBD1/CBD2 Response | |
|---|---|---|---|---|---|---|
| | CBD1 PBMCs | | CBD2 PBMCs | | | |
| Immune Cell Subtype | RM35 ADSCs + VV | PC3 Cells + VV | RM35 ADSCs + VV | PC3 Cells + VV | RM35 ADSCs + VV | PC3 Cells + VV |
| NK | 70.4 | 88.7 | 73.1 | 80.0 | 1.0 | 1.1 |
| CD56$^{high}$CD16− | 37.2 | 62.4 | 34.8 | 60.1 | 1.1 | 1.0 |
| CD56$^{low}$CD16+ | 84.5 | 94.2 | 70.2 | 78.6 | 1.2 | 1.2 |

D. HLA Blockade Suppresses CD8 T Cell Responses to Carrier Cells

As discussed above, the identification, suppression and/or elimination of factors responsible for allogeneic recognition and rejection can be used to increase the therapeutic efficacy of allogeneic stem or tumor cells, for the delivery of oncolytic viruses in an off-the-shelf manner. Allogeneic rejection determinants include the highly polymorphic and patient-specific MHC Class I and Class II molecules recognized by CD8 and CD4 T cells, as well as a broad spectrum of less polymorphic determinants, which include the MHC-like MICA and CD1a, b, c, d molecules, as well as other stress-related or stress-sensing molecules, such as butyrophilins and Annexin A2, which are recognized by various innate T cell subpopulations, such as γδ T, iNKT, and NKT cells, among others.

Elimination/blockade of allogeneic MHC I molecules was evaluated to assess whether it suppresses the allogeneic immune responses against carrier stem and tumor cells, particularly the responses of CD8 T cells that are responsible for recognizing and responding to allogeneic MHC I mismatches. 300,000 PBMCs each from incompatible and compatible donors were co-cultured for 60 hours with 10,000 adipose-derived stem cells (RM35) or cancer cells (human prostate PC3 cells) that were infected with ACAM2000 vaccinia virus at an MOI of 10 for 2 hours. A pan anti-HLA blocking antibody (anti-HLA antibody; Ultra-LEAF™ Purified anti-human HLA-A, B, C Antibody Clone W6/32, Cat. No. 311428, BioLegend, San Diego, Calif.) or an isotype control (Ultra-LEAF™ Purified Mouse IgG2a, κ Isotype Ctrl Antibody, Clone MOPC-173, Cat. No. 400264; BioLegend, San Diego, Calif.) were added to the co-cultures, to evaluate the effect of HLA blockade on the activation of anti-carrier cell responses by various innate and adaptive immune cell populations, particularly CD8 T cells. Immune activation was analyzed after co-culture of the PBMCs with pre-infected RM35 ADSCs or PC3 tumor cells for 60 hours at 37° C. and 5% $CO_2$ in the presence of 10 μg/mL isotype control or HLA blocking antibody. The immune cell subtypes were identified by multi-parameter flow cytometry analysis using CD69 as an activation marker and a set of cell type specific markers, including CD3+CD8+ (γδ and iNKT excluded) for CD8 T cells, and CD3−CD56+ for general NK cells.

Table 59 below shows the average percentages of CD69+ activated CD8 T cells and NK cells observed with the incompatible (CBD1) and compatible (CBD2) PBMCs, each co-cultured with: virus-infected stem cells (RM35 ADSCs); virus-infected stem cells+isotype control; virus-infected stem cells+HLA-blocking antibody; virus-infected tumor cells (PC3); virus-infected tumor cells+isotype control; or virus-infected tumor cells+HLA-blocking antibody. Table 60 shows the results in terms of the percentage of suppression of CD8 T and NK cell activation, mediated by HLA blockade. The % suppression was calculated using the formula:

% Suppression=(1−(avg. immune cell number with anti-HLA antibody/avg. immune cell number with isotype control))×100.

As shown in Table 59, co-cultures of the allogeneic virus-infected stem cells with either the incompatible (CBD1) or compatible (CBD2) PBMCs resulted in 7-12.5% CD69+ CD8 T cell activation, and more than 70% CD69+ NK cell activation. The addition of isotype control did not suppress or significantly affect the immune cell responses. The addition of the anti-HLA antibody to the co-cultures, however, reduced the numbers of immune cells in all co-cultures, with a greater impact on the activation of CD8 T cells, particularly in the co-cultures with the compatible PBMCs. For example, as shown in Table 60, blockade of HLA with a pan-HLA blocking antibody resulted in a 58% suppression of CD8 T cells in the virus-infected stem cell co-cultures with the incompatible PBMCs, and an 86% suppression of CD8 T cells in the virus-infected stem cell co-cultures with the compatible PBMCs. In general, virus-infected tumor cells elicited higher numbers of NK and CD8 T cells than virus-infected stem cells. The blockade of HLA yielded similar results for the PC3 cells as the stem cells, with a 58% suppression of CD8 T cell activation in the co-cultures of virus-infected PC3 cells and incompatible PBMCs, and an 82% suppression of CD8 T cell activation in the co-cultures of virus-infected PC3 cells and compatible PBMCs.

These results demonstrate that blockade of HLA with a pan-HLA blocking antibody suppresses allogeneic anti-carrier cell CD8 T cell and, to some extent, NK cell responses, with the blocking activity in general being more effective in the compatible CBD2 donor than in the incompatible CBD1 donor, particularly with respect to the CD8 T cell responses. These data are consistent with a greater involvement of innate T cell populations, and the additional allogeneic rejection determinants recognized by γδ T and NKT cells in the incompatible settings, as well as the need to eliminate them, in addition to the classical MHC class I and class II molecules recognized by classical CD8 and CD4 T cells.

Thus, a transient and/or permanent blockade or elimination of allogeneic rejection determinants, such as HLA (MHC Class I) molecules and others, can be used to generate stem or tumor cell-based carriers with enhanced immune evasion. Such carrier cells can more effectively deliver oncolytic viruses, without inducing allogeneic responses that are associated with the generation of cytotoxic T and NK cells, and the secretion of effector cytokines, such as IFNγ, that induce an anti-viral state and block the delivery and spread of the virus payload.

TABLE 59

Effects of HLA blockade on CD8 T cell and NK cell responses to virus-infected carrier cells co-cultured with incompatible and compatible PBMCs

| Conditions | CBD1 PBMCs (incompatible) | | CBD2 PBMCs (compatible) | |
|---|---|---|---|---|
| | Average % CD69+ CD8 T Cells | Average % CD69+ NK Cells | Average % CD69+ CD8 T Cells | Average % CD69+ NK Cells |
| RM35 ADSCs + VV | 12.46 | 70.37 | 7.31 | 73.07 |
| RM35 ADSCs + VV + isotype control | 10.31 | 77.95 | 8.99 | 76.48 |
| RM35 ADSCs + VV + anti-HLA antibody | 4.37 | 64.18 | 1.29 | 69.84 |
| PC3 tumor cells + VV | 32.59 | 88.66 | 14.27 | 80.03 |
| PC3 tumor cells + VV + isotype control | 33.97 | 90.41 | 15.87 | 81.60 |
| PC3 tumor cells + VV + anti-HLA antibody | 14.38 | 80.46 | 2.88 | 82.42 |

TABLE 60

% HLA Blockade-Mediated Suppression of CD8 T and NK Cell Activation

| | CBD1 PBMCs (incompatible) | | CBD2 PBMCs (compatible) | |
|---|---|---|---|---|
| | RM35 ADSCs | PC3 Tumor Cells | RM35 ADSCs | PC3 Tumor Cells |
| CD8 T Cells | 57.62 | 57.66 | 85.63 | 81.84 |
| NK Cells | 17.67 | 11.01 | 8.69 | −0.10 |

Example 9

Evading Allogeneic Recognition/Rejection by Modulation of NKG2D Signaling

In addition to MHC Class I and Class II molecules, immune responses to, and allogeneic rejection of virus-infected stem and tumor carrier cells is enhanced by the engagement of various non-MHC markers that serve as immune co-stimulatory molecules. These non-MHC markers are up-regulated on the surfaces of virally infected cells or transformed tumor cells, and modulate the ability of the carrier cells to evade immune rejection. These "stress-induced" non-MHC markers include MHC Class I-related proteins, such as human MICA and MICB, which are ligands for NKG2D receptors that are expressed by NK cells, NKT cells, γδ T cells and CD8+ T cells. Thus, NKG2D receptors can sensitize cells that express stress-induced markers/ligands, such as oncolytic virus carriers, for targeting by innate and adaptive cellular immunity.

Activation of NKG2D signaling was assessed for its effects on the ability of virus-infected stem or tumor carrier cells to evade the immune system. A human NKG2D-specific antibody was used to evaluate the effects of the engagement of NKG2D receptors on the immune responses against virus-infected carrier cells. This antibody functions as a potent co-stimulatory signal that contributes to and enhances immune recognition and activation of cellular immune responses. This NKG2D antibody is an agonist antibody that behaves like an NKG2D ligand, such as those expressed by virus-infected cells and tumor cells. Its addition, in this Example, simulates the in vivo engagement and activation of the NKG2D axis.

Adipose-derived stem cells (ADSC-RM35s) and tumor cells (human prostate PC3 cells) each were pre-infected with ACAM2000 vaccinia virus at an MOI of 10 for 2 hours. 300,000 PBMCs from the incompatible (CBD1) and compatible (CBD2) donors were co-cultured for 60 hours, at 37° C. and 5% $CO_2$, with 10,000 virus-infected RM35 ADSCs or PC3 tumor cells, in the presence of 50 μg/mL of a human NKG2D-specific antibody (Cat. No. MAB139-500, R&D Systems) or 50 μg/mL of a mouse IgGi Isotype Control (Cat. No. MAB002, R&D Systems). Immune activation then was assessed by determining the percentage of $CD69^+$ γδ T cells ($CD3^+$, γδ $TCR^+$), general NK cells ($CD3^-CD56^+$), cytokine-producing NK cell subpopulations ($CD56^{high}CD16^-$) and cytotoxic NK cell subpopulations ($CD56^{low}CD16^+$), using multi-parameter flow cytometry analysis, as described above.

The results for the co-cultures of the incompatible (CBD1) or compatible (CBD2) PBMCs with the virus-infected stem cells ("VV-ADSCs") are shown in Table 61, and the results for the co-cultures with virus-infected PC3 tumor cells ("VV-PC3") are shown in Table 62, below. The tables show the percentages of $CD69^+$ activated γδ T cells, general NK cells, $CD56^{high}CD16^-$ (cytokine-producing) NK cells, and $CD56^{low}CD16^+$ (cytotoxic) NK cells, observed in each co-culture incubated with isotype control or NKG2D-specific antibody. The percent increase in $CD69^+$ activated immune cell subpopulations with NKG2D activation was calculated using the formula:

% Increase=((avg. % immune cell subtype with NKG2D-specific antibody−avg. % immune cell subtype with isotype control)/(avg. % immune cell subtype with isotype control))×100.

As shown in Table 61, incubation with the NKG2D antibody increased the immune activation/responses to the virus-infected stem cell carriers in the incompatible (CBD1) and compatible (CBD2) settings for all immune cell subtypes, compared to the isotype control. The activation of γδ T cells and cytokine-producing $CD56^{high}CD16^-$ NK cells was the most significant, with increases of 16.5% and 27.4% in γδ T cells in the incompatible and compatible settings, respectively, and increases of 83.3% and 51.5% in $CD56^{high}CD16^-$ NK cells in the incompatible and compatible settings, respectively. The effects on the highly cytotoxic $CD56^{low}CD16^+$ NK subpopulation was minimal, which can be attributed to the NKG2D antibody blocking contact between the cytotoxic NK cells and the cell carriers. These results indicate that NKG2D signaling/engagement is involved in the regulation of immune responses against infected carrier cells.

The results in Table 62 show that incubation of the NKG2D antibody with the co-cultures of virus-infected tumor cells and incompatible or compatible PBMCs did not increase the activation of the same immune cell subpopulations. These results are consistent with the more potent immunological responses against tumor cell carriers, and their reduced ability to avoid allogeneic recognition, compared to stem cell carriers. The contrasting immune responses against stem and tumor cell carriers can be attributed to the NKG2D pathway already being more active in response to transformed/tumor cells. This is due to the higher levels of constitutive expression of NKG2D ligands, such as MIC-A/B, on tumor cells, making them easier to recognize. The addition of NKG2D antibody, which behaves like an NKG2D ligand, did not increase immune activation against tumor cell carriers in comparison to isotype control because the tumor cells already exhibit increased levels of NKG2D ligand expression.

The data indicates that the NKG2D pathway is involved in controlling the immune-evasive capabilities of virus-infected carrier cells. Thus, eliminating NKG2D ligands, such as MIC-AB and/or others, can improve the immune-evasive properties of the cell carriers. This is particularly relevant in the context of tumor cell carriers, which exhibit higher basal levels of stress-induced ligand expression. Elimination of NKG2D ligands in virus-infected untransformed stem cells also can improve their immune-evasive properties, since these cells also upregulate the expression of stress-induced ligands as virus infection progresses. To achieve this, the carrier cells can be engineered for transient or permanent suppression of expression of membrane-bound MICA/B. Alternatively, the interaction between the NKG2D receptor and its ligands can be inhibited. For example, the carrier cells can be engineered for transient or permanent expression of antagonists of MIC-A and MIC-B (e.g., kK5 (KHSV)), and/or antagonists of the NKG2D receptor (e.g., Cowpox OMCP). Alternatively, the cells can be pre-treated with an antagonist or blocking antibody, such as an anti-NKG2D monoclonal antibody (see, e.g., Kim et al. (2010) *Immunology* 130:545-555) to prevent binding by its ligand(s), acting as antagonist.

Example 10

Carrier Cells Sensitized/Engineered to Secrete Immunosuppressive Factors

Stem cells and tumor cells use various strategies for immune suppression and evasion, including IDO expression and IL-10 secretion. Virus amplification in the carrier cells, however, causes the gradual loss of cell viability and immunosuppressive potential. To overcome this limitation, the ability of a high dose of the immunosuppressive cytokine IL-10 to reverse the virus-mediated loss of immunosuppressive properties and improve the ability of virus-infected carrier cells to avoid allogeneic rejection/responses or early immune recognition, was evaluated.

Uninfected or vaccinia virus-infected carrier cells (RM35 ADSCs-stem cells, or PC3-tumor cells) were co-cultured with incompatible (CBD1) and compatible (CBD2) PBMCs, as described in Example 8 above, in the presence or absence of exogenously provided recombinant human IL-10 (mammalian expressed, carrier-free) (cat. #573202; BioLegend, San Diego, Calif.). Briefly, 300,000 PBMCs each from incompatible and compatible donors were co-cultured for 60 hours with 10,000 adipose-derived stem cells (RM35) or tumor cells (human prostate PC3 cells) that were infected with ACAM2000 vaccinia virus at an MOI of 10 for 2 hours. Immune activation was analyzed after co-culture of the PBMCs with pre-infected ADSC-RM35 or PC3 tumor cells for 60 hours at 37° C. and 5% $CO_2$ in the presence or absence of 10 nM recombinant human IL-10. The various immune cell subtypes were identified and enumerated by

TABLE 61

Effects of NKG2D activation on the % of CD69+ activated immune subpopulations in co-cultures of virus-infected stem cells with incompatible and compatible PBMCs

| | Average % CD69+ Activated Immune Cell Subtypes | | | | | |
|---|---|---|---|---|---|---|
| | CBD1 PBMCs | | | CBD2 PBMCs | | |
| Immune Cell Subtype | VV-ADSCs + isotype control | VV-ADSCs + NKG2D antibody | % Increase with NKG2D antibody | VV-ADSCs + isotype control | VV-ADSCs + NKG2D antibody | % Increase with NKG2D antibody |
| γδ T | 47.2 | 55.0 | 16.5 | 21.5 | 27.4 | 27.4 |
| NK | 72.4 | 77.1 | 6.5 | 68.2 | 77.5 | 13.6 |
| $CD56^{high}CD16^-$ | 19.8 | 36.3 | 83.3 | 23.1 | 35.0 | 51.5 |
| $CD56^{low}CD16^+$ | 83.1 | 85.6 | 3.0 | 67.3 | 76.8 | 14.1 |

TABLE 62

Effects of NKG2D activation on the % of CD69+ activated immune subpopulations in co-cultures of virus-infected tumor cells with incompatible and compatible PBMCs

| | Average % CD69+ Activated Immune Cell Subtypes | | | | | |
|---|---|---|---|---|---|---|
| | CBD1 PBMCs | | | CBD2 PBMCs | | |
| Immune Cell Subtype | VV-PC3 + isotype control | VV-PC3 + NKG2D antibody | % Increase with NKG2D antibody | VV-PC3 + isotype control | VV-PC3 + NKG2D antibody | % Increase with NKG2D antibody |
| γδ T | 81.4 | 82.6 | 1.5 | 33.1 | 33.6 | 1.5 |
| NK | 90.3 | 89.8 | -0.6 | 84.5 | 82.5 | -2.4 |
| $CD56^{high}CD16^-$ | 72.5 | 73.1 | 0.8 | 62.5 | 66.9 | 7.0 |
| $CD56^{low}CD16^+$ | 94.6 | 95.4 | 0.8 | 82.8 | 80.7 | -2.5 | multi-parameter flow cytometry analysis using CD69 as an activation marker, and the set of cell type specific markers described previously (see, Example 8). Table 63 below shows the average numbers for each of the CD69$^+$ activated immune cell subpopulations, recovered from co-cultures of incompatible or compatible PBMCs with each of: uninfected stem cells; vaccinia virus-infected stem cells; or vaccinia virus-infected stem cells+IL-10. Table 64 displays the same data for co-cultures with uninfected and vaccinia virus-infected PC3 tumor cells. Table 65 depicts the results in terms of the percent IL-10-mediated suppression of the immune cell subtypes, which was calculated using the formula:

% IL-10 Suppression=(1−(avg. immune cell number with virus-infected carrier cells+IL-10/avg. immune cell number with virus-infected carrier cells))×100.

As shown in Tables 63 and 64, the virus-infected stem and tumor cell carriers elicit an immune response across all immune cell subtypes compared to uninfected carrier cells, with a larger response in the co-cultures with the incompatible (CBD1) vs. compatible (CBD2) PBMCs. Virus-infected tumor cells elicited larger numbers of all immune cell subtypes, consistent with the fact that stem cells possess enhanced immunosuppressive and immune evasive properties. The addition of IL-10 did not prevent immune activation in response to the virus-infected carrier cells, but significantly suppressed the numbers of CD69$^+$ activated immune cells across all immune subtypes tested in both compatible and incompatible settings, and in the co-cultures with virus-infected stem cells (Table 63) or in tumor cells (Table 64). In general, the potency of the IL-10-mediated suppression was the highest in the virus-infected stem cell co-cultures with the compatible PBMCs (see, Table 65). These results are consistent with the more potent allogeneic responses against carrier cells (tumor or stem cells) in the incompatible settings (CBD1 vs. CBD2). The data indicate that engineered expression of IL-10 and other immunosuppressive factors, in the stem or tumor cell carriers, can maintain and extend the immunosuppressive properties of the carrier cells, allowing them to evade immune recognition and allogeneic rejection. This, in turn, enhances their therapeutic efficacy by improving their ability to amplify, deliver, and spread the virus to the target tumor cells, prior to being attacked by the immune system.

To achieve this, the carrier cells can be engineered for transient or permanent expression of immunosuppressive factors of human or viral origin. For example, the carrier cells can be engineered to express immunosuppressive factors of human origin, such as, but not limited to, IDO, Arginase, TRAIL, iNOS, IL-10, TGFβ, VEGF, FGF-2, PDGF, HGF, IL-6, sMICA, sMICB, sHLA-G, HLA-E, PD-L1, FAS-L, B7-H4, and single-chain antibodies (scFv) that target or deplete NK and/or NKT cells. The carrier cells also can be engineered to express immunosuppressive factors of viral origin, such as, but not limited to, ectromelia/vaccinia virus SPI-2/CrmA (inhibitor of immune FAS/TNF/Granzyme B induced apoptosis); vaccinia virus encoded N1 (IL-1/NFκB/IRF3 antagonist); HA (NCR antagonists targeting NKp30, NKp44, NKp46); IL-18 binding protein; A40R; A46R; A52R; B15R/B16R; TNFα blockers (e.g., vaccinia virus CmrC/CmrE); IFN α/β blockers (e.g., vaccinia virus B18R/B19R); IFNγ blockers (e.g., vaccinia virus B8R); and other IL-1/IL-1β/NFκB/IRF3/NCR/MHCI/TLR/NKG2D antagonists.

TABLE 63

Effects of IL-10 on average number of CD69$^+$ immune cell subtypes in uninfected and virus-infected stem cell co-cultures with incompatible and compatible PBMCs

| | Average Number of Cells | | | | | |
|---|---|---|---|---|---|---|
| | Incompatible PBMCs (CBD1) | | | Compatible PBMCs (CBD2) | | |
| Immune Cell Subtype | RM35 ADSCs | RM35 ADSCs + VV | RM35 ADSCs + VV + IL-10 | RM35 ADSCs | RM35 ADSCs + VV | RM35 ADSCs + VV + IL-10 |
| γδ T | 5.0 | 413.3 | 332.0 | 2.0 | 27.5 | 16.0 |
| iNKT | 1.0 | 42.2 | 18.5 | 2.0 | 32.5 | 4.5 |
| NKT | 3.5 | 235.4 | 191.0 | 2.0 | 42.5 | 12.0 |
| CD4 T | 6.0 | 229.6 | 102.0 | 17.0 | 76.5 | 20.0 |
| CD8 T | 1.0 | 186.4 | 118.0 | 6.0 | 118.5 | 43.0 |
| NK | 4.5 | 547.3 | 448.0 | 13.0 | 1390 | 568.5 |
| CD56$^{high}$CD16$^-$ | 0.0 | 39.6 | 25.5 | 1.5 | 43.0 | 20.0 |
| CD56$^{low}$CD16$^+$ | 3.5 | 292.0 | 305.0 | 7.5 | 759.5 | 380.5 |

TABLE 64

% Effects of IL-10 on average number of CD69+ immune cell subtypes in tumor cell co-cultures with incompatible and compatible PBMCs

| | Average Number of Cells | | | | | |
|---|---|---|---|---|---|---|
| | Incompatible PBMCs (CBD1) | | | Compatible PBMCs (CBD2) | | |
| Immune Cell Subtype | PC3 tumor cells | PC3 + VV | PC3 + VV + IL-10 | PC3 tumor cells | PC3 + VV | PC3 + VV + IL-10 |
| γδ T | 38.5 | 780.5 | 514.5 | 4.5 | 84.0 | 62.5 |
| iNKT | 6.5 | 192.5 | 64.0 | 3.5 | 92.5 | 39.5 |
| NKT | 27.5 | 1073.5 | 474.0 | 3.5 | 79.0 | 59.0 |
| CD4 T | 48.0 | 960.0 | 380.0 | 49.5 | 675.0 | 244.5 |
| CD8 T | 21.0 | 858.0 | 285.5 | 5.0 | 244.5 | 106.0 |
| NK | 67.5 | 807.0 | 529.0 | 18.5 | 1228.0 | 847.0 |
| $CD56^{high}CD16^-$ | 3.0 | 77.0 | 51.0 | 2.5 | 68.0 | 40.0 |
| $CD56^{low}CD16^+$ | 44.5 | 426.0 | 313.0 | 12.0 | 654.5 | 503.5 |

TABLE 65

% IL-10-mediated suppression of immune cell subtypes in stem and tumor cell co-cultures with incompatible and compatible PBMCs

| | % Suppression by IL-10 | | | |
|---|---|---|---|---|
| | RM35 ADSCs | | PC3 Tumor Cells | |
| Immune Cell Subtype | CBD1 PBMCs | CBD2 PBMCs | CBD1 PBMCs | CBD2 PBMCs |
| γδ T | 19.67 | 41.82 | 34.08 | 25.60 |
| iNKT | 56.15 | 86.15 | 66.75 | 57.30 |
| NKT | 18.85 | 71.76 | 55.85 | 25.32 |
| CD4 T | 55.57 | 73.86 | 60.42 | 63.78 |
| CD8 T | 36.69 | 63.71 | 66.72 | 56.65 |
| NK | 18.14 | 59.10 | 34.45 | 31.03 |
| $CD56^{high}CD16^-$ | 35.54 | 53.49 | 33.77 | 41.18 |
| $CD56^{low}CD16^+$ | −4.45 | 49.90 | 26.41 | 23.07 |

Since modifications will be apparent to those of skill in the art, it is intended that this invention be limited only by the scope of the appended claims.

The invention claimed is:

1. A carrier cell, comprising an oncolytic virus, wherein:
the virus can replicate in the cell;
the cell can be administered to a human subject;
the cell has been treated or modified or both to enhance the immunosuppressive properties or immunoprivileged properties of the cell for administration to a human subject, wherein the treated and/or modified cell is:
an engineered cell that expresses one or more single-chain antibodies that target or deplete NK and/or NKT cells and/or one or more single-chain antibodies that target or deplete γδT cells; and/or
an engineered cell that expresses one or more protein antagonists of complement proteins and/or one or more protein antagonists of neutralizing antibodies; and
optionally, the cell has been loaded with a growth factor and/or cytokine to enhance amplification of the virus in the cell.

2. The carrier cell of claim 1, that has been loaded with a growth factor and/or cytokine to enhance amplification of the virus in the cell.

3. The carrier cell of claim 1, wherein:
the cell has been treated or modified or both to enhance the immunosuppressive properties or immunoprivileged properties of the cell for administration to a human subject; and
the cell has been treated or modified to enhance amplification of the virus in the cell.

4. The carrier cell of claim 1 that is selected from among a treated or modified stem cell, immune cell, and tumor cell.

5. The carrier cell of claim 1 that is a stem cell.

6. The carrier cell of claim 4 that is a stem cell selected from among a mesenchymal, neural, totipotent, pluripotent, induced pluripotent, multipotent, oligopotent, unipotent, adipose stromal, endothelial, bone marrow, cord blood, adult peripheral blood, myoblast, small juvenile, epithelial, embryonic epithelial, and fibroblast stem cell.

7. The carrier cell of claim 4 that is a mesenchymal stem cell selected from among mesenchymal cells from adult bone marrow, adipose tissue, blood, dental pulp, neonatal umbilical cord, cord blood, placenta, placenta-derived adherent stromal cells, placenta-derived decidual stromal cells, endometrial regenerative cells, placental bipotent endothelial/mesenchymal progenitor cells, amniotic membrane or fluid mesenchymal stem cells, amniotic fluid derived progenitors, Wharton's Jelly mesenchymal stem cells, pelvic girdle stem cells, Chorionic Villus Mesenchymal Stromal cells, subcutaneous white adipose mesenchymal stem cells, pericytes, adventitial reticular stem cells, hair follicle-derived stem cells, hematopoietic stem cells, periosteum-derived mesenchymal stem cells, lateral plate mesenchymal stem cells, exfoliated deciduous teeth stem cells, periodontal ligament stem cells, dental follicle progenitor cells, stem cells from apical papilla, and muscle satellite cells.

8. The carrier cell of claim 4, that is an immune cell selected from among granulocytes, mast cells, monocytes, dendritic cells, natural killer cells, lymphocytes, T-cell receptor (TCR) transgenic cells targeting tumor-specific antigens, and CAR-T cells targeting tumor-specific antigens.

9. The carrier cell of claim 1 that is a tumor cell or tumor cell line.

10. The carrier cell of claim 9 that is a tumor cell line selected from among a human leukemia, T-cell leukemia, myelomonocytic leukemia, lymphoma, non-Hodgkin's lymphoma, Burkitt lymphoma, diffuse large B cell lymphoma, acute myeloid leukemia (AML), chronic myelogenous leukemia (CML), acute lymphoblastic leukemia (ALL), erythroleukemia, myelomonoblastic leukemia, malignant non- Hodgkin's NK Lymphoma, myeloma/plasmacytoma, multiple myeloma, and a macrophage cell line.

11. The carrier cell of claim 9 that is a modified or treated cell from a human tumor cell line selected from an NCI-60 panel, a fibrosarcoma, a hepatocarcinoma, a prostate cancer, a breast cancer, a head and neck cancer, a lung cancer, a pancreatic cancer, an ovarian cancer, a colon cancer, a gastric cancer, a gynecological cancer, a sarcoma, a melanoma, a squamous cell carcinoma, a hepatocellular carcinoma, a bladder cancer, a renal cell carcinoma, an embryonal carcinoma, a testicular teratoma, a glioblastoma, an astrocytoma, a thyroid carcinoma, or a mesothelioma cell line.

12. The carrier cell of claim 1 that is a modified or treated cell from a GM-CSF whole tumor cell vaccine (GVAX).

13. The carrier cell of claim 1, wherein the oncolytic virus is selected from among a Newcastle disease virus, parvovirus, measles virus, reovirus, vesicular stomatitis virus (VSV), adenovirus, poliovirus, herpes simplex virus (HSV), poxvirus, coxsackie virus (CXV) and Seneca Valley virus (SVV).

14. The carrier cell of claim 13, wherein the oncolytic virus is a vaccinia virus.

15. The carrier cell of claim 14, wherein the vaccinia virus is selected from among a Lister strain, Western Reserve (WR) strain, Copenhagen (Cop) strain, Bern strain, Paris strain, Tashkent strain, Tian Tan strain, Wyeth strain (DRYVAX), IHD-J strain, IHD-W strain, Brighton strain, Ankara strain, CVA382 strain, Dairen I strain, LC16m8 strain, LC16M0 strain, modified vaccinia Ankara (MVA) strain, ACAM strain, WR 65-16 strain, Connaught strain, New York City Board of Health (NYCBH) strain, EM-63 strain, NYVAC strain, Lister strain LIVP, JX-594 strain, GL-ONC1 strain, a vvDD TK mutant strain with deletions in VGF and TK, ACAM2000, and ACAM1000.

16. The carrier cell of claim 1 that has been treated to enhance or improve virus amplification, or to block induction of an anti-viral state in the subject or in the tumor microenvironment.

17. The carrier cell of claim 1 that has been treated to enhance virus amplification by pre-treatment or treatment with one or more of a cytokine or growth factor.

18. The carrier cell of claim 1 that is treated to inhibit, or is modified to express an inhibitor of, interferon-γ and/or interferon-β.

19. The carrier cell of claim 1 that has been treated to enhance virus amplification by pre-treatment or treatment to load the cell with one or more of IL-10, TGFβ, VEGF, FGF-2, PDGF, HGF, IL-6, GM-CSF, a RTK/mTOR agonist, a Wnt protein ligand, and a GSK3 inhibitor/antagonist.

20. The carrier cell of claim 16 that has been treated to block induction of an anti-viral state by pre-treatment or treatment to load the cell with one or more small molecule or protein inhibitors that interfere with IFN Type I/Type II receptors, interfere with downstream signaling, interfere with IFNAR1/IFNAR2 signaling, interfere with IFNGR1/IFNGR2 signaling, interfere with STAT1/2 signaling, interfere with Jak1 signaling, interfere with Jak2 signaling, interfere with IRF3 signaling, interfere with IRF7 signaling, interfere with IRF9 signaling, interfere with TYK2 signaling, interfere with TBK1 signaling, or interfere with other signaling pathways that effect an immune response against the oncolytic virus in the cell or subject.

21. The carrier cell of claim 16 that has been sensitized to block induction of an anti-viral state by pre-treatment or treatment to load the cell with one or more HDAC inhibitors for interfering with/deregulating IFN signaling/responsiveness.

22. The carrier cell of claim 16 that has been sensitized to block induction of an anti-viral state or enhance virus amplification by pre-treatment or treatment to load the cell with antagonists of virus-sensing and/or anti-virus defense pathways.

23. The carrier cell of claim 22, wherein the virus-sensing and/or anti-virus defense pathway(s) is/are mediated by one or more of STING, PKR, RIG-1, MDA-5, OAS-1/2/3, AIM2, MAVS, RIP-1/3, and DAI (ZBP1).

24. The carrier cell of claim 22, wherein the antagonist(s) is/are selected from one or more of K1, E3L, and K3L vaccinia proteins; NS1/NS2 influenza proteins; hepatitis C NS3-4A; arenavirus NP and Z proteins; Ebola virus VP35; HSV US11, ICP34.5 and ICP0; MCMV M45; and Borna disease virus X protein.

25. The carrier cell of claim 1 that has been sensitized to protect against inactivation/rejection determinants.

26. The carrier cell of claim 25, wherein the cell has been sensitized to protect against inactivation/rejection determinants by pre-treatment or treatment to load the cell with one or more viral major histocompatibility complex (MHC) antagonists.

27. The carrier cell of claim 26, wherein the MHC antagonist(s) is/are selected from among one or more of A4OR MHCI antagonist from vaccinia; Nef and TAT from HIV; E3-19K from adenovirus; ICP47 from HSV 1 and HSV2; CPXV012 and CPXV203 from Cowpox; ORF66 from varicella zoster virus (VZV); EBNA1, BNLF2a, BGLF5, and BILF1 from Epstein Barr virus (EBV); US2/gp24, US3/gp23, US6/gp21, US10, and US11/gp33 from human cytomegalovirus (hCMV); Rh178NIHCE from rhesus CMV (RhCMV); U21 from human herpes virus (HHV) 6 or HHV7; LANA1, ORF37/SOX, kK3/MIR1, and kK5/MIR2 from Kaposi's sarcoma associated herpes virus (KSHV); mK3 from mouse hepatitis virus-68 (MHV-68); UL41/vhs from alpha-herpesvirus, herpes simplex virus (HSV), bovine herpes virus-2 (BHV-1), and pseudorabies virus (PRV); UL49.5 from Varicellovirus, BHV-1, equine herpes virus 1 and 4 (EHV-1/4) and PRV; and m4/gp34, m6/gp48, m27, and m152/gp40 from murine CMV (mCMV).

28. The carrier cell of claim 1, wherein the cell has been sensitized to protect against inactivation/rejection determinants by pre-treatment or treatment to load the cell with antagonists of human MHC class I chain related genes MIC-A and MIC-B or with beta-2 microglobulin (B2M) antagonists of viral origin.

29. The carrier cell of claim 1, wherein the cell has been sensitized to enhance immune suppression/immune evasion by pre-treatment or treatment to load the cell with immunosuppressing factors of viral origin.

30. The carrier cell of claim 29, wherein the immunosuppressing factor is selected from among one or more of an inhibitor of immune FAS/TNF/granzyme B-induced apoptosis; an IL-1/NFκB/IRF3 antagonist; an IL-1 and toll-like receptor (TLR) antagonist; an IL-1β antagonist; a TNFα blocker; an IFNα/β blocker; and an IFNγ blocker.

31. The carrier cell of claim 1, wherein the cell has been sensitized to enhance immune suppression/immune evasion by pre-treatment or treatment to load the cell with one or more small molecule inhibitor(s) of one or more of antigen peptide transporter-1/2 (TAP-1 and TAP-2) and tapasin.

32. The carrier cell of claim 1, wherein the cell has been sensitized to protect against complement.

33. The carrier cell of claim 1 that has been engineered to express a protein antagonist of a complement protein, wherein the protein antagonist is an antibody.

34. The carrier cell of claim 33, wherein the complement protein is C3 or C5.

35. The carrier cell of claim 1 that is further engineered for improved viral amplification and/or immunomodulation by one or more of:
   a) engineering to prevent or to be unresponsive to an interferon-induced antiviral state;
   b) engineering to evade allogeneic recognition by one or more of T and NKT cells and/or one or more adaptive immune response(s) of γδ T cells;
   c) engineering to evade allogeneic recognition by NK Cells and/or one or more innate immune response(s) of γδ T cells; and
   d) engineering to express cancer or stem cell-derived factors that facilitate viral infection of otherwise non-permissive carrier cells and/or tumor cells.

36. The carrier cell of claim 35 that is a) engineered to be unresponsive to an interferon-induced antiviral state by transient or permanent suppression of Type I/Type II IFN receptors and/or downstream signaling, wherein permanent suppression can be effected by deleting the locus that is suppressed.

37. The carrier cell of claim 36, wherein suppression is effected by suppression of one or more of Type I/Type II interferon receptor expression, IFN α/β receptor expression, IFNγ receptor expression, IFNAR1/IFNAR2 receptor expression, IFNGR1/IFNGR2 receptor expression, STAT1/2 receptor expression, Jak1/2 receptor expression, IRF3 receptor expression, IRF7 receptor expression, IRF9 receptor expression, TYK2 kinase expression, and TBK1 kinase expression.

38. The carrier cell of claim 35 that is a) engineered to be unresponsive to an interferon-induced antiviral state by transient or permanent suppression of elements of the cytosolic viral DNA/RNA-sensing and anti-viral defense machinery.

39. The carrier cell of claim 35 that is engineered to prevent or to be unresponsive to an interferon-induced antiviral state by transient or permanent expression of antagonists of virus-sensing and anti-viral defense pathways mediated by STING, PKR, RIG-1, MDA-5, OAS-1/2/3, AIM2, MAVS, RIP-1/3, and DAI (ZBP1).

40. The carrier cell of claim 39, wherein the antagonist(s) is/are selected from among one or more of Kl, E3L, and K3L vaccinia proteins; NS1/NS2 influenza A proteins; hepatitis C NS3-4A; arenavirus NP and Z proteins; Ebola virus VP35; HSV US11, ICP34.5 and ICP0; MCMV M45; and Borna disease virus X protein.

41. The carrier cell of claim 35 that is b) engineered to evade allogeneic recognition by one or more of T and NKT cells and/or one or more adaptive immune response(s) of γδ T cells.

42. The carrier cell of claim 41, wherein engineering to evade allogeneic recognition by one or more of T and NKT cells and/or one or more adaptive immune response(s) of γδ T cells is effected by either or both of:
   (i) transient or permanent suppression of one or more of: MHC Class I molecules, MHC Class II molecules, and MHC-like molecules, and regulators of transcription or expression of MHC Class I, MHC Class II, and MHC-like molecules; and
   (ii) transient or permanent expression of B2M antagonists of viral origin and/or MHC antagonists of viral origin.

43. The carrier cell of claim 42, wherein:
   transient or permanent suppression of one or more of MHC Class I molecules is effected by permanent or transient suppression of HLA-A, -B and/or -C;
   transient or permanent suppression of one or more of MHC Class II molecules is effected by suppression of one or more of HLA-DP, -DQ and -DR;
   transient or permanent suppression of one or more of MHC-like molecules is effected by suppression of CD1a/b/c/d; and
   transient or permanent suppression of one or more regulators of transcription or expression of MHC Class I, MHC Class II and MHC-like molecules is effected by suppression of one or more of TAP1/2, Tapasin, Beta-2 microglobulin, CIITA, RFXANK, RFX5, and RFXAP.

44. The carrier cell of claim 42, wherein transient or permanent suppression of B2M, and/or MHC is effected by transient or permanent expression of one or more of:
   B2M antagonists of viral origin selected from UL18 from hCMV; and
   one or more MHC antagonists of viral origin selected from among one or more of A4OR MHCI antagonist from vaccinia; Nef and TAT from HIV; E3-19K from adenovirus; ICP47 from HSV 1 and HSV2; CPXV012 and CPXV203 from Cowpox; ORF66 from varicella zoster virus (VZV); EBNA1, BNLF2a, BGLF5, and BILF1 from Epstein Barr virus (EBV); US2/gp24, US3/gp23, US6/gp21, US10, and US11/gp33 from human cytomegalovirus (hCMV); Rh178/VIHCE from rhesus CMV (RhCMV); U21 from human herpes virus-6 or HHV7; LANA1, ORF37/SOX, kK3/MIR1, and kK5/MIR2 from Kaposi's sarcoma associated herpes virus (KSHV); mK3 from mouse hepatitis virus-68 (MHV-68); UL41/vhs from alpha-herpesvirus, herpes simplex virus (HSV), bovine herpes virus-2 (BHV-1), and pseudorabies virus (PRV); UL49.5 from varicella zoster virus, BHV-1, equine herpes virus 1 and 4 (EHV-1/4) and PRV; and m4/gp34, m6/gp48, m27, and m152/gp40 from murine CMV (mCMV).

45. The carrier cell of claim 35 that is c) engineered to evade allogeneic recognition by NK cells and/or one or more innate immune response(s) of γδ T cells by either or both of:
   (i) transient or permanent suppression of: membrane-bound MICA/B, or membrane-bound PVR, or membrane-bound Nectin-2, wherein permanent suppression can be effected by deleting the locus; and
   (ii) transient or permanent expression of: antagonists of MIC-A and MIC-B, antagonists of the NKG2D receptor, antagonists of NCR, ligands for the NK inhibitory receptors (KIR), or ligands for the NK inhibitory receptors NKG2a/CD94.

46. The carrier cell of claim 35 that is c) engineered to evade allogeneic recognition by NK cells by either or both of:
   (i) transient or permanent suppression of NKG2D Ligands and/or DNAM-1 ligands; and
   (ii) transient or permanent expression of:
      the antagonist of MIC-A and MIC-B kK5 (from Kaposi's sarcoma virus (KHSV));
      the antagonist of the NKG2D receptor Cowpox OMCP;
      the antagonist of NCR targeting NKp30, NKp44, and NKp46 receptors, hemagglutinin (HA from vaccinia and other viruses);
      ligands for the NK inhibitory receptors (KIR), selected from HLA-Bw4 and HLA-C2; and/or
      ligands for the NK inhibitory receptors (NKG2a/CD94), selected from HLA-E and derivatives alone, or combined with 21M HLA-B ligands to generate HLA-E binding peptides and stabilize HLA-E surface expression.

47. The carrier cell of claim 35 that is d) engineered to express cancer or stem cell-derived factors that facilitate viral infection of otherwise impermissive carrier cells and/or tumor cells.

48. The carrier cell of claim 47, wherein the cancer or stem cell-derived factors that facilitate viral infection of otherwise impermissive carrier cells and/or tumor cells are selected from among one or more growth factors and cytokines that facilitate viral infection.

49. The carrier cell of claim 47, wherein the cancer or stem cell-derived factors that facilitate viral infection of otherwise impermissive carrier cells and/or tumor cells are selected from among one or more of cancer associated antigens, oncofetal antigens, oncogene/tumor suppressors, differentiation antigens, GM-CSF, IL-10, TGFβ, VEGF, FGF-2, PDGF, HGF, IL-6, RTK/mTOR agonists, and Wnt protein ligands.

50. The carrier cell of claim 1, wherein the protein antagonists of complement proteins and/or of neutralizing antibodies are selected from among protein antagonists of complement factors (C1, C2, C3, C4, C5, MBL), vaccinia virus complement control protein (VCP), vaccinia virus complement inhibitor (B5R), scFv anti-CD1q/CD1r/CD1s, anti-C3 antibodies, anti-CS antibodies, peptidic C3 inhibitors of the compstatin family, human soluble membrane (s/m) proteins, human Factor H and derivatives, and cobra venom factors and derivatives thereof with complement inhibitory activity.

51. A method of treatment of cancer, comprising administering the carrier cell of claim 1 to a subject who has cancer that comprises a solid tumor or a hematologic malignancy.

52. The method of claim 51, wherein the carrier cell is allogeneic to the subject.

53. The method of claim 51, wherein the carrier cell is autologous to the subject.

54. The method of claim 51, wherein:
the cancer is a solid tumor or hematologic malignancy; and
the carrier cells are treated or modified to have improved viral amplification properties and/or to have enhanced immunosuppressive or immune privileged properties; and/or the carrier cells are sensitized by pretreatment with factors that promote viral amplification and/or enhance the immunosuppressive or immune privileged properties of the carrier cells.

55. The method of claim 51, wherein the cancer is selected from among leukemias, lymphomas, melanomas, carcinomas, sarcomas, myelomas, and neuroblastomas.

56. The method of claim 51, the cancer is selected from among pancreatic cancer, lung cancer, ovarian cancer, breast cancer, cervical cancer, bladder cancer, prostate cancer, brain cancer, central nervous system cancer, adenocarcinomas, liver cancer, skin cancer, hematological cancers, biliary tract cancer, bone cancer, choriocarcinoma, colon and rectal cancers, connective tissue cancer, cancer of the digestive system, endometrial cancer, esophageal cancer, eye cancer, head and neck cancer, gastric cancer, intra-epithelial neoplasm, kidney cancer, larynx cancer, oral cavity cancer, retinoblastoma, rhabdomyosarcoma, cancer of the respiratory system, stomach cancer, testicular cancer, thyroid cancer, uterine cancer, and urinary system cancers.

57. The method of claim 51, wherein a carrier cell without virus is pretreated with IFN-gamma, and is administered or used prior to administration of the carrier cell comprising virus, or concurrently with the carrier cell comprising virus.

58. The method of claim 51, wherein the carrier cell/virus combination is matched to the subject.

59. A modified carrier cell engineered, for one or more of:
a) transient or permanent expression or suppression of a gene that renders the carrier cell unresponsive to an interferon-induced antiviral response;
b) transient or permanent expression or suppression of a gene to facilitate evading allogeneic recognition by one or more of T and NKT cells and/or one or more adaptive immune response(s) of γδ T cells;
c) transient or permanent expression or suppression of a gene to facilitate evading allogeneic recognition by NK Cells and/or one or more innate immune response(s) of γδ T cells;
d) transient or permanent expression of immunosuppressive factors;
e) transient or permanent expression of factors that facilitate viral association with the carrier cell; and
f) transient or permanent expression of factors that interfere with the function of complement, and/or neutralizing antibodies.

60. The modified carrier cell of claim 59, wherein the modifications are further selected from among:
a) sensitization of the carrier cell to enhance virus amplification ability;
b) sensitization of the carrier cell to block induction of anti-viral responses;
c) protection of the carrier cell against allogeneic inactivation and/or rejection by the subject;
d) protection of the carrier cell against complement; and/or
e) rendering the carrier cell resistant to virus-mediated killing.

61. A method of selecting a carrier cell of claim 1 as suitable for delivery of an oncolytic virus to a subject having cancer, wherein the carrier cell is allogeneic to the subject, the method comprising:
identifying one or more of the following determinants (a)-(f) as indicative of a match between the carrier cell and the subject:
a) the carrier cell and the subject have identical alleles at 50% or more of the following genetic loci combined:
(i) MHC I and/or MHC II haplotypes;
(ii) MR haplotype and/or MR ligand haplotypes; and
(iii) HLA-E, CD1a, CD1b, CD1c and/or CD1d haplotypes;
b) incubating the carrier cell in a co-culture with cancerous cells from the subject results in one or more of the following:
(i) a cell to tumor migration score (CTMS) of 20% or more of the carrier cells migrating toward the cancerous cells;
(ii) a tumor to cell migration score (TCMS) of 20% or more of the cancerous cells migrating toward the carrier cells; and/or
(iii) a cumulative migration score (MRS) of [(i)+(ii)]/2 of at least 20%;
c) incubating the carrier cell in a co-culture with the oncolytic virus and cancerous cells from the subject results in one or more of the following:
(i) a virus loaded cell to tumor migration score (V-CTMS) of 20% or more of the carrier cells migrating toward the cancerous cells;

(ii) a virus loaded tumor to cell migration score (V-TCMS) of 20% or more of the cancerous cells migrating toward the carrier cells; and/or (iii) a cumulative virus loaded migration score (V-MRS) of [(i)+(ii)]/2 of at least 20%;

d) when the carrier cell is incubated in a co-culture with the oncolytic virus and immune cells obtained from the subject, an immunological viral amplification score (IVAS) representing the amount of viral amplification in the presence of immune cells obtained from the subject relative to the amount of viral amplification obtained under equivalent conditions except in the absence of immune cells obtained from the subject, is at least 20%;

e) when the carrier cell is incubated in a co-culture with the oncolytic virus and immune cells obtained from the subject, an immunological compatibility score (ICS) representing the immune response in the presence of the carrier cell relative to the immune response under equivalent conditions except in the absence of the carrier cell, is ≤200%, wherein the immune response is determined by the amount of expression of one or more of the following:

(i) IFNγ;

(ii) one or more markers associated with T cell, NK cell and/or NKT cell-mediated cytotoxicity; and/or (iii) one or more markers associated with T cell, NK cell and/or NKT cell activator/effector function(s);

f) when the carrier cell is incubated in a co-culture with the oncolytic virus and immune cells obtained from the subject, the carrier cell does not augment an anti-viral immune response and/or suppresses an anti-viral immune response relative to identical conditions except in the absence of the carrier cell, as measured by an immunological suppression score (ISS) of ≥0% according to the equation:

ISS %=[(IV+IC)−ICV]/(IV+IC)×100, wherein:

IV=the marker expression level in a co-culture of the virus+immune cells obtained from the subject;

IC=the marker expression level in a co-culture of immune cells obtained from the subject+the carrier cell;

ICV=the marker expression level in a co-culture of immune cells obtained from the subject+the carrier cell+the virus; and the marker expression level is the expression level of one or more of the markers set forth in (i), (ii) and (iii) of e);

if one or more of a)-f) is satisfied, identifying a match between the carrier cell and the subject; and selecting the carrier cell as suitable for delivery of an oncolytic virus to the subject having cancer.

62. A method of matching a subject having cancer with a carrier cell of claim 1 for delivery of an oncolytic virus to the subject, wherein the carrier cell is allogeneic to the subject, the method comprising:

determining whether the carrier cell overcomes immune barriers in the subject by detecting, in a co-culture comprising the carrier cell, the oncolytic virus and cells from the subject, a level of expression of one or more immunological markers that is ≤200% the level of expression detected under equivalent conditions except in the absence of the carrier cell, wherein the markers are selected from among one or more of:

(1) markers for T cell activation;

(2) markers for NK cell activation; and (3) markers for NKT cell activation;

wherein if the expression level of at least one marker selected from among (1), (2) and (3) in the co-culture is ≤200% the level of expression detected under equivalent conditions except in the absence of the carrier cell, the carrier cell is a match for the subject.

63. The carrier cell of claim 2 that had been pre-treated to load the cell with one or more of IL-10, TGFβ, VEGF, FGF-2, PDGF, HGF, IL-6, GM-CSF, a RTK/mTOR agonist, a Wnt protein ligand, and a GSK3 inhibitor/antagonist.

* * * * *